US012766083B2

(12) United States Patent
Shiota et al.

(10) Patent No.: US 12,766,083 B2
(45) Date of Patent: Oct. 20, 2026

(54) CYCLIC PEROXIDE, OXIDATION REACTION PRODUCT, METHOD FOR PRODUCING OXIDATION REACTION PRODUCT, AND APPLICATIONS OF THESE

(71) Applicant: MEDIPLUS PHARMA, INC., Tokyo (JP)

(72) Inventors: Gotaro Shiota, Tokyo (JP); Kenji Ito, Tokyo (JP); Hiroyuki Sekine, Tokyo (JP); Daiki Okuda, Tokyo (JP)

(73) Assignee: MEDIPLUS IP SOLUTIONS, INC., Tokyo (JP)

( * ) Notice: Subject to any disclaimer, the term of this patent is extended or adjusted under 35 U.S.C. 154(b) by 388 days.

(21) Appl. No.: 18/684,174

(22) PCT Filed: Aug. 18, 2022

(86) PCT No.: PCT/JP2022/031273
§ 371 (c)(1),
(2) Date: Feb. 15, 2024

(87) PCT Pub. No.: WO2023/022204
PCT Pub. Date: Feb. 23, 2023

(65) Prior Publication Data

US 2025/0255795 A1 Aug. 14, 2025

(30) Foreign Application Priority Data

| | | |
|---|---|---|
| Aug. 20, 2021 | (JP) | 2021-134732 |
| Dec. 1, 2021 | (JP) | 2021-195536 |
| Dec. 13, 2021 | (JP) | 2021-202053 |
| Dec. 27, 2021 | (JP) | 2021-212094 |

(51) Int. Cl.

| | |
|---|---|
| ***A61K 8/49*** | (2006.01) |
| ***A61K 31/357*** | (2006.01) |
| ***A61P 29/00*** | (2006.01) |
| ***A61Q 19/02*** | (2006.01) |
| ***A61Q 19/08*** | (2006.01) |
| ***C07D 323/00*** | (2006.01) |

(52) U.S. Cl.
CPC .......... *A61K 8/4973* (2013.01); *A61K 31/357* (2013.01); *A61P 29/00* (2018.01); *A61Q 19/02* (2013.01); *A61Q 19/08* (2013.01); *C07D 323/00* (2013.01)

(58) Field of Classification Search
CPC .... A61K 8/4973; A61K 31/357; A61Q 19/02; A61Q 19/08; A61P 29/00; C07D 323/00
See application file for complete search history.

(56) References Cited

U.S. PATENT DOCUMENTS

2015/0098963 A1 4/2015 Pernodet et al.

FOREIGN PATENT DOCUMENTS

| | | | |
|---|---|---|---|
| JP | 2005-112799 | A | 4/2005 |
| JP | 2015-189735 | A | 11/2015 |
| JP | 2018-390 | A | 1/2018 |
| JP | 2018-172432 | A | 11/2018 |
| JP | 2019-099573 | | 6/2019 |
| JP | 2020-059656 | | 4/2020 |
| JP | 2020-125374 | A | 8/2020 |
| JP | 2021-134732 | | 8/2021 |
| JP | 2021-195536 | | 12/2021 |
| JP | 2021-202053 | | 12/2021 |
| JP | 2021-212095 | | 12/2021 |
| WO | WO 02/14383 | A1 | 2/2002 |
| WO | PCT/JP2022/031273 | | 8/2022 |
| WO | WO2023/022204 | A1 | 2/2023 |

OTHER PUBLICATIONS

RN 3054404-61-1; entered Sep. 12, 2024 (Year: 2024).*
JP 2024-65685 Notice of Reasons for Refusal dated Dec. 10, 2024, 4 pages—Japanese; 4 pages—English.
JP 2023-542444 Decision of Refusal dated Mar. 14, 2024, 7 pages—Japanese; 7 pages—English.
PCT/JP2022/031273, ISR and Written Opinion dated Nov. 7, 2022, 14 pages—Japanese, 14 pages—English.
The Formation of Skin Barrier and Defective Barrier-Associate Skin Diseases, Yosuke Ishitsuka, Dept. of Dermatology, Faculty of Medicine, University of Tsukuba, dated Oct. 9, 2017, Jpn. J. Clin Immunol, 40 (6), pp. 416-427 © 2017 the Japan Society for Clinical Immunology.

* cited by examiner

*Primary Examiner* — Blessing M Fubara
(74) *Attorney, Agent, or Firm* — Andrew F. Young, Esq.; NOLTE LACKENBACH SIEGEL

(57) ABSTRACT

Provided is a highly safe cyclic peroxide. The cyclic peroxide of the present invention is characterized by being represented by the following chemical formula (I):

[Chemical Formula I]

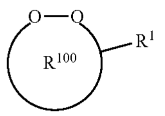

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

25 Claims, 111 Drawing Sheets

Specification includes a Sequence Listing.

$^1H$ NMR spectrum for TLC1 spot product (DMSO-$d_6$, 300 K)

$^{13}C$ NMR spectrum for TLC1 spot product (DMSO-$d_6$, 300 K

COSY NMR spectrum for TLC1 spot product (DMSO-$d_6$, 300 K)

HSQC NMR spectrum for TLC1 spot product (DMSO-$d_6$, 300 K)

HMBC NMR spectrum for TLC1 spot product (DMSO-$d_6$, 300

WITH EXPRESSION SYSTEM CELLS

N = 1

$^{1}H$ NMR spectrum for TLC1 spot product (DMSO-$d_6$, 300 K)

$^{13}C$ NMR spectrum for TLC1 spot product (DMSO-$d_6$, 300 K)

COSY NMR spectrum for TLC1 spot product (DMSO-$d_6$, 300 K)

HMBC NMR spectrum for TLC1 spot product (DMSO-$d_6$, 300 K)

$^1$H NMR spectrum for TLC1 spot product (DMSO-$d_6$, 300 K)

$^{13}C$ NMR spectrum for TLC1 spot product (DMSO-$d_6$, 300 K)

$^{13}C$ DEPT135 NMR spectrum for TLC1 spot product (DMSO-$d_6$, 300 K)

COSY NMR spectrum for TLC1 spot product (DMSO-$d_6$, 300 K)

HMBC NMR spectrum for TLC1 spot product (DMSO-$d_6$, 300 K)

$^1H$ NMR spectrum for TLC1 spot product (DMSO-$d_6$, 300 K)

Figure 4-3 $^{13}C$ NMR spectrum for TLC1 spot product (DMSO-$d_6$, 300 K)

$^{13}C$ DEPT135 NMR spectrum for TLC1 spot product (DMSO-$d_6$, 300 K)

Figure 4-5 COSY NMR spectrum for TLC1 spot product (DMSO-$d_6$, 300 K)

HMBC NMR spectrum for TLC1 spot product (DMSO-$d_6$, 300 K)

HMBC NMR spectrum for TLC1 spot product (DMSO-$d_6$, 300 K)

CYCLIC PEROXIDE, OXIDATION REACTION PRODUCT, METHOD FOR PRODUCING OXIDATION REACTION PRODUCT, AND APPLICATIONS OF THESE

CROSS REFERENCE TO RELATED APPLICATIONS

This application relates to and claims priority from PCT/JP2022/0312273 filed Aug. 18, 2022, the entire contents of which are incorporated herein by reference, including the Sequence Listing in the record, which in turn claims the priority to JP Ser. No. 2021-134732 filed Aug. 20, 2021, JP Ser. No. 2021-195536 filed Dec. 1, 2021, JP Ser. No. 2021-202053 filed Dec. 13, 2021, and JP Ser. No. 2021-212094 filed Dec. 27, 2021.

FIGURE SELECTED FOR PUBLICATION

FIG. 1

REFERENCE TO SEQUENCE LISTING

A computer readable XML file entitled "SEQUENCE_LISTING.XML", with the internal creation title TF21091WO.XML, that was created on Aug. 17, 2022, with a file size of about 16,416 bytes, contains the sequence listing for this application, has been filed with this application, and is hereby incorporated by reference in its entirety.

FIELD OF THE INVENTION

The present invention relates to a cyclic peroxide, an oxidation reaction product, a method for producing an oxidation reaction product, a whitening composition, a whitening agent, a composition for inducing expression of a skin barrier function-related gene, a composition for improving a skin barrier function, an agent for inducing a skin barrier function-related gene, an agent for improving a skin barrier function, a composition for inducing expression of an anti-oxidative stress response gene, an agent for inducing expression of an anti-oxidative stress response gene, an anti-inflammatory composition, an anti-inflammatory agent, an anti-glycation composition, and an anti-glycation agent.

BACKGROUND OF THE INVENTION

Peroxides such as hydrogen peroxide are substances used in the industry for their oxidative capacity, for example. In the field of drug discovery, for example, hydrogen peroxide has been known to be a TRP channel activator. The TRP channel (TRP receptor) is one of receptors of ion channel type present in cell membranes, and used as a target of drug discovery.

In the field of dermatology, the quantity and quality of melanin contained in skin are believed to be important as a factor to determine the color of the skin. For this reason, whitening agents that suppress melanin generation and whitening agents that reduce melanin in skin have been developed as whitening components. Patent Literature 1 describes use of a plant extract from peppermint and/or lemon balm as a whitening component that promotes melanin decomposition.

Moreover, it is known in the field of dermatology that the barrier function of skin deteriorates with aging. The deterioration of the barrier function of skin is known to be associated with skin diseases such as atopic dermatitis (Non Patent Literature 1).

Furthermore, in fields about physical aging, glycation reaction (Maillard reaction), in which protein and carbohydrate such as reducing sugar bind together in a manner independent of enzymes, is known to ultimately generate advanced glycation end products (AGEs). Proteins with AGEs, which have formed from the original proteins through the glycation reaction in vivo, are prevented from exerting the original functions in vivo by the inclusion of AGEs. Accordingly, AGEs are said to be associated with the phenomenon of aging. It has been suggested that accumulation of AGEs in skin causes sagging, wrinkles, freckles, and so on.

CITATION LIST

Patent Literature

Patent Literature 1: Japanese Patent Laid-Open No. 2020-059656

Non Patent Literature

Non Patent Literature 1: Yosuke ISHITSUKA, "The formation of skin barrier and defective barrier-associated skin diseases", 2017, Jpn. J. Clin. Immunol., 40(6), pp. 416-427

DISCLOSURE OF THE INVENTION

Problem to be Solved by the Invention

In the field of drug discovery, however, hydrogen peroxide has problems in terms of safety, including high irritancy and the possibility of explosion, because of the high reaction activity.

In the field of dermatology, no composition has been known that induces expression of a gene relating to the barrier function of skin. In addition, it has not been known that a compound containing a structure with oxidation power contributes to induction of expression of a gene relating to the barrier function of skin and improvement in the barrier function of skin.

Moreover, in fields about physical aging, it has been known that proteins with AGEs, which have formed from the original proteins through the glycation reaction in vivo, are prevented from exerting the original functions in vivo by the inclusion of AGEs, as described above. Accordingly, AGEs are said to be associated with the phenomenon of aging. It has been suggested that accumulation of AGEs in skin causes sagging, wrinkles, freckles, and so on.

In view of such circumstances, an object of the present invention is, in a first mode, to provide a highly safe cyclic peroxide, an oxidation reaction product, and a method for producing an oxidation reaction product.

An object of the present invention is, in a second mode, to provide a whitening composition and a whitening agent each containing a novel whitening component.

An object of the present invention is, in a third mode, to provide a composition for inducing expression of a skin barrier function-related gene and an agent for inducing expression of a skin barrier function-related gene each containing a novel component for inducing expression of a skin barrier function-related gene.

An object of the present invention is, in a fourth mode, to provide an anti-glycation composition and an anti-glycation agent each containing a novel anti-glycation component.

Means to Solve the Problem

Means to Solve the Problem in the First Mode

For the purpose of solving the problem in safety, the cyclic peroxide according to the first mode of the present invention is characterized by being represented by the following chemical formula (I):

[Chemical Formula I]

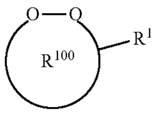

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The oxidation reaction product according to the first mode of the present invention is an oxidation reaction product characterized by containing a cyclic peptide, wherein the oxidation reaction product is obtained through oxidation of an alcohol.

The method for producing an oxidation reaction product according to the first mode of the present invention is a method for producing the oxidation reaction product of the present invention, the method including an alcohol oxidation step of oxidizing the alcohol.

Means to Solve the Problem in the Second Mode

For the purpose of providing a whitening composition and a whitening agent each containing a novel whitening component, the whitening composition according to the second mode of the present invention contains glycerin and/or a glycerin derivative, and a whitening component, wherein the whitening component contains, as an active ingredient, a cyclic peroxide represented by the following chemical formula (I):

[Chemical Formula I]

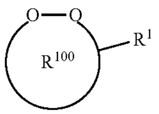

(I)

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The whitening agent according to the second mode of the present invention contains a cyclic peroxide represented by the following chemical formula (I):

[Chemical Formula I]

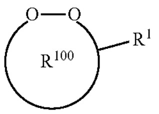

(I)

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

Means to Solve the Problem in the Third Mode

For the purpose of providing a composition for inducing expression of a skin barrier function-related gene and an agent for inducing expression of a skin barrier function-related gene each containing a novel component for inducing expression of a skin barrier function-related gene, the composition for inducing expression of a skin barrier function-related gene according to the third mode of the present invention contains glycerin and/or a glycerin derivative, and a component for inducing expression of a skin barrier function-related gene, wherein the component for inducing expression of a skin barrier function-related gene contains, as an active ingredient, a cyclic peroxide represented by the following chemical formula (I):

[Chemical Formula I]

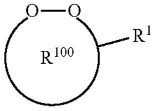

(I)

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The composition for improving a skin barrier function according to the third mode of the present invention contains the composition for inducing expression of a skin barrier function-related gene according to the third mode of the present invention.

The agent for inducing expression of a skin barrier function-related gene according to the third mode of the present invention contains a cyclic peroxide represented by the following chemical formula (I):

[Chemical Formula I]

(I)

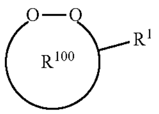

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The agent for improving a skin barrier function according to the third mode of the present invention contains the agent for inducing a skin barrier function-related gene according to the third mode of the present invention.

The composition for inducing expression of an anti-oxidative stress response gene according to the third mode of the present invention contains glycerin and/or a glycerin derivative, and a component for inducing expression of an anti-oxidative stress response gene, wherein the component for inducing expression of an anti-oxidative stress response gene contains, as an active ingredient, a cyclic peroxide represented by the following chemical formula (I):

[Chemical Formula I]

(I)

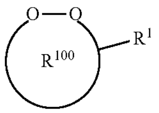

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The agent for inducing expression of an anti-oxidative stress response gene according to the third mode of the present invention contains a cyclic peroxide represented by the following chemical formula (I):

[Chemical Formula I]

(I)

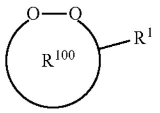

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The anti-inflammatory composition according to the third mode of the present invention contains glycerin and/or a glycerin derivative, and an anti-inflammatory component, wherein the anti-inflammatory component contains, as an active ingredient, a cyclic peroxide represented by the following chemical formula (I):

[Chemical Formula I]

(I)

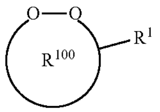

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The anti-inflammatory agent according to the third mode of the present invention contains a cyclic peroxide represented by the following chemical formula (I):

[Chemical Formula I]

(I)

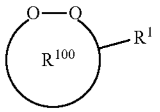

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

Means to Solve the Problem in the Fourth Mode

For the purpose of providing an anti-glycation composition and an anti-glycation agent each containing a novel anti-glycation component, the anti-glycation composition according to the fourth mode of the present invention (hereinafter, also referred to as "the composition") contains glycerin and/or a glycerin derivative, and an anti-glycation component, wherein the anti-glycation component contains, as an active ingredient, a cyclic peroxide represented by the following chemical formula (I):

[Chemical Formula I]

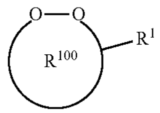

(I)

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The anti-glycation agent according to the fourth mode of the present invention contains a cyclic peroxide represented by the following chemical formula (I):

[Chemical Formula I]

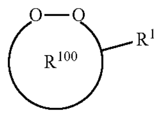

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different, or a salt thereof.

Effect of the Invention

Effect of the First Mode

The present invention can provide, in the first mode, a highly safe cyclic peroxide, an oxidation reaction product, and a method for producing an oxidation reaction product.

Effect of the Second Mode

The present invention can provide, in the second mode, a whitening composition and a whitening agent each containing a novel whitening component.

Effect of the Third Mode

The present invention can provide, in the third mode, a composition for inducing expression of a skin barrier function-related gene and an agent for inducing expression of a skin barrier function-related gene each containing a novel component for inducing expression of a skin barrier function-related gene.

Effect of the Fourth Mode

The present invention can provide, in the fourth mode, an anti-glycation composition and an anti-glycation agent each containing a novel anti-glycation component.

BRIEF DESCRIPTION OF THE DRAWINGS

FIG. 1-2 is a $^{13}C$ NMR spectrum diagram acquired from a reaction mixture resulting from ozone oxidation of glycerin (TLC1 spot product) at a temperature of 300 K (27° C.) with DMSO-$d_6$ as a solvent.

FIG. 1-3 is a $^{13}C$ DEPT135 NMR spectrum diagram acquired from a reaction mixture resulting from ozone oxidation of glycerin (TLC1 spot product) at a temperature of 300 K (27° C.) with DMSO-$d_6$ as a solvent.

FIG. 1-4 is a COSY NMR spectrum diagram acquired from a reaction mixture resulting from ozone oxidation of glycerin (TLC1 spot product) at a temperature of 300 K (27° C.) with DMSO-$d_6$ as a solvent.

FIG. 1-5 is an HSQC NMR spectrum diagram acquired from a reaction mixture resulting from ozone oxidation of glycerin (TLC1 spot product) at a temperature of 300 K (27° C.) with DMSO-$d_6$ as a solvent.

FIG. 1-6 is an HMBC NMR spectrum diagram acquired from a reaction mixture resulting from ozone oxidation of glycerin (TLC1 spot product) at a temperature of 300 K (27° C.) with DMSO-$d_6$ as a solvent.

FIG. 1-7 is a total ion chromatogram (ESI-negative mode) from precise preparative LC (liquid chromatography) for a sample obtained by adjusting (diluting) a reaction mixture (TLC1 spot product) to approximately 3% by mass with acetonitrile and a blank.

FIG. 1-8 is a series of mass spectrum diagrams for peaks F, G, and H (fraction F, fraction G, and fraction H) in FIG. 1-7.

FIG. 1-9 is a diagram showing results of examination on improvement of separation (improvement of separation conditions) in HILIC (high-performance liquid chromatography).

FIG. 1-10 is a diagram showing mass spectra for peaks 1 to 3 in FIG. 1-9 (after improvement of separation).

FIG. 1-11 is a diagram showing mass spectra for peaks 4 to 6 in FIG. 1-9 (after improvement of separation).

FIG. 1-12 is a diagram showing mass spectra for peaks 7 and 8 in FIG. 1-9 (after improvement of separation).

FIG. 1-13 is a diagram showing micro-Raman spectrum diagrams for a separated sample obtained for peak 2 (Mw=180) in FIG. 1-9 and an ozonide authentic sample in combination.

FIG. 1-14 is a $^{1}H$ NMR spectrum diagram for peak 2 (Mw=180) in FIG. 1-9.

FIG. 1-15 is a $^{13}C$ NMR spectrum diagram for peak 2 (Mw=180) in FIG. 1-9.

FIG. 1-16 is a two-dimensional ($^{1}H$-$^{13}C$ COSY) NMR spectrum diagram for peak 2 (Mw=180) in FIG. 1-9.

FIG. 1-17 is a diagram showing HILIC chromatograms for a TLC1 spot product and glyceraldehyde dimer under HILIC (high-performance liquid chromatography) conditions in FIG. 1-9 in combination.

FIG. 1-18 is a diagram showing HILIC chromatograms for a TLC1 spot product and glyceraldehyde dimer under reversed-phase HILIC (high-performance liquid chromatography) conditions in combination.

FIG. 1-19 is an enlarged view of a part of FIG. 1-18.

FIG. 1-20 is a diagram showing ESR spectrum diagrams for a TLC1 spot product and peak 2 (Mw=180) in FIG. 1-9 in combination.

FIG. 1-21 is an ESR spectrum diagram for ozonized methyl linolenate.

FIG. 1-22 is a series of ESR spectrum diagrams for peaks 1 to 8 in FIG. 1-9.

FIG. 1-23 is a diagram showing results of measurement of activity for peaks 1 to 8 in FIG. 1-9 through chemiluminescence.

FIG. 1-24 is a series of diagrams showing effects of G (glycerin), OG (ozonized glycerin), LOG (ozonized oxide), and HOG (heat-treated ozonized glycerin) added to TRPM2 (expressing cells) and Vector (TRPM2-nonexpressing cells).

FIG. 1-25 is a series of diagrams for examination on TRP channel activation in TRPM2 (expressing cells) by G and OG under the same conditions as for FIG. 1-24 except that the concentrations (% by mass) of the aqueous solutions were changed.

FIG. 1-26 is a diagram for examination on TRP channel activation in TRPM2 (expressing cells) by G, OG, LOG, and HOG.

FIG. 1-27 is a series of diagrams for examination on TRP channel activation in TRPM2 (expressing cells) by LOG and OG under the same conditions as for FIG. 1-24 except that 500 unit/ml of catalase was added for comparison with a case without addition of catalase.

FIG. 1-28 is a series of diagrams for examination on TRP channel activation in TRPM2 (expressing cells) by OG and LOG under the same conditions as for FIG. 1-24 except that the concentrations (% by mass) of the aqueous solutions were changed.

FIG. 1-29 is a series of diagrams for examination on TRP channel activation in TRPM2 (expressing cells) by LOG at 0.1% by mass under the same conditions as for FIG. 1-24 except that 100 unit/ml of catalase was added or 1 μm of PJ34 (product name, from ChemScene) was added for comparison with a case without addition of catalase and PJ34.

FIG. 1-30 is a series of diagrams for examination on TRP channel activation in TRPM2 (expressing cells) by LOG at 0.1% by mass under the same conditions as for FIG. 1-24 except that 100 μm of dipyridyl (α,α'-dipyridyl) was added for comparison with a case without addition of dipyridyl.

FIG. 1-31 is a series of diagrams for examination on TRP channel activation in different cells by LOG under the same conditions as for FIG. 1-24 except that the concentration of the aqueous solution was changed and TRPM1 HEK (expressing cells) or HEK (expressing cells) was used in place of TRPM2 (expressing cells).

FIG. 1-32 is a series of diagrams for examination on TRP channel activation in TRPM2 (expressing cells) and TRPMA1 (expressing cells) by F7 at different concentrations in the same manner as for FIG. 1-31.

FIG. 1-33 is a series of diagrams for examination on TRP channel activation in TRPM2 (expressing cells) and TRPMA1 (expressing cells) by F7 at different concentrations in the same manner as for FIG. 1-31.

FIG. 2-1 is a series of graphs showing melanin measurement values over time in Example 2-1.

FIG. 2-2 is a series of graphs showing the changes of melanin measurement values over time in Example 2-1.

FIG. 2-3 is a $^{1}H$ NMR spectrum diagram acquired from a reaction mixture resulting from ozone oxidation of glycerin (TLC1 spot product) at a temperature of 300 K (27° C.) with DMSO-$d_6$ as a solvent.

FIG. 2-4 is a $^{13}C$ NMR spectrum diagram acquired from a reaction mixture resulting from ozone oxidation of glycerin (TLC1 spot product) at a temperature of 300 K (27° C.) with DMSO-$d_6$ as a solvent.

FIG. 2-5 is a $^{13}C$ DEPT135 NMR spectrum diagram acquired from a reaction mixture resulting from ozone oxidation of glycerin (TLC1 spot product) at a temperature of 300 K (27° C.) with DMSO-$d_6$ as a solvent.

FIG. 2-6 is a COSY NMR spectrum diagram acquired from a reaction mixture resulting from ozone oxidation of glycerin (TLC1 spot product) at a temperature of 300 K (27° C.) with DMSO-$d_6$ as a solvent.

FIG. 2-7 is an HSQC NMR spectrum diagram acquired from a reaction mixture resulting from ozone oxidation of glycerin (TLC1 spot product) at a temperature of 300 K (27° C.) with DMSO-$d_6$ as a solvent.

FIG. 2-8 is an HMBC NMR spectrum diagram acquired from a reaction mixture resulting from ozone oxidation of glycerin (TLC1 spot product) at a temperature of 300 K (27° C.) with DMSO-$d_6$ as a solvent.

FIG. 2-9 is a total ion chromatogram (ESI-negative mode) from precise preparative LC (liquid chromatography) for a sample obtained by adjusting (diluting) a reaction mixture (TLC1 spot product) to approximately 3% by mass with acetonitrile and a blank.

FIG. 2-10 is a series of mass spectrum diagrams for peaks F, G, and H (fraction F, fraction G, and fraction H) in FIG. 2-9.

FIG. 2-11 is a diagram showing results of examination on improvement of separation (improvement of separation conditions) in HILIC (high-performance liquid chromatography).

FIG. 2-12 is a diagram showing mass spectra for peaks 1 to 3 in FIG. 2-11 (after improvement of separation).

FIG. 2-13 is a diagram showing mass spectra for peaks 4 to 6 in FIG. 2-11 (after improvement of separation).

FIG. 2-14 is a diagram showing mass spectra for peaks 7 and 8 in FIG. 2-11 (after improvement of separation).

FIG. 2-15 is a diagram showing micro-Raman spectrum diagrams for a separated sample obtained for peak 2 (Mw=180) in FIG. 2-11 and an ozonide authentic sample in combination.

FIG. 2-16 is a $^{1}H$ NMR spectrum diagram for peak 2 (Mw=180) in FIG. 2-11.

FIG. 2-17 is a $^{13}C$ NMR spectrum diagram for peak 2 (Mw=180) in FIG. 2-11.

FIG. 2-18 is a two-dimensional ($^{1}H$-$^{13}C$ COSY) NMR spectrum diagram for peak 2 (Mw=180) in FIG. 2-11.

FIG. 2-19 is a diagram showing HILIC chromatograms for a TLC1 spot product and glyceraldehyde dimer under HILIC (high-performance liquid chromatography) conditions in FIG. 2-11 in combination.

FIG. 2-20 is a diagram showing HILIC chromatograms for a TLC1 spot product and glyceraldehyde dimer under reversed-phase HILIC (high-performance liquid chromatography) conditions in combination.

FIG. 2-21 is an enlarged view of a part of FIG. 2-20.

FIG. 2-22 is a diagram showing ESR spectrum diagrams for a TLC1 spot product and peak 2 (Mw=180) in FIG. 2-9 in combination.

FIG. 2-23 is an ESR spectrum diagram for ozonized methyl linolenate.

FIG. 2-24 is a series of ESR spectrum diagrams for peaks 1 to 8 in FIG. 2-11.

FIG. 2-25 is a diagram showing results of measurement of activity for peaks 1 to 8 in FIG. 2-11 through chemiluminescence.

FIG. 3-1 is a series of graphs showing expression levels of skin barrier function-related genes in Example 3-1.

FIG. 3-2 is a series of graphs showing expression levels of anti-oxidative stress response genes in Example 3-1.

FIG. 3-3 is a series of graphs showing peptide contents in terms of glutathione in Example 3-1.

FIG. 3-4 is a graph showing viabilities of cells in Example 3-1.

FIG. 3-5 is a graph showing production levels of IL-1$\alpha$ in Example 3-1.

FIG. 3-6 is a graph showing production levels of prostaglandin E2 in Example 3-1.

FIG. 3-7 is a $^{1}H$ NMR spectrum diagram acquired from a reaction mixture resulting from ozone oxidation of glycerin (TLC1 spot product) at a temperature of 300 K (27° C.) with DMSO-$d_6$ as a solvent.

FIG. 3-8 is a $^{13}C$ NMR spectrum diagram acquired from a reaction mixture resulting from ozone oxidation of glycerin (TLC1 spot product) at a temperature of 300 K (27° C.) with DMSO-$d_6$ as a solvent.

FIG. 3-9 is a $^{13}C$ DEPT135 NMR spectrum diagram acquired from a reaction mixture resulting from ozone oxidation of glycerin (TLC1 spot product) at a temperature of 300 K (27° C.) with DMSO-$d_6$ as a solvent.

FIG. 3-10 is a COSY NMR spectrum diagram acquired from a reaction mixture resulting from ozone oxidation of glycerin (TLC1 spot product) at a temperature of 300 K (27° C.) with DMSO-$d_6$ as a solvent.

FIG. 3-11 is an HSQC NMR spectrum diagram acquired from a reaction mixture resulting from ozone oxidation of glycerin (TLC1 spot product) at a temperature of 300 K (27° C.) with DMSO-$d_6$ as a solvent.

FIG. 3-12 is an HMBC NMR spectrum diagram acquired from a reaction mixture resulting from ozone oxidation of glycerin (TLC1 spot product) at a temperature of 300 K (27° C.) with DMSO-$d_6$ as a solvent.

FIG. 3-13 is a total ion chromatogram (ESI-negative mode) from precise preparative LC (liquid chromatography) for a sample obtained by adjusting (diluting) a reaction mixture (TLC1 spot product) to approximately 3% by mass with acetonitrile and a blank.

FIG. 3-14 is a series of mass spectrum diagrams for peaks F, G, and H (fraction F, fraction G, and fraction H) in FIG. 3-13.

FIG. 3-15 is a diagram showing results of examination on improvement of separation (improvement of separation conditions) in HILIC (high-performance liquid chromatography).

FIG. 3-16 is a diagram showing mass spectra for peaks 1 to 3 in FIG. 3-15 (after improvement of separation).

FIG. 3-17 is a diagram showing mass spectra for peaks 4 to 6 in FIG. 3-15 (after improvement of separation).

FIG. 3-18 is a diagram showing mass spectra for peaks 7 and 8 in FIG. 3-15 (after improvement of separation).

FIG. 3-19 is a diagram showing micro-Raman spectrum diagrams for a separated sample obtained for peak 2 (Mw=180) in FIG. 3-15 and an ozonide authentic sample in combination.

FIG. 3-20 is a $^{1}H$ NMR spectrum diagram for peak 2 (Mw=180) in FIG. 3-15.

FIG. 3-21 is a $^{13}C$ NMR spectrum diagram for peak 2 (Mw=180) in FIG. 3-15.

FIG. 3-22 is a two-dimensional ($^{1}H$-$^{13}C$ COSY) NMR spectrum diagram for peak 2 (Mw=180) in FIG. 3-15.

FIG. 3-23 is a diagram showing HILIC chromatograms for a TLC1 spot product and glyceraldehyde dimer under HILIC (high-performance liquid chromatography) conditions in FIG. 3-15 in combination.

FIG. 3-24 is a diagram showing HILIC chromatograms for a TLC1 spot product and glyceraldehyde dimer under reversed-phase HILIC (high-performance liquid chromatography) conditions in combination.

FIG. 3-25 is an enlarged view of a part of FIG. 3-24.

FIG. 3-26 is a diagram showing ESR spectrum diagrams for a TLC1 spot product and peak 2 (Mw=180) in FIG. 3-9 in combination.

FIG. 3-27 is an ESR spectrum diagram for ozonized methyl linolenate.

FIG. 3-28 is a series of ESR spectrum diagrams for peaks 1 to 8 in FIG. 3-15.

FIG. 3-29 is a diagram showing results of measurement of activity for peaks 1 to 8 in FIG. 3-15 through chemiluminescence.

FIG. 4-1 is a graph showing anti-glycation rates in Example 4-1.

FIG. 4-2 is a $^{1}H$ NMR spectrum diagram acquired from a reaction mixture resulting from ozone oxidation of glycerin (TLC1 spot product) at a temperature of 300 K (27° C.) with DMSO-$d_6$ as a solvent.

FIG. 4-3 is a $^{13}C$ NMR spectrum diagram acquired from a reaction mixture resulting from ozone oxidation of glycerin (TLC1 spot product) at a temperature of 300 K (27° C.) with DMSO-$d_6$ as a solvent.

FIG. 4-4 is a $^{13}C$ DEPT135 NMR spectrum diagram acquired from a reaction mixture resulting from ozone oxidation of glycerin (TLC1 spot product) at a temperature of 300 K (27° C.) with DMSO-$d_6$ as a solvent.

FIG. 4-5 is a COSY NMR spectrum diagram acquired from a reaction mixture resulting from ozone oxidation of glycerin (TLC1 spot product) at a temperature of 300 K (27° C.) with DMSO-$d_6$ as a solvent.

FIG. 4-6 is an HSQC NMR spectrum diagram acquired from a reaction mixture resulting from ozone oxidation of glycerin (TLC1 spot product) at a temperature of 300 K (27° C.) with DMSO-$d_6$ as a solvent.

FIG. 4-7 is an HMBC NMR spectrum diagram acquired from a reaction mixture resulting from ozone oxidation of glycerin (TLC1 spot product) at a temperature of 300 K (27° C.) with DMSO-$d_6$ as a solvent.

FIG. 4-8 is a total ion chromatogram (ESI-negative mode) from precise preparative LC (liquid chromatography) for a sample obtained by adjusting (diluting) a reaction mixture (TLC1 spot product) to approximately 3% by mass with acetonitrile and a blank.

FIG. 4-9 is a series of mass spectrum diagrams for peaks F, G, and H (fraction F, fraction G, and fraction H) in FIG. 4-8.

FIG. 4-10 is a diagram showing results of examination on improvement of separation (improvement of separation conditions) in HILIC (high-performance liquid chromatography).

FIG. 4-11 is a diagram showing mass spectra for peaks 1 to 3 in FIG. 4-10 (after improvement of separation).

FIG. 4-12 is a diagram showing mass spectra for peaks 4 to 6 in FIG. 4-10 (after improvement of separation).

FIG. 4-13 is a diagram showing mass spectra for peaks 7 and 8 in FIG. 4-10 (after improvement of separation).

FIG. 4-14 is a diagram showing micro-Raman spectrum diagrams for a separated sample obtained for peak 2 (Mw=180) in FIG. 4-10 and an ozonide authentic sample in combination.

FIG. 4-15 is a $^1$H NMR spectrum diagram for peak 2 (Mw=180) in FIG. 4-10.

FIG. 4-16 is a $^{13}$C NMR spectrum diagram for peak 2 (Mw=180) in FIG. 4-10.

FIG. 4-17 is a two-dimensional ($^1$H-$^{13}$C COSY) NMR spectrum diagram for peak 2 (Mw=180) in FIG. 4-10.

FIG. 4-18 is a diagram showing HILIC chromatograms for a TLC1 spot product and glyceraldehyde dimer under HILIC (high-performance liquid chromatography) conditions in FIG. 4-10 in combination.

FIG. 4-19 is a diagram showing HILIC chromatograms for a TLC1 spot product and glyceraldehyde dimer under reversed-phase HILIC (high-performance liquid chromatography) conditions in combination.

FIG. 4-20 is an enlarged view of a part of FIG. 4-19.

FIG. 4-21 is a diagram showing ESR spectrum diagrams for a TLC1 spot product and peak 2 (Mw=180) in FIG. 4-4 in combination.

FIG. 4-22 is an ESR spectrum diagram for ozonized methyl linolenate.

FIG. 4-23 is a series of ESR spectrum diagrams for peaks 1 to 8 in FIG. 4-10.

FIG. 4-24 is a diagram showing results of measurement of activity for peaks 1 to 8 in FIG. 4-10 through chemiluminescence.

DESCRIPTION OF THE PREFERRED EMBODIMENT

Figure 1:
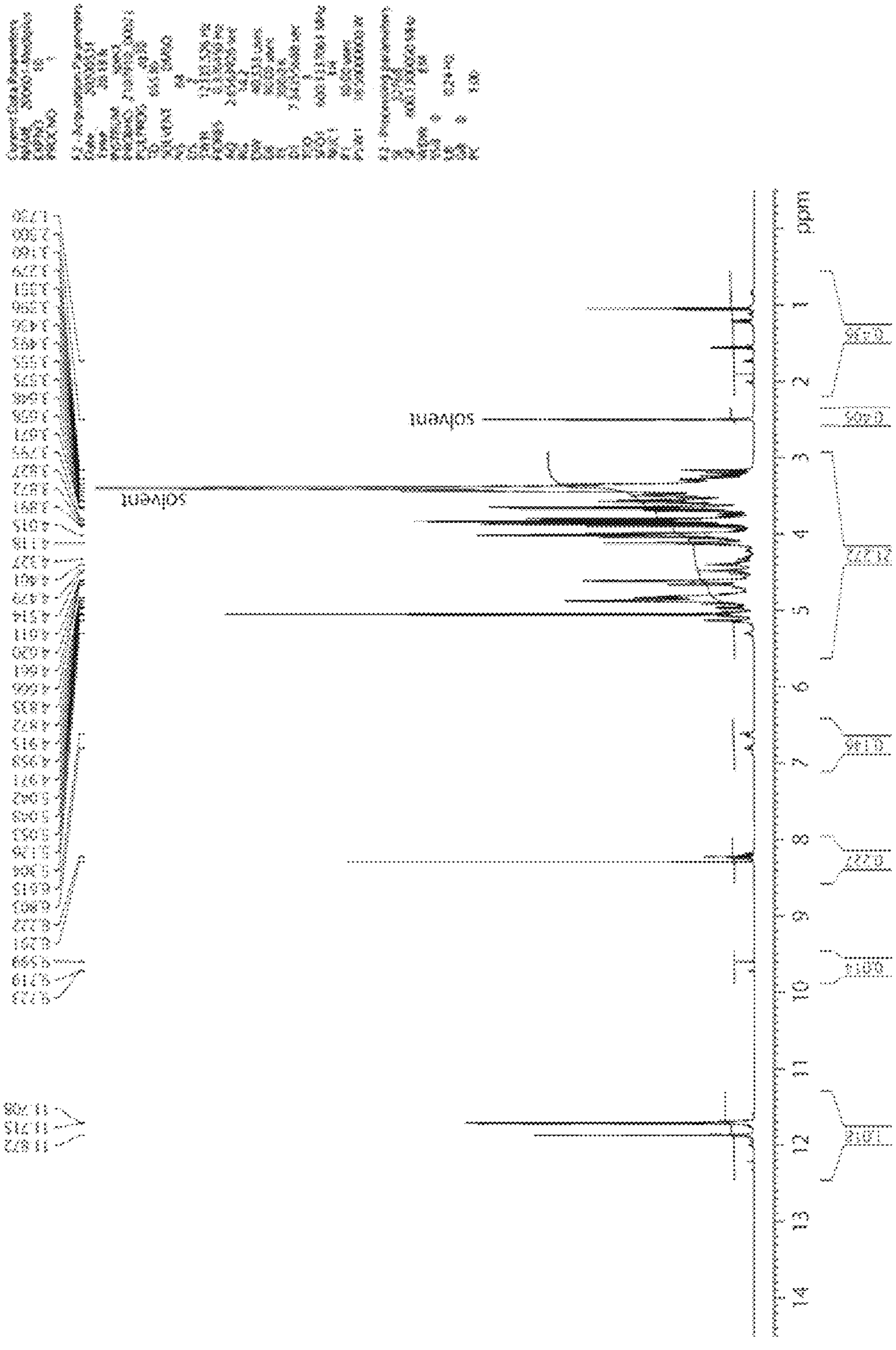
FIG. 1-1 is a $^1H$ NMR spectrum diagram acquired from a reaction mixture resulting from ozone oxidation of glycerin (TLC1 spot product) at a temperature of 300 K (27° C.) with DMSO-$d_6$ as a solvent.

Hereinafter, the present invention will be more specifically described with examples. However, the present invention is not limited to the following description.

First Mode for Carrying Out the Invention

First, the first mode for carrying out the present invention will be described. However, the first mode of the present invention is not limited to the following description.

In the first mode of the present invention, if isomers such as tautomers or stereoisomers (examples: geometric isomers, conformers, and optical isomers) are present for a compound, any of the isomers can be used for the first mode of the present invention, unless otherwise specified. In the first mode of the present invention, if a substance can form a salt, the salt can also be used for the first mode of the present invention, unless otherwise specified. The salt may be an acid addition salt, or a base addition salt. Moreover, the acid to form the acid addition salt may be an inorganic acid or an organic acid, and the base to form the base addition salt may be an inorganic base or an organic base. Examples of the inorganic acid include, but are not limited to, sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluoric acid, chloric acid, bromic acid, iodic acid, perfluoric acid, perchloric acid, perbromic acid, and periodic acid. Examples of the organic acid include, but are not limited to, similarly, p-toluenesulfonic acid, methanesulfonic acid, oxalic acid, p-bromobenzenesulfonic acid, carbonic acid, succinic acid, citric acid, benzoic acid, and acetic acid. Examples of the inorganic base include, but are not limited to, ammonium hydroxide, alkali metal hydroxide, alkaline earth metal hydroxide, carbonate, and hydrogen carbonate, and more specific examples thereof include sodium hydroxide, potassium hydroxide, potassium carbonate, sodium carbonate, sodium hydrogen carbonate, potassium hydrogen carbonate, calcium hydroxide, and calcium carbonate. Examples of the organic base include, but are not limited to, similarly, ethanolamine, triethylamine, and tris(hydroxymethyl)aminomethane. The method for producing those salts is not limited to a particular method, and, for example, such a salt can be produced in such a manner that an acid or base as shown above is appropriately allowed to add to the compound with a known method.

Examples of the aromatic ring having no heteroatom in the first mode of the present invention include a benzene ring, a naphthalene ring, an anthracene ring, a phenanthrene ring, and a pyrene ring. Examples of the heteroaromatic ring include a pyridine ring and a thiophene ring. The nitrogen-containing aromatic ring may be free of a positive charge, or have a positive charge. Examples of the nitrogen-containing aromatic ring being free of a positive charge include a pyrroline ring, a pyridine ring, a pyridazine ring, a pyrimidine ring, a pyrazine ring, a quinoline ring, an isoquinoline ring, an acridine ring, a 3,4-benzoquinoline ring, a 5,6-benzoquinoline ring, a 6,7-benzoquinoline ring, a 7,8-benzoquinoline ring, a 3,4-benzoisoquinoline ring, a 5,6-benzoisoquinoline ring, a 6,7-benzoisoquinoline ring, and a 7,8-benzoisoquinoline ring. Examples of the nitrogen-containing aromatic ring having a positive charge include a pyrrolinium ring, a pyridinium ring, a pyridazinium ring, a pyrimidinium ring, a pyrazinium ring, a quinolinium ring, an isoquinolinium ring, an acridinium ring, a 3,4-benzoquinolinium ring, a 5,6-benzoquinolinium ring, a 6,7-benzoquinolinium ring, a 7,8-benzoquinolinium ring, a 3,4-benzoisoquinolinium ring, a 5,6-benzoisoquinolinium ring, a 6,7-benzoisoquinolinium ring, and a 7,8-benzoisoquinolinium ring. Examples of the oxygen-containing aromatic ring or sulfur-containing aromatic ring include an aromatic ring formed by replacing at least one carbon atom or nitrogen atom in the aromatic ring containing no heteroatom or the nitrogen-containing aromatic ring with at least one of an oxygen atom and a sulfur atom.

Examples of the "substituent" in the first mode of the present invention include a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), and an alkylthio group (—SR, wherein R is an alkyl group).

In the first mode of the present invention, each chain substituent (e.g., an alkyl group and a hydrocarbon group such as an unsaturated aliphatic hydrocarbon group) may be linear or branched, unless otherwise specified, and the number of carbon atoms is not limited and may be, for example, 1 to 40, 1 to 32, 1 to 24, 1 to 18, 1 to 12, one to six, or one or two (two or more for an unsaturated hydrocarbon group). In the first mode of the present invention, the number of ring members (the number of atoms constituting a ring) of each cyclic group (e.g., an aryl group, a heteroaryl group) is not limited and may be, for example, 5 to 32, 5 to 24, 6 to 18, 6 to 12, or 6 to 10. If isomers are present for a substituent or the like, the substituent or the like may be any of the isomers; when a substituent or the like is simply referred to as a "butyl group", for example, the substituent or the like may be a n-butyl group, or a sec-butyl group, or a tert-butyl group; when a substituent or the like is simply referred to as a "naphthyl group", the substituent or the like may be a 1-naphthyl group or a 2-naphthyl group.

The first mode of the present invention will be more specifically described with examples below. However, the first mode of the present invention is not limited to the description given below. Description of one part of the first mode of the present invention can be referred to for description of another part and vice versa, unless otherwise stated. Herein, use of the expression "A to B" is intended to include the numerical values or physical values before and after "to". Herein, the expression "A and/or B" encompasses "only A", "only B", and "both A and B".

[1. Cyclic Peroxide]

The cyclic peroxide according to the first mode of the present invention, is, as described above, characterized by being represented by the following chemical formula (I):

[Chemical Formula I]

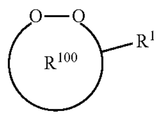

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The heteroatom is an atom other than carbon and hydrogen, and may be, for example, one selected from the group consisting of an oxygen atom, a nitrogen atom, a sulfur atom, a selenium atom, a boron atom, and a silicon atom. The substituent is not limited and may contain, for example, a hydroxy group, and may be, for example, one selected from the group consisting of a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), and an alkylthio group (—SR, wherein R is an alkyl group) shown above.

In the cyclic peroxide according to the first mode of the present invention, for example, $R^{100}$ in the chemical formula (I) may be a cyclic structure having 5 to 10 ring members.

The cyclic peroxide according to the first mode of the present invention may be, for example, a cyclic peroxide represented by the following chemical formula (II):

[Chemical Formula II]

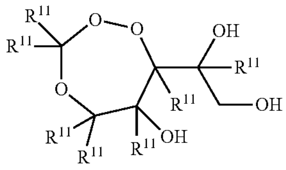

(II)

wherein the $R^{11}$ groups are the same or different, each being a hydrogen atom or a substituent, and two $R^{11}$ groups bound to the same carbon atom optionally together form an oxo group (=O) or a thioxo group (=S).

In the cyclic peroxide according to the first mode of the present invention, the substituent for each of the $R^{11}$ groups in the chemical formula (II) may be, for example, a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

The cyclic peroxide according to the first mode of the present invention may be, for example, a cyclic peroxide represented by a chemical formula (1) below. The cyclic peroxide represented by the following chemical formula (1) corresponds to the case that the $R^{11}$ groups in the chemical formula (II) are each a hydrogen atom:

[Chemical Formula I]

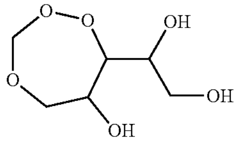

(1)

The method for producing the cyclic peroxide according to the first mode of the present invention is not limited to a particular method, and, for example, the cyclic peroxide according to the first mode of the present invention can be produced by oxidizing an alcohol with the method described later for producing an oxidation reaction product according to the first mode of the present invention. In this case, for example, an oxidation reaction product produced may be directly used without purification; alternatively, only the cyclic peroxide according to the first mode of the present invention may be isolated and purified for use.

The phenomenon that a cyclic peroxide is obtained through oxidation of an alcohol, for example, through ozone oxidation of glycerin was discovered for the first time by the present inventors. Although the mechanism that gives a cyclic peroxide is unclear, for example, longer reaction time in oxidation reaction of an alcohol is expected to give a reaction product differing from those from conventional reactions, as described later.

The cyclic peroxide according to the first mode of the present invention can be isolated and, for example, formulated because the cyclic peroxide according to the first mode of the present invention is more chemically stable and allows easier handling than radicals and the like.

Generally speaking, cyclic peroxides are substances industrially used, for example, for their oxidative capacity. In particular, artemisinin, which has the same seven-membered ring (trioxolane) backbone as the cyclic peroxide according to the first mode of the present invention, led to the winning of Nobel prize in 2015 for the usefulness against malaria, and derivatives of artemisinin have been still under research.

However, supply of artemisinin, which is extracted and purified from natural products, is unstable. In addition, artemisinin is neither water-soluble nor liposoluble, and hence causes many problems in formulation. Hydrogen peroxide, an example of water-soluble substances with high oxidation power, as described above, is highly reactive and unstable, and the usage thereof for living bodies is only limited to topical agents for disinfection.

On the other hand, the first mode of the present invention can provide, for example, a cyclic peroxide and oxidation reaction product that are highly safe and superior in water solubility, and a method for producing such an oxidation reaction product. Examples of evaluation methods for the fact that the cyclic peroxide according to the first mode of the present invention or the oxidation reaction product according to the first mode of the present invention is water-soluble and exerts oxidative capacity include, as described later in Example 1, a method for evaluating activation on TRP channels, which are used as a target of drug discovery. Regarding the mechanism that causes the TRP channel activation, for example, the cyclic peroxide according to the first mode of the present invention or the oxidation reaction product according to the first mode of the present invention causes the TRP channel activation through the slow decomposition thereof and the resulting generation of hydrogen peroxide, though the mechanism is not limited to this mode.

[2. Oxidation Reaction Product]

The oxidation reaction product according to the first mode of the present invention is an oxidation reaction product characterized by containing a cyclic peroxide, wherein the oxidation reaction product is obtained through oxidation of an alcohol. However, the method for producing the oxidation reaction product according to the first mode of the present invention may be performed with any method without limitation to oxidation of an alcohol, and any substance produced with any production method may be employed as long as the substance has the same structure.

The oxidation of an alcohol is not limited to a particular method. For example, the oxidation of an alcohol may be at least one of ozone oxidation and hydrogen peroxide oxidation. However, as described above, the method for producing the oxidation reaction product according to the first mode of the present invention may be performed with any method without limitation to ozone oxidation and hydrogen peroxide oxidation of an alcohol, and any substance produced with any production method may be employed as long as the substance has the same structure.

The oxidation reaction product according to the first mode of the present invention may be, for example, a mixture containing a plurality of oxidation reaction products.

The oxidation reaction product according to the first mode of the present invention may have, for example, oxidative capacity.

The oxidation reaction product according to the first mode of the present invention may have, for example, reductive capacity.

The oxidation reaction product according to the first mode of the present invention may contain, for example, a TRP channel activator.

The alcohol to be used as a raw material of the oxidation reaction product according to the first mode of the present invention is not limited. The alcohol for the oxidation reaction product according to the first mode of the present invention may be, for example, a saturated alcohol.

The alcohol for the oxidation reaction product according to the first mode of the present invention may be, for example, a polyhydric alcohol.

The alcohol for the oxidation reaction product according to the first mode of the present invention may be, for example, at least one of glycerin and a glycerin derivative.

The oxidation reaction product according to the first mode of the present invention may contain, for example, an oxidation reaction product formed by binding of two or more molecules of the alcohol.

The oxidation reaction product according to the first mode of the present invention may contain, for example, the cyclic peroxide according to the first mode of the present invention.

The alcohol to be used as a raw material of the oxidation reaction product according to the first mode of the present invention is not limited, and may be, for example, a saturated alcohol as described above, or an unsaturated alcohol. The alcohol may be liner or branched, and may contain a cyclic structure or not. The alcohol may be, for example, a polyhydric alcohol or a monohydric alcohol. The number of hydroxy groups of the polyhydric alcohol is not limited, and the polyhydric alcohol may be, for example, dihydric, trihydric, or tetrahydric. Examples of the monohydric saturated alcohol include a saturated alcohol having 1 to 40, 1 to 32, 1 to 24, 1 to 18, 1 to 12, one to six, or one or two carbon atoms, the saturated alcohol may be linear or branched, and may contain a cyclic structure or not, and specific examples thereof include methanol, ethanol, n-propyl alcohol, isopropyl alcohol, n-butyl alcohol, sec-butyl alcohol, and tert-butyl alcohol. Examples of the saturated polyhydric alcohol include a saturated polyhydric alcohol having 1 to 40, 1 to 32, 1 to 24, 1 to 18, 1 to 12, one to six, or one or two carbon atoms, the saturated polyhydric alcohol may be linear or branched, and may contain a cyclic structure or not, and specific examples thereof include ethylene glycol (ethane-1,2-diol), propylene glycol (propane-1,2-diol), glycerin, and a glycerin derivative. The glycerin derivative is not limited, and may be, for example, a polymer of glycerin or a compound formed by substituting at least one of the hydrogen atoms of glycerin with a substituent (e.g., an alkyl group). Examples of the glycerin derivative include diglycerin and polyglycerin.

The oxidation reaction product according to the first mode of the present invention may be, for example, a substance having reductive capacity, as described above. For example, the oxidation reaction product according to the first mode of the present invention may have reductive capacity through inclusion of a functional group, wherein the reductive capacity is derived from the functional group, which has reductive capacity. Specifically, for example, the oxidation reaction product according to the first mode of the present invention may have reductive capacity through inclusion of an aldehyde group (formyl group), or have reductive capacity derived from the keto form because of the keto-enol tautomerism of the TRP channel activator according to the first mode of the present invention. For example, the oxidation reaction product according to the first mode of the present invention that has been obtained in Example 1 shown later contains an acetal structure as the backbone, as confirmed by NMR, hence being inferred to color through DNPH (dinitrophenylhydrazine: derived from ketone and aldehyde) reaction derived from ketone and aldehyde.

The oxidation reaction product according to the first mode of the present invention may be, for example, a substance formed by binding of two or more molecules of the alcohol, as described above. Specifically, for example, a structure formed by binding of two or more molecules of the alcohol and oxidizing the resultant is acceptable. The mode of "binding" of two or more molecules of the alcohol is not limited, and may be, for example, addition or condensation.

The oxidation reaction product according to the first mode of the present invention can be isolated and, for example, formulated because the oxidation reaction product according to the first mode of the present invention is more chemically stable and allows easier handling than radicals and the like.

[3. Method for Producing Oxidation Reaction Product]

The method for producing an oxidation reaction product according to the first mode of the present invention is, as described above, a method for producing the oxidation reaction product according to the first mode of the present invention, the method including an alcohol oxidation step of oxidizing the alcohol.

The oxidation of the alcohol in the alcohol oxidation step is not limited to a particular method. In the method for producing an oxidation reaction product according to the first mode of the present invention, for example, the alcohol may be oxidized through at least one of ozone oxidation and hydrogen peroxide oxidation in the alcohol oxidation step.

In the method for producing an oxidation reaction product according to the first mode of the present invention, the reaction time in the alcohol oxidation step is not limited. The reaction time in the alcohol oxidation step may be, for example, 24 hours or more or 1 day or more, 48 hours or more or 2 days or more, 72 hours or more or 3 days or more, 120 hours or more or 5 days or more, or 168 hours or more or 7 days or more. The upper limit value of the reaction time in the alcohol oxidation step is not limited, and the reaction time may be, for example, 720 hours or less or 30 days or less, or 360 hours or less or 15 days or less.

In order to obtain a reaction product containing the cyclic peroxide according to the first mode of the present invention in the method for producing an oxidation reaction product according to the first mode of the present invention, it is preferable to employ longer reaction time for the alcohol oxidation step. For example, longer reaction time in the alcohol oxidation step is inferred to allow production of the cyclic peroxide according to the first mode of the present invention, which cannot be obtained through conventional ozone oxidation reaction or the like of glycerin. For production efficiency in the method for producing an oxidation reaction product according to the first mode of the present invention, it is preferable to avoid excessively long reaction time for the alcohol oxidation step.

The method for producing an oxidation reaction product according to the first mode of the present invention includes an alcohol oxidation step of oxidizing the alcohol, as described above. However, the oxidation reaction product according to the first mode of the present invention is not limited to substances produced with the production method, as described above, and any substance produced with any production method may be employed as long as the substance has the same structure. The method for producing an oxidation reaction product according to the first mode of the present invention will be more specifically described with reference to examples below.

The case that ozone oxidation is performed with use of glycerin as the alcohol will be described as an example below. However, the description below is an example as mentioned, and the method for producing an oxidation reaction product according to the first mode of the present invention is not limited to the description below. For example, the method below can be performed in the same manner even with use of another alcohol in place of glycerin. For example, the method for oxidizing the alcohol in the alcohol oxidation step of the method for producing an oxidation reaction product according to the first mode of the present invention is not limited to a particular method, and any oxidizing method is available, without limitation only to ozone oxidation. The oxidizing method may be, for example, at least one of ozone oxidation and hydrogen peroxide oxidation. Not only the type of the alcohol and the method for oxidizing the alcohol, for example, but also the concentrations of substances, reaction temperature, reaction time, and other reaction conditions can be appropriately changed.

The oxidation reaction product according to the first mode of the present invention can be produced with a production method including a step of oxidizing glycerin, for example, by bringing glycerin into contact with ozone, more specifically, mixing glycerin and ozone (corresponding to the "alcohol oxidation step" in the first mode of the present invention). The step of oxidizing glycerin may be, for example, a step of oxidizing glycerin by bringing a glycerin solution and a gas containing ozone into gas-liquid contact.

It is preferable for the glycerin solution to contain glycerin at high concentration. For the glycerin solution of high concentration, for example, a glycerin solution having a glycerin concentration of 75% or more can be used, and, as a specific example, a 84 to 87% by weight glycerin solution as a product in accordance with the Japanese Pharmacopeia is preferable, a concentrated glycerin solution having a glycerin concentration of 98% by weigh or more as a product in accordance with the Japanese Pharmacopeia is more preferable, and a purified glycerin solution having a concentration of 98.5% by weight or more is even more preferable. If having a relatively higher glycerin concentration, the glycerin solution can be treated with ozone at higher concentration. The solvent to glycerin in the glycerin solution is not limited, and is, for example, an aqueous solvent such as water.

It is preferable for the gas containing ozone to contain ozone at high concentration. Any method may be used for producing the gas of high ozone concentration without limitation, and, for example, an ozone generator that generates ozone by silent discharge in oxygen gas can be used. If oxygen gas is used, for example, an oxygen tank for medical use may be used, and oxygen gas produced by an oxygen generator may be used.

Any method may be used for bringing the glycerin solution and the gas containing ozone into gas-liquid contact without limitation, and an example is a method in which a tank is charged with a glycerin solution of high concentration (e.g., 98% by weight or more) and the gas of high ozone concentration is released as fine bubbles into the tank with use of an air diffuser. Specifically, for example, an ozone-treated glycerin solution having a concentration of approximately 4000 ppm in terms of hydrogen peroxide concentration can be produced by aerating the concentrated glycerin solution with a gas having an ozone concentration of approximately 37000 ppm for approximately 7 days. The aeration time is not limited, and, for example, an ozone-treated glycerin solution containing the oxidation reaction product according to the first mode of the present invention at higher concentration can be produced by aerating for a relatively long time.

The oxidation reaction product according to the first mode of the present invention may be directly used without separating from a mixture after the reaction (e.g., the ozone-treated glycerin solution), or used after separating the oxidation reaction product according to the first mode of the present invention from the mixture after the reaction. The separation method is not limited to a particular method, and, for example, the oxidation reaction product according to the first mode of the present invention can be separated from the mixture after the reaction through chromatography such as preparative thin-layer chromatography.

Conventional production of a substance having oxidation power such as peroxide needs a pathway including complex systems. The method for producing an oxidation reaction product according to the first mode of the present invention allows, for example, an oxidation reaction product having oxidation power to be produced in a very simple and easy manner.

The oxidation reaction product according to the first mode of the present invention is capable of generating, for example, hydrogen peroxide. For example, the oxidation reaction product according to the first mode of the present invention can generate 1 to 4000 ppm, 10 to 4000 ppm, or 100 to 4000 ppm of hydrogen peroxide per approximately 4000 ppm of the oxidation reaction product according to the first mode of the present invention in terms of hydrogen peroxide concentration.

[4. Method for Using Cyclic Peroxide and Oxidation Reaction Product]

The cyclic peroxide according to the first mode of the present invention and the oxidation reaction product according to the first mode of the present invention are not limited to particular using method. If being capable of causing TRP channel activation, for example, the cyclic peroxide according to the first mode of the present invention or the oxidation reaction product according to the first mode of the present invention may be used as a TRP channel activator. The usage method in this case is not limited, and may be, for example, the same as the method for using common TRP channel activators. Being highly safe as described above, the cyclic peroxide according to the first mode of the present invention and the oxidation reaction product according to the first mode of the present invention can be safely used. In the usage method, for example, the cyclic peroxide according to the first mode of the present invention and the oxidation reaction product according to the first mode of the present invention may be directly used without separating from a mixture after the reaction, or used after separating the cyclic peroxide according to the first mode of the present invention or the oxidation reaction product according to the first mode of the present invention from the mixture after the reaction, as described above.

Being highly safe with the explosivity, irritancy, and the like reduced as described above, the cyclic peroxide according to the first mode of the present invention and the oxidation reaction product according to the first mode of the present invention are very useful. For example, the cyclic peroxide according to the first mode of the present invention and the oxidation reaction product according to the first mode of the present invention can act on ion channels involved in itch, pain, and the like (e.g., TRPA1), hence being available in development of medicaments, for example.

The cyclic peroxide according to the first mode of the present invention and the oxidation reaction product according to the first mode of the present invention are not limited to those applications, and applicable as a cosmetic, a pharmaceutical, a food, or a dietary supplement or the like for various applications.

[Second Mode for Carrying Out the Invention]

Second, the second mode for carrying out the present invention will be described. However, the second mode of the present invention is not limited to the following description.

In the second mode of the present invention, if isomers such as tautomers or stereoisomers (examples: geometric isomers, conformers, and optical isomers) are present for a compound, any of the isomers can be used for the second mode of the present invention, unless otherwise specified. In the second mode of the present invention, if a substance can form a salt, the salt can also be used for the second mode of the present invention, unless otherwise specified. The salt may be an acid addition salt, or a base addition salt. Moreover, the acid to form the acid addition salt may be an inorganic acid or an organic acid, and the base to form the base addition salt may be an inorganic base or an organic base. Examples of the inorganic acid include, but are not limited to, sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluoric acid, chloric acid, bromic acid, iodic acid, perfluoric acid, perchloric acid, perbromic acid, and periodic acid. Examples of the organic acid include, but are not limited to, similarly, p-toluenesulfonic acid, methanesulfonic acid, oxalic acid, p-bromobenzenesulfonic acid, carbonic acid, succinic acid, citric acid, benzoic acid, and acetic acid. Examples of the inorganic base include, but are not limited to, ammonium hydroxide, alkali metal hydroxide, alkaline earth metal hydroxide, carbonate, and hydrogen carbonate, and more specific examples thereof include sodium hydroxide, potassium hydroxide, potassium carbonate, sodium carbonate, sodium hydrogen carbonate, potassium hydrogen carbonate, calcium hydroxide, and calcium carbonate. Examples of the organic base include, but are not limited to, similarly, ethanolamine, triethylamine, and tris (hydroxymethyl)aminomethane. The method for producing those salts is not limited to a particular method, and, for example, such a salt can be produced in such a manner that an acid or base as shown above is appropriately allowed to add to the compound with a known method.

Examples of the aromatic ring having no heteroatom in the second mode of the present invention include a benzene ring, a naphthalene ring, an anthracene ring, a phenanthrene ring, and a pyrene ring. Examples of the heteroaromatic ring include a pyridine ring and a thiophene ring. The nitrogen-containing aromatic ring may be free of a positive charge, or have a positive charge. Examples of the nitrogen-containing aromatic ring being free of a positive charge include a pyrroline ring, a pyridine ring, a pyridazine ring, a pyrimidine ring, a pyrazine ring, a quinoline ring, an isoquinoline ring, an acridine ring, a 3,4-benzoquinoline ring, a 5,6-benzoquinoline ring, a 6,7-benzoquinoline ring, a 7,8-benzoquinoline ring, a 3,4-benzoisoquinoline ring, a 5,6-benzoisoquinoline ring, a 6,7-benzoisoquinoline ring, and a 7,8-benzoisoquinoline ring. Examples of the nitrogen-containing aromatic ring having a positive charge include a pyrrolinium ring, a pyridinium ring, a pyridazinium ring, a pyrimidinium ring, a pyrazinium ring, a quinolinium ring, an isoquinolinium ring, an acridinium ring, a 3,4-benzoquinolinium ring, a 5,6-benzoquinolinium ring, a 6,7-benzoquinolinium ring, a 7,8-benzoquinolinium ring, a 3,4-benzoisoquinolinium ring, a 5,6-benzoisoquinolinium ring, a 6,7-benzoisoquinolinium ring, and a 7,8-benzoisoquinolinium ring. Examples of the oxygen-containing aromatic ring or sulfur-containing aromatic ring include an aromatic ring formed by replacing at least one carbon atom or nitrogen atom in the aromatic ring containing no heteroatom or the nitrogen-containing aromatic ring with at least one of an oxygen atom and a sulfur atom.

Examples of the "substituent" in the second mode of the present invention include a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), and an alkylthio group (—SR, wherein R is an alkyl group).

In the second mode of the present invention, each chain substituent (e.g., an alkyl group and a hydrocarbon group such as an unsaturated aliphatic hydrocarbon group) may be linear or branched, unless otherwise specified, and the number of carbon atoms is not limited and may be, for example, 1 to 40, 1 to 32, 1 to 24, 1 to 18, 1 to 12, one to six, or one or two (two or more for an unsaturated hydrocarbon group). Herein, the number of ring members (the number of atoms constituting a ring) of each cyclic group (e.g., an aryl group, a heteroaryl group) is not limited and may be, for example, 5 to 32, 5 to 24, 6 to 18, 6 to 12, or 6 to 10. If isomers are present for a substituent or the like, the substituent or the like may be any of the isomers; when a substituent or the like is simply referred to as a "butyl group", for example, the substituent or the like may be a n-butyl group, or a sec-butyl group, or a tert-butyl group; when a substituent or the like is simply referred to as a "naphthyl group", the substituent or the like may be a 1-naphthyl group or a 2-naphthyl group.

In the second mode of the present invention, the term "whitening" means prevention and/or amelioration of pigmentation. Specifically, the term "whitening" means prevention and/or amelioration of, for example: pigmentation symptoms due to enhanced generation or production of melanin, excessive accumulation of melanin, and/or abnormal deposition of melanin, such as freckles, dullness, ephelides, tanning, skin inflammation, and dark patches caused by skin irritation; and pigmentation symptoms due to diseases that cause pigmentation such as melasma in skin because of a drug such as steroid.

The second mode of the present invention will be more specifically described with examples below. However, the second mode of the present invention is not limited to the description given below. Description of one part of the second mode of the present invention can be referred to for description of another part and vice versa, unless otherwise stated. Herein, use of the expression "A to B" is intended to include the numerical values or physical values before and after "to". Herein, the expression "A and/or B" encompasses "only A", "only B", and "both A and B".

<Whitening Composition>

The whitening composition (hereinafter referred to as "the composition") according to the second mode of the present invention contains glycerin and/or a glycerin derivative, and a whitening component, wherein the whitening component contains a cyclic peroxide or a salt thereof as an active ingredient. The composition according to the second mode of the present invention is characterized by containing the cyclic peroxide or a salt thereof, and other configurations and conditions are not limited. The cyclic peroxide is inferred to promote the decomposition of melanin, as described later. Accordingly, when being applied to skin, for example, the composition according to the second mode of the present invention can give a whitening effect to the skin.

The whitening composition according to the second mode of the present invention can be said to be, for example, a composition for improving freckles, dullness, or ephelides, a composition for suppressing melanin generation, a composition for decomposing melanin, a composition for promoting melanin excretion, a composition for reducing skin pigmentation, or a composition for skin whitening.

[1. Whitening Component]

As described above, the composition according to the second mode of the present invention contains a whitening component. The composition according to the second mode of the present invention may contain, as an active ingredient of the whitening component, the cyclic peroxide, or an oxidation reaction product containing the cyclic peroxide as described later, or both of them. The cyclic peroxide may be a compound represented by a chemical formula (I) below, or a cyclic peroxide contained in an oxidation reaction product, wherein the oxidation reaction product is obtained through oxidation of an alcohol, described later.

The amount of the whitening component contained in the composition according to the second mode of the present invention is, for example, 0.001 to 10 w/v %, 0.05 to 5 w/v %, or 0.01 to 1 w/v %. The amount of the cyclic peroxide contained in the composition according to the second mode of the present invention is, for example, 0.001 to 10 w/v %, 0.05 to 5 w/v %, or 0.01 to 1 w/v %.

[2. Cyclic Peroxide]

The cyclic peroxide is represented by the following chemical formula (I):

[Chemical Formula I]

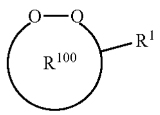

(I)

wherein

- $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and
- $R^1$ is a substituent, wherein one $R^1$ group, a plurality of $R^1$ groups, or no $R^1$ group is present, and if a plurality of $R^1$ groups is present, the $R^1$ groups are the same or different.

The heteroatom is an atom other than carbon and hydrogen, and may be, for example, one selected from the group consisting of an oxygen atom, a nitrogen atom, a sulfur atom, a selenium atom, a boron atom, and a silicon atom. The substituent is not limited and may contain, for example, a hydroxy group, and may be, for example, one selected from the group consisting of a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), and an alkylthio group (—SR, wherein R is an alkyl group) shown above.

In the cyclic peroxide, for example, $R^{100}$ in the chemical formula (I) may be a cyclic structure having 5 to 10 ring members.

The cyclic peroxide may be, for example, a cyclic peroxide represented by the following chemical formula (II):

[Chemical Formula II]

(II)

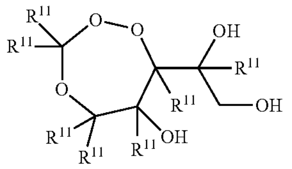

wherein the $R^{11}$ groups are the same or different, each being a hydrogen atom or a substituent, and two $R^{11}$ groups bound to the same carbon atom optionally together form an oxo group (=O) or a thioxo group (=S).

In the cyclic peroxide, the substituent for each of the $R^{11}$ groups in the chemical formula may be, for example, a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

The cyclic peroxide may be, for example, a cyclic peroxide represented by a chemical formula (1) below. The cyclic peroxide represented by the following chemical formula (1) corresponds to the case that the $R^{11}$ groups in the chemical formula (II) are each a hydrogen atom:

[Chemical Formula I]

(1)

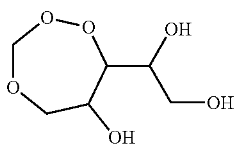

The method for producing the cyclic peroxide is not limited to a particular method, and, for example, the cyclic peroxide can be produced by oxidizing an alcohol with a method described later for producing an oxidation reaction product. In this case, for example, an oxidation reaction product produced may be directly used without purification; alternatively, only the cyclic peroxide may be isolated and purified for use.

The phenomenon that a cyclic peroxide is obtained through oxidation of an alcohol, for example, through ozone oxidation of glycerin was discovered for the first time by the present inventors. Although the mechanism that gives a cyclic peroxide is unclear, for example, longer reaction time in oxidation reaction of an alcohol is expected to give a reaction product differing from those from conventional reactions, as described later.

The cyclic peroxide can be isolated and, for example, formulated because the cyclic peroxide is more chemically stable and allows easier handling than radicals and the like.

Generally speaking, cyclic peroxides are substances industrially used, for example, for their oxidative capacity. In particular, artemisinin, which has the same seven-membered ring (trioxolane) backbone as the cyclic peroxide, led to the winning of Nobel prize in 2015 for the usefulness against malaria, and derivatives of artemisinin have been still under research.

However, supply of artemisinin, which is extracted and purified from natural products, is unstable. In addition, artemisinin is neither water-soluble nor liposoluble, and hence causes many problems in formulation. Hydrogen peroxide, an example of water-soluble substances with high oxidation power, is highly reactive and unstable, and the usage thereof for living bodies is only limited to topical agents for disinfection.

On the other hand, the second mode of the present invention uses, for example, a cyclic peroxide and oxidation reaction product that are highly safe and superior in water solubility, and hence is preferably applicable to living bodies. The second mode of the present invention is inferred to allow melanin to be decomposed through the oxidative capacity of the cyclic peroxide, thereby causing whitening action. The whitening action can be evaluated according to Example 2 shown later.

In the composition according to the second mode of the present invention, the cyclic peroxide may be in the form of a salt or a solvate such as a hydrate. The description of the cyclic peroxide can be referred to for description of the salt of the cyclic peroxide or a solvate of any of them.

[3. Oxidation Reaction Product]

The oxidation reaction product is an oxidation reaction product characterized by containing a cyclic peroxide, wherein the oxidation reaction product is obtained through oxidation of an alcohol, as described above. However, the method for producing the oxidation reaction product may be performed with any method without limitation to oxidation of an alcohol, and any substance produced with any production method may be employed as long as the substance has the same structure.

The oxidation of an alcohol is not limited to a particular method. For example, the oxidation of an alcohol may be at least one of ozone oxidation and hydrogen peroxide oxidation. However, as described above, the method for producing the oxidation reaction product may be performed with any method without limitation to ozone oxidation and hydrogen peroxide oxidation of an alcohol, and any substance produced with any production method may be employed as long as the substance has the same structure.

The oxidation reaction product may be, for example, a mixture containing a plurality of oxidation reaction products.

The oxidation reaction product may have, for example, oxidative capacity.

The oxidation reaction product may have, for example, reductive capacity.

The oxidation reaction product may contain, for example, a substance having melanin decomposition activity, melanin generation-suppressing activity, and/or melanin excretion-promoting activity.

The alcohol to be used as a raw material of the oxidation reaction product is not limited. The alcohol for the oxidation reaction product may be, for example, a saturated alcohol.

The alcohol for the oxidation reaction product may be, for example, a polyhydric alcohol.

The alcohol for the oxidation reaction product may be, for example, at least one of glycerin and a glycerin derivative.

The oxidation reaction product may contain, for example, an oxidation reaction product formed by binding of two or more molecules of the alcohol.

The oxidation reaction product may contain, for example, the cyclic peroxide.

The alcohol to be used as a raw material of the oxidation reaction product is not limited, and may be, for example, a saturated alcohol as described above, or an unsaturated alcohol. The alcohol may be liner or branched, and may contain a cyclic structure or not. The alcohol may be, for example, a polyhydric alcohol or a monohydric alcohol. The number of hydroxy groups of the polyhydric alcohol is not limited, and the polyhydric alcohol may be, for example, dihydric, trihydric, or tetrahydric. Examples of the monohydric saturated alcohol include a saturated alcohol having 1 to 40, 1 to 32, 1 to 24, 1 to 18, 1 to 12, one to six, or one or two carbon atoms, the saturated alcohol may be linear or branched, and may contain a cyclic structure or not, and specific examples thereof include methanol, ethanol, n-propyl alcohol, isopropyl alcohol, n-butyl alcohol, sec-butyl alcohol, and tert-butyl alcohol. Examples of the saturated polyhydric alcohol include a saturated polyhydric alcohol having 1 to 40, 1 to 32, 1 to 24, 1 to 18, 1 to 12, one to six, or one or two carbon atoms, the saturated polyhydric alcohol may be linear or branched, and may contain a cyclic structure or not, and specific examples thereof include ethylene glycol (ethane-1,2-diol), propylene glycol (propane-1,2-diol), glycerin, and a glycerin derivative. The glycerin derivative is not limited, and may be, for example, a polymer of glycerin or a compound formed by substituting at least one of the hydrogen atoms of glycerin with a substituent (e.g., an alkyl group). Examples of the glycerin derivative include diglycerin and polyglycerin. The glycerin derivative may be an oxidized form of glycerin.

The oxidation reaction product may be, for example, a substance having reductive capacity, as described above. For example, the oxidation reaction product may have reductive capacity through inclusion of a functional group, wherein the reductive capacity is derived from the functional group, which has reductive capacity. Specifically, for example, the oxidation reaction product may have reductive capacity through inclusion of an aldehyde group (formyl group), or have reductive capacity derived from the keto form because of the keto-enol tautomerism. For example, the oxidation reaction product that has been obtained in Example 2 shown later contains an acetal structure as the backbone, as confirmed by NMR, hence being inferred to color through DNPH (dinitrophenylhydrazine: derived from ketone and aldehyde) reaction derived from ketone and aldehyde.

The oxidation reaction product may be, for example, a substance formed by binding of two or more molecules of the alcohol, as described above. Specifically, for example, a structure formed by binding of two or more molecules of the alcohol and oxidizing the resultant is acceptable. The mode of "binding" of two or more molecules of the alcohol is not limited, and may be, for example, addition or condensation.

The oxidation reaction product can be isolated and, for example, formulated because the oxidation reaction product is more chemically stable and allows easier handling than radicals and the like.

[4. Method for Producing Oxidation Reaction Product]

The method for producing an oxidation reaction product is, as described above, a method for producing the oxidation reaction product, the method including an alcohol oxidation step of oxidizing the alcohol.

The oxidation of the alcohol in the alcohol oxidation step is not limited to a particular method. In the method for producing an oxidation reaction product, for example, the alcohol may be oxidized through at least one of ozone oxidation and hydrogen peroxide oxidation in the alcohol oxidation step.

In the method for producing an oxidation reaction product, the reaction time in the alcohol oxidation step is not limited. The reaction time in the alcohol oxidation step may be, for example, 24 hours or more or 1 day or more, 48 hours or more or 2 days or more, 72 hours or more or 3 days or more, 120 hours or more or 5 days or more, or 168 hours or more or 7 days or more. The upper limit value of the reaction time in the alcohol oxidation step is not limited, and the reaction time may be, for example, 720 hours or less or 30 days or less, or 360 hours or less or 15 days or less.

In order to obtain a reaction product containing the cyclic peroxide in the method for producing an oxidation reaction product, it is preferable to employ longer reaction time for the alcohol oxidation step. For example, longer reaction time in the alcohol oxidation step is inferred to allow production of the cyclic peroxide, which cannot be obtained through conventional ozone oxidation reaction or the like of glycerin. For production efficiency in the method for producing an oxidation reaction product, it is preferable to avoid excessively long reaction time for the alcohol oxidation step.

The method for producing an oxidation reaction product includes an alcohol oxidation step of oxidizing the alcohol, as described above. However, the oxidation reaction product is not limited to substances produced with the production method, as described above, and any substance produced with any production method may be employed as long as the substance has the same structure. The method for producing an oxidation reaction product will be more specifically described with reference to examples below.

The case that ozone oxidation is performed with use of glycerin as the alcohol will be described as an example below. However, the description below is an example as mentioned, and the method for producing an oxidation reaction product is not limited to the description below. For example, the method below can be performed in the same manner even with use of another alcohol in place of glycerin. For example, the method for oxidizing the alcohol in the alcohol oxidation step of the method for producing an oxidation reaction product is not limited to a particular method, and any oxidizing method is available, without limitation only to ozone oxidation. The oxidizing method may be, for example, at least one of ozone oxidation and hydrogen peroxide oxidation. Not only the type of the alcohol and the method for oxidizing the alcohol, for example, but also the concentrations of substances, reaction temperature, reaction time, and other reaction conditions can be appropriately changed.

The oxidation reaction product can be produced with a production method including a step of oxidizing glycerin, for example, by bringing glycerin into contact with ozone, more specifically, mixing glycerin and ozone (corresponding to the "alcohol oxidation step"). The step of oxidizing glycerin may be, for example, a step of oxidizing glycerin by bringing a glycerin solution and a gas containing ozone into gas-liquid contact.

It is preferable for the glycerin solution to contain glycerin at high concentration. For the glycerin solution of high concentration, for example, a glycerin solution having a glycerin concentration of 75% or more can be used, and, as a specific example, a 84 to 87% by weight glycerin solution as a product in accordance with the Japanese Pharmacopeia is preferable, a concentrated glycerin solution having a glycerin concentration of 98% by weigh or more as a product in accordance with the Japanese Pharmacopeia is more preferable, and a purified glycerin solution having a concentration of 98.5% by weight or more is even more preferable. If having a relatively higher glycerin concentration, the glycerin solution can be treated with ozone at higher concentration. The solvent to glycerin in the glycerin solution is not limited, and is, for example, an aqueous solvent such as water.

It is preferable for the gas containing ozone to contain ozone at high concentration. Any method may be used for producing the gas of high ozone concentration without limitation, and, for example, an ozone generator that generates ozone by silent discharge in oxygen gas can be used. If oxygen gas is used, for example, an oxygen tank for medical use may be used, and oxygen gas produced by an oxygen generator may be used.

Any method may be used for bringing the glycerin solution and the gas containing ozone into gas-liquid contact without limitation, and an example is a method in which a tank is charged with a glycerin solution of high concentration (e.g., 98% by weight or more) and the gas of high ozone concentration is released as fine bubbles into the tank with use of an air diffuser. Specifically, for example, an ozone-treated glycerin solution having a concentration of approximately 4000 ppm in terms of hydrogen peroxide concentration can be produced by aerating the concentrated glycerin solution with a gas having an ozone concentration of approximately 37000 ppm for approximately 7 days. The aeration time is not limited, and, for example, an ozone-treated glycerin solution containing the oxidation reaction product at higher concentration can be produced by aerating for a relatively long time.

The oxidation reaction product may be directly used without separating from a mixture after the reaction (e.g., the ozone-treated glycerin solution), or used after separating the oxidation reaction product from the mixture after the reaction. The separation is not limited to a particular method, and, for example, the oxidation reaction product can be separated from the mixture after the reaction through chromatography such as preparative thin-layer chromatography.

Conventional production of a substance having oxidation power such as peroxide needs a pathway including complex systems. The method for producing an oxidation reaction product allows, for example, an oxidation reaction product having oxidation power to be produced in a very simple and easy manner.

The oxidation reaction product is capable of generating, for example, hydrogen peroxide. For example, the oxidation reaction product can generate 1 to 4000 ppm, 10 to 4000 ppm, or 100 to 4000 ppm of hydrogen peroxide per approximately 4000 ppm of the oxidation reaction product in terms of hydrogen peroxide concentration.

[5. Glycerin]

In the composition according to the second mode of the present invention, the glycerin may be glycerin or a glycerin derivative described above. The composition according to the second mode of the present invention can stably retain the cyclic peroxide by allowing the cyclic peroxide to coexist with the glycerin.

The amount of the glycerin contained in the composition according to the second mode of the present invention is, for example, 0.1 to 100 w/v %, and preferably 0.1 to 50 w/v %.

[6. Additional Whitening Component]

The composition according to the second mode of the present invention may contain, as an active ingredient of the whitening component, an additional whitening component in addition to the cyclic peroxide and/or the oxidation reaction product containing the cyclic peroxide. Examples of the additional whitening component include arbutin, tranexamic acid, and ascorbic acid or a derivative thereof.

[7. Additional Component]

The composition according to the second mode of the present invention may contain an additional component that is added to dosage forms for application to skin. Specific examples of the additional component include a component that is added to topical agents for skin, and a component that is added to cosmetics (including quasi drugs). Examples of the component that is added to topical agents for skin include pharmaceutically acceptable carriers. Another example of the additional component is a component that is added in application to skin or in transdermal application, and specific examples thereof include aqueous solvents such as water, alcohols, moisturizers, oils, softeners (emollients), surfactants (solubilizers, emulsifying agents), salts, thickeners, pH adjusters, ultraviolet absorbers, drugs, buffers, coloring agents, preservatives, and fragrances.

[8. Dosage Form, Usage, and Applications]

The composition according to the second mode of the present invention is, for example, solid or liquid. Examples of the form of the composition according to the second mode of the present invention include a lotion dosage form, an emulsified dosage form such as an emulsion and a cream, an oil dosage form, a gel dosage form, an ointment, a pack, and a cleansing agent.

A subject for using the composition according to the second mode of the present invention is a human or a non-human animal. The composition according to the second mode of the present invention can be used for a site containing melanin in the subject, and a specific example of the site is skin. The amount of use of the composition according to the second mode of the present invention is not limited, and can be a typical amount of use for a dosage form to be employed for the composition according to the second mode of the present invention.

The composition according to the second mode of the present invention can be preferably used for applications of topical agents for skin such as cosmetics.

<Whitening Agent>

The whitening agent according to the second mode of the present invention contains a cyclic peroxide or a salt thereof. The whitening agent according to the second mode of the present invention is characterized by containing a cyclic peroxide or a salt thereof, and other configurations and conditions are not limited. The cyclic peroxide is inferred to promote the decomposition of melanin. Accordingly, when being applied to skin, for example, the whitening agent according to the second mode of the present invention can give a whitening effect to the skin.

The whitening agent according to the second mode of the present invention can be said to be, for example, an agent for improving freckles, dullness, or ephelides, an agent for suppressing melanin generation, an agent for decomposing melanin, an agent for reducing skin pigmentation, or a whitening agent.

In the whitening agent according to the second mode of the present invention, the cyclic peroxide may be a compound represented by a chemical formula (I) below, or a cyclic peroxide contained in the oxidation reaction product described above, wherein the oxidation reaction product is obtained through oxidation of an alcohol:

[Chemical Formula I]

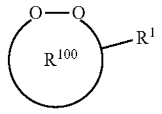

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The description of the composition according to the second mode of the present invention can be referred to for description of the cyclic peroxide and the oxidation reaction product.

The description of the composition according to the second mode of the present invention can be referred to for description of dosage forms and applications of the whitening agent according to the second mode of the present invention.

<Whitening Method>

The whitening method according to the second mode of the present invention uses the whitening composition according to the second mode of the present invention and/or the whitening agent according to the second mode of the present invention. The whitening method according to the second mode of the present invention is characterized by the use of the whitening composition according to the second mode of the present invention and/or the whitening agent according to the second mode of the present invention, and other steps and conditions are not limited. The cyclic peroxide contained in the composition and/or whitening agent according to the second mode of the present invention is inferred to promote the decomposition of melanin. Accordingly, when being applied to skin, for example, the whitening agent according to the second mode of the present invention can give a whitening effect to the skin.

The whitening method according to the second mode of the present invention can be performed by using the whitening composition and/or the whitening agent for the skin of a subject. More specifically, the whitening method according to the second mode of the present invention can be performed by bringing the whitening composition and/or the whitening agent into contact with the skin of a subject.

<Use>

The second mode of the present invention is the whitening composition according to the second mode of the present invention and/or the whitening agent according to the second mode of the present invention for use in whitening, or use thereof for whitening.

Third Mode for Carrying Out the Invention

Second, the third mode for carrying out the present invention will be described. However, the third mode of the present invention is not limited to the following description.

In the third mode of the present invention, if isomers such as tautomers or stereoisomers (examples: geometric isomers, conformers, and optical isomers) are present for a compound, any of the isomers can be used for the present invention, unless otherwise specified. In the third mode of the present invention, if a substance can form a salt, the salt can also be used for the third mode of the present invention, unless otherwise specified. The salt may be an acid addition salt, or a base addition salt. Moreover, the acid to form the acid addition salt may be an inorganic acid or an organic acid, and the base to form the base addition salt may be an inorganic base or an organic base. Examples of the inorganic acid include, but are not limited to, sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluoric acid, chloric acid, bromic acid, iodic acid, perfluoric acid, perchloric acid, perbromic acid, and periodic acid. Examples of the organic acid include, but are not limited to, similarly, p-toluenesulfonic acid, methanesulfonic acid, oxalic acid, p-bromobenzenesulfonic acid, carbonic acid, succinic acid, citric acid, benzoic acid, and acetic acid. Examples of the inorganic base include, but are not limited to, ammonium hydroxide, alkali metal hydroxide, alkaline earth metal hydroxide, carbonate, and hydrogen carbonate, and more specific examples thereof include sodium hydroxide, potassium hydroxide, potassium carbonate, sodium carbonate, sodium hydrogen carbonate, potassium hydrogen carbonate, calcium hydroxide, and calcium carbonate. Examples of the organic base include, but are not limited to, similarly, ethanolamine, triethylamine, and tris(hydroxymethyl)aminomethane. The method for producing those salts is not limited to a particular method, and, for example, such a salt can be produced in such a manner that an acid or base as shown above is appropriately allowed to add to the compound with a known method.

Examples of the aromatic ring having no heteroatom in the third mode of the present invention include a benzene ring, a naphthalene ring, an anthracene ring, a phenanthrene ring, and a pyrene ring. Examples of the heteroaromatic ring include a pyridine ring and a thiophene ring. The nitrogen-containing aromatic ring may be free of a positive charge, or have a positive charge. Examples of the nitrogen-containing aromatic ring being free of a positive charge include a pyrroline ring, a pyridine ring, a pyridazine ring, a pyrimidine ring, a pyrazine ring, a quinoline ring, an isoquinoline ring, an acridine ring, a 3,4-benzoquinoline ring, a 5,6-benzoquinoline ring, a 6,7-benzoquinoline ring, a 7,8-benzoquinoline ring, a 3,4-benzoisoquinoline ring, a 5,6-benzoisoquinoline ring, a 6,7-benzoisoquinoline ring, and a 7,8-benzoisoquinoline ring. Examples of the nitrogen-containing aromatic ring having a positive charge include a pyrrolinium ring, a pyridinium ring, a pyridazinium ring, a pyrimidinium ring, a pyrazinium ring, a quinolinium ring, an isoquinolinium ring, an acridinium ring, a 3,4-benzoquinolinium ring, a 5,6-benzoquinolinium ring, a 6,7-benzoquinolinium ring, a 7,8-benzoquinolinium ring, a 3,4-benzoisoquinolinium ring, a 5,6-benzoisoquinolinium ring, a 6,7-benzoisoquinolinium ring, and a 7,8-benzoisoquinolinium ring. Examples of the oxygen-containing aromatic ring or sulfur-containing aromatic ring include an aromatic ring formed by replacing at least one carbon atom or nitrogen atom in the aromatic ring containing no heteroatom or the nitrogen-containing aromatic ring with at least one of an oxygen atom and a sulfur atom.

Examples of the "substituent" in the third mode of the present invention include a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), and an alkylthio group (—SR, wherein R is an alkyl group).

In the third mode of the present invention, each chain substituent (e.g., an alkyl group and a hydrocarbon group such as an unsaturated aliphatic hydrocarbon group) may be linear or branched, unless otherwise specified, and the number of carbon atoms is not limited and may be, for example, 1 to 40, 1 to 32, 1 to 24, 1 to 18, 1 to 12, one to six, or one or two (two or more for an unsaturated hydrocarbon group). Herein, the number of ring members (the number of atoms constituting a ring) of each cyclic group (e.g., an aryl group, a heteroaryl group) is not limited and may be, for example, 5 to 32, 5 to 24, 6 to 18, 6 to 12, or 6 to 10. If isomers are present for a substituent or the like, the substituent or the like may be any of the isomers: when a substituent or the like is simply referred to as a "butyl group", for example, the substituent or the like may be a n-butyl group, or a sec-butyl group, or a tert-butyl group; when a substituent or the like is simply referred to as a "naphthyl group", the substituent or the like may be a 1-naphthyl group or a 2-naphthyl group.

In the third mode of the present invention, the term "skin barrier function" means a function to prevent moisture in the interior of skin from vaporizing out and/or a function to prevent the invasion of substances from the surroundings into skin.

In the third mode of the present invention, the term "oxidative stress" means a stress caused by a reactive oxygen species. Specific examples of the oxidative stress include disorder of biomolecules (e.g., proteins, lipids, nucleic acids) and disorder of organelles because of the reactive oxygen species.

In the third mode of the present invention, the phrase "inducing expression of a gene" may mean change from a state without expression of a gene of interest to a state with expression of the gene of interest, or increase in the expression level of a gene of interest.

In the third mode of the present invention, the term "treatment" means therapeutic treatment and/or preventive treatment. Herein, the term "therapy" means treating, curing, preventing, inhibiting, remitting from, or ameliorating a disease, pathological condition, or a disorder, or stopping, inhibiting, reducing, or retarding the progression of a disease, pathological condition, or a disorder. Herein, the term "prevention" means lowering the probability of the onset of a disease or pathological condition, or retarding the onset of a disease or pathological condition. The "therapy" may be therapy for a patient presenting with a target disease, or therapy for a model animal with a target disease.

The third mode of the present invention will be more specifically described with examples below. However, the third mode of the present invention is not limited to the description given below. Description of one part of the third mode of the present invention can be referred to for description of another part and vice versa, unless otherwise stated. Herein, use of the expression "A to B" is intended to include the numerical values or physical values before and after "to". Herein, the expression "A and/or B" encompasses "only A", "only B", and "both A and B".

<Composition for Inducing Expression of Skin Barrier Function-Related Gene>

The composition for inducing expression of a skin barrier function-related gene according to the third mode of the present invention (hereinafter, referred to as "the first composition") contains glycerin and/or a glycerin derivative, and a component for inducing expression of a skin barrier function-related gene, wherein the component for inducing expression of a skin barrier function-related gene contains a cyclic peroxide or a salt thereof as an active ingredient. The first composition according to the third mode of the present invention is characterized by containing the cyclic peroxide or a salt thereof, and other configurations and conditions are not limited. As described later, the cyclic peroxide induces expression of a protein important for skin barrier functions such as a pro-filaggrin gene, which is a skin barrier function-related gene. Accordingly, when being applied to skin, for example, the first composition according to the third mode of the present invention can give an effect to induce expression of a skin barrier function-related gene to the skin.

[1. Expression Inducer Component for Skin Barrier Function-Related Gene]

The first composition according to the third mode of the present invention contains a component for inducing expression of a skin barrier function-related gene, as described above. The first composition according to the third mode of the present invention may contain, as an active ingredient of the component for inducing expression of a skin barrier function-related gene, the cyclic peroxide, or an oxidation reaction product containing the cyclic peroxide as described later, or both of them. The cyclic peroxide may be a compound represented by a chemical formula (I) below, or a cyclic peroxide contained in an oxidation reaction product described later, wherein the oxidation reaction product is obtained through oxidation of an alcohol, or both of them.

The amount of the component for inducing expression of a skin barrier function-related gene contained in the first composition according to the third mode of the present invention can be any effective amount that allows induction of expression of a skin barrier function-related gene, and is, for example, 0.001 to 10 w/v %, 0.05 to 5 w/v %, or 0.01 to 1 w/v %. The amount of the cyclic peroxide contained in the first composition according to the third mode of the present invention can be any effective amount that allows induction of expression of a skin barrier function-related gene, and is, for example, 0.001 to 10 w/v %, 0.05 to 5 w/v %, or 0.01 to 1 w/v %.

[2. Cyclic Peroxide]

The cyclic peroxide is represented by the following chemical formula (I):

[Chemical Formula I]

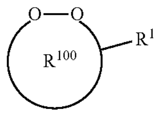

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The heteroatom is an atom other than carbon and hydrogen, and may be, for example, one selected from the group consisting of an oxygen atom, a nitrogen atom, a sulfur atom, a selenium atom, a boron atom, and a silicon atom. The substituent is not limited and may contain, for example, a hydroxy group, and may be, for example, one selected from the group consisting of a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), and an alkylthio group (—SR, wherein R is an alkyl group) shown above.

In the cyclic peroxide, for example, $R^{100}$ in the chemical formula (I) may be a cyclic structure having 5 to 10 ring members.

The cyclic peroxide may be, for example, a cyclic peroxide represented by the following chemical formula (II):

[Chemical Formula II]

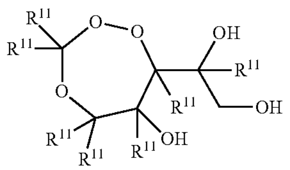

(II)

wherein the $R^{11}$ groups are the same or different, each being a hydrogen atom or a substituent, and two $R^{11}$ groups bound to the same carbon atom optionally together form an oxo group (═O) or a thioxo group (═S).

In the cyclic peroxide, the substituent for each of the $R^{11}$ groups in the chemical formula (II) may be, for example, a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

The cyclic peroxide may be, for example, a cyclic peroxide represented by a chemical formula (1) below. The cyclic peroxide represented by the following chemical formula (1) corresponds to the case that the $R^{11}$ groups in the chemical formula (II) are each a hydrogen atom.

[Chemical Formula I]

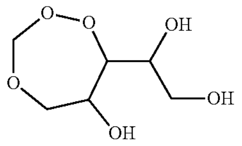

(1)

The method for producing the cyclic peroxide is not limited to a particular method, and, for example, the cyclic peroxide can be produced by oxidizing an alcohol with a method described later for producing an oxidation reaction product. In this case, for example, an oxidation reaction product produced may be directly used without purification; alternatively, only the cyclic peroxide may be isolated and purified for use.

The phenomenon that a cyclic peroxide is obtained through oxidation of an alcohol, for example, through ozone oxidation of glycerin was discovered for the first time by the present inventors. Although the mechanism that gives a cyclic peroxide is unclear, for example, longer reaction time in oxidation reaction of an alcohol is expected to give a reaction product differing from those from conventional reactions, as described later.

The cyclic peroxide can be isolated and, for example, formulated because the cyclic peroxide is more chemically stable and allows easier handling than radicals and the like.

Generally speaking, cyclic peroxides are substances industrially used, for example, for their oxidative capacity. In particular, artemisinin, which has the same seven-membered ring (trioxolane) backbone as the cyclic peroxide, led to the winning of Nobel prize in 2015 for the usefulness against malaria, and derivatives of artemisinin have been still under research.

However, supply of artemisinin, which is extracted and purified from natural products, is unstable. In addition, artemisinin is neither water-soluble nor liposoluble, and hence causes many problems in formulation. Hydrogen peroxide, an example of water-soluble substances with high oxidation power, is highly reactive and unstable, and the usage thereof for living bodies is only limited to topical agents for disinfection.

On the other hand, the third mode of the present invention can be preferably used for living bodies because a cyclic peroxide and oxidation reaction product that are highly safe and superior in water solubility are used. The third mode of the present invention is inferred to cause an action to induce expression of a skin barrier function-related gene through the oxidative capacity of the cyclic peroxide. The action to induce expression of a skin barrier function-related gene can be evaluated according to Example 3 shown later.

In the first composition according to the third mode of the present invention, the cyclic peroxide may be in the form of a salt or a solvate such as a hydrate. The description of the cyclic peroxide can be referred to for description of the salt of the cyclic peroxide or a solvate of any of them.

[3. Oxidation Reaction Product]

The oxidation reaction product is an oxidation reaction product characterized by containing a cyclic peroxide, wherein the oxidation reaction product is obtained through oxidation of an alcohol, as described above. However, the method for producing the oxidation reaction product may be performed with any method without limitation to oxidation of an alcohol, and any substance produced with any production method may be employed as long as the substance has the same structure.

The oxidation of an alcohol is not limited to a particular method. For example, the oxidation of an alcohol may be at least one of ozone oxidation and hydrogen peroxide oxidation. However, as described above, the method for producing the oxidation reaction product may be performed with any method without limitation to ozone oxidation and hydrogen peroxide oxidation of an alcohol, and any substance produced with any production method may be employed as long as the substance has the same structure.

The oxidation reaction product may be, for example, a mixture containing a plurality of oxidation reaction products.

The oxidation reaction product may have, for example, oxidative capacity.

The oxidation reaction product may have, for example, reductive capacity.

The alcohol to be used as a raw material of the oxidation reaction product is not limited. The alcohol for the oxidation reaction product may be, for example, a saturated alcohol.

The alcohol for the oxidation reaction product may be, for example, a polyhydric alcohol.

The alcohol for the oxidation reaction product may be, for example, at least one of glycerin and a glycerin derivative.

The oxidation reaction product may contain, for example, an oxidation reaction product formed by binding of two or more molecules of the alcohol.

The oxidation reaction product may contain, for example, the cyclic peroxide.

The alcohol to be used as a raw material of the oxidation reaction product is not limited, and may be, for example, a saturated alcohol as described above, or an unsaturated alcohol. The alcohol may be liner or branched, and may contain a cyclic structure or not. The alcohol may be, for example, a polyhydric alcohol or a monohydric alcohol. The number of hydroxy groups of the polyhydric alcohol is not limited, and the polyhydric alcohol may be, for example, dihydric, trihydric, or tetrahydric. Examples of the monohydric saturated alcohol include a saturated alcohol having 1 to 40, 1 to 32, 1 to 24, 1 to 18, 1 to 12, one to six, or one or two carbon atoms, the saturated alcohol may be linear or branched, and may contain a cyclic structure or not, and specific examples thereof include methanol, ethanol, n-propyl alcohol, isopropyl alcohol, n-butyl alcohol, sec-butyl alcohol, and tert-butyl alcohol. Examples of the saturated polyhydric alcohol include a saturated polyhydric alcohol having 1 to 40, 1 to 32, 1 to 24, 1 to 18, 1 to 12, one to six, or one or two carbon atoms, the saturated polyhydric alcohol may be linear or branched, and may contain a cyclic structure or not, and specific examples thereof include ethylene glycol (ethane-1,2-diol), propylene glycol (propane-1,2-diol), glycerin, and a glycerin derivative. The glycerin derivative is not limited, and may be, for example, a polymer of glycerin or a compound formed by substituting at least one of the hydrogen atoms of glycerin with a substituent (e.g., an alkyl group). Examples of the glycerin derivative include diglycerin and polyglycerin. The glycerin derivative may be an oxidized form of glycerin.

The oxidation reaction product may be, for example, a substance having reductive capacity, as described above. For example, the oxidation reaction product may have reductive capacity through inclusion of a functional group, wherein the reductive capacity is derived from the functional group, which has reductive capacity. Specifically, for example, the oxidation reaction product may have reductive capacity through inclusion of an aldehyde group (formyl group), or have reductive capacity derived from the keto form because of the keto-enol tautomerism. For example, the oxidation reaction product that has been obtained in Example 3 shown later contains an acetal structure as the backbone, as confirmed by NMR, hence being inferred to color through DNPH (dinitrophenylhydrazine: derived from ketone and aldehyde) reaction derived from ketone and aldehyde.

The oxidation reaction product may be, for example, a substance formed by binding of two or more molecules of the alcohol, as described above. Specifically, for example, a structure formed by binding of two or more molecules of the alcohol and oxidizing the resultant is acceptable. The mode of "binding" of two or more molecules of the alcohol is not limited, and may be, for example, addition or condensation.

The oxidation reaction product can be isolated and, for example, formulated because the oxidation reaction product is more chemically stable and allows easier handling than radicals and the like.

[4. Method for Producing Oxidation Reaction Product]

The method for producing an oxidation reaction product is, as described above, a method for producing the oxidation reaction product, the method including an alcohol oxidation step of oxidizing the alcohol.

The oxidation of the alcohol in the alcohol oxidation step is not limited to a particular method. In the method for producing an oxidation reaction product, for example, the alcohol may be oxidized through at least one of ozone oxidation and hydrogen peroxide oxidation in the alcohol oxidation step.

In the method for producing an oxidation reaction product, the reaction time in the alcohol oxidation step is not limited. The reaction time in the alcohol oxidation step may be, for example, 24 hours or more or 1 day or more, 48 hours or more or 2 days or more, 72 hours or more or 3 days or more, 120 hours or more or 5 days or more, or 168 hours or more or 7 days or more. The upper limit value of the reaction time in the alcohol oxidation step is not limited, and the reaction time may be, for example, 720 hours or less or 30 days or less, or 360 hours or less or 15 days or less.

In order to obtain a reaction product containing the cyclic peroxide in the method for producing an oxidation reaction product, it is preferable to employ longer reaction time for the alcohol oxidation step. For example, longer reaction time in the alcohol oxidation step is inferred to allow production of the cyclic peroxide, which cannot be obtained through conventional ozone oxidation reaction or the like of glycerin. For production efficiency in the method for producing an oxidation reaction product, it is preferable to avoid excessively long reaction time for the alcohol oxidation step.

The method for producing an oxidation reaction product includes an alcohol oxidation step of oxidizing the alcohol, as described above. However, the oxidation reaction product is not limited to substances produced with the production method, as described above, and any substance produced with any production method may be employed as long as the substance has the same structure. The method for producing an oxidation reaction product will be more specifically described with reference to examples below.

The case that ozone oxidation is performed with use of glycerin as the alcohol will be described as an example below. However, the description below is an example as mentioned, and the method for producing an oxidation reaction product is not limited to the description below. For example, the method below can be performed in the same manner even with use of another alcohol in place of glycerin. For example, the method for oxidizing the alcohol in the alcohol oxidation step of the method for producing an oxidation reaction product is not limited to a particular method, and any oxidizing method is available, without limitation only to ozone oxidation. The oxidizing method may be, for example, at least one of ozone oxidation and hydrogen peroxide oxidation. Not only the type of the alcohol and the method for oxidizing the alcohol, for example, but also the concentrations of substances, reaction temperature, reaction time, and other reaction conditions can be appropriately changed.

The oxidation reaction product can be produced with a production method including a step of oxidizing glycerin, for example, by bringing glycerin into contact with ozone, more specifically, mixing glycerin and ozone (corresponding to the "alcohol oxidation step"). The step of oxidizing glycerin may be, for example, a step of oxidizing glycerin by bringing a glycerin solution and a gas containing ozone into gas-liquid contact.

It is preferable for the glycerin solution to contain glycerin at high concentration. For the glycerin solution of high concentration, for example, a glycerin solution having a glycerin concentration of 75% or more can be used, and, as a specific example, a 84 to 87% by weight glycerin solution as a product in accordance with the Japanese Pharmacopeia is preferable, a concentrated glycerin solution having a glycerin concentration of 98% by weigh or more as a product in accordance with the Japanese Pharmacopeia is more preferable, and a purified glycerin solution having a concentration of 98.5% by weight or more is even more preferable. If having a relatively higher glycerin concentration, the glycerin solution can be treated with ozone at higher concentration. The solvent to glycerin in the glycerin solution is not limited, and is, for example, an aqueous solvent such as water.

It is preferable for the gas containing ozone to contain ozone at high concentration. Any method may be used for producing the gas of high ozone concentration without limitation, and, for example, an ozone generator that generates ozone by silent discharge in oxygen gas can be used. If oxygen gas is used, for example, an oxygen tank for medical use may be used, and oxygen gas produced by an oxygen generator may be used.

Any method may be used for bringing the glycerin solution and the gas containing ozone into gas-liquid contact without limitation, and an example is a method in which a tank is charged with a glycerin solution of high concentration (e.g., 98% by weight or more) and the gas of high ozone concentration is released as fine bubbles into the tank with use of an air diffuser. Specifically, for example, an ozone-treated glycerin solution having a concentration of approximately 4000 ppm in terms of hydrogen peroxide concentration can be produced by aerating the concentrated glycerin solution with a gas having an ozone concentration of approximately 37000 ppm for approximately 7 days. The aeration time is not limited, and, for example, an ozone-treated glycerin solution containing the oxidation reaction product at higher concentration can be produced by aerating for a relatively long time.

The oxidation reaction product may be directly used without separating from a mixture after the reaction (e.g., the ozone-treated glycerin solution), or used after separating the oxidation reaction product from the mixture after the reaction. The separation method is not limited to a particular method, and, for example, the oxidation reaction product can be separated from the mixture after the reaction through chromatography such as preparative thin-layer chromatography.

Conventional production of a substance having oxidation power such as peroxide needs a pathway including complex systems. The method for producing an oxidation reaction product allows, for example, an oxidation reaction product having oxidation power to be produced in a very simple and easy manner.

The oxidation reaction product is capable of generating, for example, hydrogen peroxide. For example, the oxidation reaction product can generate 1 to 4000 ppm, 10 to 4000 ppm, or 100 to 4000 ppm of hydrogen peroxide per approximately 4000 ppm of the oxidation reaction product in terms of hydrogen peroxide concentration.

[5. Glycerin]

In the first composition according to the third mode of the present invention, the glycerin may be glycerin or a glycerin derivative described above. The first composition according to the third mode of the present invention can stably retain the cyclic peroxide by allowing the cyclic peroxide to coexist with the glycerin.

The amount of the glycerin contained in the first composition according to the third mode of the present invention is, for example, 0.1 to 100 w/v %, and preferably 0.1 to 50 w/v %.

[6. Skin Barrier Function-Related Gene]

The skin barrier function-related gene can be any gene encoding a protein that contributes to the barrier function of skin. Examples of the skin barrier function-related gene include a pro-filaggrin gene, an involucrin gene, and a serine palmitoyltransferase gene. One gene or a plurality of genes may be induced to be expressed as the skin barrier function-related gene by the first composition according to the third mode of the present invention. Examples of the pro-filaggrin gene, involucrin gene, and serine palmitoyltransferase gene include, as human genes, polynucleotides each consisting of a nucleotide sequence specified with a GenBank Accession Number shown in the following.

Profilaggrin gene: NM_002016.2

Involucrin gene: NM_005547.2

Serine palmitoyltransferase gene. NM_004863.3

[7. Additional Component]

The first composition according to the third mode of the present invention may contain an additional component that is added to dosage forms for application to skin. Specific examples of the additional component include a component that is added to topical agents for skin, and a component that is added to cosmetics (including quasi drugs). Examples of the component that is added to topical agents for skin include pharmaceutically acceptable carriers. Another example of the additional component is a component that is added in application to skin or in transdermal application, and specific examples thereof include aqueous solvents such as water, alcohols, moisturizers, oils, softeners (emollients), surfactants (solubilizers, emulsifying agents), salts, thickeners, pH adjusters, ultraviolet absorbers, drugs, buffers, coloring agents, preservatives, and fragrances.

[8. Dosage Form, Usage, and Applications]

The first composition according to the third mode of the present invention is, for example, solid or liquid. Examples of the form of the first composition according to the third mode of the present invention include a lotion dosage form, an emulsified dosage form such as an emulsion and a cream, an oil dosage form, a gel dosage form, an ointment, a pack, and a cleansing agent.

A subject for using the first composition according to the third mode of the present invention is a human or a non-human animal. The first composition according to the third mode of the present invention can be used, for example, to skin of the subject. The amount of use of the first composition according to the third mode of the present invention is not limited, and can be a typical amount of use for a dosage form to be employed for the first composition according to the third mode of the present invention.

The first composition according to the third mode of the present invention can be preferably used for applications of topical agents for skin such as cosmetics.

<Agent for Inducing Expression of Skin Barrier Function-Related Gene>

The agent for inducing expression of a skin barrier function-related gene according to the third mode of the present invention (hereinafter, referred to as "the first inducing agent") contains a cyclic peroxide or a salt thereof. The agent for inducing expression of a skin barrier function-related gene according to the third mode of the present invention is characterized by containing a cyclic peroxide or a salt thereof, and other configurations and conditions are not limited. As described above, the cyclic peroxide induces expression of a protein important for skin barrier functions such as a pro-filaggrin gene, which is the skin barrier function-related gene. Accordingly, when being applied to skin, for example, the first inducing agent according to the third mode of the present invention can give an effect to induce expression of a skin barrier function-related gene to the skin.

The amount of the component for inducing expression of a skin barrier function-related gene contained in the first inducing agent according to the third mode of the present invention can be any effective amount that allows induction of expression of a skin barrier function-related gene, and is, for example, 0.001 to 10 w/v %, 0.05 to 5 w/v %, or 0.01 to 1 w/v %. The amount of the cyclic peroxide contained in the first inducing agent according to the third mode of the present invention can be any effective amount that allows induction of expression of a skin barrier function-related gene, and is, for example, 0.001 to 10 w/v %, 0.05 to 5 w/v %, or 0.01 to 1 w/v %.

The cyclic peroxide in the first inducing agent according to the third mode of the present invention may be a compound represented by a chemical formula (I) below, or the cyclic peroxide contained in the oxidation reaction product described above, wherein the oxidation reaction product is obtained through oxidation of an alcohol:

[Chemical Formula I]

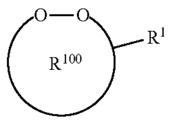

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The description of the first composition according to the third mode of the present invention can be referred to for description of the cyclic peroxide and the oxidation reaction product.

The description of the first composition according to the third mode of the present invention can be referred to for description of dosage forms and applications of the first inducing agent according to the third mode of the present invention.

<Composition for Improving Skin Barrier Function>

The composition for improving a skin barrier function according to the third mode of the present invention (hereinafter, referred to as "the second composition") contains glycerin and/or a glycerin derivative, and a component for improving a skin barrier function, wherein the component for improving a skin barrier function contains a cyclic peroxide or a salt thereof as an active ingredient. The second composition according to the third mode of the present invention is characterized by containing the cyclic peroxide or a salt thereof, and other configurations and conditions are not limited. As described above, the cyclic peroxide induces expression of a protein important for skin barrier functions such as a pro-filaggrin gene, which is a skin barrier function-related gene. Accordingly, when being applied to skin, for example, the second composition according to the third mode of the present invention can give an effect to induce expression of a skin barrier function-related gene to the skin, thereby improving the skin barrier function.

The amount of the component for improving a skin barrier function contained in the second composition according to the third mode of the present invention can be any effective amount that allows a skin barrier function to be improved, and is, for example, 0.001 to 10 w/v %, 0.05 to 5 w/v %, or 0.01 to 1 w/v %. The amount of the cyclic peroxide contained in the second composition according to the third mode of the present invention can be any effective amount that allows a skin barrier function to be improved, and is, for example, 0.001 to 10 w/v %, 0.05 to 5 w/v %, or 0.01 to 1 w/v %.

The cyclic peroxide in the second composition according to the third mode of the present invention may be a compound represented by a chemical formula (I) below, or the cyclic peroxide contained in the oxidation reaction product described above, wherein the oxidation reaction product is obtained through oxidation of an alcohol:

[Chemical Formula I]

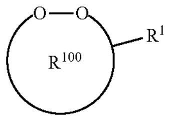

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The description of the first composition according to the third mode of the present invention can be referred to for description of the cyclic peroxide, the oxidation reaction product, and glycerin.

The description of the first composition according to the third mode of the present invention can be referred to for description of dosage forms and applications of the second composition according to the third mode of the present invention.

The second composition according to the third mode of the present invention can improve a skin barrier function. Accordingly, the second composition according to the third mode of the present invention can be preferably used for treating, for example, atopic dermatitis or psoriasis vulgaris, which involves the lowering of the skin barrier function.

<Agent for Improving Skin Barrier Function>

The agent for improving a skin barrier function according to the third mode of the present invention (hereinafter, referred to as "the improving agent") contains a cyclic peroxide or a salt thereof. The agent for improving a skin barrier function according to the third mode of the present invention is characterized by containing a cyclic peroxide or a salt thereof, and other configurations and conditions are not limited. As described above, the cyclic peroxide induces expression of a protein important for skin barrier functions such as a pro-filaggrin gene, which is the skin barrier function-related gene. Accordingly, when being applied to skin, for example, the improving agent according to the third mode of the present invention can give an effect to induce expression of a skin barrier function-related gene to the skin, thereby improving the skin barrier function.

The amount of the component for improving a skin barrier function contained in the improving agent according to the third mode of the present invention can be any effective amount that allows a skin barrier function to be improved, and is, for example, 0.001 to 10 w/v %, 0.05 to 5 w/v %, or 0.01 to 1 w/v %. The amount of the cyclic peroxide contained in the improving agent according to the third mode of the present invention can be any effective amount that allows a skin barrier function to be improved, and is, for example, 0.001 to 10 w/v %, 0.05 to 5 w/v %, or 0.01 to 1 w/v %.

The cyclic peroxide in the improving agent according to the third mode of the present invention may be a compound represented by a chemical formula (I) below, or the cyclic peroxide contained in the oxidation reaction product described above, wherein the oxidation reaction product is obtained through oxidation of an alcohol:

[Chemical Formula I]

(I)

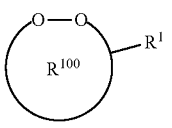

wherein

- $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and
- $R^1$ is a substituent, wherein one $R^1$ group, a plurality of $R^1$ groups, or no $R^1$ group is present, and if a plurality of $R^1$ groups is present, the $R^1$ groups are the same or different.

The description of the first composition according to the third mode of the present invention can be referred to for description of the cyclic peroxide and the oxidation reaction product.

The descriptions of the first composition and second composition according to the third mode of the present invention can be referred to for description of dosage forms and applications of the improving agent according to the third mode of the present invention.

<Composition for Inducing Expression of Anti-Oxidative Stress Response Gene>

The composition for inducing expression of an anti-oxidative stress response gene according to the third mode of the present invention (hereinafter, referred to as "the third composition") contains glycerin and/or a glycerin derivative, and a component for inducing expression of an anti-oxidative stress response gene, wherein the component for inducing expression of an anti-oxidative stress response gene contains a cyclic peroxide or a salt thereof as an active ingredient. The third composition according to the third mode of the present invention is characterized by containing the cyclic peroxide or a salt thereof, and other configurations and conditions are not limited. As described above, the cyclic peroxide induces expression of a protein important for anti-oxidative stress response such as a heme oxygenase-1 gene and an NAD(P)H quinone oxidoreductase-1 gene, each of which is an anti-oxidative stress response gene. Accordingly, when being applied to skin, for example, the third composition according to the third mode of the present invention can give an effect to induce expression of an anti-oxidative stress response gene to the skin, thereby improving the anti-oxidative stress response.

The amount of the component for inducing expression of an anti-oxidative stress response gene contained in the third composition according to the third mode of the present invention can be any effective amount that allows induction of expression of an anti-oxidative stress response gene, and is, for example, 0.001 to 10 w/v %, 0.05 to 5 w/v %, or 0.01 to 1 w/v %. The amount of the cyclic peroxide contained in the third composition according to the third mode of the present invention can be any effective amount that allows induction of expression of an anti-oxidative stress response gene, and is, for example, 0.001 to 10 w/v %, 0.05 to 5 w/v %, or 0.01 to 1 w/v %.

The cyclic peroxide in the third composition according to the third mode of the present invention may be a compound represented by a chemical formula (I) below, or the cyclic peroxide contained in the oxidation reaction product described above, wherein the oxidation reaction product is obtained through oxidation of an alcohol:

[Chemical Formula I]

(I)

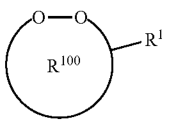

wherein

- $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and
- $R^1$ is a substituent, wherein one $R^1$ group, a plurality of $R^1$ groups, or no $R^1$ group is present, and if a plurality of $R^1$ groups is present, the $R^1$ groups are the same or different.

The anti-oxidative stress response gene can be any gene encoding a protein that contributes to oxidative stress response. Examples of the anti-oxidative stress response gene include a heme oxygenase-1 (HO-1) gene and an NAD(P)H quinone oxidoreductase-1 (NQO-1) gene, and/or a glutathione gene. One gene or a plurality of genes may be induced to be expressed as the anti-oxidative stress response gene by the third composition according to the third mode of the present invention. Examples of the heme oxygenase-1 gene and NAD(P)H quinone oxidoreductase-1 gene include, as human genes, polynucleotides each consisting of a nucleotide sequence specified with a GenBank Accession Number shown in the following.

Heme oxygenase-1 gene: NM_002133.3

NAD(P)H quinone oxidoreductase-1 gene: NM_000903.3

The description of the first composition according to the third mode of the present invention can be referred to for description of the cyclic peroxide, the oxidation reaction product, and glycerin.

The description of the first composition according to the third mode of the present invention can be referred to for description of dosage forms and applications of the third composition according to the third mode of the present invention.

The third composition according to the third mode of the present invention can improve anti-oxidative stress response. Accordingly, the third composition according to the third mode of the present invention can be preferably used for treating, for example, atopic dermatitis, which involves the lowering of the anti-oxidative stress response.

<Agent for Inducing Expression of Anti-Oxidative Stress Function Gene>

The agent for inducing expression of an anti-oxidative stress response gene according to the third mode of the present invention (hereinafter, referred to as "the second inducing agent") contains a cyclic peroxide or a salt thereof. The agent for inducing expression of an anti-oxidative stress response gene according to the third mode of the present invention is characterized by containing a cyclic peroxide or a salt thereof, and other configurations and conditions are not limited. As described above, the cyclic peroxide induces expression of a protein important for anti-oxidative stress response such as a heme oxygenase-1 gene and an NAD (P)H quinone oxidoreductase-1 gene, each of which is the anti-oxidative stress response gene. Accordingly, when being applied to skin, for example, the second inducing agent according to the third mode of the present invention can give an effect to induce expression of an anti-oxidative stress response gene to the skin, thereby improving the anti-oxidative stress response.

The amount of the component for inducing expression of an anti-oxidative stress response gene contained in the second inducing agent according to the third mode of the present invention can be any effective amount that allows induction of expression of an anti-oxidative stress response gene, and is, for example, 0.001 to 10 w/v %, 0.05 to 5 w/v %, or 0.01 to 1 w/v %. The amount of the cyclic peroxide contained in the second inducing agent according to the third mode of the present invention can be any effective amount that allows induction of expression of an anti-oxidative stress response gene, and is, for example, 0.001 to 10 w/v %, 0.05 to 5 w/v %, or 0.01 to 1 w/v %.

The cyclic peroxide in the second inducing agent according to the third mode of the present invention may be a compound represented by a chemical formula (I) below, or the cyclic peroxide contained in the oxidation reaction product described above, wherein the oxidation reaction product is obtained through oxidation of an alcohol:

[Chemical Formula I]

(I)

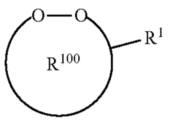

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The description of the first composition according to the third mode of the present invention can be referred to for description of the cyclic peroxide and the oxidation reaction product.

The description of the first composition and third composition according to the third mode of the present invention can be referred to for description of dosage forms and applications of the second inducing agent according to the third mode of the present invention.

<Anti-Inflammatory Composition>

The anti-inflammatory composition according to the third mode of the present invention (hereinafter, referred to as "the fourth composition") contains glycerin and/or a glycerin derivative, and an anti-inflammatory component, wherein the anti-inflammatory component contains a cyclic peroxide or a salt thereof as an active ingredient. The fourth composition according to the third mode of the present invention is characterized by containing the cyclic peroxide or a salt thereof, and other configurations and conditions are not limited. As described later, the cyclic peroxide suppresses production of the anti-inflammatory cytokine IL-1α and prostaglandin E2. Accordingly, when being applied to skin, for example, the fourth composition according to the third mode of the present invention can give an anti-inflammatory effect to the skin.

The amount of the anti-inflammatory component contained in the anti-inflammatory composition according to the third mode of the present invention can be any amount that allows suppression of inflammation, and is, for example, 0.001 to 10 w/v %, 0.05 to 5 w/v %, or 0.01 to 1 w/v %. The amount of the cyclic peroxide contained in the anti-inflammatory composition according to the third mode of the present invention can be any amount that allows suppression of inflammation, and is, for example, 0.001 to 10 w/v %, 0.05 to 5 w/v %, or 0.01 to 1 w/v %.

The cyclic peroxide in the fourth composition according to the third mode of the present invention may be a compound represented by a chemical formula (I) below, or the cyclic peroxide contained in the oxidation reaction product described above, wherein the oxidation reaction product is obtained through oxidation of an alcohol:

[Chemical Formula I]

(I)

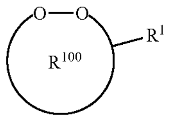

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The fourth composition according to the third mode of the present invention suppresses, for example, expression and/or production of the proinflammatory cytokine. Examples of the proinflammatory cytokine include IL-1α. Accordingly, the fourth composition according to the third mode of the present invention can be said to be, for example, a composition for suppressing expression of an IL-1α gene and/or a composition for suppressing production of IL-1α. In addition, the fourth composition according to the third mode of the present invention suppresses, for example, production of a chemical mediator that evokes inflammation. Examples of the chemical mediator include prostaglandin E2. Accordingly, the fourth composition according to the third mode of the present invention can be said to be, for example, a composition for suppressing production of prostaglandin E2.

The description of the first composition according to the third mode of the present invention can be referred to for description of the cyclic peroxide, the oxidation reaction product, and glycerin.

The description of the first composition according to the third mode of the present invention can be referred to for description of dosage forms and applications of the fourth composition according to the third mode of the present invention.

The fourth composition according to the third mode of the present invention can suppress inflammation. Accordingly, the fourth composition according to the third mode of the present invention can be preferably used for treating an inflammatory disease such as atopic dermatitis and psoriasis vulgaris. In addition, the fourth composition according to the third mode of the present invention can suppress inflammation in a preferable manner in epidermal keratinocytes present in skin. Accordingly, the fourth composition according to the third mode of the present invention can be said to be, for example, a composition for suppressing inflammation in epidermal keratinocytes.

<Anti-Inflammatory Agent>

The anti-inflammatory agent according to the third mode of the present invention contains a cyclic peroxide or a salt thereof. The agent for inducing expression of an anti-oxidative stress response gene according to the third mode of the present invention is characterized by containing a cyclic peroxide or a salt thereof, and other configurations and conditions are not limited. As described above, the cyclic peroxide suppresses production of the anti-inflammatory cytokine IL-1α. Accordingly, when being applied to skin, for example, the anti-inflammatory agent according to the third mode of the present invention can give an anti-inflammatory effect to the skin.

The amount of the anti-inflammatory component contained in the anti-inflammatory agent according to the third mode of the present invention can be any amount that allows suppression of inflammation, and is, for example, 0.001 to 10 w/v %, 0.05 to 5 w/v %, or 0.01 to 1 w/v %. The amount of the cyclic peroxide contained in the anti-inflammatory agent according to the third mode of the present invention can be any amount that allows suppression of inflammation, and is, for example, 0.001 to 10 w/v %, 0.05 to 5 w/v %, or 0.01 to 1 w/v %.

The cyclic peroxide in the anti-inflammatory agent according to the third mode of the present invention may be a compound represented by a chemical formula (I) below, or the cyclic peroxide contained in the oxidation reaction product described above, wherein the oxidation reaction product is obtained through oxidation of an alcohol:

[Chemical Formula I]

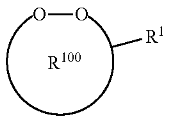

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The anti-inflammatory agent according to the third mode of the present invention suppresses, for example, expression and/or production of the proinflammatory cytokine. Examples of the proinflammatory cytokine include IL-1α. Accordingly, the anti-inflammatory agent according to the third mode of the present invention can be said to be, for example, an agent for suppressing expression of an IL-1α gene and/or an agent for suppressing production of IL-1α. In addition, the anti-inflammatory agent according to the third mode of the present invention suppresses production of a chemical mediator that evokes inflammation. Examples of the chemical mediator include prostaglandin E2. Accordingly, the anti-inflammatory agent according to the third mode of the present invention can be said to be, for example, an agent for suppressing production of prostaglandin E2.

The description of the first composition according to the third mode of the present invention can be referred to for description of the cyclic peroxide and the oxidation reaction product.

The descriptions of the first composition and fourth composition according to the third mode of the present invention can be referred to for description of dosage forms and applications of the anti-inflammatory agent according to the third mode of the present invention.

<Method for Inducing Expression of Skin Barrier Function-Related Gene>

The method for inducing expression of a skin barrier function-related gene according to the third mode of the present invention (hereinafter, referred to as "the first inducing method") uses the composition for inducing expression of a skin barrier function-related gene according to the third mode of the present invention and/or the agent for inducing expression of a skin barrier function-related gene according to the third mode of the present invention. The first inducing method according to the third mode of the present invention is characterized by the use of the first composition according to the third mode of the present invention and/or the first inducing agent according to the third mode of the present invention, and other steps and conditions are not limited. The cyclic peroxide contained in the first composition and/or first inducing agent according to the third mode of the present invention induces expression of a protein important for skin barrier functions such as a pro-filaggrin gene, which is a skin barrier function-related gene. Accordingly, when being applied to skin, for example, the first inducing method according to the third mode of the present invention can give an effect to induce expression of a skin barrier function-related gene to the skin.

The first inducing method according to the third mode of the present invention can be performed, for example, by using the first composition and/or the first inducing agent for the skin of a subject. More specifically, the first inducing method according to the third mode of the present invention can be performed by bringing the first composition and/or the first inducing agent into contact with the skin of a subject.

The first inducing method according to the third mode of the present invention is performed, for example, in vitro or in vivo.

<Method for Improving Skin Barrier Function>

The method for improving a skin barrier function according to the third mode of the present invention (hereinafter, referred to as "the improving method") uses the composition for improving a skin barrier function according to the third mode of the present invention and/or the agent for improving a skin barrier function according to the third mode of the present invention. The improving method according to the third mode of the present invention is characterized by the use of the second composition according to the third mode of the present invention and/or the improving agent according to the third mode of the present invention, and other steps and conditions are not limited. The cyclic peroxide contained in the second composition and/or improving agent according to the third mode of the present invention induces expression of a protein important for skin barrier functions such as a pro-filaggrin gene, which is a skin barrier function-related gene. Accordingly, when being applied to skin, for example, the improving method according to the third mode of the present invention can give an effect to induce expression of a skin barrier function-related gene to the skin, thereby improving the barrier function of the skin.

The improving method according to the third mode of the present invention can be performed, for example, by using the second composition and/or the improving agent for the skin of a subject. More specifically, the improving method according to the third mode of the present invention can be performed by bringing the second composition and/or the improving agent into contact with the skin of a subject.

The improving method according to the third mode of the present invention is performed, for example, in vino or in vivo.

<Method for Inducing Expression of Anti-Oxidative Stress Response Gene>

The method for inducing expression of an anti-oxidative stress response gene according to the third mode of the present invention (hereinafter, referred to as "the second inducing method") uses the composition for inducing expression of an anti-oxidative stress response gene according to the third mode of the present invention and/or the agent for inducing expression of an anti-oxidative stress response gene according to the third mode of the present invention. The second inducing method according to the third mode of the present invention is characterized by the use of the third composition according to the third mode of the present invention and/or the third inducing agent according to the third mode of the present invention, and other steps and conditions are not limited. The cyclic peroxide contained in the third composition and/or third inducing agent according to the third mode of the present invention induces expression of a protein important for anti-oxidative stress response such as a heme oxygenase-1 gene and an NAD(P)H quinone oxidoreductase-1 gene, each of which is an anti-oxidative stress response gene. Accordingly, when being applied to skin, for example, the second inducing method according to the third mode of the present invention can give an effect to induce expression of an anti-oxidative stress response gene to the skin, thereby improving the anti-oxidative stress response.

The second inducing method according to the third mode of the present invention can be performed, for example, by using the third composition and/or the third inducing agent for the skin of a subject. More specifically, the second inducing method according to the third mode of the present invention can be performed by bringing the third composition and/or the third inducing agent into contact with the skin of a subject.

The second inducing method according to the third mode of the present invention can be performed, for example, in vitro or in vivo.

<Method for Suppressing Inflammation>

The method for suppressing inflammation according to the third mode of the present invention (hereinafter, referred to as "the suppressing method") uses the fourth composition according to the third mode of the present invention and/or the anti-inflammatory agent according to the third mode of the present invention. The suppressing method according to the third mode of the present invention is characterized by the use of the fourth composition according to the third mode of the present invention and/or the anti-inflammatory agent according to the third mode of the present invention, and other steps and conditions are not limited. The cyclic peroxide contained in the fourth composition and/or anti-inflammatory agent according to the third mode of the present invention suppresses production of the anti-inflammatory cytokine IL-1α and expression of prostaglandin E2. Accordingly, when being applied to skin, for example, the suppressing method according to the third mode of the present invention can give an anti-inflammatory effect to the skin.

The suppressing method according to the third mode of the present invention allows, for example expression and/or production of the proinflammatory cytokine to be suppressed. Examples of the proinflammatory cytokine include IL-1α. Accordingly, the suppressing method according to the third mode of the present invention can be said to be, for example, a method for suppressing expression of an IL-1α gene and/or a method for suppressing production of IL-1α. In addition, the suppressing method according to the third mode of the present invention allows, for example, production of a chemical mediator that evokes inflammation to be suppressed. Examples of the chemical mediator include prostaglandin E2. Accordingly, the suppressing method according to the third mode of the present invention can be said to be, for example, a method for suppressing production of prostaglandin E2.

The suppressing method according to the third mode of the present invention can be performed, for example, by using the fourth composition and/or the anti-inflammatory agent for the skin of a subject. More specifically, the suppressing method according to the third mode of the present invention can be performed by bringing the fourth composition and/or the anti-inflammatory agent into contact with the skin of a subject.

The suppressing method according to the third mode of the present invention is performed, for example, in vitro or in vivo.

<Method for Treating Inflammatory Disease>

The method for treating an inflammatory disease according to the third mode of the present invention (hereinafter, referred to as "the treating method") includes an administration step of administering the anti-inflammatory composition according to the third mode of the present invention and/or the anti-inflammatory agent according to the third mode of the present invention to a subject. The treating method according to the third mode of the present invention is characterized by the administration of the fourth composition according to the third mode of the present invention and/or the anti-inflammatory agent according to the third mode of the present invention (hereinafter, also referred to as "the medicament", collectively), and other steps and conditions are not limited. The treating method according to the third mode of the present invention allows inflammation to be suppressed because the medicament is used. Accordingly, the treating method according to the third mode of the present invention allows an inflammatory disease to be treated.

The treating method according to the third mode of the present invention includes an administration step of administering the medicament, specifically, includes an administration step of administering the medicament to a subject. The medicament may be administered in vitro, or administered in vivo. For a subject and conditions for the administration of the medicament, for example, the description of a subject and conditions for the administration of the first composition according to the third mode of the present invention can be referred to. The subject is, for example, a subject desired to be treated. As a specific example, the subject may be a patient affected by the inflammatory disease, or a patient predicted to be affected by the inflammatory disease, or a patient with uncertainty on whether to be affected by the inflammatory disease.

<Use>

The third mode of the present invention is the composition for inducing expression of a skin barrier function-related gene according to the third mode of the present invention and/or the agent for inducing expression of a skin barrier function-related gene according to the third mode of the present invention for use in inducing expression of a skin barrier function-related gene, or use thereof for inducing expression of a skin barrier function-related gene. The third mode of the present invention is the composition for improving a skin barrier function according to the third mode of the present invention and/or the agent for improving a skin barrier function according to the third mode of the present invention for use in improving a skin barrier function, or use thereof for improving a skin barrier function. The third mode of the present invention is the composition for inducing expression of an anti-oxidative stress response gene according to the third mode of the present invention and/or the agent for inducing expression of an anti-oxidative stress response gene according to the third mode of the present invention for use in inducing expression of an anti-oxidative stress response gene, or use thereof for inducing expression of an anti-oxidative stress response gene. The third mode of the present invention is the anti-inflammatory composition according to the third mode of the present invention and/or the anti-inflammatory agent according to the third mode of the present invention for use in suppressing inflammation, or use thereof for suppressing inflammation. The third mode of the present invention is the anti-inflammatory composition according to the third mode of the present invention and/or the anti-inflammatory agent according to the third mode of the present invention for use in treating an inflammatory disease, or use thereof for treating an inflammatory disease.

Fourth Mode for Carrying Out the Invention

Second, the fourth mode for carrying out the present invention will be described. However, the fourth mode of the present invention is not limited to the following description.

In the fourth mode of the present invention, if isomers such as tautomers or stereoisomers (examples: geometric isomers, conformers, and optical isomers) are present for a compound, any of the isomers can be used for the fourth mode of the present invention, unless otherwise specified. In the fourth mode of the present invention, if a substance can form a salt, the salt can also be used for the fourth mode of the present invention, unless otherwise specified. The salt may be an acid addition salt, or a base addition salt. Moreover, the acid to form the acid addition salt may be an inorganic acid or an organic acid, and the base to form the base addition salt may be an inorganic base or an organic base. Examples of the inorganic acid include, but are not limited to, sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluoric acid, chloric acid, bromic acid, iodic acid, perfluoric acid, perchloric acid, perbromic acid, and periodic acid. Examples of the organic acid include, but are not limited to, similarly, p-toluenesulfonic acid, methanesulfonic acid, oxalic acid, p-bromobenzenesulfonic acid, carbonic acid, succinic acid, citric acid, benzoic acid, and acetic acid. Examples of the inorganic base include, but are not limited to, ammonium hydroxide, alkali metal hydroxide, alkaline earth metal hydroxide, carbonate, and hydrogen carbonate, and more specific examples thereof include sodium hydroxide, potassium hydroxide, potassium carbonate, sodium carbonate, sodium hydrogen carbonate, potassium hydrogen carbonate, calcium hydroxide, and calcium carbonate. Examples of the organic base include, but are not limited to, similarly, ethanolamine, triethylamine, and tris(hydroxymethyl)aminomethane. Production of those salts is not limited to a particular method, and, for example, such a salt can be produced in such a manner that an acid or base as shown above is appropriately allowed to add to the compound with a known method.

Examples of the aromatic ring having no heteroatom in the fourth mode of the present invention include a benzene ring, a naphthalene ring, an anthracene ring, a phenanthrene ring, and a pyrene ring. Examples of the heteroaromatic ring include a pyridine ring and a thiophene ring. The nitrogen-containing aromatic ring may be free of a positive charge, or have a positive charge. Examples of the nitrogen-containing aromatic ring being free of a positive charge include a pyrroline ring, a pyridine ring, a pyridazine ring, a pyrimidine ring, a pyrazine ring, a quinoline ring, an isoquinoline ring, an acridine ring, a 3,4-benzoquinoline ring, a 5,6-benzoquinoline ring, a 6,7-benzoquinoline ring, a 7,8-benzoquinoline ring, a 3,4-benzoisoquinoline ring, a 5,6-benzoisoquinoline ring, a 6,7-benzoisoquinoline ring, and a 7,8-benzoisoquinoline ring. Examples of the nitrogen-containing aromatic ring having a positive charge include a pyrrolinium ring, a pyridinium ring, a pyridazinium ring, a pyrimidinium ring, a pyrazinium ring, a quinolinium ring, an isoquinolinium ring, an acridinium ring, a 3,4-benzoquinolinium ring, a 5,6-benzoquinolinium ring, a 6,7-benzoquinolinium ring, a 7,8-benzoquinolinium ring, a 3,4-benzoisoquinolinium ring, a 5,6-benzoisoquinolinium ring, a 6,7-benzoisoquinolinium ring, and a 7,8-benzoisoquinolinium ring. Examples of the oxygen-containing aromatic ring or sulfur-containing aromatic ring include an aromatic ring formed by replacing at least one carbon atom or nitrogen atom in the aromatic ring containing no heteroatom or the nitrogen-containing aromatic ring with at least one of an oxygen atom and a sulfur atom.

Examples of the "substituent" in the fourth mode of the present invention include a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), and an alkylthio group (—SR, wherein R is an alkyl group).

In the fourth mode of the present invention, each chain substituent (e.g., an alkyl group and a hydrocarbon group such as an unsaturated aliphatic hydrocarbon group) may be linear or branched, unless otherwise specified, and the number of carbon atoms is not limited and may be, for example, 1 to 40, 1 to 32, 1 to 24, 1 to 18, 1 to 12, one to six, or one or two (two or more for an unsaturated hydrocarbon group). Herein, the number of ring members (the number of atoms constituting a ring) of each cyclic group (e.g., an aryl group, a heteroaryl group) is not limited and may be, for example, 5 to 32, 5 to 24, 6 to 18, 6 to 12, or 6 to 10. If isomers are present for a substituent or the like, the substituent or the like may be any of the isomers; when a substituent or the like is simply referred to as a "butyl group", for example, the substituent or the like may be a n-butyl group, or a sec-butyl group, or a tert-butyl group; when a substituent or the like is simply referred to as a "naphthyl group", the substituent or the like may be a 1-naphthyl group or a 2-naphthyl group.

In the fourth mode of the present invention, the term "protein" or "polypeptide" refers to a polymer composed of unmodified amino acids (natural amino acids), modified amino acids, and/or artificial amino acids. The polypeptide is, for example, a peptide having a length of 10 or more amino acids.

In the fourth mode of the present invention, the term "glycation" means that a protein, a polypeptide, and/or an amino acid is modified with a sugar. Examples of the sugar include a reducing sugar such as glucose, fructose, and lactose.

In the fourth mode of the present invention, the term "glycation reaction" refers to condensation reaction between an amino group-containing compound and a carbonyl group-containing compound (aminocarbonylation reaction). Examples of the amino group-containing compound include a protein, a polypeptide, or an amino acid. Examples of the carbonyl group-containing compound include a reducing sugar. The glycation reaction can be referred to as, for example, Maillard reaction.

In the fourth mode of the present invention, the term "glycation reaction product" refers to a substance generated through glycation reaction. Examples of the glycation reaction product include an intermediate product and end product that are generated in the glycation reaction. Examples of the glycation reaction product include a protein or polypeptide with any of the AGEs; a protein or polypeptide having a crosslinking structure formed by any of the AGEs; and a glycated protein generated through glycation reaction. Examples of the intermediate reaction product include a substance in the course of glycation reaction, and specific examples thereof include glyoxal, methylglyoxal, and 3-deoxyglucosone. The AGEs include pentosidine, crossline, pyrropyridine, pyraline, carboxymethyllysine (CML), carboxyethyllysine (CEL), carboxyethyllysine, carboxymethylarginine (CMA), argpyrimidine, imidazolone compounds, glyoxal-lysine dimer (GOLD), and methylglyoxal-lysine dimer (MOLD).

The fourth mode of the present invention will be more specifically described with examples below. However, the fourth mode of the present invention is not limited to the description given below. Description of one part of the fourth mode of the present invention can be referred to for description of another part and vice versa, unless otherwise stated. Herein, use of the expression "A to B" is intended to include the numerical values or physical values before and after "to". Herein, the expression "A and/or B" encompasses "only A", "only B", and "both A and B".

<Anti-Glycation Composition>

The anti-glycation composition according to the fourth mode of the present invention contains glycerin and/or a glycerin derivative, and an anti-glycation component, wherein the anti-glycation component contains a cyclic peroxide or a salt thereof as an active ingredient. The composition according to the fourth mode of the present invention is characterized by containing the cyclic peroxide or a salt thereof, and other configurations and conditions are not limited. As described later, the cyclic peroxide has decomposing ability to crosslinking structures formed by AGEs. Accordingly, the composition according to the fourth mode of the present invention can give an anti-glycation effect.

Being capable of decomposing AGEs generated through glycation reaction, the composition according to the fourth mode of the present invention can be said to be, for example, a decomposer composition for advanced glycation end products (AGEs), a decomposer composition for a glycation reaction product, or a decomposer composition for a protein or polypeptide with a crosslinking structure formed by an advanced glycation end product. Being capable of repairing a protein or polypeptide, for example, by removing AGEs or a crosslinking structure formed by an AGE in a glycated protein, the composition according to the fourth mode of the present invention can be said to be a repairer composition for a glycated protein or glycated peptide.

[1. Anti-Glycation Component]

As described above, the composition according to the fourth mode of the present invention contains an anti-glycation component. The composition according to the fourth mode of the present invention may contain, as an active ingredient of the anti-glycation component, the cyclic peroxide, or an oxidation reaction product containing the cyclic peroxide as described later, or both of them. The cyclic peroxide may be a compound represented by a chemical formula (I) below, or a cyclic peroxide contained in an oxidation reaction product described later, wherein the oxidation reaction product is obtained through oxidation of an alcohol.

The amount of the anti-glycation component contained in the composition according to the fourth mode of the present invention can be any effective amount that allows anti-glycation, more specifically, any effective amount that allows AGEs to be decomposed, and is, for example, 0.001 to 10 w/v %, 0.05 to 5 w/v %, or 0.01 to 1 w/v %. The amount of the cyclic peroxide contained in the composition according to the fourth mode of the present invention can be any effective amount that allows anti-glycation, and is, for example, 0.001 to 10 w/v %, 0.05 to 5 w/v %, or 0.01 to 1 w/v %.

The anti-glycation component may exhibit anti-glycation activity by suppressing the glycation reaction to inhibit the generation of AGEs or the generation of crosslinking structures by AGEs, or exhibit anti-glycation activity by decomposing AGEs generated through the glycation reaction or crosslinking structures formed by AGEs, or exhibit both the activities.

[2. Cyclic Peroxide]

The cyclic peroxide is represented by the following chemical formula (I):

[Chemical Formula I]

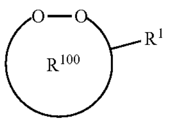

(I)

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The heteroatom is an atom other than carbon and hydrogen, and may be, for example, one selected from the group consisting of an oxygen atom, a nitrogen atom, a sulfur atom, a selenium atom, a boron atom, and a silicon atom. The substituent is not limited and may contain, for example, a hydroxy group, and may be, for example, one selected from the group consisting of a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), and an alkylthio group (—SR, wherein R is an alkyl group) shown above.

In the cyclic peroxide, for example, $R^{100}$ in the chemical formula (I) may be a cyclic structure having 5 to 10 ring members.

The cyclic peroxide may be, for example, a cyclic peroxide represented by the following chemical formula (II):

[Chemical Formula II]

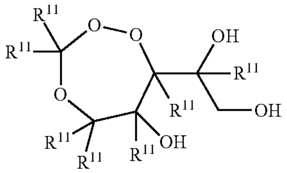

(II)

wherein the $R^{11}$ groups are the same or different, each being a hydrogen atom or a substituent, and two $R^{11}$ groups bound to the same carbon atom optionally together form an oxo group (═O) or a thioxo group (═S).

In the cyclic peroxide, the substituent for each of the $R^{11}$ groups in the chemical formula (II) may be, for example, a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

The cyclic peroxide may be, for example, a cyclic peroxide represented by a chemical formula (1) below. The cyclic peroxide represented by the following chemical formula (1) corresponds to the case that the $R^{11}$ groups in the chemical formula (II) are each a hydrogen atom:

[Chemical Formula 1]

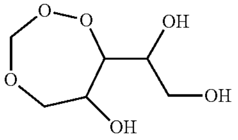

(1)

The method for producing the cyclic peroxide is not limited to a particular method, and, for example, the cyclic peroxide can be produced by oxidizing an alcohol with a method described later for producing an oxidation reaction product. In this case, for example, an oxidation reaction product produced may be directly used without purification; alternatively, only the cyclic peroxide may be isolated and purified for use.

The phenomenon that a cyclic peroxide is obtained through oxidation of an alcohol, for example, through ozone oxidation of glycerin was discovered for the first time by the present inventors. Although the mechanism that gives a cyclic peroxide is unclear, for example, longer reaction time in oxidation reaction of an alcohol is expected to give a reaction product differing from those from conventional reactions, as described later.

The cyclic peroxide can be isolated and, for example, formulated because the cyclic peroxide is more chemically stable and allows easier handling than radicals and the like.

Generally speaking, cyclic peroxides are substances industrially used, for example, for their oxidative capacity. In particular, artemisinin, which has the same seven-membered ring (trioxolane) backbone as the cyclic peroxide, led to the winning of Nobel prize in 2015 for the usefulness against malaria, and derivatives of artemisinin have been still under research.

However, supply of artemisinin, which is extracted and purified from natural products, is unstable. In addition, artemisinin is neither water-soluble nor liposoluble, and hence causes many problems in formulation. Hydrogen peroxide, an example of water-soluble substances with high oxidation power, is highly reactive and unstable, and the usage thereof for living bodies is only limited to topical agents for disinfection.

On the other hand, the fourth mode of the present invention uses, for example, a cyclic peroxide and oxidation reaction product that are highly safe and superior in water solubility, and hence is preferably applicable to living bodies. The fourth mode of the present invention is inferred to show anti-glycation action through the oxidative capacity of the cyclic peroxide. The anti-glycation action can be evaluated according to Example 4 shown later.

In the composition according to the fourth mode of the present invention, the cyclic peroxide may be in the form of a salt or a solvate such as a hydrate. The description of the cyclic peroxide can be referred to for description of the salt of the cyclic peroxide or a solvate of any of them.

[3. Oxidation Reaction Product]

The oxidation reaction product is an oxidation reaction product characterized by containing a cyclic peroxide, wherein the oxidation reaction product is obtained through oxidation of an alcohol, as described above. However, the method for producing the oxidation reaction product may be performed with any method without limitation to oxidation of an alcohol, and any substance produced with any production method may be employed as long as the substance has the same structure.

The oxidation of an alcohol is not limited to a particular method. For example, the oxidation of an alcohol may be at least one of ozone oxidation and hydrogen peroxide oxidation. However, as described above, the method for producing the oxidation reaction product may be performed with any method without limitation to ozone oxidation and hydrogen peroxide oxidation of an alcohol, and any substance produced with any production method may be employed as long as the substance has the same structure.

The oxidation reaction product may be, for example, a mixture containing a plurality of oxidation reaction products.

The oxidation reaction product may have, for example, oxidative capacity.

The oxidation reaction product may have, for example, reductive capacity.

The alcohol to be used as a raw material of the oxidation reaction product is not limited. The alcohol for the oxidation reaction product may be, for example, a saturated alcohol.

The alcohol for the oxidation reaction product may be, for example, a polyhydric alcohol.

The alcohol for the oxidation reaction product may be, for example, at least one of glycerin and a glycerin derivative.

The oxidation reaction product may contain, for example, an oxidation reaction product formed by binding of two or more molecules of the alcohol.

The oxidation reaction product may contain, for example, the cyclic peroxide.

The alcohol to be used as a raw material of the oxidation reaction product is not limited, and may be, for example, a saturated alcohol as described above, or an unsaturated alcohol. The alcohol may be liner or branched, and may contain a cyclic structure or not. The alcohol may be, for example, a polyhydric alcohol or a monohydric alcohol. The number of hydroxy groups of the polyhydric alcohol is not limited, and the polyhydric alcohol may be, for example, dihydric, trihydric, or tetrahydric. Examples of the monohydric saturated alcohol include a saturated alcohol having 1 to 40, 1 to 32, 1 to 24, 1 to 18, 1 to 12, one to six, or one or two carbon atoms, the saturated alcohol may be linear or branched, and may contain a cyclic structure or not, and specific examples thereof include methanol, ethanol, n-propyl alcohol, isopropyl alcohol, n-butyl alcohol, sec-butyl alcohol, and tert-butyl alcohol. Examples of the saturated polyhydric alcohol include a saturated polyhydric alcohol having 1 to 40, 1 to 32, 1 to 24, 1 to 18, 1 to 12, one to six, or one or two carbon atoms, the saturated polyhydric alcohol may be linear or branched, and may contain a cyclic structure or not, and specific examples thereof include ethylene glycol (ethane-1,2-diol), propylene glycol (propane-1,2-diol), glycerin, and a glycerin derivative. The glycerin derivative is not limited, and may be, for example, a polymer of glycerin or a compound formed by substituting at least one of the hydrogen atoms of glycerin with a substituent (e.g., an alkyl group). Examples of the glycerin derivative include diglycerin and polyglycerin. The glycerin derivative may be an oxidized form of glycerin.

The oxidation reaction product may be, for example, a substance having reductive capacity, as described above. For example, the oxidation reaction product may have reductive capacity through inclusion of a functional group, wherein the reductive capacity is derived from the functional group, which has reductive capacity. Specifically, for example, the oxidation reaction product may have reductive capacity through inclusion of an aldehyde group (formyl group), or have reductive capacity derived from the keto form because of the keto-enol tautomerism. For example, the oxidation reaction product that has been obtained in Example 4 shown later contains an acetal structure as the backbone, as confirmed by NMR, hence being inferred to color through DNPH (dinitrophenylhydrazine: derived from ketone and aldehyde) reaction derived from ketone and aldehyde.

The oxidation reaction product may be, for example, a substance formed by binding of two or more molecules of the alcohol, as described above. Specifically, for example, a structure formed by binding of two or more molecules of the alcohol and oxidizing the resultant is acceptable. The mode of “binding” of two or more molecules of the alcohol is not limited, and may be, for example, addition or condensation.

The oxidation reaction product can be isolated and, for example, formulated because the oxidation reaction product is more chemically stable and allows easier handling than radicals and the like.

[4. Method for Producing Oxidation Reaction Product]

The method for producing an oxidation reaction product is, as described above, a method for producing the oxidation reaction product, the method including an alcohol oxidation step of oxidizing the alcohol.

The oxidation of the alcohol in the alcohol oxidation step is not limited to a particular method. In the method for producing an oxidation reaction product, for example, the alcohol may be oxidized through at least one of ozone oxidation and hydrogen peroxide oxidation in the alcohol oxidation step.

In the method for producing an oxidation reaction product, the reaction time in the alcohol oxidation step is not limited. The reaction time in the alcohol oxidation step may be, for example, 24 hours or more or 1 day or more, 48 hours or more or 2 days or more, 72 hours or more or 3 days or more, 120 hours or more or 5 days or more, or 168 hours or more or 7 days or more. The upper limit value of the reaction time in the alcohol oxidation step is not limited, and the reaction time may be, for example, 720 hours or less or 30 days or less, or 360 hours or less or 15 days or less.

In order to obtain a reaction product containing the cyclic peroxide in the method for producing an oxidation reaction product, it is preferable to employ longer reaction time for the alcohol oxidation step. For example, longer reaction time in the alcohol oxidation step is inferred to allow production of the cyclic peroxide, which cannot be obtained through conventional ozone oxidation reaction or the like of glycerin. For production efficiency in the method for producing an oxidation reaction product, it is preferable to avoid excessively long reaction time for the alcohol oxidation step.

The method for producing an oxidation reaction product includes an alcohol oxidation step of oxidizing the alcohol, as described above. However, the oxidation reaction product is not limited to substances produced with the production method, as described above, and any substance produced with any production method may be employed as long as the substance has the same structure. The method for producing an oxidation reaction product will be more specifically described with reference to examples below.

The case that ozone oxidation is performed with use of glycerin as the alcohol will be described as an example below. However, the description below is an example as mentioned, and the method for producing an oxidation reaction product is not limited to the description below. For example, the method below can be performed in the same manner even with use of another alcohol in place of glycerin. For example, the oxidation of the alcohol in the alcohol oxidation step of the method for producing an oxidation reaction product is not limited to a particular method, and any oxidizing method is available, without limitation only to ozone oxidation. The oxidizing method may be, for example, at least one of ozone oxidation and hydrogen peroxide oxidation. Not only the type of the alcohol and the method for oxidizing the alcohol, for example, but also the concentrations of substances, reaction temperature, reaction time, and other reaction conditions can be appropriately changed.

The oxidation reaction product can be produced with a production method including a step of oxidizing glycerin, for example, by bringing glycerin into contact with ozone, more specifically, mixing glycerin and ozone (corresponding to the "alcohol oxidation step"). The step of oxidizing glycerin may be, for example, a step of oxidizing glycerin by bringing a glycerin solution and a gas containing ozone into gas-liquid contact.

It is preferable for the glycerin solution to contain glycerin at high concentration. For the glycerin solution of high concentration, for example, a glycerin solution having a glycerin concentration of 75% or more can be used, and, as a specific example, a 84 to 87% by weight glycerin solution as a product in accordance with the Japanese Pharmacopeia is preferable, a concentrated glycerin solution having a glycerin concentration of 98% by weigh or more as a product in accordance with the Japanese Pharmacopeia is more preferable, and a purified glycerin solution having a concentration of 98.5% by weight or more is even more preferable. If having a relatively higher glycerin concentration, the glycerin solution can be treated with ozone at higher concentration. The solvent to glycerin in the glycerin solution is not limited, and is, for example, an aqueous solvent such as water.

It is preferable for the gas containing ozone to contain ozone at high concentration. Any method may be used for producing the gas of high ozone concentration without limitation, and, for example, an ozone generator that generates ozone by silent discharge in oxygen gas can be used. If oxygen gas is used, for example, an oxygen tank for medical use may be used, and oxygen gas produced by an oxygen generator may be used.

Any method may be used for bringing the glycerin solution and the gas containing ozone into gas-liquid contact without limitation, and an example is a method in which a tank is charged with a glycerin solution of high concentration (e.g., 98% by weight or more) and the gas of high ozone concentration is released as fine bubbles into the tank with use of an air diffuser. Specifically, for example, an ozone-treated glycerin solution having a concentration of approximately 4000 ppm in terms of hydrogen peroxide concentration can be produced by aerating the concentrated glycerin solution with a gas having an ozone concentration of approximately 37000 ppm for approximately 7 days. The aeration time is not limited, and, for example, an ozone-treated glycerin solution containing the oxidation reaction product at higher concentration can be produced by aerating for a relatively long time.

The oxidation reaction product may be directly used without separating from a mixture after the reaction (e.g., the ozone-treated glycerin solution), or used after separating the oxidation reaction product from the mixture after the reaction. The separation is not limited to a particular method, and, for example, the oxidation reaction product can be separated from the mixture after the reaction through chromatography such as preparative thin-layer chromatography.

Conventional production of a substance having oxidation power such as peroxide needs a pathway including complex systems. The method for producing an oxidation reaction product allows, for example, an oxidation reaction product having oxidation power to be produced in a very simple and easy manner.

The oxidation reaction product is capable of generating, for example, hydrogen peroxide. For example, the oxidation reaction product can generate 1 to 4000 ppm, 10 to 4000 ppm, or 100 to 4000 ppm of hydrogen peroxide per approximately 4000 ppm of the oxidation reaction product in terms of hydrogen peroxide concentration.

[5. Glycerin]

In the composition according to the fourth mode of the present invention, the glycerin may be glycerin or a glycerin derivative described above. The composition according to the fourth mode of the present invention can stably retain the cyclic peroxide by allowing the cyclic peroxide to coexist with the glycerin.

The amount of the glycerin contained in the composition according to the fourth mode of the present invention is, for example, 0.1 to 100 w/v %, and preferably 0.1 to 50 w/v %.

[6. Additional Component]

The composition according to the fourth mode of the present invention may contain an additional component that is added to dosage forms for application to skin. Specific examples of the additional component include a component that is added to topical agents for skin, and a component that is added to cosmetics (including quasi drugs). Examples of the component that is added to topical agents for skin include pharmaceutically acceptable carriers. Another example of the additional component is a component that is added in application to skin or in transdermal application, and specific examples thereof include aqueous solvents such as water, alcohols, moisturizers, oils, softeners (emollients), surfactants (solubilizers, emulsifying agents), salts, thickeners, pH adjusters, ultraviolet absorbers, drugs, buffers, coloring agents, preservatives, and fragrances.

[7. Dosage Form, Usage, and Applications]

The composition according to the fourth mode of the present invention is, for example, solid or liquid. Examples of the form of the composition according to the fourth mode of the present invention include a lotion dosage form, an emulsified dosage form such as an emulsion and a cream, an oil dosage form, a gel dosage form, an ointment, a pack, and a cleansing agent.

A subject for using the composition according to the fourth mode of the present invention is a human or a non-human animal. The composition according to the fourth mode of the present invention can be used, for example, skin of the subject. The amount of use of the composition according to the fourth mode of the present invention is not limited, and can be a typical amount of use for a dosage form to be employed for the composition according to the fourth mode of the present invention.

The composition according to the fourth mode of the present invention can be preferably used for applications of topical agents for skin such as cosmetics.

<Anti-Glycation Agent>

The anti-glycation agent according to the fourth mode of the present invention contains a cyclic peroxide or a salt thereof. The anti-glycation agent according to the fourth mode of the present invention is characterized by containing a cyclic peroxide or a salt thereof, and other configurations and conditions are not limited. As described later, the cyclic peroxide has decomposing ability to crosslinking structures formed by AGEs. Accordingly, the anti-glycation agent according to the fourth mode of the present invention can give an anti-glycation effect.

Being capable of decomposing AGEs generated through glycation reaction, the anti-glycation agent according to the fourth mode of the present invention can be said to be, for example, a decomposer for advanced glycation end products (AGEs), a decomposer for a glycation reaction product, or a decomposer for a protein or polypeptide with a crosslinking structure formed by an advanced glycation end product. Being capable of repairing a protein or polypeptide, for example, by removing AGEs or a crosslinking structure formed by an AGE in a glycated protein, the anti-glycation agent according to the fourth mode of the present invention can be said to be a repairer for a glycated protein or glycated peptide.

The amount of the anti-glycation component contained in the anti-glycation agent according to the fourth mode of the present invention can be any effective amount that allows anti-glycation, more specifically, any effective amount that allows AGEs to be decomposed, and is, for example, 0.001 to 10 w/v %, 0.05 to 5 w/v %, or 0.01 to 1 w/v %. The amount of the cyclic peroxide contained in the anti-glycation agent according to the fourth mode of the present invention can be any effective amount that allows anti-glycation, and is, for example, 0.001 to 10 w/v %, 0.05 to 5 w/v %, or 0.01 to 1 w/v %.

In the anti-glycation agent according to the fourth mode of the present invention, the cyclic peroxide may be a compound represented by a chemical formula (I) below, or the cyclic peroxide contained in the oxidation reaction product described above, wherein the oxidation reaction product is obtained through oxidation of an alcohol:

[Chemical Formula I]

(I)

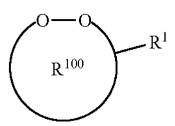

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

The description of the composition according to the fourth mode of the present invention can be referred to for description of the cyclic peroxide and the oxidation reaction product.

The description of the composition according to the fourth mode of the present invention can be referred to for description of dosage forms and applications of the anti-glycation agent according to the fourth mode of the present invention.

<Anti-Glycation Method>

The anti-glycation method according to the fourth mode of the present invention uses the anti-glycation composition according to the fourth mode of the present invention and/or the anti-glycation agent according to the fourth mode of the present invention. The anti-glycation method according to the fourth mode of the present invention is characterized by the use of the composition according to the fourth mode of the present invention and/or the anti-glycation agent according to the fourth mode of the present invention, and other steps and conditions are not limited. As described later, the cyclic peroxide contained in the composition and/or anti-glycation agent according to the fourth mode of the present invention has decomposing ability to crosslinking structures formed by AGEs. Accordingly, the anti-glycation method according to the fourth mode of the present invention can give an anti-glycation effect.

The anti-glycation method according to the fourth mode of the present invention can be performed, for example, by using the composition and/or the anti-glycation agent for the skin of a subject. More specifically, the anti-glycation method according to the fourth mode of the present invention can be performed by bringing the composition and/or the anti-glycation agent into contact with the skin of a subject.

The anti-glycation method according to the fourth mode of the present invention can be performed, for example, in vitro or in vivo.

<Use>

The fourth mode of the present invention is the anti-glycation composition according to the fourth mode of the present invention and/or the anti-glycation agent according to the fourth mode of the present invention for use in anti-glycation, or use thereof for anti-glycation.

EXAMPLES

Hereinafter, examples of the present invention will be described. However, the present invention is not limited to the following examples.

Example of First Mode

First, an example of the first mode of the present invention will be described. However, the first mode of the present invention is not limited to the example below. Commercially available reagents were used in accordance with their protocols, unless otherwise specified.

Example 1

An oxidation reaction product containing the cyclic peroxide according to the first mode of the present invention was produced through ozone oxidation of glycerin. Then, the oxidative capacity of and TRP channel activation by the oxidation reaction product produced were examined. The present example corresponds to an example of production and use of the cyclic peroxide according to the first mode of the present invention, and to an example of production and use of the oxidation reaction product according to the first mode of the present invention, and further to an example of the method for producing an oxidation reaction product according to the first mode of the present invention.

(1) Production of Oxidation Reaction Product Containing Cyclic Peroxide According to the First Mode of the Present Invention Concentrated glycerin and ozone were brought into gas-liquid contact, and an ozone-treated glycerin solution containing the oxidation reaction product according to the first mode of the present invention (ozone gel) was produced in a manner shown below. Here, the concentrated glycerin was a product containing glycerin at a concentration of 98% by weight or more in accordance with the Japanese Pharmacopeia. The oxidation reaction product according to the first mode of the present invention, an oxidation reaction product produced in the present example, contained the cyclic peroxide according to first mode of the present invention, as described later.

A Teflon® tank having a capacity of 50 L was used as a contactor. An air diffuser was set on the bottom of the tank so that ozone could be fed as fine bubbles into the tank. A gas of high oxygen concentration, which contained oxygen at a concentration as high as 90% by volume or more, was used as a raw material, and a silent discharge ozone generator capable of generating 100 g of ozone per hour was used.

The tank was charged with 22 kg of the concentrated glycerin, the gas of high oxygen concentration was sent to the ozone generator at 20 L per minute to generate a gas containing ozone, and the gas generated was released into the tank via the air diffuser for 7 days or more to give a glycerin solution dissolving an ozone-oxidized form of glycerin therein at a final concentration of 4000 ppm. The ozone-oxidized form of glycerin corresponds to the oxidation reaction product according to the first mode of the present invention. As described later, the cyclic peroxide according to the first mode of the present invention was contained in that ozone-oxidized form.

(2) Analysis of Reaction Mixture

Glycerin was removed from the glycerin solution dissolving the ozone-oxidized form of glycerin therein, which had been produced in "(1) Production of Oxidation Reaction Product Containing Cyclic Peroxide According to the First Mode of the Present Invention", by using a silica gel column, and thus a reaction mixture containing the cyclic peroxide according to the first mode of the present invention was obtained (hereinafter, occasionally referred to as "the TLC1 spot product"). As described later, the TLC1 spot product was directly used without separating the cyclic peroxide according to the first mode of the present invention from the TLC1 spot product to examine the oxidative capacity of and TRP channel activation by the cyclic peroxide according to the first mode of the present invention.

Figures 1, 2:
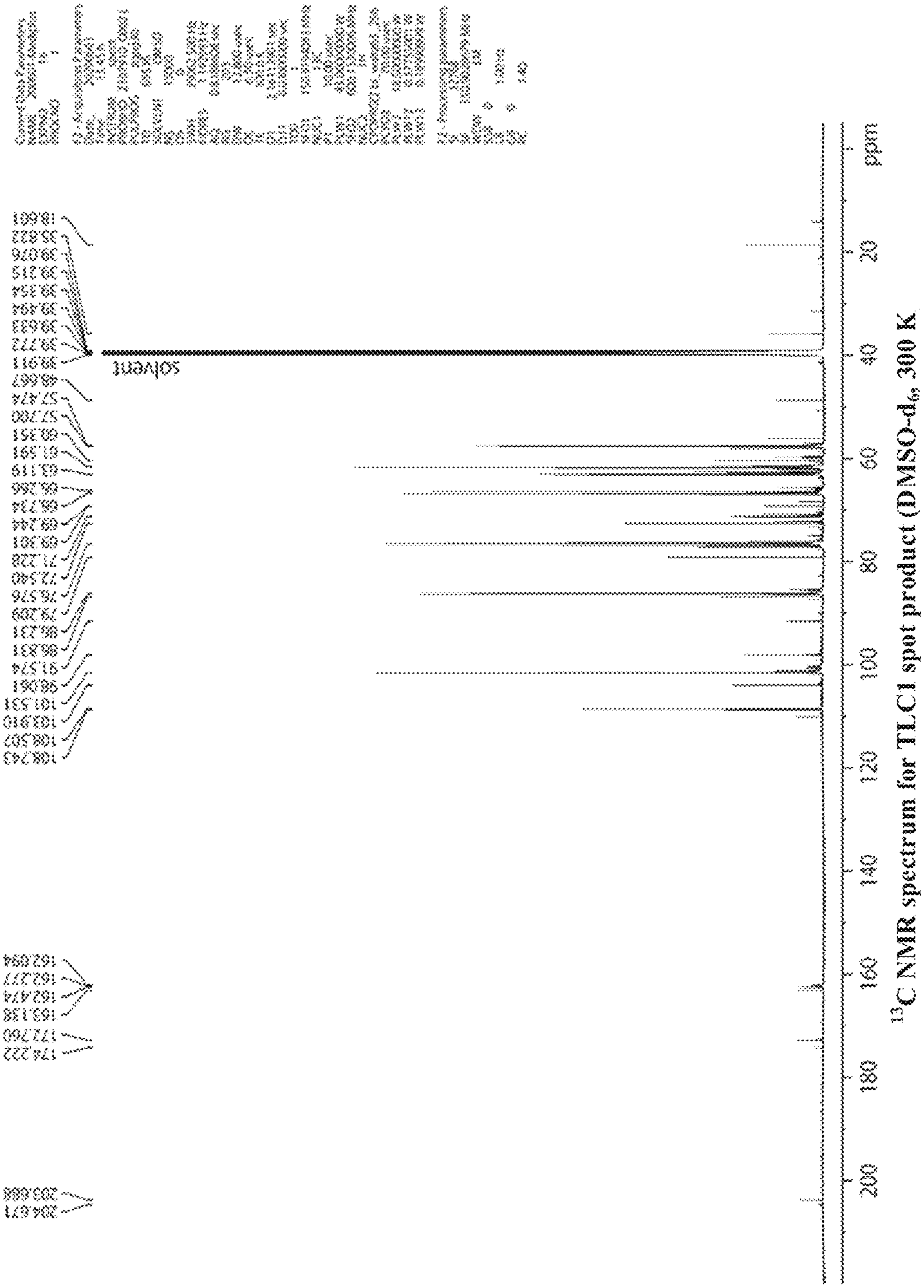
Figures 1, 2, 3:
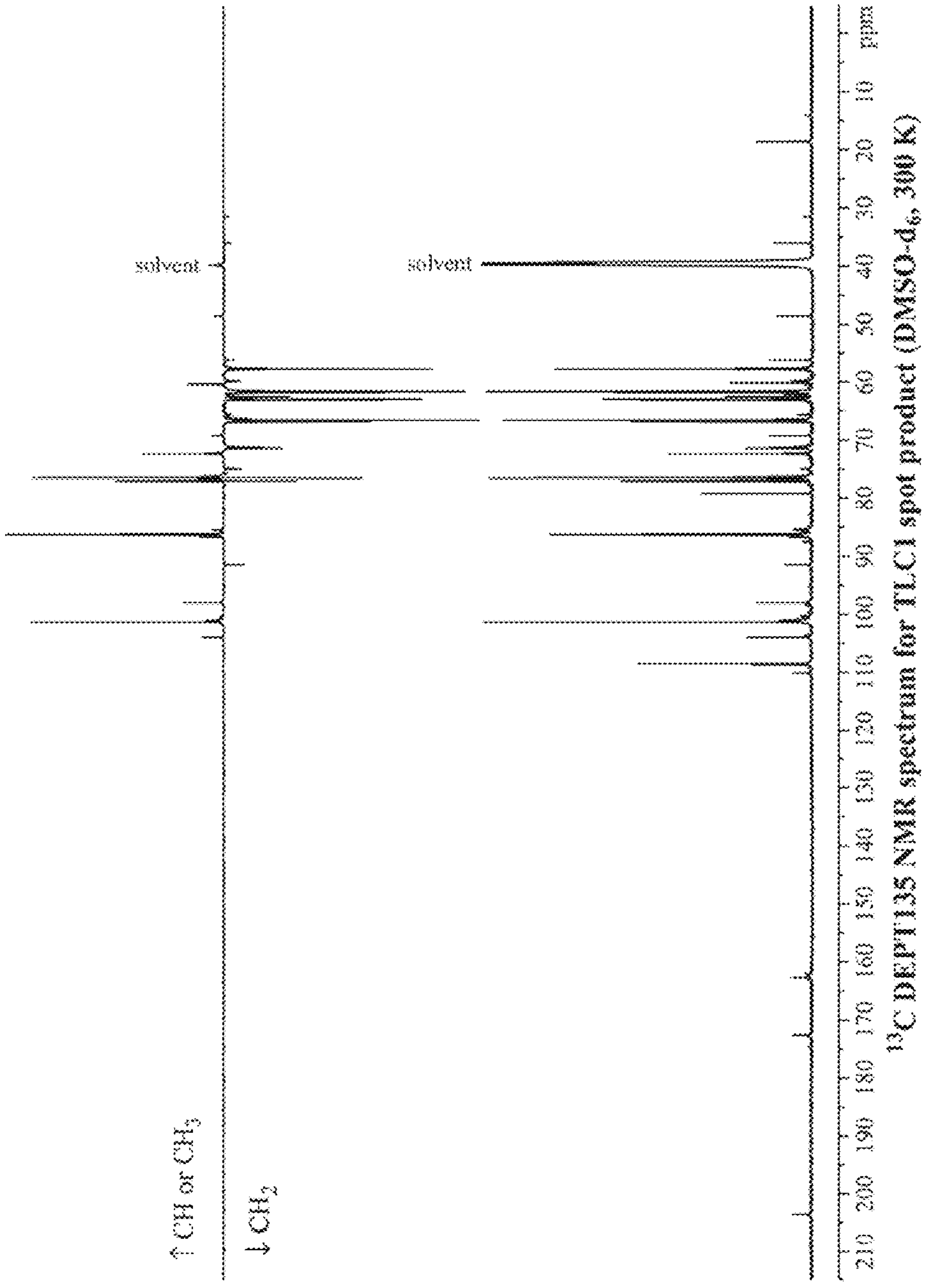

NMR spectra for the reaction mixture (TLC1 spot product) were determined with use of DMSO-$d_6$ as a solvent at a temperature of 300 K (27° C.). FIG. 1-1 to FIG. 1-6 show the spectrum diagrams. FIG. 1-1 is the $^1$H NMR spectrum diagram. FIG. 1-2 is the $^{13}$C NMR spectrum diagram. FIG. 1-3 is the $^{13}$C DEPT135 NMR spectrum diagram. FIG. 1-4 is the COSY NMR spectrum diagram. FIG. 1-5 is the HSQC NMR spectrum diagram. FIG. 1-6is the HMBC NMR spectrum diagram. Complex peaks were observed as shown in FIG. 1-1 to FIG. 1-6, and hence the TLC1 spot product was expected to be a mixture of a plurality of substances. LCMS found that the TLC1 spot product contained a component of m/z 198,203.

(3) Separation and Analysis of Reaction Mixture

The reaction mixture (TLC1 spot product) was adjusted (diluted) to approximately 3% by mass with acetonitrile, and filtered through a membrane filter, and the resulting filtrate was subjected to LC measurement for optimization of separation conditions. Subsequently, peaks found in LC measurement under the optimized conditions were checked for mass, and precise separation was performed for Mw=180 (peak 2). Thereafter, the resulting fractionated solution was freeze-dried, and the dried product of the fraction was subjected to microscopic LR measurement and various NMR measurements. The measurement apparatuses (analyzers) and measurement conditions were as follows.

[Measurement Apparatuses (Analyzers)]

1) Precise preparative LC: Waters, ACQUITY UPLC H-class Bio
2) Microscopic LR: SNOM/AFM/Raman multifunction apparatus, alpha300RSA manufactured by WITec
3) NMR: Bruker Biospin, AVANCE III-600 with Cryo Probe

[Measurement Conditions]

1) Precise Preparative LC

Column: Shodex Asahipak NH2P-50 (4.6 mmφ×250 mm, 5 μm)
Composition of eluent: water/acetonitrile gradient
Time (min): 0 5 15 20
Water: 5 10 50 50
Acetonitrile: 95 90 50 50
Flow rate: 1.0 mL/min
Detector: MS (QDa)
Column temperature: 40° C.
Injection volume: 50 μL
Ionization method: ESI (NEG.)
Mass range in measurement (m/z): 50 to 500

2) Microscopic LR

Excitation wavelength: 532 nm
Wavelength range in measurement: approximately 125 to 3800 $cm^{-1}$
Objective lens: ×100
Detector: EMCCD

3) NMR

Observation frequency: 600 MHz ($^1$H), 150 MHz ($^{13}$C)
Solvent for measurement: methanol-$d_4$
Measurement temperature: 300 K
Chemical shift standard: solvent for measurement [3.30 ppm ($^1$H), 49.80 ppm ($^{13}$C)]

FIG. 1-7 shows total ion chromatograms (ESI-negative mode) from the precise preparative LC (liquid chromatography) for the sample and a blank, the sample being obtained by adjusting (diluting) the reaction mixture (TLC1 spot product) to approximately 3% by mass with acetonitrile. In FIG. 1-7, the ordinate shows intensity and the abscissa shows retention time (minutes). In FIG. 1-7, "Synthesized OG" in the bottom shows a chromatogram for the sample of the TLC1 spot product, and the top shows a chromatogram for the blank (acetonitrile). As shown in the figure, components of A to L were found from the TLC1 spot product. These components A to L were separated and checked for the presence or absence of coloring with potassium iodide starch test paper, and the result showed that component H exhibited the strongest coloring.

FIG. 1-8 shows mass spectra for peaks F, G, and H (fraction F, fraction G, and fraction H) in FIG. 1-7 in combination. In FIG. 1-8, the ordinate shows intensity and the abscissa shows mass-charge ratios (m/z). As shown in the figure, it was found that peak F had Mw=180, peak G had Mw=226, and peak H had Mw=256.

Moreover, FIG. 1-9 shows results of examination on improvement of separation (improvement of separation conditions) in HILIC (high-performance liquid chromatography). In FIG. 1-9, the ordinate shows intensity and the abscissa shows retention time (minutes), and the same applies to FIG. 1-17 to FIG. 1-19. In FIG. 1-9, the top is a chromatogram before improvement of separation (under the same conditions as for FIG. 1-8), and the bottom is a chromatogram after improvement of separation. As shown in the figure, peaks 1 to 8 were found after improvement of separation. The molecular weights of the peaks were confirmed to be those as shown in FIG. 1-9 from mass spectra shown later.

FIG. 1-10 shows mass spectra for peaks 1 to 3 in FIG. 1-9 (after improvement of separation). In FIG. 1-10, the top, middle, and bottom are mass spectra for peak 1, peak 2, and peak 3, respectively. As shown in the figure, it was found that peak 1 had Mw=196, peak 2 had Mw=180, and peak 3 had Mw=240.

FIG. 1-11 shows mass spectra for peaks 4 to 6 in FIG. 1-9 (after improvement of separation). In FIG. 1-11, the top, middle, and bottom are mass spectra for peak 4, peak 5, and peak 6, respectively. As shown in the figure, it was found that peak 4 had Mw=240, peak 5 had Mw=240, and peak 6 had Mw=226.

FIG. 1-12 shows mass spectra for peaks 7 and 8 in FIG. 1-9 (after improvement of separation). In FIG. 1-12, the top and bottom are mass spectra for peak 7 and peak 8, respectively. As shown in the figure, it was found that peaks 7 and 8 both had Mw=256.

FIG. 1-13 shows micro-Raman spectrum diagrams for a separated sample obtained from peak 2 (Mw=180) in FIG. 1-9 and an ozonide authentic sample (ozonized oleic acid) in combination. In FIG. 1-13, the ordinate shows intensity and the abscissa shows Raman shifts (1/cm). As shown in FIG. 1-13, peak 2 (Mw=180) exhibited a micro-Raman spectrum similar to that for ozonide, and hence expected to have a structure similar to that of ozonide. The micro-Raman spectrum for peak 2 (Mw=180) exhibited a pattern differing from that for peroxide, and hence peak 2 (Mw=180) was expected not to correspond to peroxide. From NMR shown later, peak 2 (Mw=180) was found to correspond to the cyclic peroxide according to the first mode of the present invention.

FIG. 1-14 shows a $^{1}$H NMR spectrum diagram for peak 2 (Mw=180) in FIG. 1-9. Methanol-$d_4$ ($CD_3OD$) was used for the solvent for measurement. In the figure, the top spectrum diagram is an enlarged view of a part around 3.4 to 4.9 ppm in the bottom spectrum diagram. From the attribution of the $^{1}$H NMR, the result of Mw=180, and other instrumental analysis data, the structure of the oxidation reaction product for peak 2 (Mw=180) was demonstrated to be that of a cyclic peroxide represented by a chemical formula (1) below. The peaks indicated with signs A to F in the $^{1}$H NMR spectrum diagram in FIG. 1-14 were attributed to peaks for hydrogen atoms bound to the carbon atoms indicated with the same signs A to F in a chemical formula (1) below, which is shown in FIG. 1-14. It was expected that a slight amount of the raw material glycerin remained, and the peak was also detected.

[Chemical Formula 1M]

(1)

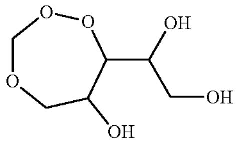

Molecular Weight: 180.16

FIG. 1-15 shows a $^{13}$C NMR spectrum diagram for peak 2 (Mw=180) in FIG. 1-9. Methanol-$d_4$ ($CD_3OD$) was used for the solvent for measurement. In the figure, the top spectrum diagram is an enlarged view of a part around 60 to 105 ppm in the bottom spectrum diagram. From the attribution of the $^{13}$C NMR, the result of Mw=180, and other instrumental analysis data, the structure of the oxidation reaction product for peak 2 (Mw=180) was demonstrated to be that of the cyclic peroxide represented by the chemical formula (1). The peaks indicated with signs A to F in the $^{13}$C NMR spectrum diagram in FIG. 1-15 were attributed to peaks for the carbon atoms indicated with the same signs A to F in a chemical formula (1) below, which is shown in FIG. 1-15. It was expected that a slight amount of the raw material glycerin remained, and the peak was also detected.

FIG. 1-16 shows a two-dimensional ($^{1}$H-$^{13}$C COSY) NMR spectrum diagram for peak 2 (Mw=180) in FIG. 1-9. Methanol-$d_4$ ($CD_3OD$) was used for the solvent for measurement. From the attribution of the two-dimensional NMR, the result of Mw=180, and other instrumental analysis data, the structure of the oxidation reaction product for peak 2 (Mw=180) was demonstrated to be that of the cyclic peroxide represented by the chemical formula (1). The peaks indicated with signs A to F in the two-dimensional NMR spectrum diagram in FIG. 1-16 were attributed to peaks for the carbon atoms indicated with the same signs A to F and hydrogen atoms bound to the carbon atoms in a chemical formula (1) below, which is shown in FIG. 1-16. It was expected that a slight amount of the raw material glycerin remained, and the peak was also detected.

FIG. 1-17 shows HILIC chromatograms for the TLC1 spot product and glyceraldehyde dimer under the HILIC (high-performance liquid chromatography) conditions in FIG. 1-9 in combination. In FIG. 1-17, the "Synthesized OG" in the top shows a HILIC chromatogram for the TLC1 spot product. The bottom is a HILIC chromatogram for glyceraldehyde dimer. As shown in the figure, no glyceraldehyde dimer was detected under the HILIC conditions in FIG. 1-9.

FIG. 1-18 shows HILIC chromatograms for the TLC1 spot product and glyceraldehyde dimer under reversed-phase HILIC (high-performance liquid chromatography) conditions in combination. FIG. 1-19 shows an enlarged view of a part of FIG. 1-18. The "Synthesized OG" in the top in each of FIG. 1-18 and FIG. 1-19 is a HILIC chromatogram for the TLC1 spot product. The bottom is a HILIC chromatogram for glyceraldehyde dimer. As shown in the figures, the component separation of the TLC1 spot product was not found under the reversed-phase HILIC conditions. This was probably because the retention power of the column was weak and as a result the elution time of the TLC1 spot product was short. On the other hand, the retention time of glyceraldehyde dimer was slightly different from that of the TLC1 spot product (Synthesized OG). From the results, the TLC1 spot product was inferred to contain no glyceraldehyde dimer.

FIG. 1-20 shows ESR spectrum diagrams for the TLC1 spot product and peak 2 (Mw=180) in FIG. 1-9 in combination. In FIG. 1-20, the ordinate shows intensity and the abscissa shows magnetic flux density (G). Water was used for the solvent for measurement. As shown in the figure, the spectrum for the TLC1 spot product and that for the peak 2 (Mw=180) component in FIG. 1-9 almost completely matched, and the positions of the appearance of peaks in the former were almost identical to those in the latter. The TLC1 spot product and the peak 2 (Mw=180) component in FIG. 1-9 both exhibited a spectrum for DMPO (spin-trapping agent), the spectrum characterized by six lines. This spectral pattern is similar to that for ozonide.

FIG. 1-21 shows an ESR spectrum diagram for ozonized methyl linolenate. Acetone was used for the solvent for measurement. Ozonized methyl linolenate is a known degree of ozonide. As shown in the figure, the ESR spectrum diagram for ozonized methyl linolenate exhibited a spectrum for DMPO (spin-trapping agent), the spectrum characterized by six lines characteristic to ozonide. This spectral pattern is similar to those for the TLC1 spot product and peak 2 (Mw=180) in FIG. 1-20.

FIG. 1-22 shows ESR spectrum diagrams for peaks 1 to 8 in FIG. 1-9. Water was used for the solvent for measurement. The uppermost is an ESR spectrum diagram for a blank (only the solvent) for comparison. As shown in the figure, the components of peaks 1 to 8 were all found to have radical activity.

The graph in FIG. 1-23 shows results of measurement of activity for peaks 1 to 8 in FIG. 1-9 through chemiluminescence. In the figure, the ordinate shows all-wavelength emission intensity (relative intensity). The numbers “1” to “8” in the abscissa indicate fractions of peaks 1 to 8. The numerical values under the numbers indicate the molecular weights of the fractions found from mass spectra. As shown in the figure, it was found from the chemiluminescence that components with activity were generated in addition to the component having a molecular weight of 180.

(4) Examination on TRP Channel Activation

The TLC1 spot product produced in “(1) Production of Oxidation Reaction Product Containing Cyclic Peroxide According to the First Mode of the Present Invention” was directly used without separation (purification) to examine the TRP channel activation. Hereinafter, “OG” indicates glycerin not ozone-oxidized. Hereinafter, “OG” indicates a product formed by ozone-oxidizing glycerin with an oxygen generator (ozonized glycerin). In production of “OG”, the ozone oxidation of glycerin with an oxygen generator was performed with use of a gas having an ozone concentration of approximately 37000 ppm, which had been obtained through a process in which a high concentration of oxygen (oxygen concentration: 70% or more) was given to air with an oxygen generator and the oxygen was ozonized via an ozone generator, under Conditions A below. Hereinafter, “LOG” indicates a product formed by further oxidizing “OG”. Production of “LOG” by oxidation of “OG” was performed with use of a gas having an ozone concentration of approximately 37000 ppm, which had been obtained through a process in which oxygen from an oxygen tank (oxygen concentration: 99% or more) was ozonized via an ozone generator, under Conditions B below. That is, “LOG” shown below is the same as the glycerin solution dissolving an ozone-oxidized form of glycerin therein at a final concentration of 4000 ppm, the glycerin solution produced in “(1) Production of Oxidation Reaction Product Containing Cyclic Peroxide According to the First Mode of the Present Invention”. Therefore, it follows that “LOG” shown below is a glycerin solution of the TLC1 spot product. Hereinafter, “HOG” indicates a product formed by heating “OG” at 80° C. for 168 hours (heat treatment).

(Conditions A: Production of “OG”)

A tank was charged with glycerin at a concentration of 98% by weight (“G”, specifically, non-ozonized glycerin). Subsequently, “G” in the tank was aerated with the gas having an ozone concentration of approximately 37000 ppm by using an air diffuser for approximately 7 days to give a glycerin solution dissolving an ozonized form of glycerin therein at a final concentration of 4000 ppm. This ozone-treated glycerin solution was used as “OG”.

(Conditions B: Production of “LOG”)

A tank was charged with “OG” produced under Conditions A. Subsequently, “G” in the tank was aerated with the gas having an ozone concentration of approximately 37000 ppm by using an air diffuser for approximately 7 days to produce an ozone-treated glycerin solution at 2000 ppm in terms of hydrogen peroxide concentration. This ozone-treated glycerin solution was used as “LOG”.

FIG. 1-24 shows effects of G, OG, LOG, and HOG added to TRPM2 (expressing cells) and Vector (TRPM2-nonexpressing cells). In FIG. 1-24, the left graph is a graph for TRPM2 (expressing cells), and the right graph is a graph for Vector (TRPM2-nonexpressing cells). Each abscissa shows time (seconds). The time when G, OG, LOG, and HOG were added is 120 seconds (2 minutes). G, OG, LOG, and HOG were each used as a 10% by mass aqueous solution. Each ordinate shows variations of intracellular $Ca^{2+}$ concentration. Furthermore, the bottom graph in FIG. 1-24 shows net intracellular $Ca^{2+}$ increase rates. As shown in the figure, G, OG, and LOG gave higher intracellular $Ca^{2+}$ increase rates than HOG, hence confirmed to cause high TRP channel activation, and OG and LOG were confirmed to cause higher TRP channel activation than G.

G and OG were examined for TRP channel activation to TRPM2 (expressing cells) under the same conditions as for FIG. 1-24 except that the concentrations (% by mass) of the aqueous solutions were changed. FIG. 1-25 shows the results. The left graph in FIG. 1-25 shows the result for G, and the right graph in FIG. 1-25 shows the result for OG. Each abscissa shows time (seconds). Each ordinate shows variations of intracellular $Ca^{2+}$ concentration. The bottom graph in FIG. 1-25 shows the correlation between concentrations (abscissa, % by mass) and net intracellular $Ca^{2+}$ increase rates (ordinate) for G and OG. As shown in the figure, G caused higher TRP channel activation at high concentrations, whereas OG caused high TRP channel activation even at low concentrations.

G, OG, LOG, and HOG were examined for TRP channel activation in TRPM2 (expressing cells) under the same conditions as for FIG. 1-24 except that the concentrations of the aqueous solutions were changed from 10% by mass to 1% by mass. FIG. 1-26 shows the results. The abscissa shows time (seconds). The ordinate shows variations of intracellular $Ca^{2+}$ concentration. As shown in FIG. 1-26, only LOG caused high TRP channel activation under the conditions.

LOG and OG were examined for TRP channel activation in TRPM2 (expressing cells) under the same conditions as for FIG. 1-24 except that 500 unit/ml of catalase was added for comparison with a case without addition of catalase. FIG. 1-27 shows the results. The left graph in FIG. 1-27 shows the result for LOG, and the right graph in FIG. 1-27 shows the result for OG. Each abscissa shows time (seconds). Each ordinate shows variations of intracellular $Ca^{2+}$ concentration. The bottom graph in FIG. 1-27 shows net intracellular $Ca^{2+}$ increase rates (ordinate) with addition of catalase (+) and those without addition of catalase for LOG and OG. As shown in the figure, it was conformed that addition of catalase resulted in the loss of TRP channel activation by both OG and LOG.

OG and LOG were examined for TRP channel activation in TRPM2 (expressing cells) under the same conditions as for FIG. 1-24 except that the concentrations (% by mass) of the aqueous solutions were changed. FIG. 1-28 shows the results. The left graph in FIG. 1-28 shows the result for OG, and the right graph in FIG. 1-28 shows the result for LOG. Each abscissa shows time (seconds). Each ordinate shows variations of intracellular $Ca^{2+}$ concentration. The bottom graph in FIG. 1-28 shows the correlation between concentrations (abscissa) and variations of intracellular $Ca^{2+}$ concentration (ordinate) for OG and LOG. As shown in the figure, LOG caused high TRP channel activation even at 1000-fold dilution, whereas OG did not cause TRP channel activation at the same concentration.

LOG at 0.1% by mass was examined for TRP channel activation in TRPM2 (expressing cells) under the same conditions as for FIG. 1-24 except that 100 unit/ml of catalase was added or 1 μm of PJ34 (product name, from ChemScene) was added for comparison with a case without addition of catalase and PJ34. FIG. 1-29 shows the results. The upper left graph in FIG. 1-29 shows the result of comparison between the case with addition of catalase and the case without addition of catalase. The lower left graph in FIG. 1-29 shows the result of comparison between the case with addition of PJ34 and the case without addition of PJ34. Each abscissa shows time (seconds). Each ordinate shows variations of intracellular $Ca^{2+}$ concentration. The upper right graph in FIG. 1-29 shows net intracellular $Ca^{2+}$ increase rates (ordinate) with addition of catalase and those without addition of catalase (Control). The lower right graph in FIG. 1-29 shows net intracellular $Ca^{2+}$ increase rates (ordinate) with addition of PJ34 and those without addition of PJ34 (Control). As shown in the figure, it was confirmed that addition of any of catalase and PJ34 resulted in the loss of TRP channel activation. PJ34 is a substance represented by the following chemical formula.

[Chemical Formula PJ34]

PJ34

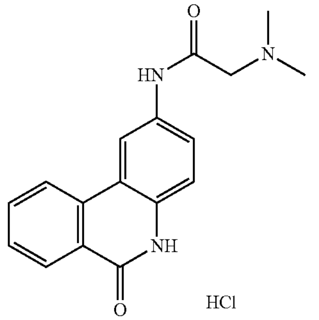

LOG at 0.1% by mass was examined for TRP channel activation in TRPM2 (expressing cells) under the same conditions as for FIG. 1-24 except that 100 μm of dipyridyl (α,α'-dipyridyl) was added for comparison with a case without addition of dipyridyl. FIG. 1-30 shows the results. The left graph in FIG. 1-30 shows the result of comparison between the case with addition of dipyridyl and the case without addition of dipyridyl. Each abscissa shows time (seconds). Each ordinate shows variations of intracellular $Ca^{2+}$ concentration. The right graph in FIG. 1-30 shows net intracellular $Ca^{2+}$ increase rates (ordinate) with addition of dipyridyl and those without addition of dipyridyl (Control). As shown in the figure, it was confirmed that addition of dipyridyl resulted in the loss of TRP channel activation.

LOG was examined for TRP channel activation in different cells under the same conditions as for FIG. 1-24 except that the concentration of the aqueous solution was changed and TRPM1 HEK (expressing cells) or HEK (expressing cells) was used in place of TRPM2 (expressing cells). FIG. 1-31 shows the results. The upper left graph in FIG. 1-31 shows the result for TRPM1 HEK (expressing cells), and the right graph in FIG. 1-31 shows the result for HEK (expressing cells). Each abscissa shows time (seconds). Each ordinate shows variations of intracellular $Ca^{2+}$ concentration. The bottom graph in FIG. 1-31 shows the correlation between concentrations (abscissa, % by mass) and net intracellular $Ca^{2+}$ increase rates (ordinate) for LOG. As shown in the figure, LOG caused TRP channel activation in TRPM1 HEK (expressing cells), but hardly caused TRP channel activation in HEK (expressing cells).

The TLC1 spot product was further purified to make the component having a molecular weight of 180 a main component. The component at various concentrations was examined for TRP channel activation in TRPM2 (expressing cells) and TRPMA1 (expressing cells) in the same manner as for FIG. 1-31. FIG. 1-32 and FIG. 1-33 show the results. In FIG. 1-32 and FIG. 1-33, "F7" indicates the component obtained by purifying the TLC1 spot product to make the component having a molecular weight of 180 a main component. As shown in FIG. 1-32 and FIG. 1-33, F7 did not cause TRP channel activation in TRPM2, but caused TRP channel activation in TRPA1 (expressing cells).

Thus, as demonstrated in Example 1, a TRP channel activator having oxidation power was successfully produced not from an olefin but from glycerin, which is a substance without any double bond, by ozone oxidation in a simpler manner.

The TLC1 spot product was separated into components corresponding to peaks 1 to 8 in FIG. 1-9, with which glycerin solutions each having the same concentration as OG described above were prepared, and examined for TRP channel activation in the same manner. The results found all the components corresponding to peaks 1 to 8 to cause TRP channel activation, and thus have oxidation power. However, OG, which was a mixture of the components corresponding to peaks 1 to 8, was confirmed to cause stronger TRP channel activation than any of the components, and thus have strong oxidation power.

Example of Second Mode

Second, Example 2 will be described. However, the second mode of the present invention is not limited to the example below. Commercially available reagents were used in accordance with their protocols, unless otherwise specified.

Example 2

An oxidation reaction product containing the cyclic peroxide was produced through ozone oxidation of glycerin. Then, the whitening effect of the oxidation reaction product produced was examined. The present example corresponds to an example of production and use of the cyclic peroxide, and to an example of production and use of the oxidation reaction product, and further to an example of the method for producing an oxidation reaction product.

(1) Production of the Oxidation Reaction Product Containing Cyclic Peroxide

Concentrated glycerin and ozone were brought into gas-liquid contact, and an ozone-treated glycerin solution containing the oxidation reaction product (ozonized glycerin) was produced in a manner shown below. Here, the concentrated glycerin was a product containing glycerin at a concentration of 98% by weight or more in accordance with the Japanese Pharmacopeia. The oxidation reaction product according to the second mode of the present invention, an oxidation reaction product produced in the present example, contained the cyclic peroxide according to the second mode of the present invention, as described later.

A Teflon® tank having a capacity of 50 L was used as a contactor. An air diffuser was set on the bottom of the tank so that ozone could be fed as fine bubbles into the tank. A gas of high oxygen concentration, which contained oxygen at a concentration as high as 90% by volume or more, was used as a raw material, and a silent discharge ozone generator capable of generating 100 g of ozone per hour was used.

The tank was charged with 22 kg of the concentrated glycerin, the gas of high oxygen concentration was sent to the ozone generator at 20 L per minute to generate a gas containing ozone, and the gas generated was released into the tank via the air diffuser for 7 days or more to give a glycerin solution dissolving an ozone-oxidized form of glycerin therein at a final concentration of 4000 ppm. The ozone-oxidized form of glycerin corresponds to the oxidation reaction product. As described later, the cyclic peroxide was contained in that ozone-oxidized form. The ozone-oxidized form of glycerin containing the peroxide was examined for whitening activity.

(2) Examination on Whitening Action

Forty-eight healthy individuals (females, 41 years or older and 59 years or younger) participated as test subjects. The test subjects were well informed with description documents (including a consent form) in advance, and a written consent was acquired from each test subject.

For examination of the whitening action, a test product of Example 2-1A, a test product of Example 2-1B, a test product of Reference Example 2-1A, and a test product of Reference Example 2-1B were prepared. Specifically, the test product of Example 2-4A was prepared by adding water in an amount equal to that of the ozonized glycerin in Example 2(1) to give a 50% ozonized glycerin aqueous solution and further adding pentylene glycol and xanthan gum thereto. The test product of Example 2-1B was prepared by adding water in an amount 9 times that of the ozonized glycerin in Example 2(1) to give a 10% ozonized glycerin aqueous solution and further adding pentylene glycol, xanthan gum, and Na hyaluronate thereto. As a result, the test product of Example 2-1A and the test product of Example 2-1B each contained the ozone-oxidized form in the ozonized glycerin obtained in Example 2(1) at a final concentration of 80 ppm or 800 ppm. The test product of Reference Example 2-1A and the test product of Reference Example 2-1B were prepared in the same manner except that the concentrated glycerin was used in place of the ozonized glycerin.

The test subjects were divided into two groups below (24 test subjects in each group). Each test subject took two pushes (approximately 1 ml) of a test product on the hands and applied the test product to a specified half of the face after every face washing performed twice per day (morning and night). After the initiation of the test, the test subjects neither changed cosmetics other than test products (such as lotions, emulsions, sera, creams) nor began use of a new facial product before the end of the test. The validation test was conducted during April to June, thus under an environment to cause melanin generation over time. This test had been reviewed by an ethics review board and approved before being conducted in compliance with the Declaration of Helsinki and Ethical Guidelines for Medical and Health Research Involving Human Subjects.

(Test Group 1)

Half of face: test product of Example 2-1A

Another half of face: test product of Reference Example 2-1A (Test Group 2)

Half of face: test product of Example 2-1B

Another half of face: test product of Reference Example 2-1B

Each test subject was subjected to quintuple melanin measurement for freckle sites in the left and right cheeks on the day of initiation of application of test products (week 0) and 4 weeks and 8 weeks after the initiation of application. The melanin measurement was performed by using a Mexameter® MX18 (Courage+Khazaka electronic GmbH, Cologne, Germany). Subsequently, the maximum value and the minimum value of the five measurement values were excluded. Then, the mean of the three residual measurement values was employed as a melanin measurement value for the test subject. In addition, the changes of melanin measurement values from those at the initiation of the test were determined. Statistical test was carried out with Student t-test, and cases with $p<0.05$ were determined to be significant differences. FIG. 2-1 and FIG. 2-2 show the results.

FIG. 2-1 is a series of graphs showing melanin measurement values over time. In FIG. 2-1, (A) shows the results for Example 2-1A and Reference Example 2-1A, and (B) shows the results for Example 2-1B and Reference Example 2-4B. In each of FIGS. 2-1(A) and 2-1(B), the abscissa shows numbers of weeks after the initiation of the test, and the ordinate shows melanin measurement values (Melanin index). FIG. 2-2 is a series of graphs showing the changes of melanin measurement values over time. In FIG. 2-2, (A) shows the results for Example 2-4A and Reference Example 2-4A, and (B) shows the results for Example 2-4B and Reference Example 2-4B. In each of FIGS. 2-2(A) and 2-2(B), the abscissa shows numbers of weeks after the initiation of the test, and the ordinate shows the changes of melanin measurement values ($\Delta$Melanin index). As shown in FIG. 2-1 and FIG. 2-2, the respective skin regions to which the test product of Example 2-1A and the test product of Example 2-1B had been applied exhibited lower melanin measurement values than the respective skin regions to which the test product of Reference Example 2-1A and the test product of Reference Example 2-1B had been applied, and the reductions increased over time. These results revealed that the cyclic peroxide contained in the ozone-oxidized form has an activity to reduce the amount of melanin in skin, in other words, exhibits whitening action.

The compound having a molecular weight of 180 (chemical formula (1)), which is described later, can be eliminated from ozonized glycerin by performing heat treatment of the ozonized glycerin. In light of this, an ozonized glycerin after the heat treatment was examined on change in melanin measurement values, and found to have lost the activity to give lower melanin measurement values. Accordingly, the compound having a molecular weight of 180 (chemical formula (1)), which is described later, can be said to be an active ingredient responsible for the whitening action. Being a cyclic peroxide, the compound having a molecular weight of 180 was inferred to exhibit the whitening action by decomposing melanin through the oxidative capacity.

(3) Analysis of Reaction Mixture

To identify the active ingredient of the whitening component in the ozonized glycerin, a cyclic peroxide that was not found for glycerin was extracted from the ozonized glycerin in Example 2(1), and analyzed. Glycerin was removed from the glycerin solution dissolving the ozone-oxidized form of glycerin therein, which had been produced in "Example 2(1) Production of the Oxidation Reaction Product Containing Cyclic Peroxide", by using a silica gel column, and thus a reaction mixture containing the cyclic peroxide was obtained (hereinafter, occasionally referred to as "the TLC1 spot product").

Figures 1, 2, 3, 4:
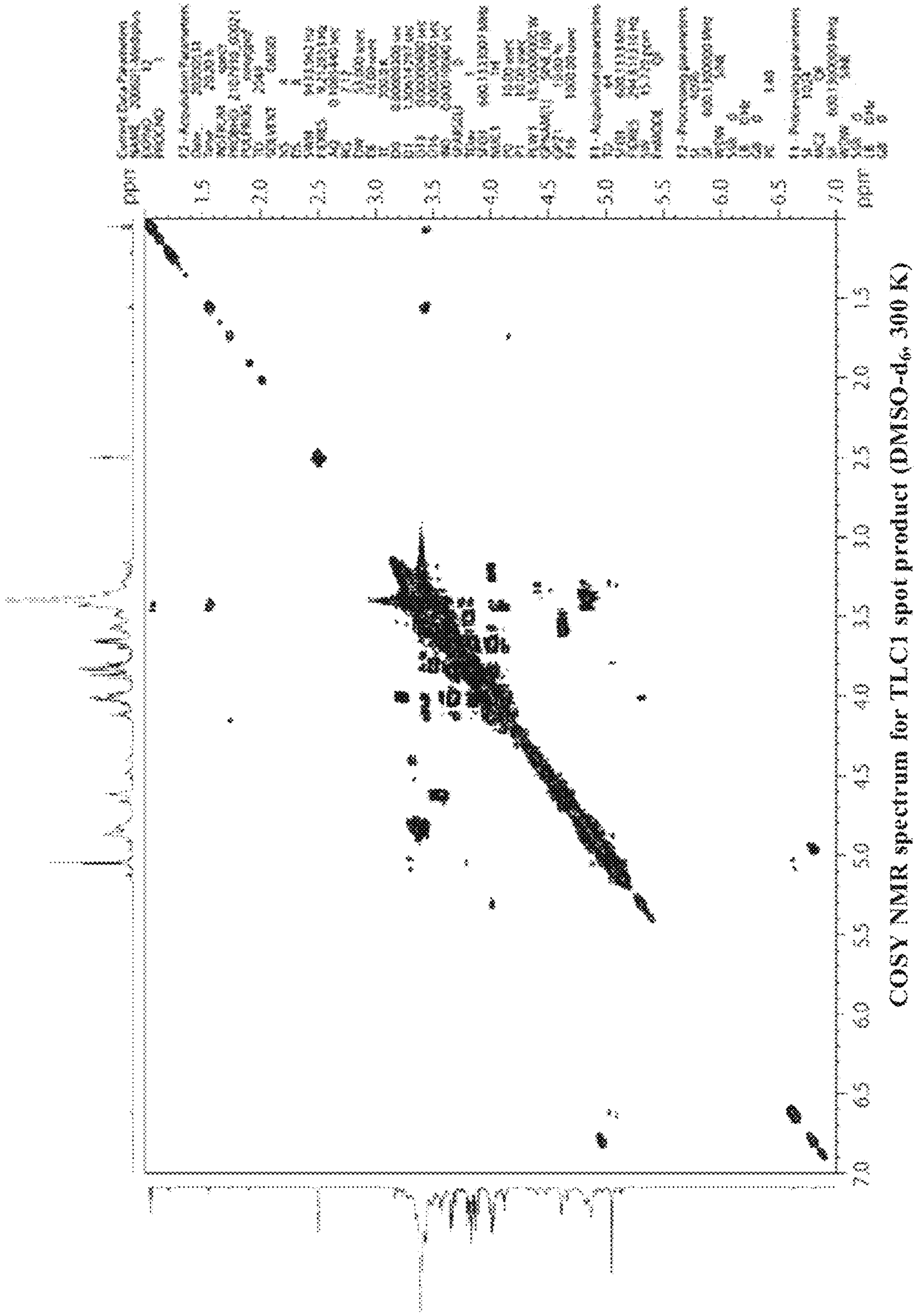

NMR spectra for the reaction mixture (TLC1 spot product) were determined with use of DMSO-$d_6$ as a solvent at a temperature of 300 K (27° C.). FIG. 2-3 to FIG. 2-8 show the spectrum diagrams. FIG. 2-3 is the $^1$H NMR spectrum diagram. FIG. 2-4 is the $^{13}$C NMR spectrum diagram. FIG. 2-5 is the $^{13}$C DEPT135 NMR spectrum diagram. FIG. 2-6 is the COSY NMR spectrum diagram. FIG. 2-7 is the HSQC NMR spectrum diagram. FIG. 2-8 is the HMBC NMR spectrum diagram. Complex peaks were observed as shown in FIG. 2-3 to FIG. 2-8, and hence the TLC1 spot product was expected to be a mixture of a plurality of substances. LCMS found that the TLC1 spot product contained a component of m/z 198,203.

(4) Separation and Analysis of Reaction Mixture

The reaction mixture (TLC1 spot product) was adjusted (diluted) to approximately 3% by mass with acetonitrile, and filtered through a membrane filter, and the resulting filtrate was subjected to LC measurement for optimization of separation conditions. Subsequently, peaks found in LC measurement under the optimized conditions were checked for mass, and precise separation was performed for Mw=180 (peak 2). Thereafter, the resulting fractionated solution was freeze-dried, and the dried product of the fraction was subjected to microscopic LR measurement and various NMR measurements. The measurement apparatuses (analyzers) and measurement conditions were as follows.

[Measurement Apparatuses (Analyzers)]

1) Precise preparative LC: Waters, ACQUITY UPLC H-class Bio
2) Microscopic LR: SNOM/AFM/Raman multifunction apparatus, alpha300RSA manufactured by WITec
3) NMR: Bruker Biospin, AVANCE III-600 with Cryo Probe

[Measurement Conditions]

1) Precise Preparative LC

Column: Shodex Asahipak NH2P-50 (4.6 mmφ×250 mm, 5 μm)
Composition of eluent: water/acetonitrile gradient
Time (min): 0 5 15 20
Water: 5 10 50 50
Acetonitrile: 95 90 50 50
Flow rate: 1.0 mL/min
Detector: MS (QDa)
Column temperature: 40° C.
Injection volume: 50 μL
Ionization method: ESI (NEG.)
Mass range in measurement (m/z): 50 to 500

2) Microscopic LR

Excitation wavelength: 532 nm
Wavelength range in measurement: approximately 125 to 3800 $cm^{-1}$
Objective lens: ×100
Detector: EMCCD

3) NMR

Observation frequency: 600 MHz ($^1$H), 150 MHz ($^{13}$C)
Solvent for measurement: methanol-$d_4$
Measurement temperature: 300 K
Chemical shift standard: solvent for measurement [3.30 ppm ($^1$H), 49.80 ppm ($^{13}$C)]

FIG. 2-9 shows total ion chromatograms (ESI-negative mode) from the precise preparative LC (liquid chromatography) for the sample and a blank, the sample being obtained by adjusting (diluting) the reaction mixture (TLC1 spot product) to approximately 3% by mass with acetonitrile. In FIG. 2-9, the ordinate shows intensity and the abscissa shows retention time (minutes). In FIG. 2-9, "Synthesized OG" in the bottom shows a chromatogram for the sample of the TLC1 spot product, and the top shows a chromatogram for the blank (acetonitrile). As shown in the figure, components of A to L were found from the TLC1 spot product. These components A to L were separated and checked for the presence or absence of coloring with potassium iodide starch test paper, and the result showed that component H exhibited the strongest coloring.

FIG. 2-10 shows mass spectra for peaks F, G, and H (fraction F, fraction G, and fraction H) in FIG. 2-9 in combination. In FIG. 2-10, the ordinate shows intensity and the abscissa shows mass-charge ratios (m/z). As shown in the figure, it was found that peak F had Mw=180, peak G had Mw=226, and peak H had Mw=256.

Moreover, FIG. 2-11 shows results of examination on improvement of separation (improvement of separation conditions) in HILIC (high-performance liquid chromatography). In FIG. 2-11, the ordinate shows intensity and the abscissa shows retention time (minutes), and the same applies to FIG. 2-19 to FIG. 2-21. In FIG. 2-11, the top is a chromatogram before improvement of separation (under the same conditions as for FIG. 2-10), and the bottom is a chromatogram after improvement of separation. As shown in the figure, peaks 1 to 8 were found after improvement of separation. The molecular weights of the peaks were confirmed to be those as shown in FIG. 2-11 from mass spectra shown later.

FIG. 2-12 shows mass spectra for peaks 1 to 3 in FIG. 2-11 (after improvement of separation). In FIG. 2-12, the top, middle, and bottom are mass spectra for peak 1, peak 2, and peak 3, respectively. As shown in the figure, it was found that peak 1 had Mw=196, peak 2 had Mw=180, and peak 3 had Mw=240.

FIG. 2-13 shows mass spectra for peaks 4 to 6 in FIG. 2-11 (after improvement of separation). In FIG. 2-13, the top, middle, and bottom are mass spectra for peak 4, peak 5, and peak 6, respectively. As shown in the figure, it was found that peak 4 had Mw=240, peak 5 had Mw=240, and peak 6 had Mw=226.

FIG. 2-14 shows mass spectra for peaks 7 and 8 in FIG. 2-11 (after improvement of separation). In FIG. 2-14, the top and bottom are mass spectra for peak 7 and peak 8, respectively. As shown in the figure, it was found that peaks 7 and 8 both had Mw=256.

FIG. 2-15 shows micro-Raman spectrum diagrams for a separated sample obtained from peak 2 (Mw=180) in FIG. 2-11 and an ozonide authentic sample (ozonized oleic acid) in combination. In FIG. 2-15, the ordinate shows intensity and the abscissa shows Raman shifts (1/cm). As shown in FIG. 2-15, peak 2 (Mw=180) exhibited a micro-Raman spectrum similar to that for ozonide, and hence expected to have a structure similar to that of ozonide. The micro-Raman spectrum for peak 2 (Mw=180) exhibited a pattern differing from that for peroxide, and hence peak 2 (Mw=180) was expected not to correspond to peroxide. From NMR shown later, peak 2 (Mw=180) was found to correspond to the cyclic peroxide.

FIG. 2-16 shows a $^{1}$H NMR spectrum diagram for peak 2 (Mw=180) in FIG. 2-11. Methanol-$d_4$ ($CD_3OD$) was used for the solvent for measurement. In the figure, the top spectrum diagram is an enlarged view of a part around 3.4 to 4.9 ppm in the bottom spectrum diagram. From the attribution of the $^{1}$H NMR, the result of Mw=180, and other instrumental analysis data, the structure of the oxidation reaction product for peak 2 (Mw=180) was demonstrated to be that of a cyclic peroxide represented by a chemical formula (1) below. The peaks indicated with signs A to F in the $^{1}$H NMR spectrum diagram in FIG. 2-16 were attributed to peaks for hydrogen bound to the carbon atoms indicated with the same signs A to F in a chemical formula (1) below, which is shown in FIG. 2-16. It was expected that a slight amount of the raw material glycerin remained, and the peak was also detected.

[Chemical Formula 1M]

(1)

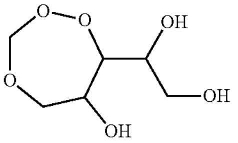

Molecular Weight: 180.16

FIG. 2-17 shows a $^{13}$C NMR spectrum diagram for peak 2 (Mw=180) in FIG. 2-11. Methanol-$d_4$ ($CD_3OD$) was used for the solvent for measurement. In the figure, the top spectrum diagram is an enlarged view of a part around 60 to 105 ppm in the bottom spectrum diagram. From the attribution of the $^{13}$C NMR, the result of Mw=180, and other instrumental analysis data, the structure of the oxidation reaction product for peak 2 (Mw=180) was demonstrated to be that of the cyclic peroxide represented by the chemical formula (1). The peaks indicated with signs A to F in the $^{13}$C NMR spectrum diagram in FIG. 2-17 were attributed to peaks for the carbon atoms indicated with the same signs A to F in a chemical formula (1) below, which is shown in FIG. 2-17. It was expected that a slight amount of the raw material glycerin remained, and the peak was also detected.

FIG. 2-18 shows a two-dimensional ($^{1}$H-$^{13}$C COSY) NMR spectrum diagram for peak 2 (Mw=180) in FIG. 2-11. Methanol-$d_4$ ($CD_3OD$) was used for the solvent for measurement. From the attribution of the two-dimensional NMR, the result of Mw=180, and other instrumental analysis data, the structure of the oxidation reaction product for peak 2 (Mw=180) was demonstrated to be that of the cyclic peroxide represented by the chemical formula (1). The peaks indicated with signs A to F in the two-dimensional NMR spectrum diagram in FIG. 2-18 were attributed to peaks for the carbon atoms indicated with the same signs A to F and hydrogen atoms bound to the carbon atoms in a chemical formula (1) below, which is shown in FIG. 2-18. It was expected that a slight amount of the raw material glycerin remained, and the peak was also detected.

FIG. 2-19 shows HILIC chromatograms for the TLC1 spot product and glyceraldehyde dimer under the HILIC (high-performance liquid chromatography) conditions in FIG. 2-11 in combination. In FIG. 2-19, the "Synthesized OG" in the top shows a HILIC chromatogram for the TLC1 spot product. The bottom is a HILIC chromatogram for glyceraldehyde dimer. As shown in the figure, no glyceraldehyde dimer was detected under the HILIC conditions in FIG. 2-11.

FIG. 2-20 shows HILIC chromatograms for the TLC1 spot product and glyceraldehyde dimer under reversed-phase HILIC (high-performance liquid chromatography) conditions in combination. FIG. 2-21 shows an enlarged view of a part of FIG. 2-20. The "Synthesized OG" in the top in each of FIG. 2-20 and FIG. 2-21 is a HILIC chromatogram for the TLC1 spot product. The bottom is a HILIC chromatogram for glyceraldehyde dimer. As shown in the figures, the component separation of the TLC1 spot product was not found under the reversed-phase HILIC conditions. This was probably because the retention power of the column was weak and as a result the elution time of the TLC1 spot product was short. On the other hand, the retention time of glyceraldehyde dimer was slightly different from that of the TLC1 spot product (Synthesized OG). From the results, the TLC1 spot product was inferred to contain no glyceraldehyde dimer.

FIG. 2-22 shows ESR spectrum diagrams for the TLC1 spot product and peak 2 (Mw=180) in FIG. 2-11 in combination. In FIG. 2-22, the ordinate shows intensity and the abscissa shows magnetic flux density (G). Water was used for the solvent for measurement. As shown in the figure, the spectrum for the TLC1 spot product and that for the peak 2 (Mw=180) component in FIG. 2-11 almost completely matched, and the positions of the appearance of peaks in the former were almost identical to those in the latter. The TLC1 spot product and the peak 2 (Mw=180) component in FIG. 2-11 both exhibited a spectrum for DMPO (spin-trapping agent), the spectrum characterized by six lines. This spectral pattern is similar to that for ozonide.

FIG. 2-23 shows an ESR spectrum diagram for ozonized methyl linolenate. Acetone was used for the solvent for measurement. Ozonized methyl linolenate is a known ozonide. As shown in the figure, the ESR spectrum diagram for ozonized methyl linolenate exhibited a spectrum for DMPO (spin-trapping agent), the spectrum characterized by six lines characteristic to ozonide. This spectral pattern is similar to those for the TLC1 spot product and peak 2 (Mw=180) in FIG. 2-22.

FIG. 2-24 shows ESR spectrum diagrams for peaks 1 to 8 in FIG. 2-11. Water was used for the solvent for measurement. The uppermost is an ESR spectrum diagram for a blank (only the solvent) for comparison. As shown in the figure, the components of peaks 1 to 8 were all found to have radical activity.

The graph in FIG. 2-25 shows results of measurement of activity for peaks 1 to 8 in FIG. 2-11 through chemiluminescence. In the figure, the ordinate shows all-wavelength emission intensity (relative intensity). The numbers "1" to "8" in the abscissa indicate fractions of peaks 1 to 8. The numerical values under the numbers indicate the molecular weights of the fractions found from mass spectra. As shown in the figure, it was found from the chemiluminescence that components with activity were generated in addition to the component having a molecular weight of 180.

Example of Third Mode

Third, Example 3 will be described. However, the third mode of the present invention is not limited to the example below. Commercially available reagents were used in accordance with their protocols, unless otherwise specified.

Example 3-1

An oxidation reaction product containing the cyclic peroxide was produced through ozone oxidation of glycerin. Then, the oxidation reaction product produced was examined for action to induce expression of a skin barrier function-related gene. The present example corresponds to an example of production and use of the cyclic peroxide, and to an example of production and use of the oxidation reaction product, and further to an example of the method for producing an oxidation reaction product.

(1) Production of the Oxidation Reaction Product Containing Cyclic Peroxide

Concentrated glycerin and ozone were brought into gas-liquid contact, and an ozone-treated glycerin solution containing the oxidation reaction product (ozonized glycerin) was produced in a manner shown below. Here, the concentrated glycerin was a product containing glycerin at a concentration of 98% by weight or more in accordance with the Japanese Pharmacopeia. The oxidation reaction product according to the third mode of the present invention, an oxidation reaction product produced in the present example, contained the cyclic peroxide according to the third mode of the present invention, as described later.

A Teflon® tank having a capacity of 50 L was used as a contactor. An air diffuser was set on the bottom of the tank so that ozone could be fed as fine bubbles into the tank. A gas of high oxygen concentration, which contained oxygen at a concentration as high as 90% by volume or more, was used as a raw material, and a silent discharge ozone generator capable of generating 100 g of ozone per hour was used.

The tank was charged with 22 kg of the concentrated glycerin, the gas of high oxygen concentration was sent to the ozone generator at 20 L per minute to generate a gas containing ozone, and the gas generated was released into the tank via the air diffuser for 7 days or more to give a glycerin solution dissolving an ozone-oxidized form of glycerin therein at a final concentration of 4000 ppm. The ozone-oxidized form of glycerin corresponds to the oxidation reaction product. As described later, the cyclic peroxide was contained in that ozone-oxidized form. The ozone-oxidized form of glycerin with the peroxide was examined for the action to induce expression of a skin barrier function gene.

(2) Examination on Action to Induce Expression of Skin Barrier Function Gene

Whether the ozonized glycerin was capable of inducing expression of a skin barrier function gene was examined with human epidermal keratinocytes. Specifically, normal human epidermal cells (NHEK: manufactured by Kurabo Industries Ltd.) were suspended in a medium (HuMedia-KG2 (KG2), manufactured by Kurabo Industries Ltd.), then seeded on a 96-well plate to reach $2.0\times10^4$ cells/well/100 μl, and cultured under conditions of 37° C. and 5% $CO_2$ (the same conditions were used for the subsequent cultures) for 24 hours. After the culture, the medium in each well was replaced with KG2 medium (100 μl/well) containing the ozonized glycerin in Example 3-1(1) at a specific concentration (1, 2, or 4 (v/v)/o), and culture was further performed for 24 hours. Subsequently, the medium in each well was removed, the cells were then washed with phosphate buffer (PBS(−)), and RNA was extracted by using an RNA extraction kit (Ambion® Cells-to-CT™ Kits, manufactured by Thermo Fisher Scientific). From the RNA obtained, cDNA was synthesized through reverse transcription reaction.

Real-time PCR reagents and a PCR apparatus (StepOne™ Real-Time PCR System, manufactured by Applied Biosystems) were applied to the cDNA to calculate mRNA expression levels of a pro-filaggrin gene, an involucrin gene, and a serine palmitoyltransferase gene (ΔΔCt method). Primer sets shown below were used for the amplification of mRNA for the genes, and the expression level of each gene was calculated as a relative value to the mRNA expression level of a GAPDH gene. For a comparative example, the same operations were performed except that the concentrated glycerin was used in place of the ozonized glycerin. FIG. 3-1 shows the results.

```
-Primer set for pro-filaggrin gene
Forward primer
                                          (SEQ ID NO: 1)
5'-CATGGCAGCTATGGTAGTGCAGA-3'

Reverse primer
                                          (SEQ ID NO: 2)
5'-ACCAAACGCACTTGCTTTACAGA-3'

-Primer set for involucrin gene
Forward primer
                                          (SEQ ID NO: 3)
5'-GCTGGAGCAGCCTGTGTTTG-3'

Reverse primer
                                          (SEQ ID NO: 4)
5'-CTGGACACTGCGGGTGGTTA-3'

-Primer set for serine palmitoyltransferase gene
Forward primer
                                          (SEQ ID NO: 5)
5'-GCCTGTCAGCAGCTCATACCAA-3'

Reverse primer
                                          (SEQ ID NO: 6)
5'-GGCCTGTCCAGTAGAGGTACCAA-3'

-Primer set for GAPDH gene
                                          (SEQ ID NO: 7)
Forward primer
5'-GCACCGTCAAGGCTGAGAAC-3'

Reverse primer
                                          (SEQ ID NO: 8)
5'-TGGTGAAGACGCCAGTGGA-3'
```

FIG. 3-1 is a series of graphs showing expression levels of the skin barrier function-related genes. In FIG. 3-1, (A) shows expression levels of the pro-filaggrin gene, (B) shows expression levels of the involucrin gene, and (C) shows the result for the serine palmitoyltransferase gene. In each of FIGS. 3-1(A) to 3-1(C), the abscissa shows sample concentrations, and the ordinate shows relative expression levels of the corresponding gene. As shown in FIGS. 3-1(A) to 3-1(C), the group treated with the ozonized glycerin (OG) exhibited higher expression levels of the pro-filaggrin gene, the involucrin gene, and the serine palmitoyltransferase gene than the group treated with the comparative example (Glycerin). These results revealed that the ozonized glycerin is capable of inducing expression of the skin barrier function-related genes. As shown later by comparison of components between the ozonized glycerin and the concentrated glycerin, the ozonized glycerin differed from the concentrated glycerin in that, for example, the ozonized glycerin contained a compound of a chemical formula (1) described later. Accordingly, it was demonstrated that the compound of the chemical formula (1) contained in the ozonized glycerin induces expression of the skin barrier function-related genes.

(3) Examination on Action to Induce Expression of Anti-Oxidative Stress Response Gene Whether the ozonized glycerin was capable of inducing expression of an anti-oxidative stress response gene was examined with human epidermal keratinocytes. cDNA was prepared in the same manner as in Example 3-1(2). For the cDNA, mRNA expression levels of a heme oxygenase-1 gene and an NAD(P)H quinone oxidoreductase-1 gene were calculated in the same manner as in Example 3-1(2) (ΔΔCt method). Primer sets shown below were used for the amplification of mRNA for the genes, and the expression level of each gene was calculated as a relative value to the mRNA expression level of a GAPDH gene. For a comparative example, the same operations were performed except that the concentrated glycerin was used in place of the ozonized glycerin. FIG. 3-2 shows the results.

```
-Primer set for heme oxygenase-1 gene
Forward primer
                                    (SEQ ID NO: 9)
5'-TTGCCAGTGCCACCAAGTTC-3'

Reverse primer
                                   (SEQ ID NO: 10)
5'-TCAGCAGCTCCTGCAACTCC-3'

-Primer set for NAD(P)H quinone oxidoreductase-1
gene
Forward primer
                                   (SEQ ID NO: 11)
5'-GTGGCAGTGGCTCCATGTACTC-3'

Reverse primer
                                   (SEQ ID NO: 12)
5'-GAGTGTGCCCAATGCTATATGTCAG-3'
```

FIG. 3-2 is a series of graphs showing expression levels of the anti-oxidative stress response genes. In FIG. 3-1, (A) shows expression levels of the heme oxygenase-1 gene, and (B) shows expression levels of the NAD(P)H quinone oxidoreductase-1 gene. In each of FIGS. 3-2(A) and 3-2(B), the abscissa shows sample concentrations, and the ordinate shows relative expression levels of the corresponding gene. As shown in FIGS. 3-2(A) and 3-2(B), the group treated with the ozonized glycerin (OG) exhibited higher expression levels of the heme oxygenase-1 gene and the NAD(P)H quinone oxidoreductase-1 gene than the group treated with the comparative example (Glycerin). These results revealed that the ozonized glycerin is capable of inducing expression of the anti-oxidative stress response genes. As shown later by comparison of components between the ozonized glycerin and the concentrated glycerin, the ozonized glycerin differed from the concentrated glycerin in that, for example, the ozonized glycerin contained a compound of a chemical formula (1) described later. Accordingly, it was demonstrated that the compound of the chemical formula (1) contained in the ozonized glycerin induces expression of the anti-oxidative stress response genes.

Subsequently, culture was performed in the same manner as in Example 3-1(2) in the presence of KG2 medium containing the ozonized glycerin at a specific concentration for 24 hours or 48 hours. After the culture, the medium in each well was removed. Then, 0.5% Triton® X-100 solution was added at 100 μl/well to lyse the cells in each cell, preparing a cell lysate. Into a new plate, 175 μl of reaction solution (2 mmol/l NADPH, 0.12 units/ml glutathione reductase, and 0.1 mol/l phosphate buffer containing 0.5 mmol/l EDTA) and 25 μl of the cell lysate were added and then mixed together, and the resultant was incubated at 37° C. for 10 minutes. Thereafter, 25 μl of a coloring solution (10 mmol/l (5,5'-dithio-bis-(2-nitrobenzoic acid): DTNB) was added, and the absorbance (405 nm) was measured by using an absorptiometer. From the absorbance acquired, the amount of glutathione was calculated. The amount of glutathione was calculated as a relative amount to the total amount of assayed proteins. FIG. 3-3 shows the results.

FIG. 3-3 is a series of graphs showing peptide contents in terms of glutathione. In FIG. 3-3, (A) shows peptide expression levels after the culture for 24 hours, and (B) shows peptide expression levels after the culture for 48 hours. In each of FIGS. 3-3(A) and 3-3(B), the abscissa shows sample concentrations, and the ordinate shows relative peptide expression levels in terms of glutathione. As shown in FIGS. 3-3 (A) and 3-3(B), the group treated with the ozonized glycerin (OG) exhibited higher peptide expression levels in terms of glutathione than the group treated with the comparative example (Glycerin). These results revealed that the ozonized glycerin is capable of inducing expression of the anti-oxidative protein. As shown later by comparison of components between the ozonized glycerin and the concentrated glycerin, the ozonized glycerin differed from the concentrated glycerin in that, for example, the ozonized glycerin contained a compound of a chemical formula (1) described later. Accordingly, it was demonstrated that the compound of the chemical formula (1) contained in the ozonized glycerin induces expression of the anti-oxidative protein glutathione.

(4) Cytotoxicity Check

The ozonized glycerin was confirmed to have no cytotoxicity by using human epidermal keratinocytes. Specifically, culture was performed in the same manner as in Example 3-1(3) in the presence of KG2 medium containing the ozonized glycerin at a specific concentration for 24 hours or 48 hours. After the culture, the medium in each well was removed. Subsequently, a medium containing 0.003% Neutral Red (NR: manufactured by Sigma-Aldrich Co. LLC) was added, and culture was performed at 37° C. for 2 hours. Each well was washed with PBS(−), 100 μl/l of 1 mol/l hydrochloric acid solution containing 30 (v/v) % methanol was then added, and NR was extracted. The absorbance (measurement wavelength: 550 nm, reference wavelength: 650 nm) of the resulting extract was measured by using the absorptiometer, and the cell viability was calculated. FIG. 3-4 shows the results.

FIG. 3-4 is a graph showing viabilities of cells. In FIG. 3-4, the abscissa shows sample concentrations, and the ordinate shows relative expression levels of glutathione. As shown in FIG. 3-4, the group treated with the ozonized glycerin (OG) exhibited cell viabilities comparable to those of the group treated with the comparative example (Glycerin). These results confirmed the ozonized glycerin to exhibit no cytotoxicity.

(5) Examination on Anti-Inflammatory Action

The ozonized glycerin was confirmed to exhibit anti-inflammatory action by using human epidermal keratinocytes. Specifically, a three-dimensionally cultured epidermis (LabCyte EPI-MODEL, manufactured by J-TEC (Japan Tissue Engineering Co., Ltd.)) was set on a 24-well plate to which 500 μl of an assay medium attached had been added, and cultured for conditioning under conditions of 37° C. and 5% $CO_2$ overnight. After the culture, 30 μl of an assay medium containing the ozonized glycerin at a specific concentration (0 or 1 (v/v)/o) was applied to the horny layer side, and culture was performed at 37° C. for 24 hours. After the culture, the assay medium containing the ozonized glycerin was removed with a cotton swab, and the surface of the horny layer was further washed once with 500 μl of PBS(−). Subsequently, the surface of the horny layer was removed of PBS(−) with a cotton swab, and then irradiated with UVB (280 to 315 nm, 600 mJ/$cm^2$). Furthermore, the three-dimensionally cultured epidermis was transferred to a plate to which 500 μl of a fresh assay medium had been added, and then further cultured under conditions of 37° C. and 5% $CO_2$ for 24 hours.

Subsequently, the three-dimensionally cultured epidermis was transferred to a well plate to each well of which 500 μl of alamarBlue® Reagent (manufactured by Thermo Fisher Scientific) solution (100-fold diluted with an assay medium) had been added, and further cultured under conditions of 37° C. and 5% $CO_2$ for 2 hours. Thereafter, the fluorescence intensity of the three-dimensionally cultured epidermis was measured by using a fluorophotometer (Ex/Em=570 nm/590 nm), and the cell viability was determined. In addition, the culture supernatant in the culture was used for quantification by ELISA for interleukin-1α (IL-1α: R&D Systems, Inc.) and prostaglandin E2 ($PGE_2$: manufactured by Cayman Chemical Company). For comparative examples, quantification was performed after the same operations except that irradiation with UVB was not performed or PBS(−) or an assay medium containing 40% glycerin was used in place of the assay medium containing the ozonized glycerin. FIG. 3-5 and FIG. 3-6 show the results.

Figures 1, 2, 3, 4, 5:
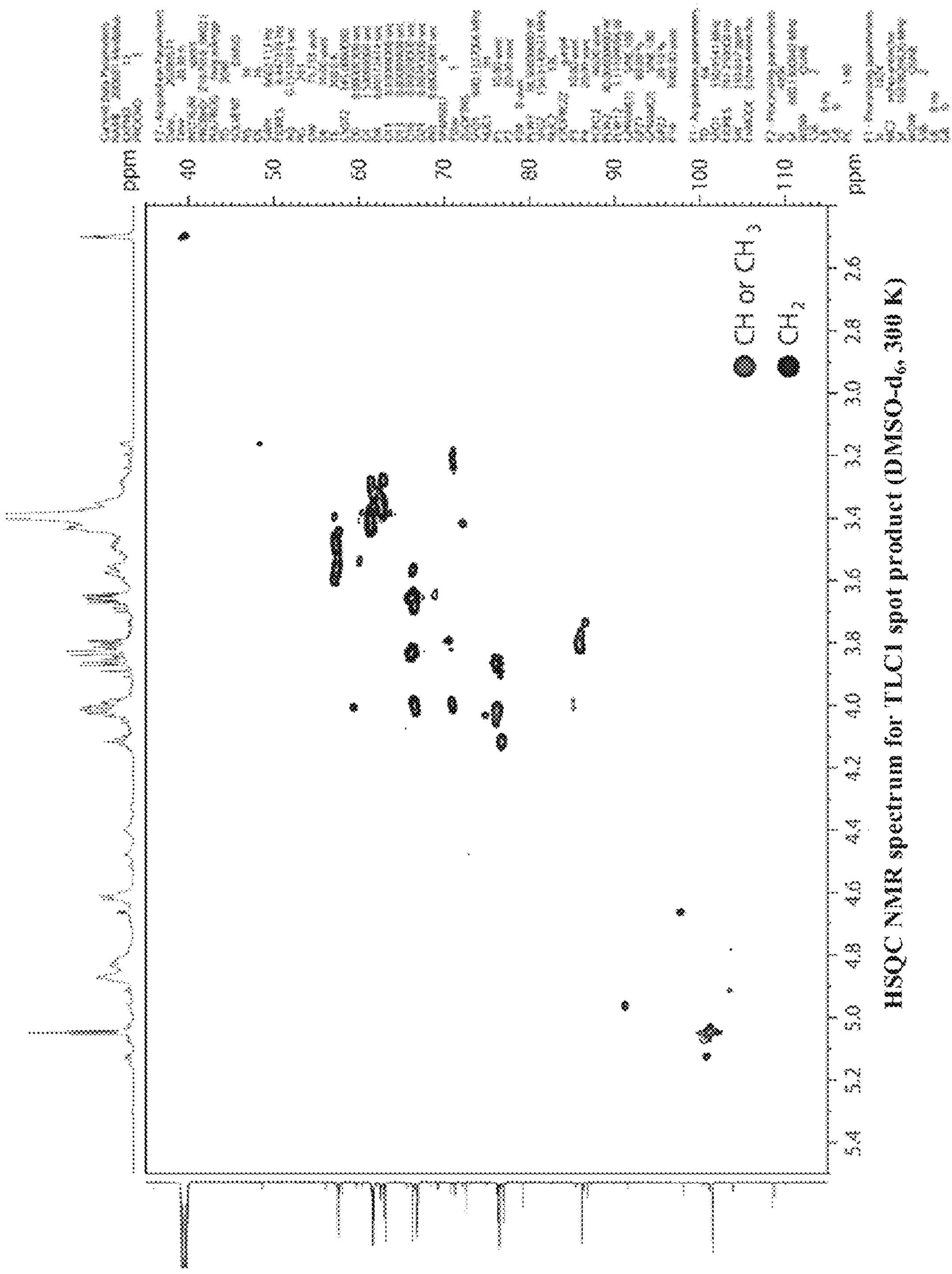

FIG. 3-5 is a graph showing production levels of IL-1α. FIG. 3-6 is a graph showing production levels of prostaglandin E2. In each of FIG. 3-5 and FIG. 3-6, the abscissa shows UV treatment, and sample types and concentrations, and the ordinate shows production levels of IL-1α or production levels of $PGE_2$. As shown in FIG. 3-5 and FIG. 3-6, the group treated with the ozonized glycerin (OG) exhibited lower production levels of IL-1α and lower production levels of $PGE_2$ than the group treated with the comparative group (Glycerin). These results revealed that the ozonized glycerin exhibits anti-inflammatory action. As shown later by comparison of components between the ozonized glycerin and the concentrated glycerin, the ozonized glycerin differed from the concentrated glycerin in that, for example, the ozonized glycerin contained a compound of a chemical formula (1) described later. Accordingly, it was concluded that the compound of the chemical formula (1) contained in the ozonized glycerin exhibits anti-inflammatory action.

Example 3-2

The active ingredient in the ozonized glycerin was confirmed to be a cyclic peroxide.

(1) Analysis of Reaction Mixture

To identify the active ingredient of the component for inducing expression of a skin barrier function-related gene in the ozonized glycerin, a cyclic peroxide that was not found for glycerin was extracted from the ozonized glycerin in Example 3-1(1), and analyzed. Glycerin was removed from the glycerin solution dissolving the ozone-oxidized form of glycerin therein, which had been produced in “Example 3-1(1) Production of the Oxidation Reaction Product Containing Cyclic Peroxide”, by using a silica gel column, and thus a reaction mixture containing the cyclic peroxide was obtained (hereinafter, occasionally referred to as “the TLC1 spot product”).

NMR spectra for the reaction mixture (TLC1 spot product) were determined with use of DMSO-$d_6$ as a solvent at a temperature of 300 K (27° C.). FIG. 3-7 to FIG. 3-12 show the spectrum diagrams. FIG. 3-7 is the $^1$H NMR spectrum diagram. FIG. 3-8 is the $^{13}$C NMR spectrum diagram. FIG. 3-9 is the $^{13}$C DEPT135 NMR spectrum diagram. FIG. 3-10 is the COSY NMR spectrum diagram. FIG. 3-11 is the HSQC NMR spectrum diagram. FIG. 3-12 is the HMBC NMR spectrum diagram. Complex peaks were observed as shown in FIG. 3-7 to FIG. 3-12, and hence the TLC1 spot product was expected to be a mixture of a plurality of substances. LCMS found that the TLC1 spot product contained a component of m/z 198,203.

(2) Separation and Analysis of Reaction Mixture

The reaction mixture (TLC1 spot product) was adjusted (diluted) to approximately 3% by mass with acetonitrile, and filtered through a membrane filter, and the resulting filtrate was subjected to LC measurement for optimization of separation conditions. Subsequently, peaks found in LC measurement under the optimized conditions were checked for mass, and precise separation was performed for Mw=180 (peak 2). Thereafter, the resulting fractionated solution was freeze-dried, and the dried product of the fraction was subjected to microscopic LR measurement and various NMR measurements. The measurement apparatuses (analyzers) and measurement conditions were as follows.

[Measurement Apparatuses (Analyzers)]

1) Precise preparative LC: Waters, ACQUITY UPLC H-class Bio
2) Microscopic LR: SNOM/AFM/Raman multifunction apparatus, alpha300RSA manufactured by WITec
3) NMR: Bruker Biospin, AVANCE III-600 with Cryo Probe

[Measurement Conditions]

1) Precise Preparative LC
Column: Shodex Asahipak NH2P-50 (4.6 mmφ×250 mm, 5 μm)
Composition of eluent: water/acetonitrile gradient
Time (min): 0 5 15 20
Water: 5 10 50 50
Acetonitrile: 95 90 50 50
Flow rate: 1.0 mL/min
Detector: MS (QDa)
Column temperature: 40° C.
Injection volume: 50 μL
Ionization method: ESI (NEG.)
Mass range in measurement (m/z): 50 to 500

2) Microscopic LR
Excitation wavelength: 532 nm
Wavelength range in measurement; approximately 125 to 3800 $cm^{-1}$
Objective lens: ×100
Detector: EMCCD 3) NMR
Observation frequency: 600 MHz ($^1$H), 150 MHz ($^{13}$C)
Solvent for measurement: methanol-$d_4$
Measurement temperature: 300 K
Chemical shift standard: solvent for measurement [3.30 ppm ($^1$H), 49.80 ppm ($^{13}$C)]

FIG. 3-13 shows total ion chromatograms (ESI-negative mode) from the precise preparative LC (liquid chromatography) for the sample and a blank, the sample being obtained by adjusting (diluting) the reaction mixture (TLC1 spot product) to approximately 3% by mass with acetonitrile. In FIG. 3-13, the ordinate shows intensity and the abscissa shows retention time (minutes). In FIG. 3-13, “Synthesized OG” in the bottom shows a chromatogram for the sample of the TLC1 spot product, and the top shows a chromatogram for the blank (acetonitrile). As shown in the figure, components of A to L were found from the TLC1 spot product. These components A to L were separated and checked for the presence or absence of coloring with potassium iodide starch test paper, and the result showed that component H exhibited the strongest coloring.

FIG. 3-14 shows mass spectra for peaks F, G, and H (fraction F, fraction G, and fraction H) in FIG. 3-13 in combination. In FIG. 3-14, the ordinate shows intensity and the abscissa shows mass-charge ratios (m/z). As shown in the figure, it was found that peak F had Mw=180, peak G had Mw=226, and peak H had Mw=256.

Moreover, FIG. 3-15 shows results of examination on improvement of separation (improvement of separation conditions) in HILIC (high-performance liquid chromatography). In FIG. 3-15, the ordinate shows intensity and the abscissa shows retention time (minutes), and the same applies to FIG. 3-23 to FIG. 3-25. In FIG. 3-15, the top is a chromatogram before improvement of separation (under the same conditions as for FIG. 3-14), and the bottom is a chromatogram after improvement of separation. As shown in the figure, peaks 1 to 8 were found after improvement of separation. The molecular weights of the peaks were confirmed to be those as shown in FIG. 3-15 from mass spectra shown later.

FIG. 3-16 shows mass spectra for peaks 1 to 3 in FIG. 3-15 (after improvement of separation). In FIG. 3-16, the top, middle, and bottom are mass spectra for peak 1, peak 2, and peak 3, respectively. As shown in the figure, it was found that peak 1 had Mw=196, peak 2 had Mw=180, and peak 3 had Mw=240.

FIG. 3-17 shows mass spectra for peaks 4 to 6 in FIG. 3-15 (after improvement of separation). In FIG. 3-17, the top, middle, and bottom are mass spectra for peak 4, peak 5, and peak 6, respectively. As shown in the figure, it was found that peak 4 had Mw=240, peak 5 had Mw=240, and peak 6 had Mw=226.

FIG. 3-18 shows mass spectra for peaks 7 and 8 in FIG. 3-15 (after improvement of separation). In FIG. 3-18, the top and bottom are mass spectra for peak 7 and peak 8, respectively. As shown in the figure, it was found that peaks 7 and 8 both had Mw=256.

FIG. 3-19 shows micro-Raman spectrum diagrams for a separated sample obtained from peak 2 (Mw=180) in FIG. 3-15 and an ozonide authentic sample (ozonized oleic acid) in combination. In FIG. 3-19, the ordinate shows intensity and the abscissa shows Raman shifts (1/cm). As shown in FIG. 3-19, peak 2 (Mw=180) exhibited a micro-Raman spectrum similar to that for ozonide, and hence expected to have a structure similar to that of ozonide. The micro-Raman spectrum for peak 2 (Mw=180) exhibited a pattern differing from that for peroxide, and hence peak 2 (Mw=180) was expected not to correspond to peroxide. From NMR shown later, peak 2 (Mw=180) was found to correspond to the cyclic peroxide.

FIG. 3-20 shows a $^{1}H$ NMR spectrum diagram for peak 2 (Mw=180) in FIG. 3-15. Methanol-$d_4$ ($CD_3OD$) was used for the solvent for measurement. In the figure, the top spectrum diagram is an enlarged view of a part around 3.4 to 4.9 ppm in the bottom spectrum diagram. From the attribution of the $^{1}H$ NMR, the result of Mw=180, and other instrumental analysis data, the structure of the oxidation reaction product for peak 2 (Mw=180) was demonstrated to be that of a cyclic peroxide represented by a chemical formula (1) below. The peaks indicated with signs A to F in the $^{1}H$ NMR spectrum diagram in FIG. 3-20 were attributed to peaks for hydrogen atoms bound to the carbon atoms indicated with the same signs A to F in a chemical formula (1) below, which is shown in FIG. 3-20. It was expected that a slight amount of the raw material glycerin remained, and the peak was also detected.

[Chemical Formula 1M]

(1)

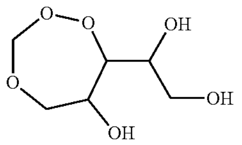

Molecular Weight: 180.16

FIG. 3-21 shows a $^{13}C$ NMR spectrum diagram for peak 2 (Mw=180) in FIG. 3-15.Methanol-$d_4$ ($CD_3OD$) was used for the solvent for measurement. In the figure, the top spectrum diagram is an enlarged view of a part around 60 to 105 ppm in the bottom spectrum diagram. From the attribution of the $^{13}C$ NMR, the result of Mw=180, and other instrumental analysis data, the structure of the oxidation reaction product for peak 2 (Mw=180) was demonstrated to be that of the cyclic peroxide represented by the chemical formula (1). The peaks indicated with signs A to F in the $^{13}C$ NMR spectrum diagram in FIG. 3-21 were attributed to peaks for the carbon atoms indicated with the same signs A to F in a chemical formula (1) below, which is shown in FIG. 3-21. It was expected that a slight amount of the raw material glycerin remained, and the peak was also detected.

FIG. 3-22 shows a two-dimensional ($^{1}H$-$^{13}C$ COSY) NMR spectrum diagram for peak 2 (Mw=180) in FIG. 3-15. Methanol-$d_4$ ($CD_3OD$) was used for the solvent for measurement. From the attribution of the two-dimensional NMR, the result of Mw=180, and other instrumental analysis data, the structure of the oxidation reaction product for peak 2 (Mw=180) was demonstrated to be that of the cyclic peroxide represented by the chemical formula (1). The peaks indicated with signs A to F in the two-dimensional NMR spectrum diagram in FIG. 3-22 were attributed to peaks for the carbon atoms indicated with the same signs A to F and hydrogen atoms bound to the carbon atoms in a chemical formula (1) below, which is shown in FIG. 3-22. It was expected that a slight amount of the raw material glycerin remained, and the peak was also detected.

FIG. 3-23 shows HILIC chromatograms for the TLC1 spot product and glyceraldehyde dimer under the HILIC (high-performance liquid chromatography) conditions in FIG. 3-15 in combination. In FIG. 3-23, the "Synthesized OG" in the top shows a HILIC chromatogram for the TLC1 spot product. The bottom is a HILIC chromatogram for glyceraldehyde dimer. As shown in the figure, no glyceraldehyde dimer was detected under the HILIC conditions in FIG. 3-23.

FIG. 3-24 shows HILIC chromatograms for the TLC1 spot product and glyceraldehyde dimer under reversed-phase HILIC (high-performance liquid chromatography) conditions in combination. FIG. 3-25 shows an enlarged view of a part of FIG. 3-24. The "Synthesized OG" in the top in each of FIG. 3-24 and FIG. 3-25 is a HILIC chromatogram for the TLC1 spot product. The bottom is a HILIC chromatogram for glyceraldehyde dimer. As shown in the figures, the component separation of the TLC1 spot product was not found under the reversed-phase HILIC conditions. This was probably because the retention power of the column was weak and as a result the elution time of the TLC1 spot product was short. On the other hand, the retention time of glyceraldehyde dimer was slightly different from that of the TLC1 spot product (Synthesized OG). From the results, the TLC1 spot product was inferred to contain no glyceraldehyde dimer.

FIG. 3-26 shows ESR spectrum diagrams for the TLC1 spot product and peak 2 (Mw=180) in FIG. 3-15 in combination. In FIG. 3-26, the ordinate shows intensity and the abscissa shows magnetic flux density (G). Water was used for the solvent for measurement. As shown in the figure, the spectrum for the TLC1 spot product and that for the peak 2 (Mw=180) component in FIG. 3-15 almost completely matched, and the positions of the appearance of peaks in the former were almost identical to those in the latter. The TLC1 spot product and the peak 2 (Mw=180) component in FIG. 3-15 both exhibited a spectrum for DMPO (spin-trapping agent), the spectrum characterized by six lines. This spectral pattern is similar to that for ozonide.

FIG. 3-27 shows an ESR spectrum diagram for ozonized methyl linolenate. Acetone was used for the solvent for measurement. Ozonized methyl linolenate is a known ozonide. As shown in the figure, the ESR spectrum diagram for ozonized methyl linolenate exhibited a spectrum for DMPO (spin-trapping agent), the spectrum characterized by six lines characteristic to ozonide. This spectral pattern is similar to those for the TLC1 spot product and peak 2 (Mw=180) in FIG. 3-26.

FIG. 3-28 shows ESR spectrum diagrams for peaks 1 to 8 in FIG. 3-15. Water was used for the solvent for measurement. The uppermost is an ESR spectrum diagram for a blank (only the solvent) for comparison. As shown in the figure, the components of peaks 1 to 8 were all found to have radical activity.

The graph in FIG. 3-29 shows results of measurement of activity for peaks 1 to 8 in FIG. 3-15 through chemiluminescence. In the figure, the ordinate shows all-wavelength emission intensity (relative intensity). The numbers “1” to “8” in the abscissa indicate fractions of peaks 1 to 8. The numerical values under the numbers indicate the molecular weights of the fractions found from mass spectra. As shown in the figure, it was found from the chemiluminescence that components with activity were generated in addition to the component having a molecular weight of 180.

Example of Fourth Mode

Fourth, Example 4 will be described. However, the fourth mode of the present invention is not limited to the example below. Commercially available reagents were used in accordance with their protocols, unless otherwise specified.

Example 4-1

An oxidation reaction product containing the cyclic peroxide was produced through ozone oxidation of glycerin. Then, the oxidation reaction product produced was examined for anti-glycation action. The present example corresponds to an example of production and use of the cyclic peroxide, and to an example of production and use of the oxidation reaction product, and further to an example of the method for producing an oxidation reaction product.

(1) Production of the Oxidation Reaction Product Containing Cyclic Peroxide

Concentrated glycerin and ozone were brought into gas-liquid contact, and an ozone-treated glycerin solution containing the oxidation reaction product (ozonized glycerin) was produced in a manner shown below. Here, the concentrated glycerin was a product containing glycerin at a concentration of 98% by weight or more in accordance with the Japanese Pharmacopeia. The oxidation reaction product according to the fourth mode of the present invention, an oxidation reaction product produced in the present example, contained the cyclic peroxide according to the fourth mode of the present invention, as described later.

A Teflon® tank having a capacity of 50 L was used as a contactor. An air diffuser was set on the bottom of the tank so that ozone could be fed as fine bubbles into the tank. A gas of high oxygen concentration, which contained oxygen at a concentration as high as 90% by volume or more, was used as a raw material, and a silent discharge ozone generator capable of generating 100 g of ozone per hour was used.

The tank was charged with 22 kg of the concentrated glycerin, the gas of high oxygen concentration was sent to the ozone generator at 20 L per minute to generate a gas containing ozone, and the gas generated was released into the tank via the air diffuser for 7 days or more to give a glycerin solution dissolving an ozone-oxidized form of glycerin therein at a final concentration of 4000 ppm. The ozone-oxidized form of glycerin corresponds to the oxidation reaction product. As described later, the cyclic peroxide was contained in that ozone-oxidized form. The ozone-oxidized form of glycerin containing the peroxide was examined for decomposition activity to AGEs.

(2) Examination on Cleavage Activity to Crosslinking Structures Formed by AGEs

Cleavage activities to crosslinking structures formed by AGEs were measured in accordance with Reference 1 (Sara Vasan et al. Nature, 382, pp. 275-278 (1996)). Specifically, 1-phenyl-1,2-propanedione (PPD), which is a reaction substrate for an AGEs crosslinking model having an α-diketone structure, was used as a substrate, and cleavage activities to crosslinking structures formed by AGEs were measured by detecting cleavage of PPD. As a positive control, N-phenacylthiazolium bromide (PTB) was used, which is known to have cleavage activity to crosslinking structures formed by AGEs.

Mixed were 100 μl of sample solution shown below (n=5), 20 μl of 10 mmol/L PPD (solvent: 50% acetonitrile), and 80 μl of 2 mol/l phosphate buffer (pH 7.4), and reacted at 37° C. for 2 hours. After the reaction, 40 μl of 2 mol/l hydrochloric acid was added to each of the resulting reaction solutions to terminate the reaction. After the termination of the reaction, 20 μl of 100 mmol/l sodium dehydroacetate was added as an internal standard to each of the reaction solutions.

(Sample Solutions)

- Diluted solutions of ozonized glycerin: solutions obtained by diluting the ozonized glycerin in Example 4-1(1) with water to reach an ozone-oxidized form concentration of 10, 100, or 1000 ppm
- Concentrated glycerin solution
- 5 or 10 mmol/l PTB (solvent: 50% acetonitrile)
- Hydrogen peroxide solutions: solutions obtained by diluting with water to reach an $H_2O_2$ concentration of 1 or 10 mmol/l Subsequently, the mixed solutions obtained were centrifuged at 20° C. and 3,000×g for 10 minutes, and a 20-μl portion of each supernatant was collected as a measurement sample, and the amounts of benzoic acid in the measurement samples were analyzed by reversed-phase HPLC. The reversed-phase HPLC performed was under measurement conditions shown below. Measurement samples each containing benzoic acid at a known concentration were analyzed in the same manner.

(Measurement Conditions for Reversed-Phase HPLC)

Column: Cadenza CD-C18 75 mm×4.6 mmID (manufactured by Imtakt Corporation)

Mobile phase: 0.2% acetic acid/acetonitrile (70:30) (containing 2 mmol/l EDTA-2Na)

Flow rate: 1 ml/min

Measurement wavelength: 230 nm

A calibration curve was prepared from peak areas of chromatograms acquired from the measurement samples each containing benzoic acid at a known concentration (benzoic acid: 2.4 minutes), and the benzoic acid contents of the measurement samples derived from the different sample solutions were quantified. To subtract background benzoic acid contents, the sample solutions were subjected to quantification in the same manner. On the assumption that 1 mol of PPD generates 1 mol of benzoic acid, anti-glycation rates (crosslink cleavage rates) were calculated from an expression (1) below. FIG. 4-1 shows the results.

$$\text{Anti-glycation rate (\%)} = \{(A - B)/C\} \times 100 \quad (1)$$

A: Amount of benzoic acid in measurement sample

B: Amount of benzoic acid in sample solution

C: Amount of reacted PPD (amount of substrate)

FIG. 4-1 is a graph showing anti-glycation rates. In FIG. 4-1, the abscissa shows sample solution types and concentrations, and the ordinate shows anti-glycation rates. As shown in FIG. 4-1, the ozonized glycerin exhibited concentration-dependent increase in the anti-glycation rate. The ozonized glycerin exhibited anti-glycation rates comparable to or higher than those for the positive controls PTB and hydrogen peroxide solutions ($H_2O_2$). These results revealed that the ozonized glycerin exhibits very strong cleavage activity to crosslinking structures formed by AGEs, in other words, anti-glycation activity. As shown later by comparison of components between the ozonized glycerin and the concentrated glycerin, the ozonized glycerin differed from the concentrated glycerin in that, for example, the ozonized glycerin contained a compound of a chemical formula (1) described later. Accordingly, it was demonstrated that the compound of the chemical formula (1) contained in the ozonized glycerin exhibits anti-glycation activity.

Thus, the oxidation reaction product containing the cyclic peroxide obtained through ozone oxidation of glycerin, specifically, the compound of the chemical formula (1) was revealed to exhibit anti-glycation activity.

Example 4-2

The active ingredient in the ozonized glycerin was confirmed to be a cyclic peroxide.

(1) Analysis Reaction Mixture

To identify the active ingredient of the anti-glycation component in the ozonized glycerin, a cyclic peroxide that was not found for glycerin was extracted from the ozonized glycerin in Example 4-1(1), and analyzed. Glycerin was removed from the glycerin solution dissolving the ozone-oxidized form of glycerin therein, which had been produced in “Example 4-1(1) Production of the Oxidation Reaction Product Containing Cyclic Peroxide”, by using a silica gel column, and thus a reaction mixture containing the cyclic peroxide was obtained (hereinafter, occasionally referred to as “the TLC1 spot product”).

Figures 1, 2, 3, 4, 5, 6:
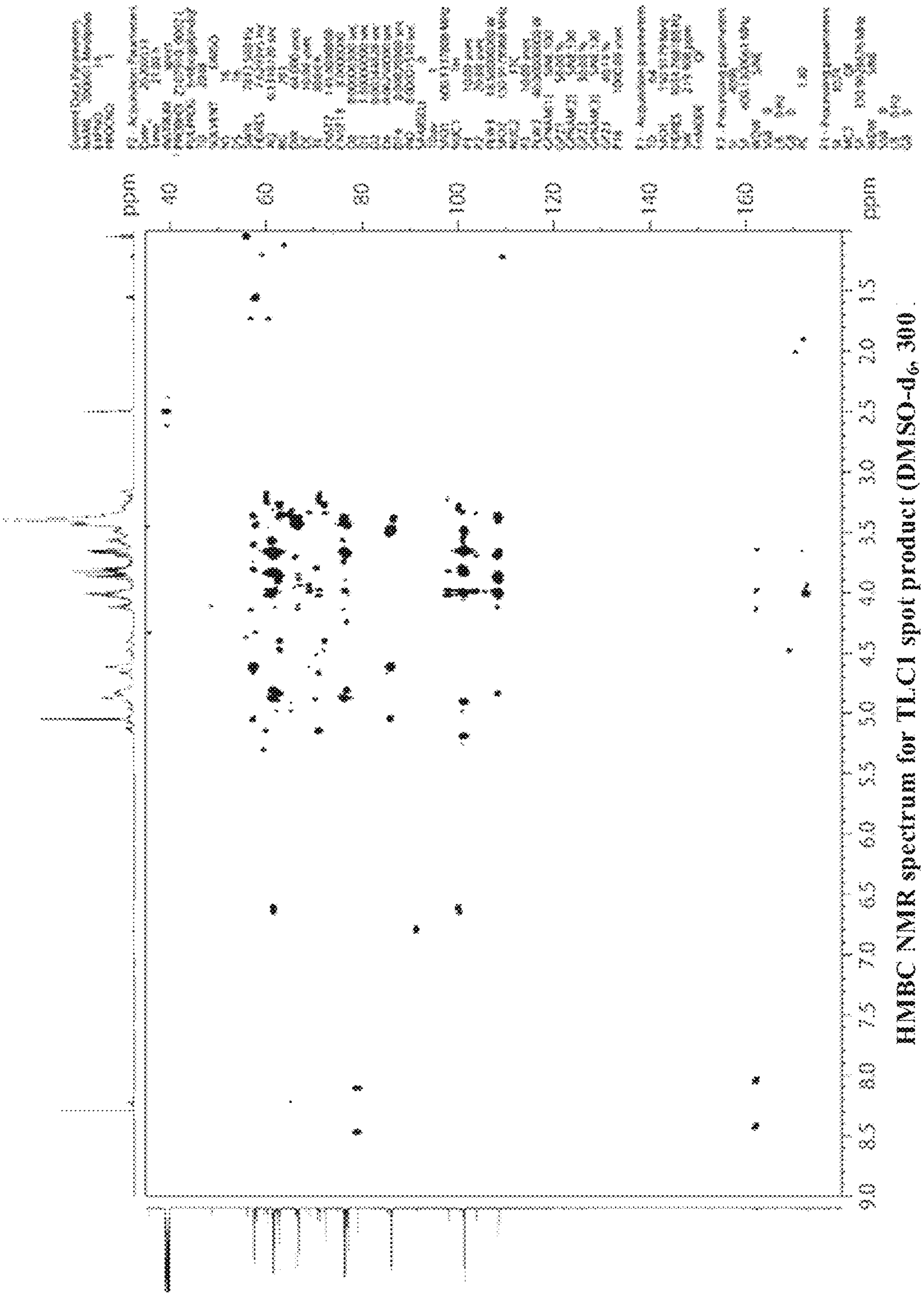
Figures 1, 2, 3, 4, 5, 6, 7:
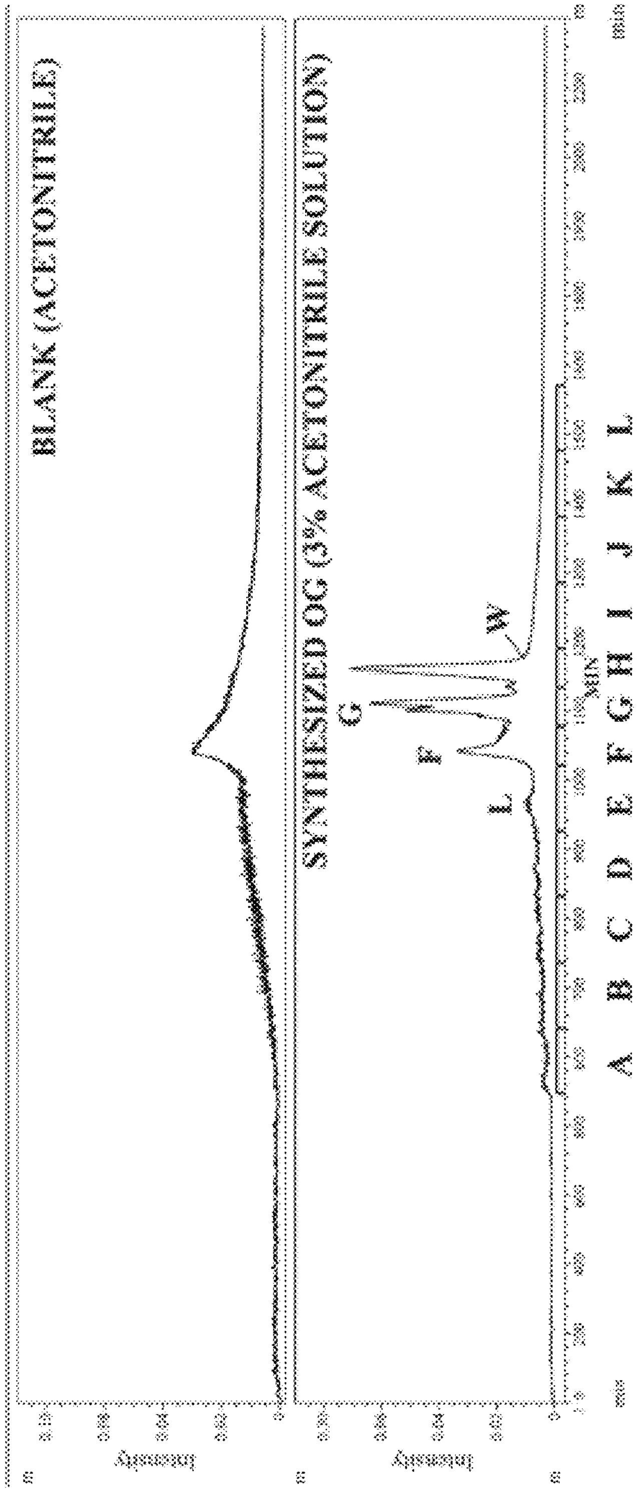
Figures 1, 2, 3, 4, 5, 6, 7, 8:
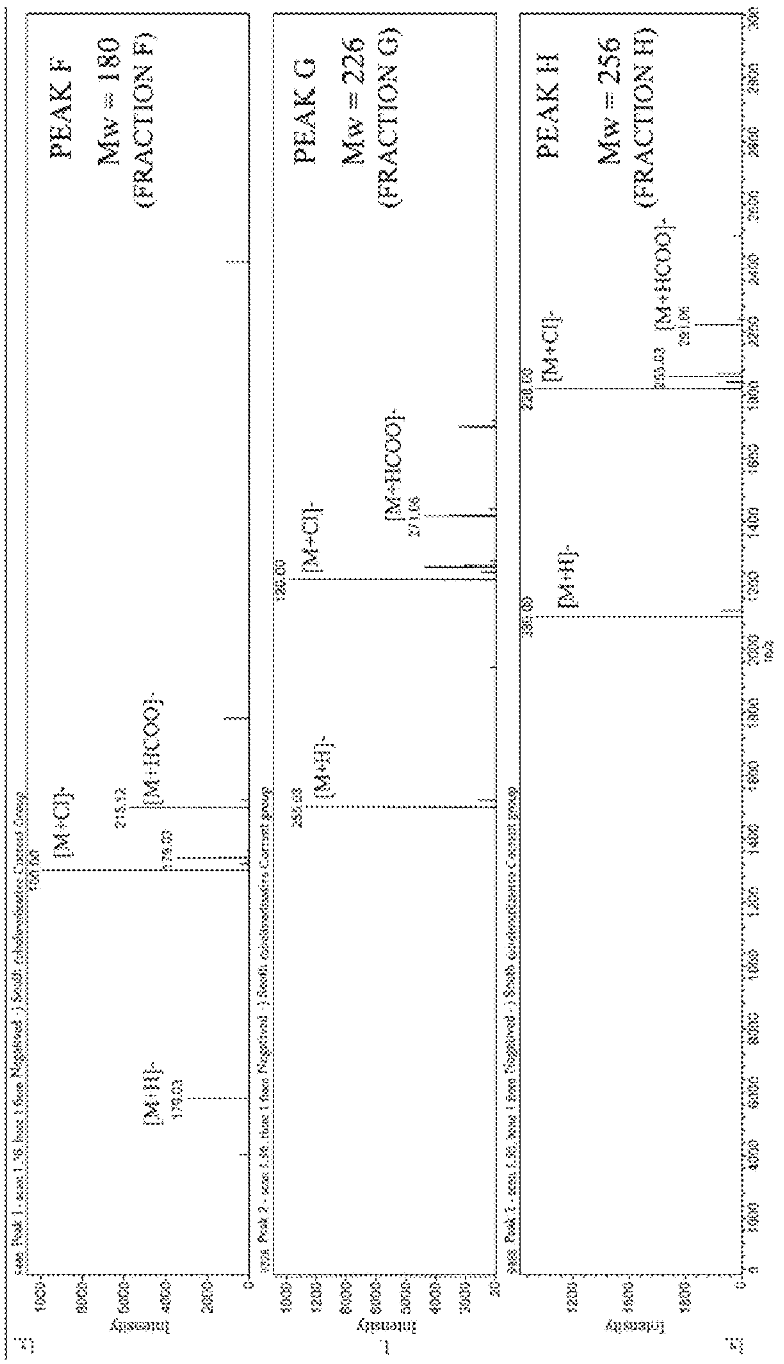
Figures 1, 2, 3, 4, 5, 6, 7, 8, 9:
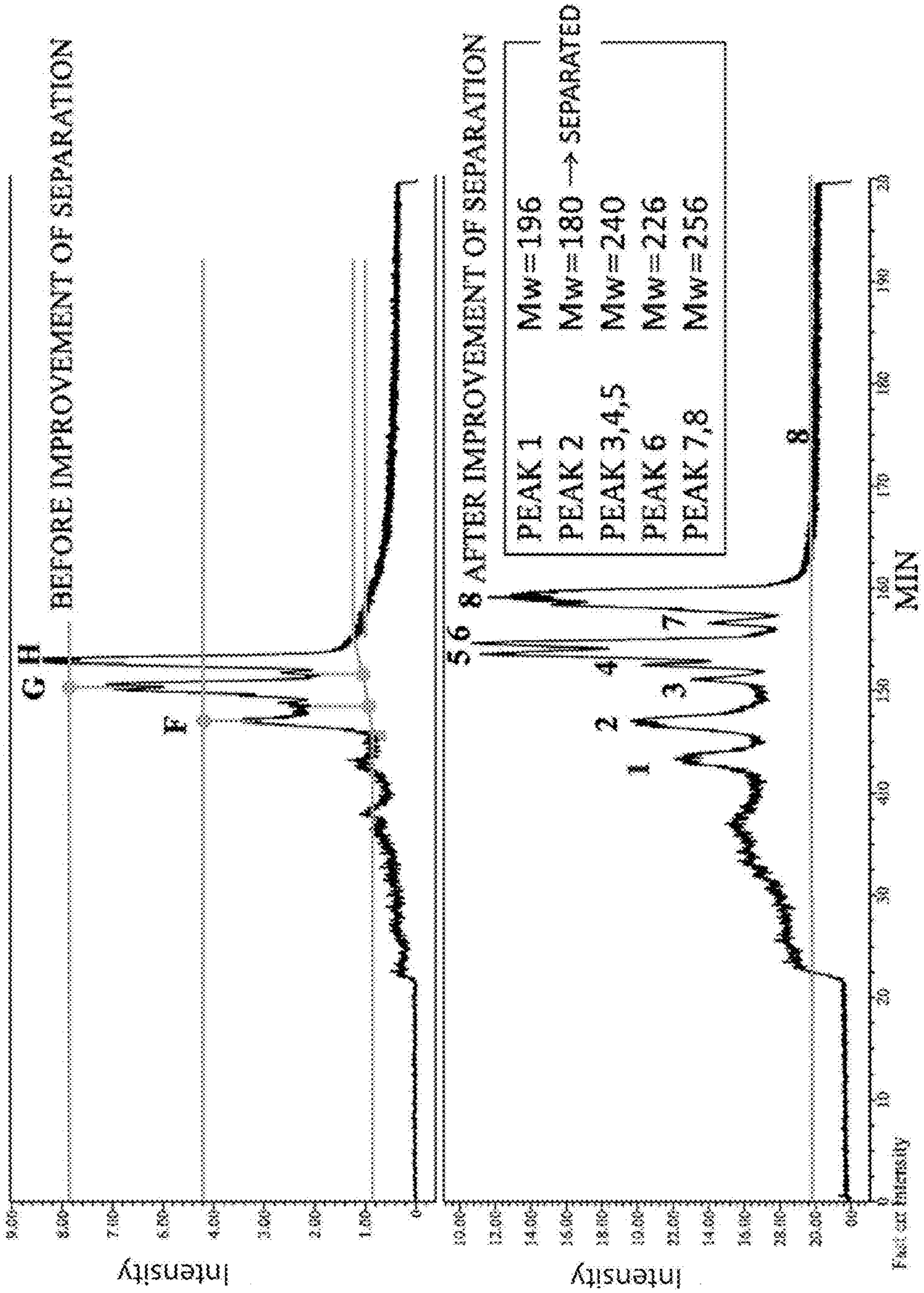
Figures 1, 2, 3, 4, 5, 6, 7, 8, 9, 10:
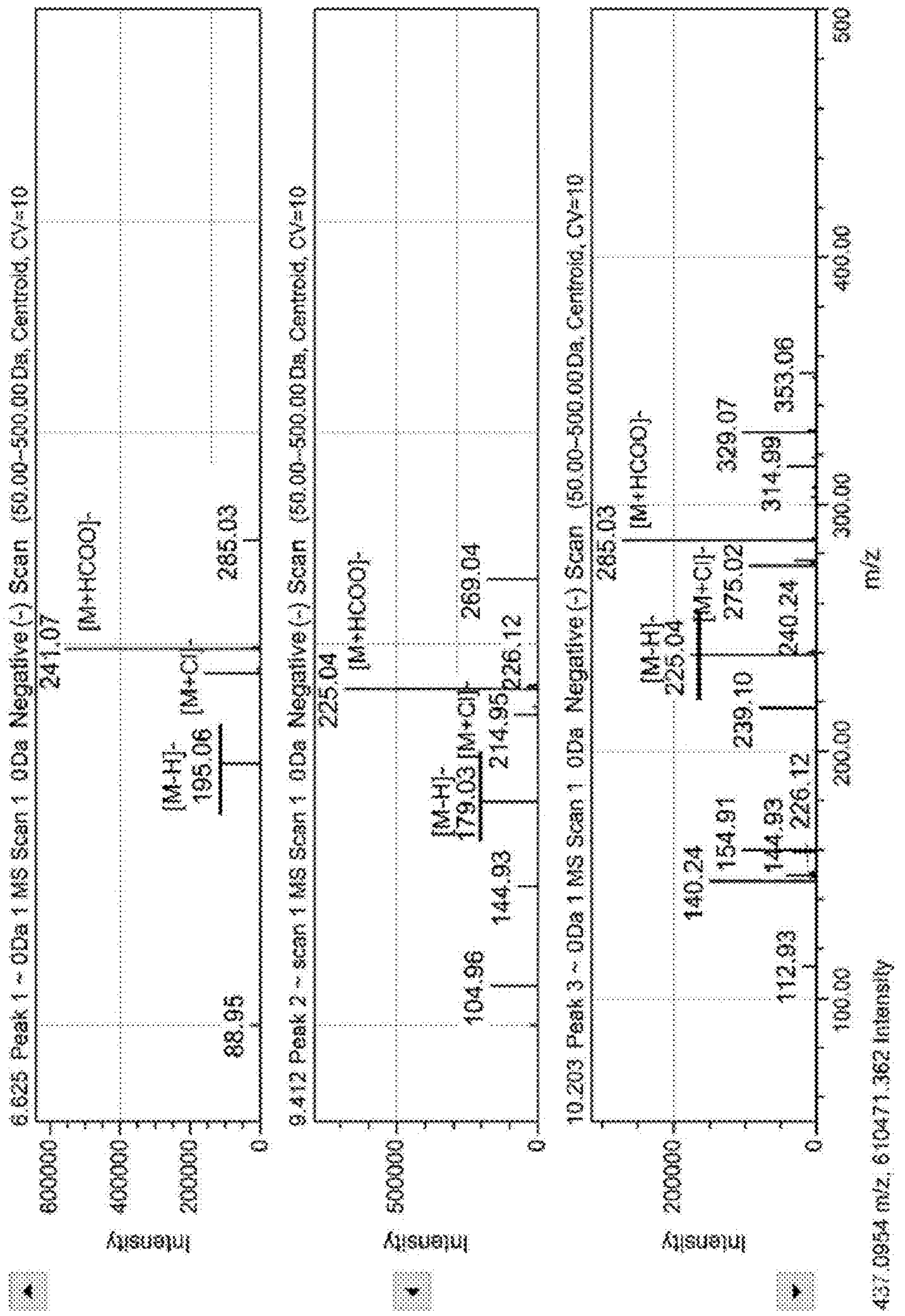
Figures 1, 2, 3, 4, 5, 6, 7, 8, 9, 10, 11:
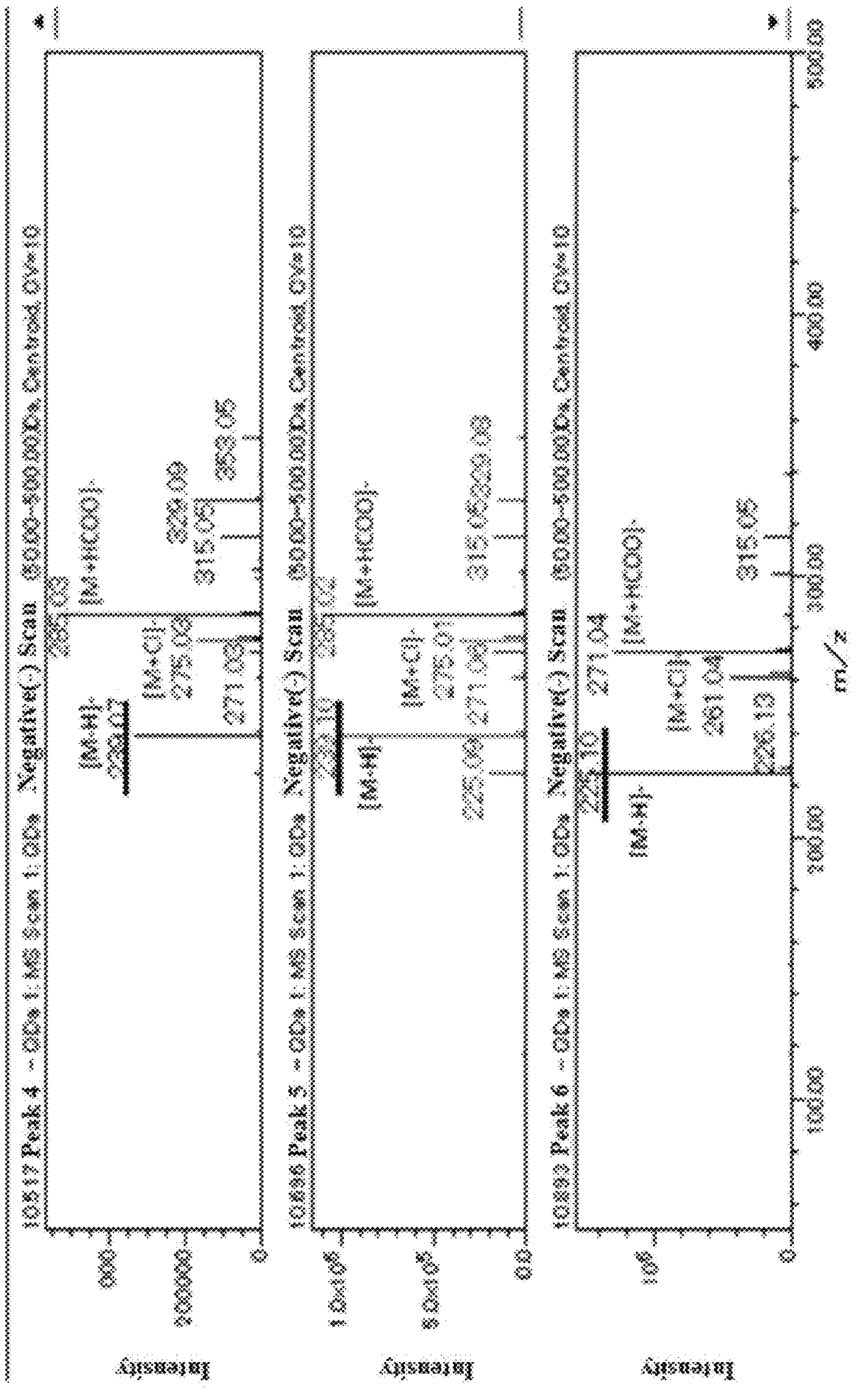
Figures 1, 2, 3, 4, 5, 6, 7, 8, 9, 10, 11, 12:
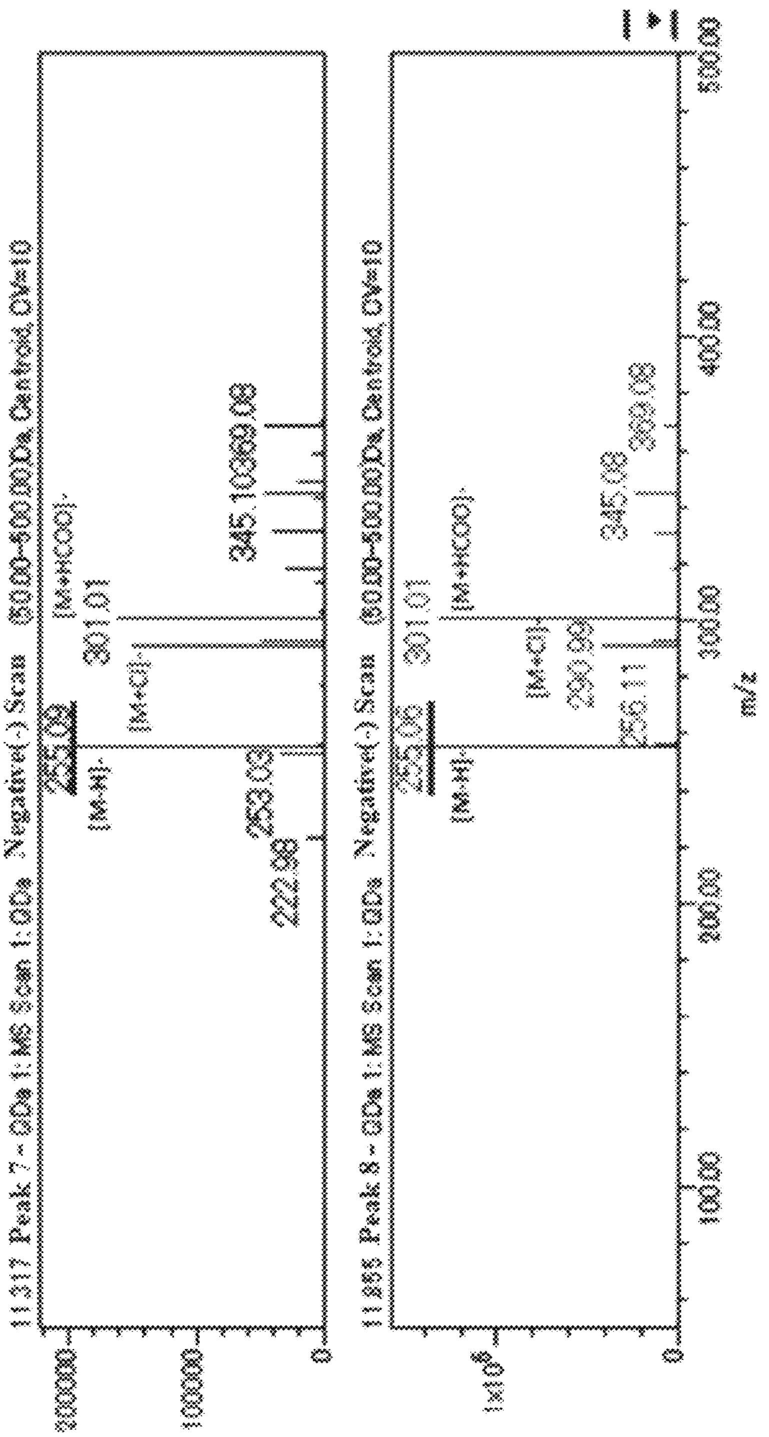
Figures 1, 2, 3, 4, 5, 6, 7, 8, 9, 10, 11, 12, 13:
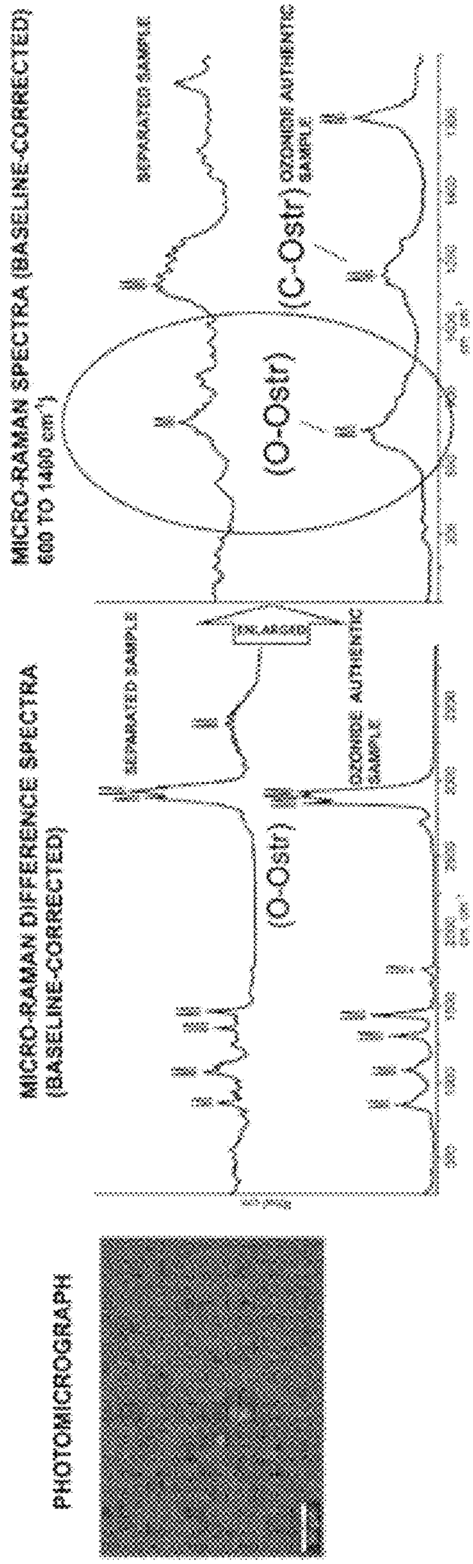
Figures 1, 2, 3, 4, 5, 6, 7, 8, 9, 10, 11, 12, 13, 14:
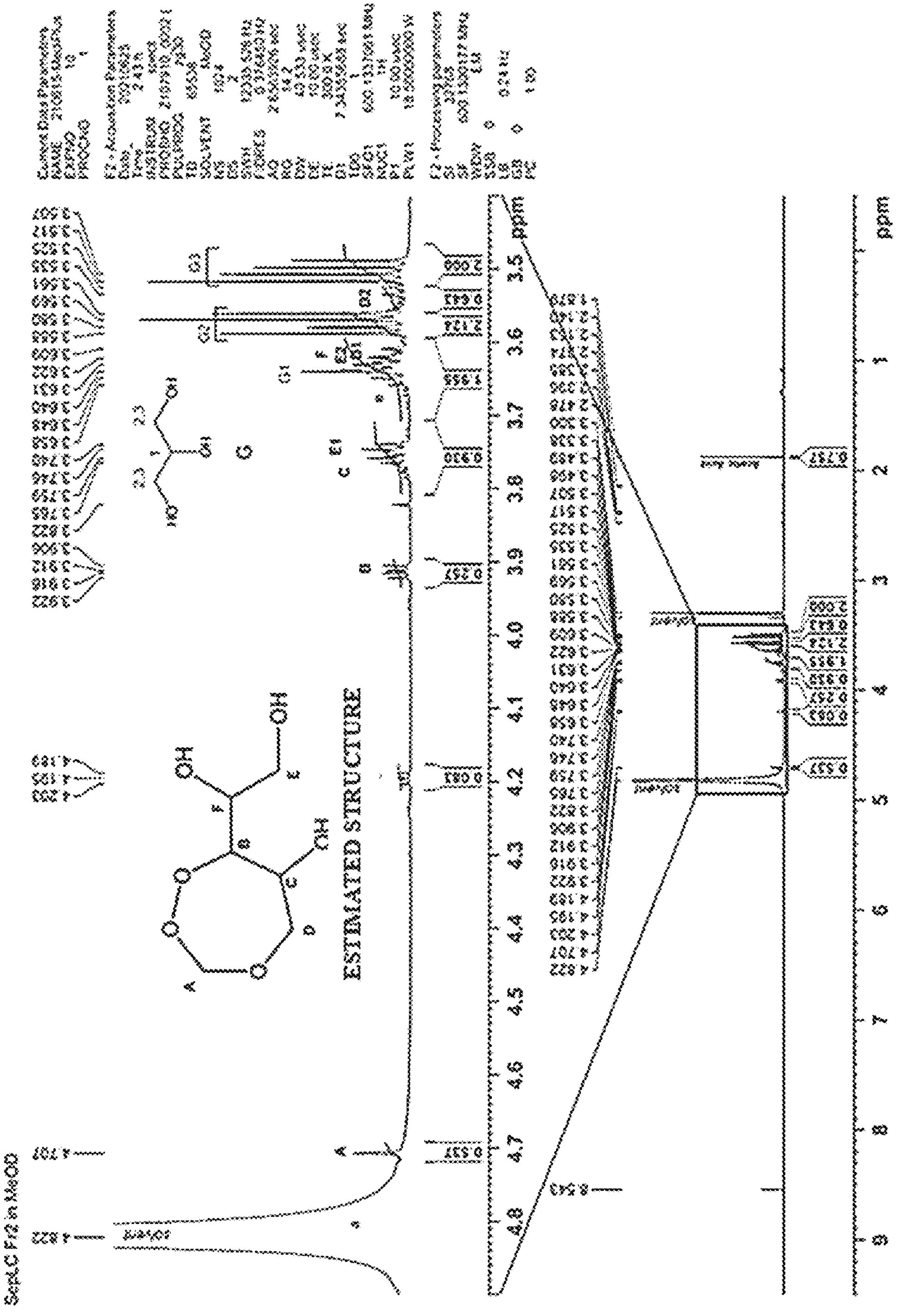
Figures 1, 2, 3, 4, 5, 6, 7, 8, 9, 10, 11, 12, 13, 14, 15:
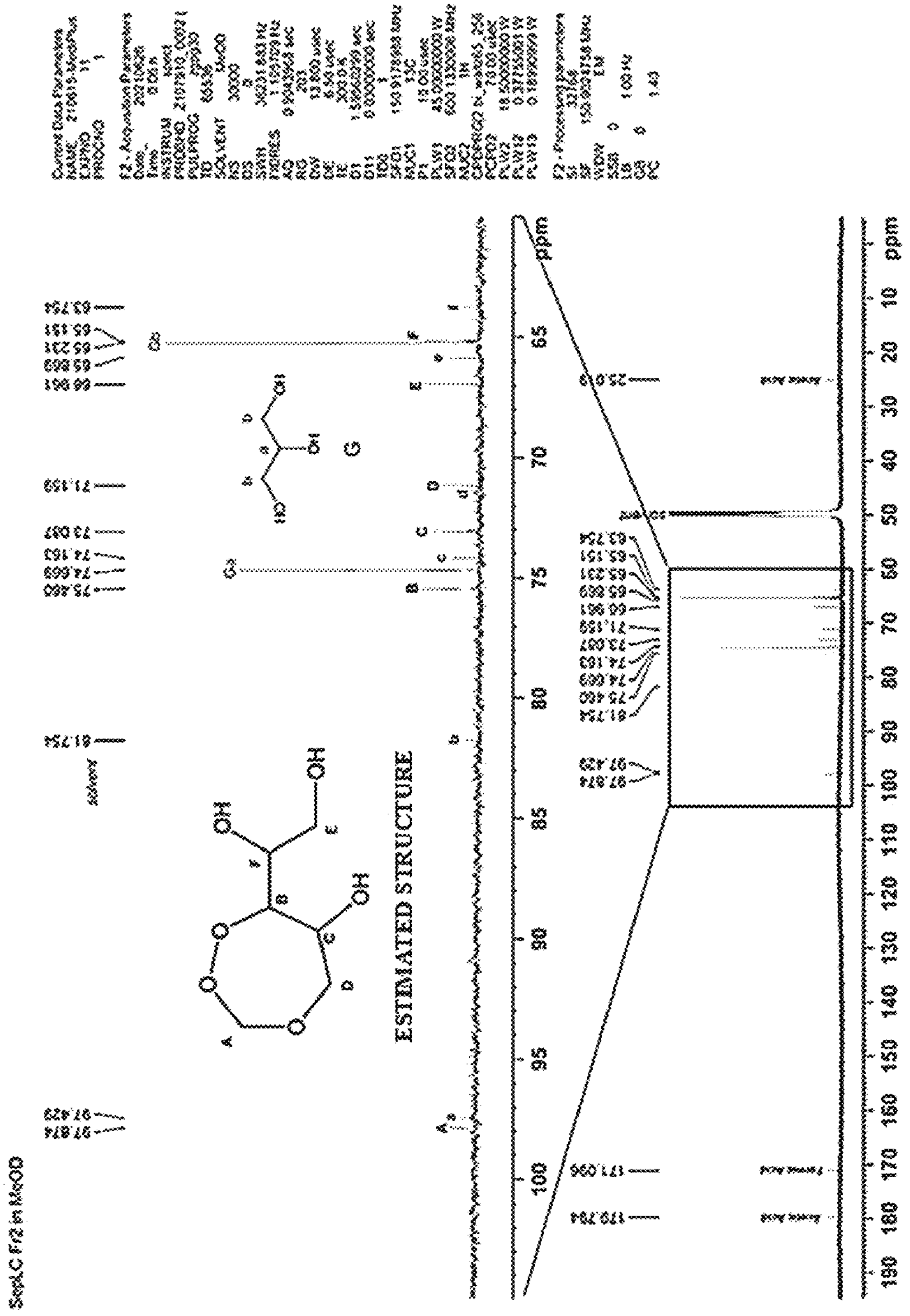
Figures 1, 2, 3, 4, 5, 6, 7, 8, 9, 10, 11, 12, 13, 14, 15, 16:
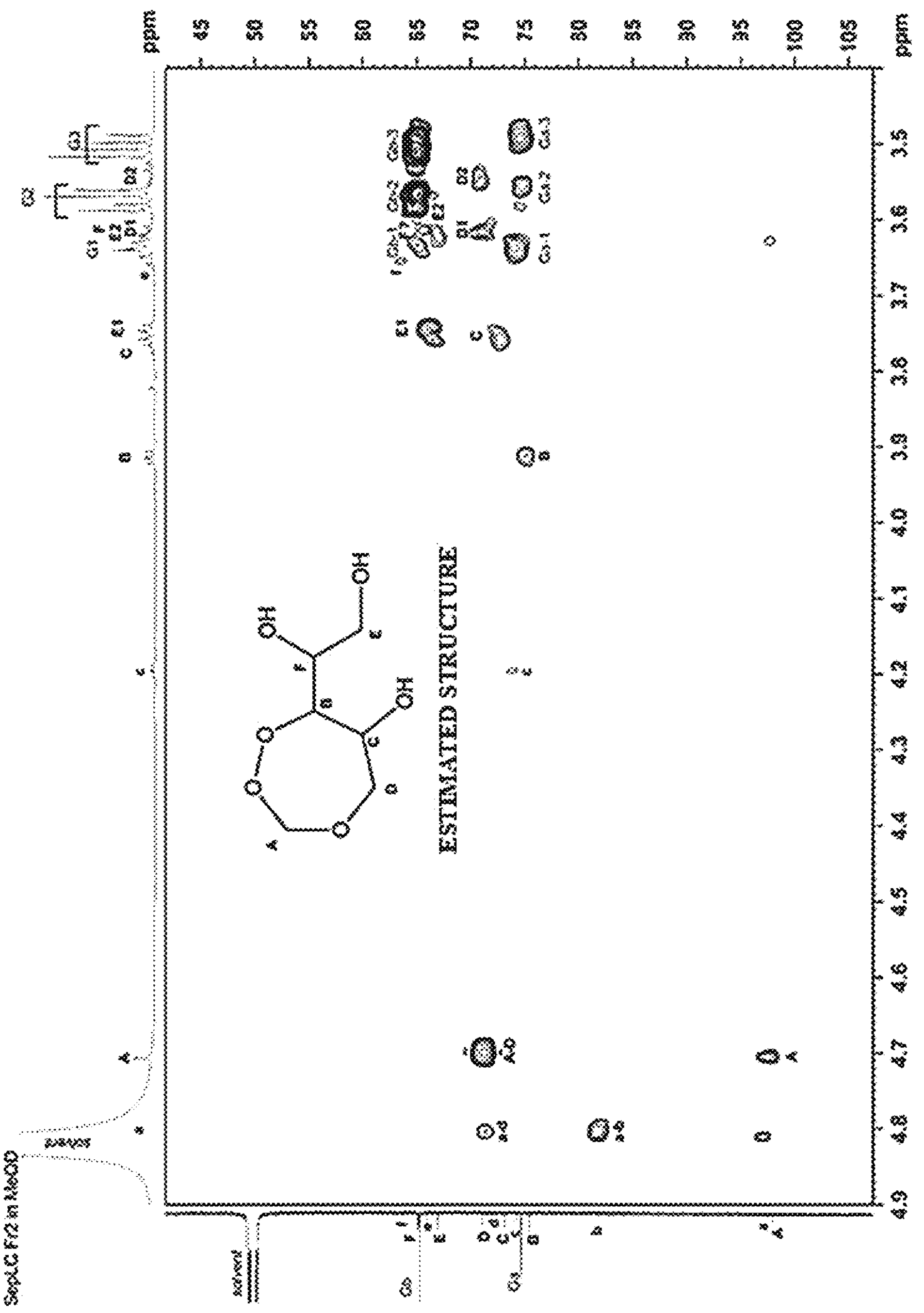
Figures 1, 2, 3, 4, 5, 6, 7, 8, 9, 10, 11, 12, 13, 14, 15, 16, 17:
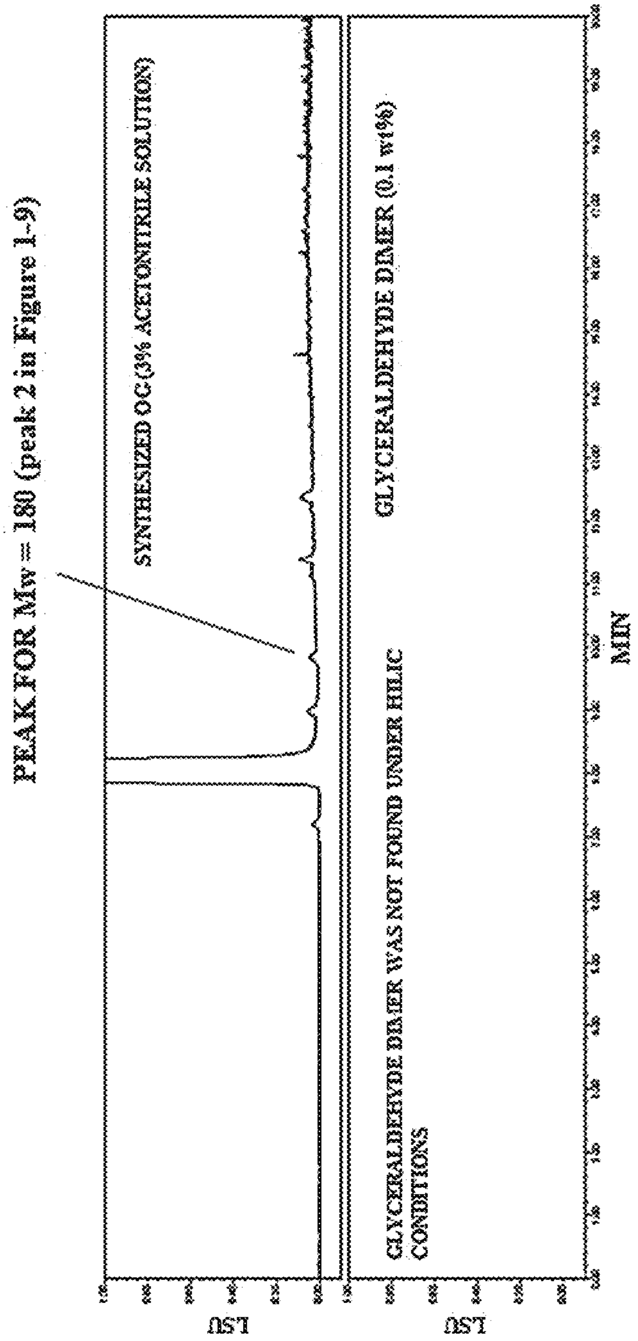
Figures 1, 2, 3, 4, 5, 6, 7, 8, 9, 10, 11, 12, 13, 14, 15, 16, 17, 18:
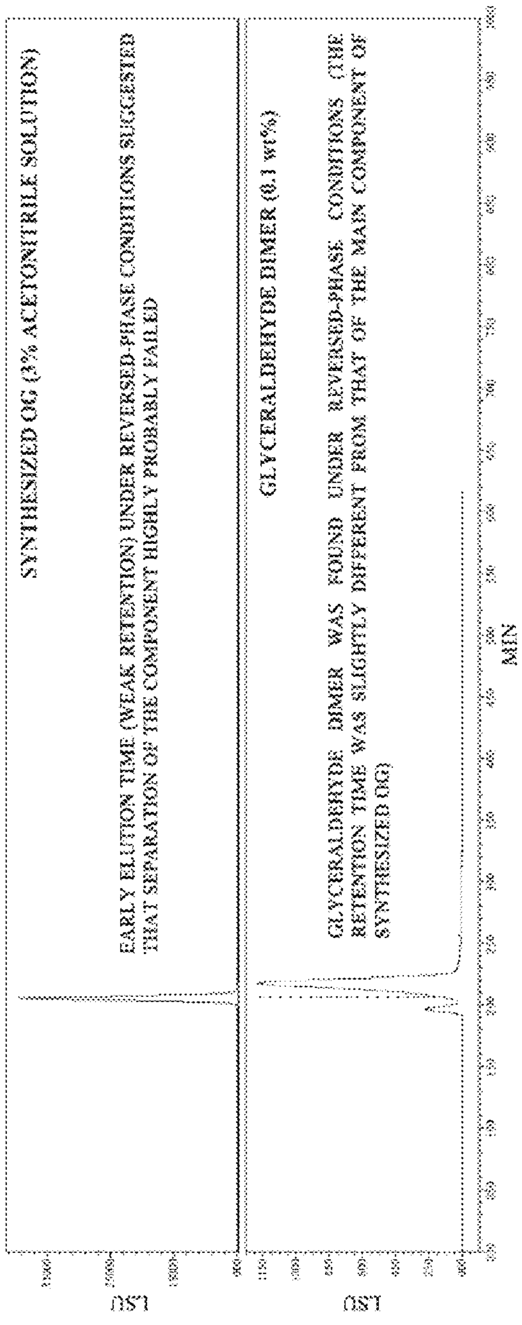
Figures 1, 2, 3, 4, 5, 6, 7, 8, 9, 10, 11, 12, 13, 14, 15, 16, 17, 18, 19:
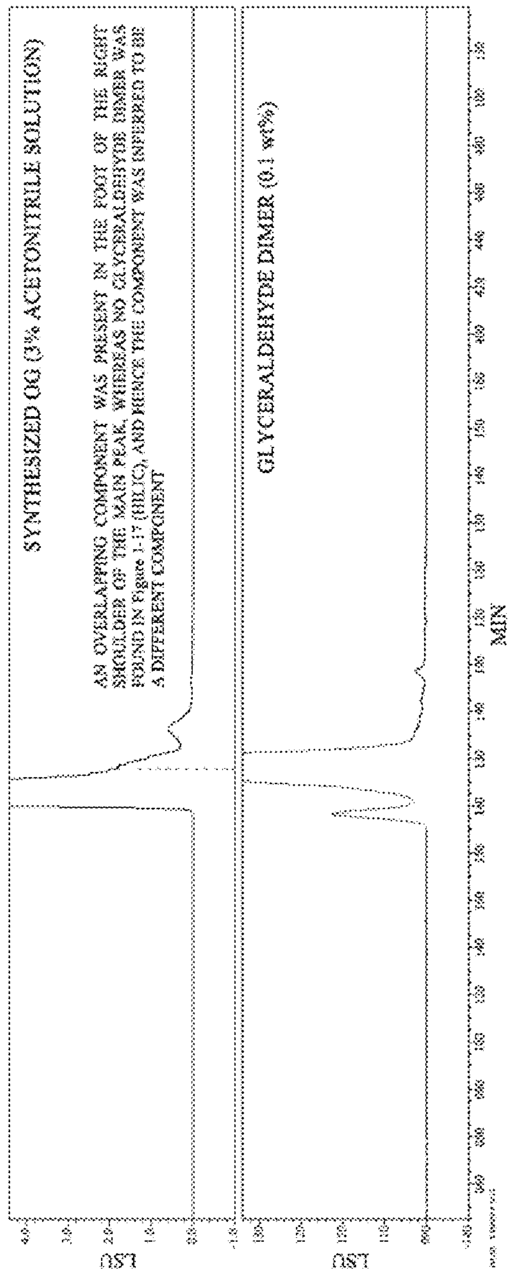
Figures 1, 2, 3, 4, 5, 6, 7, 8, 9, 10, 11, 12, 13, 14, 15, 16, 17, 18, 19, 20:
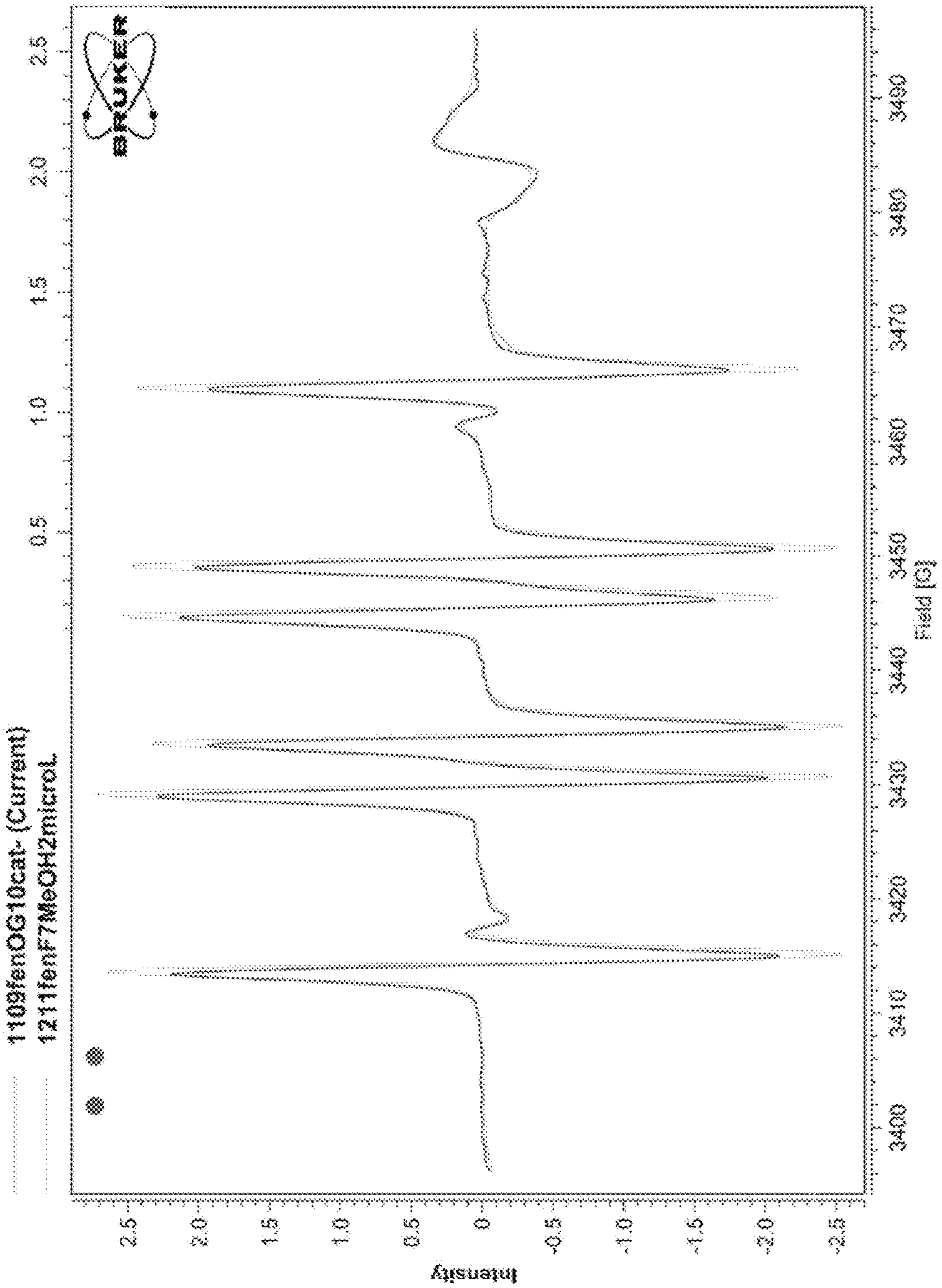
Figures 1, 2, 3, 4, 5, 6, 7, 8, 9, 10, 11, 12, 13, 14, 15, 16, 17, 18, 19, 20, 21:
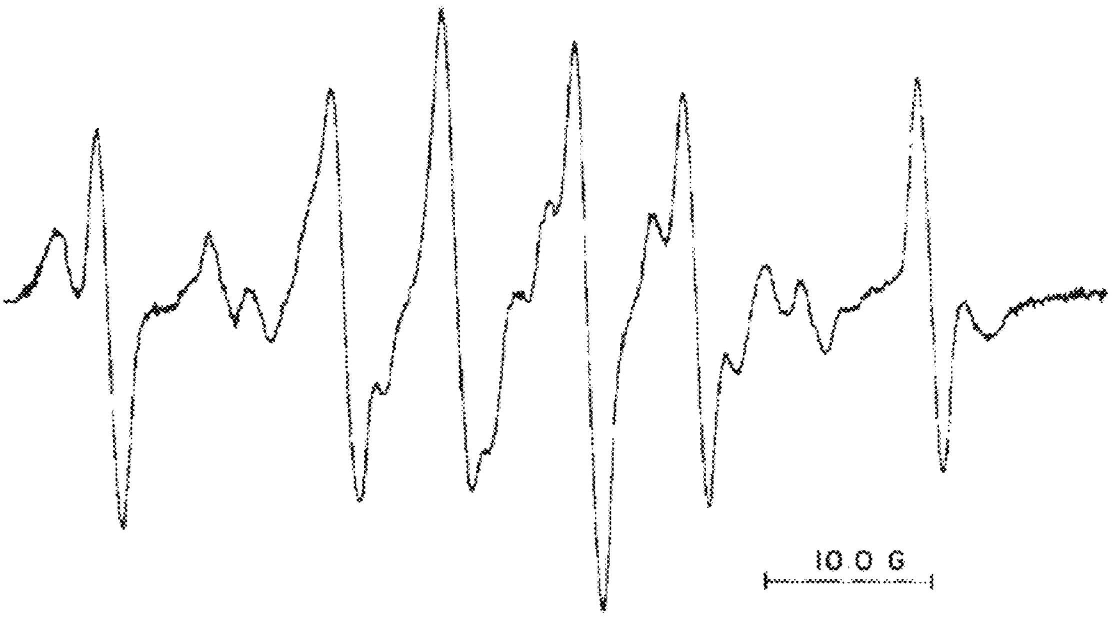
Figures 1, 2, 3, 4, 5, 6, 7, 8, 9, 10, 11, 12, 13, 14, 15, 16, 17, 18, 19, 20, 21, 22:
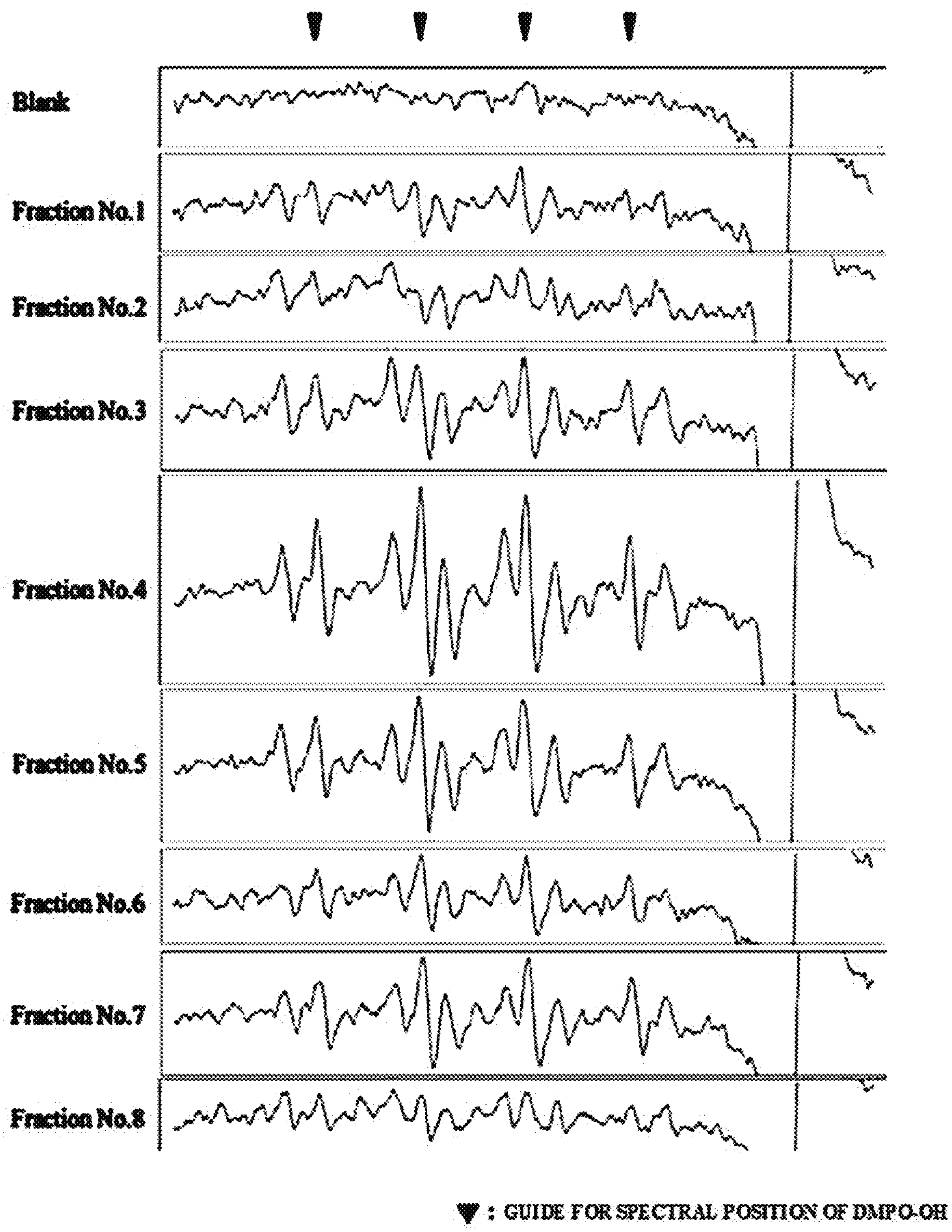
Figures 1, 2, 3, 4, 5, 6, 7, 8, 9, 10, 11, 12, 13, 14, 15, 16, 17, 18, 19, 20, 21, 22, 23:
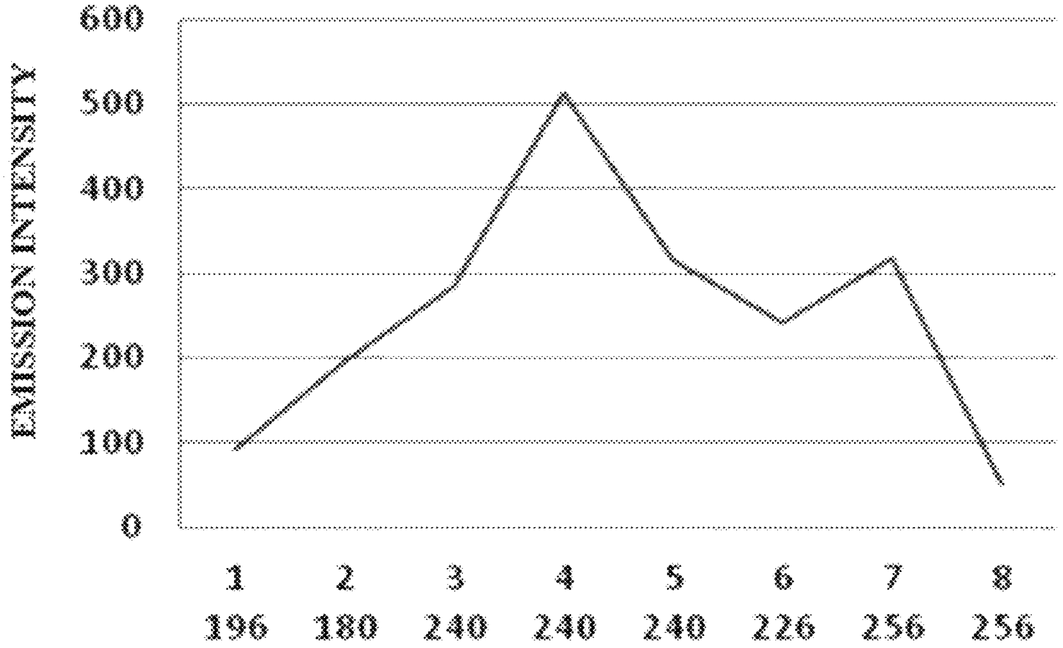
Figures 1, 2, 3, 4, 5, 6, 7, 8, 9, 10, 11, 12, 13, 14, 15, 16, 17, 18, 19, 20, 21, 22, 23, 24:
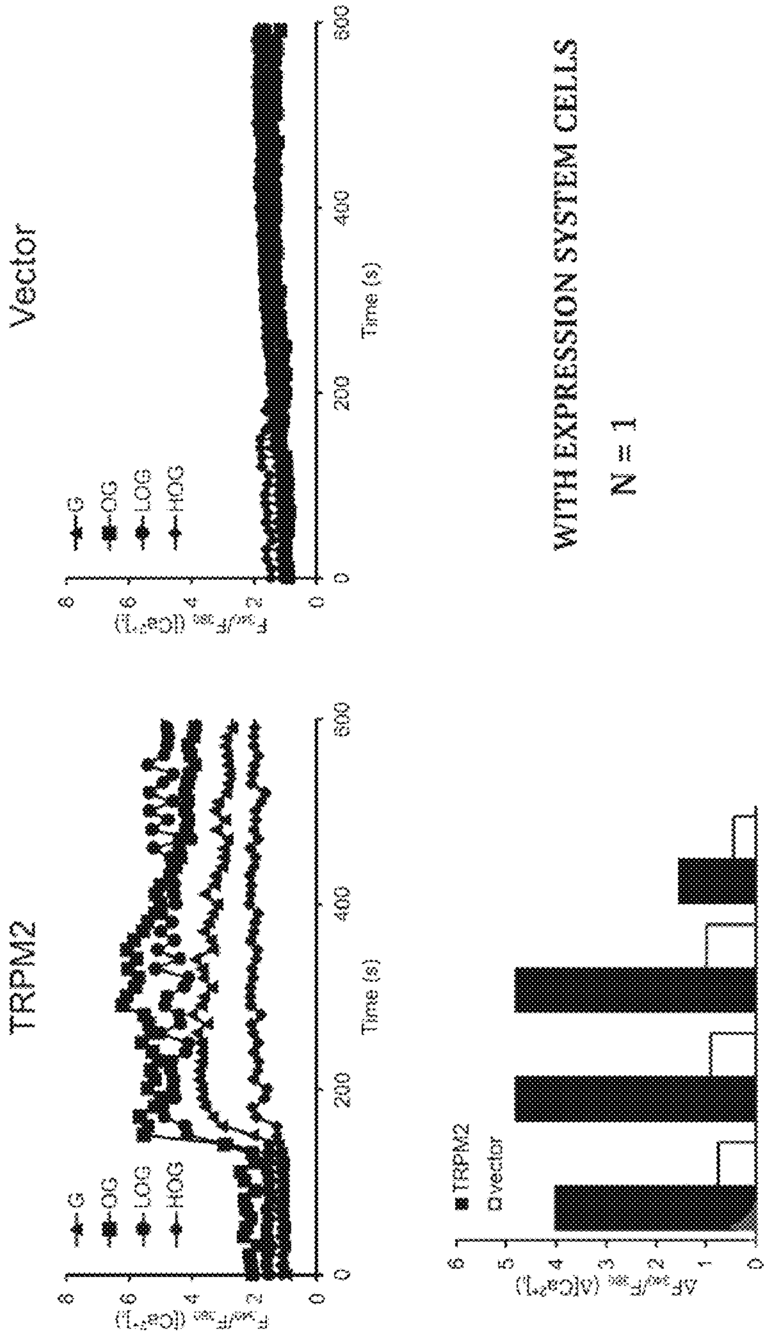
Figures 1, 2, 3, 4, 5, 6, 7, 8, 9, 10, 11, 12, 13, 14, 15, 16, 17, 18, 19, 20, 21, 22, 23, 24, 25:
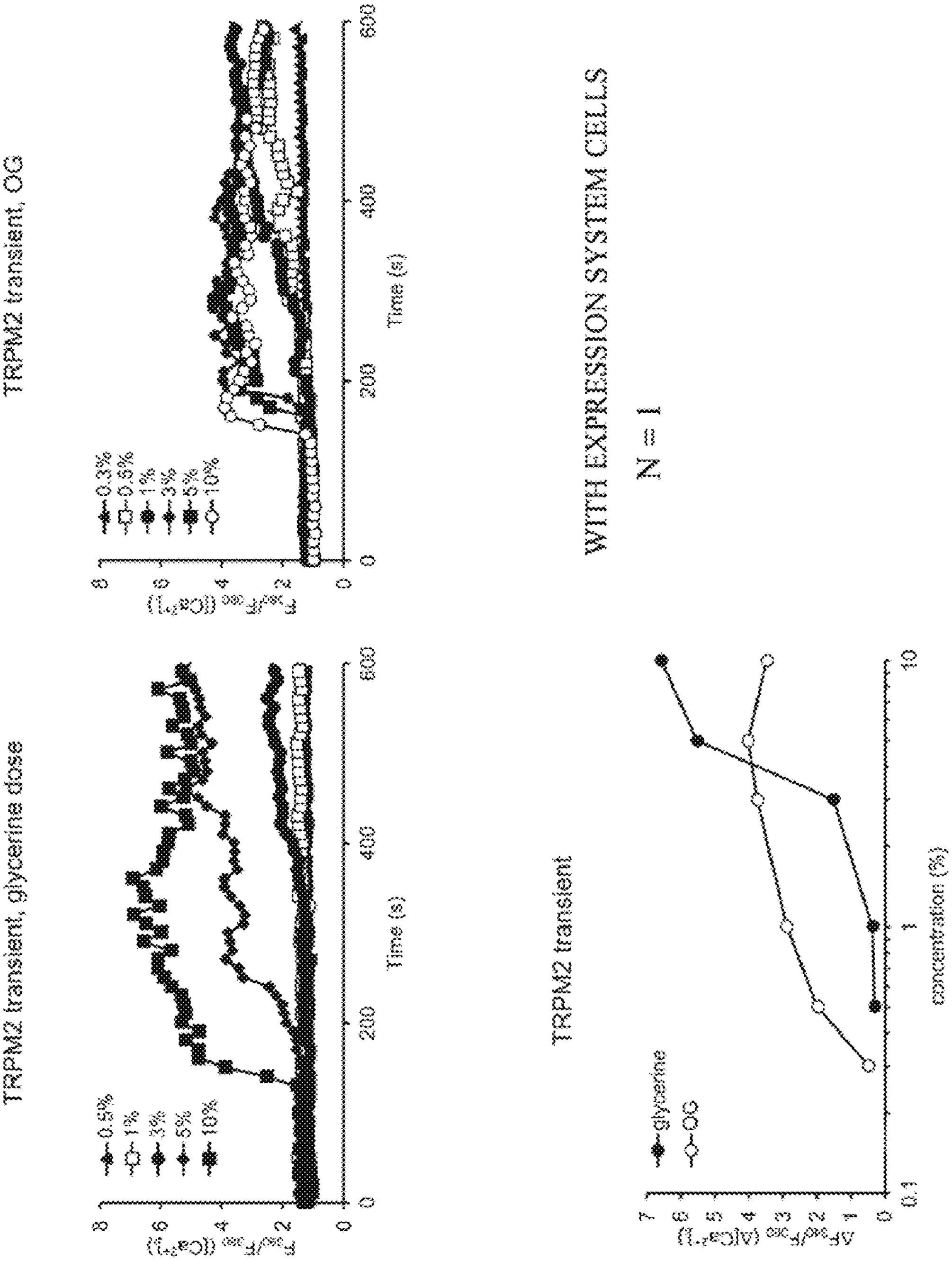
Figures 1, 2, 3, 4, 5, 6, 7, 8, 9, 10, 11, 12, 13, 14, 15, 16, 17, 18, 19, 20, 21, 22, 23, 24, 25, 26:
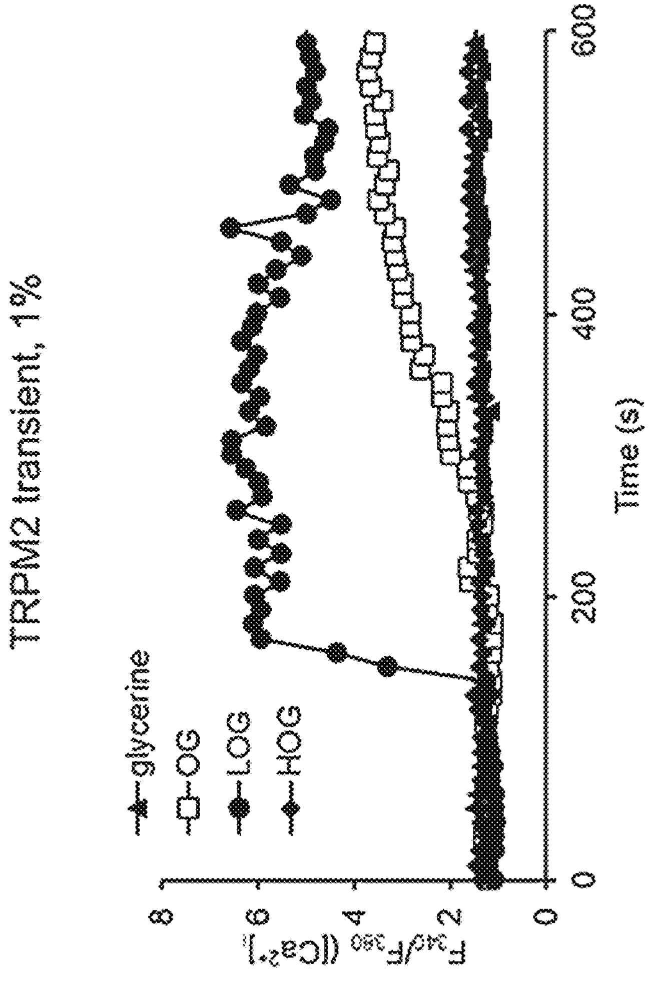
Figures 1, 2, 3, 4, 5, 6, 7, 8, 9, 10, 11, 12, 13, 14, 15, 16, 17, 18, 19, 20, 21, 22, 23, 24, 25, 26, 27:
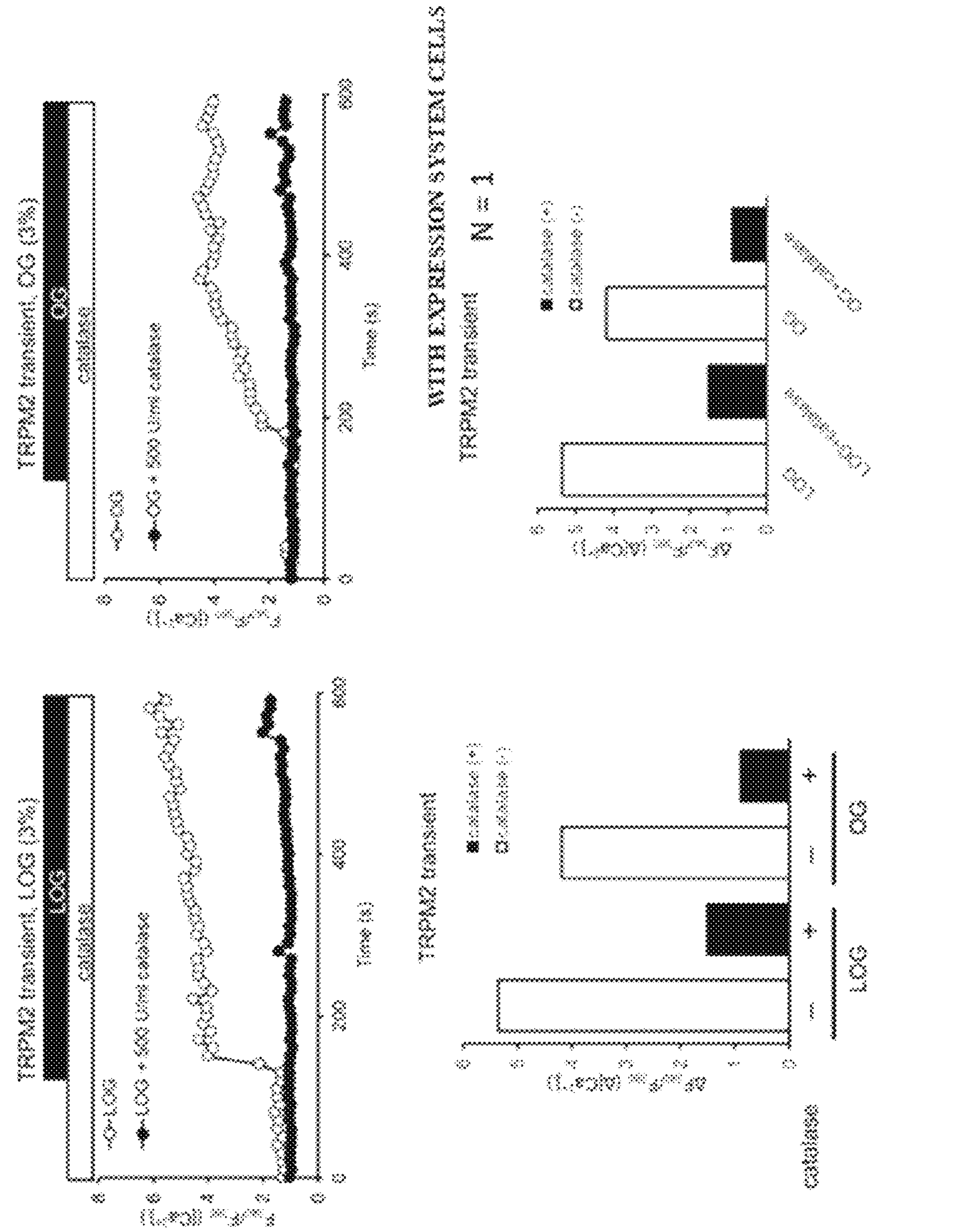
Figures 1, 2, 3, 4, 5, 6, 7, 8, 9, 10, 11, 12, 13, 14, 15, 16, 17, 18, 19, 20, 21, 22, 23, 24, 25, 26, 27, 28:
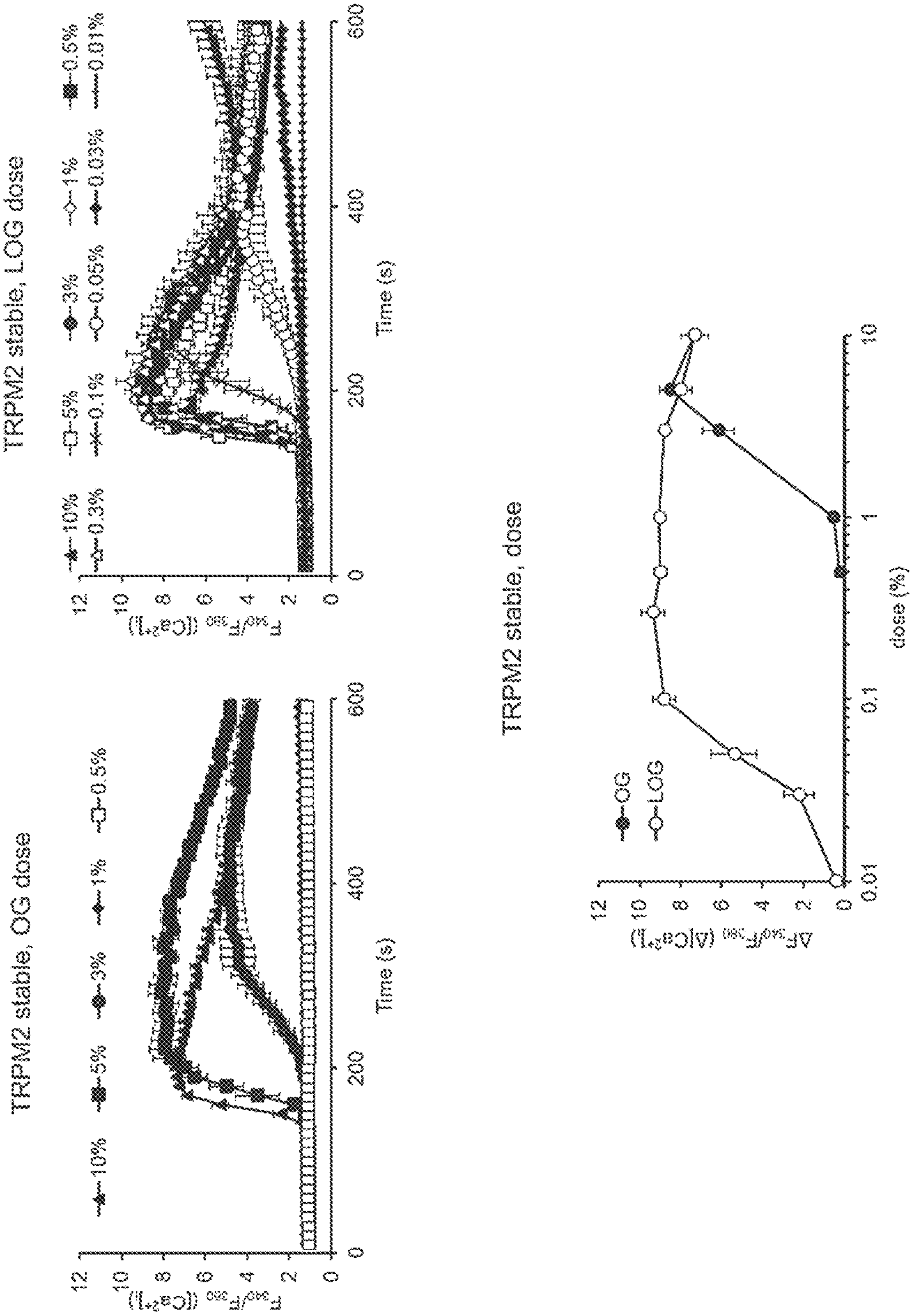
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29:
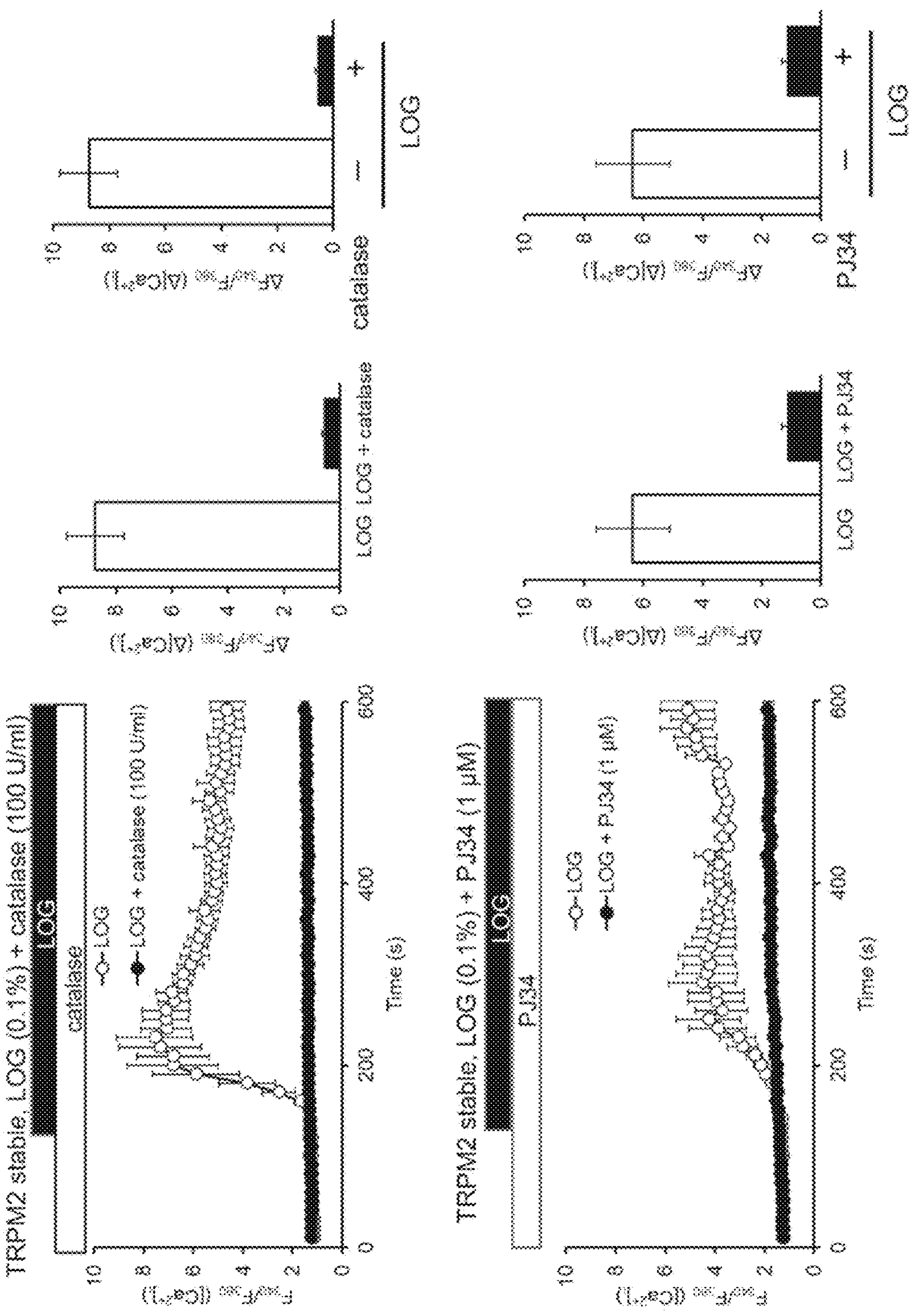
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30:
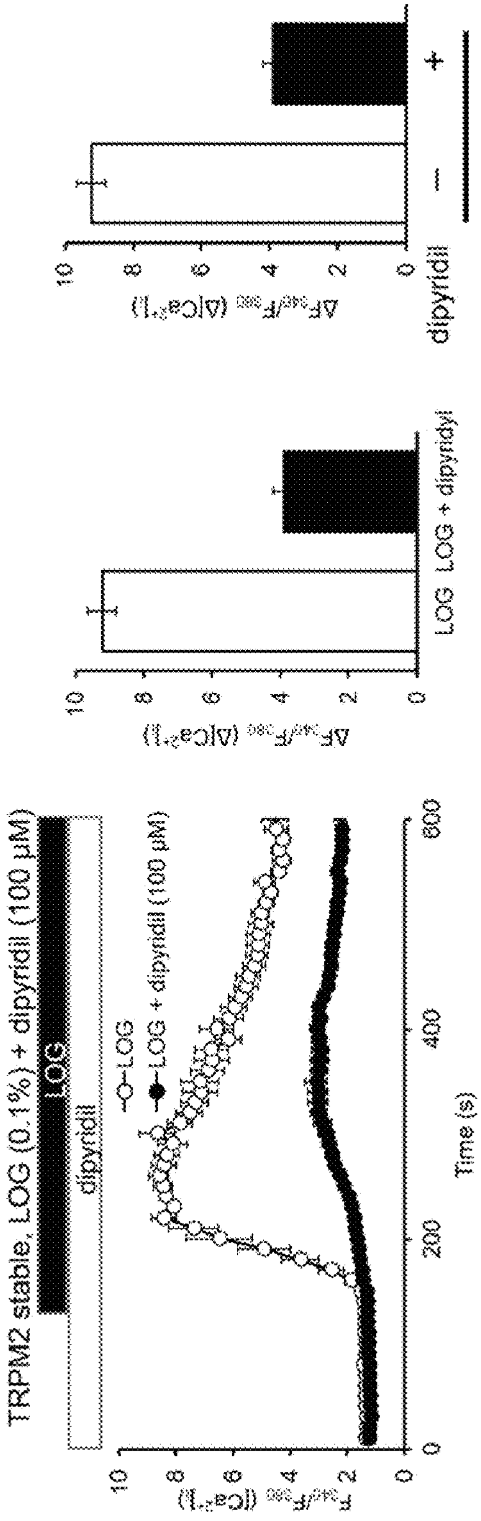
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31:
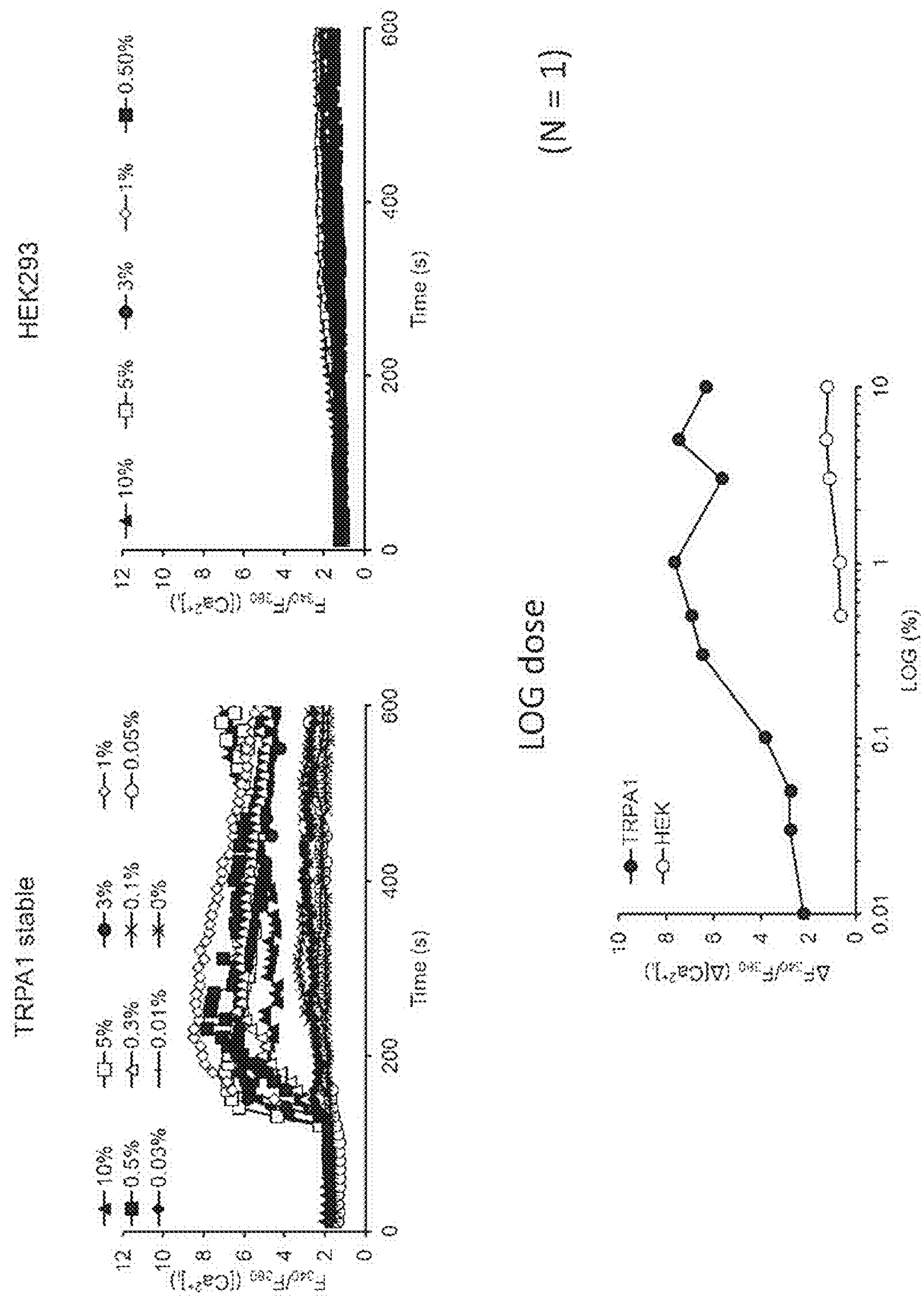
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
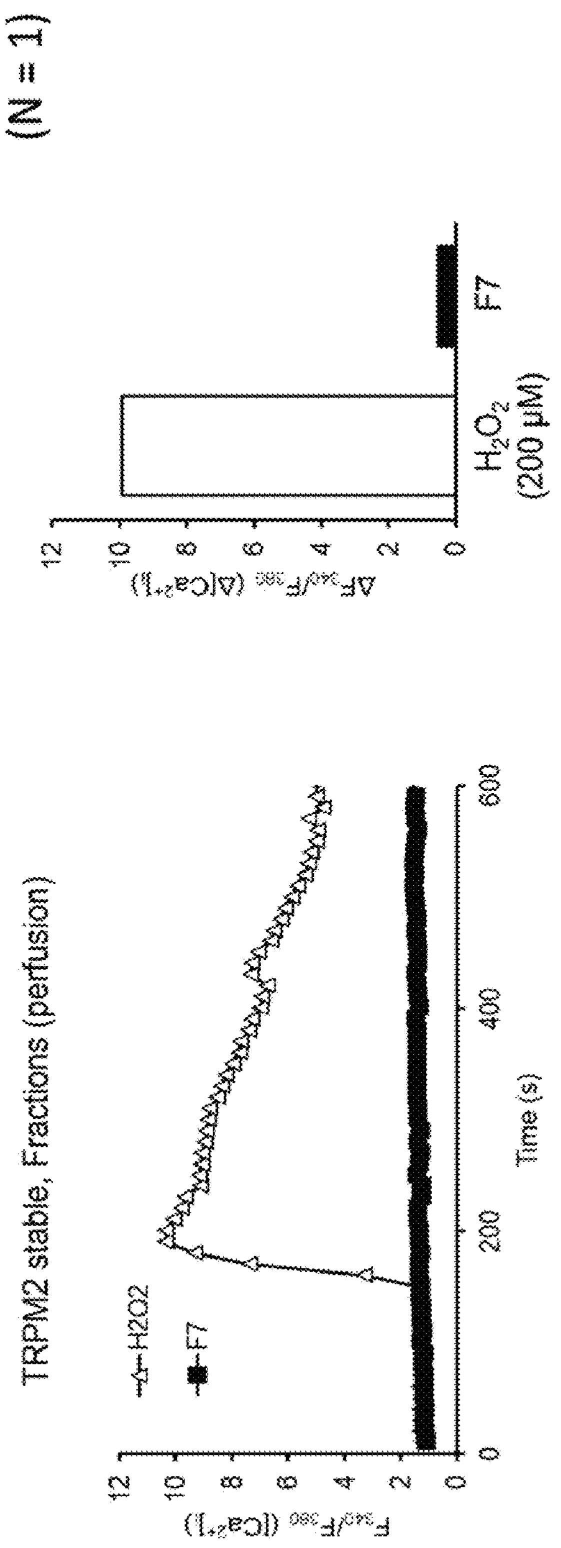
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
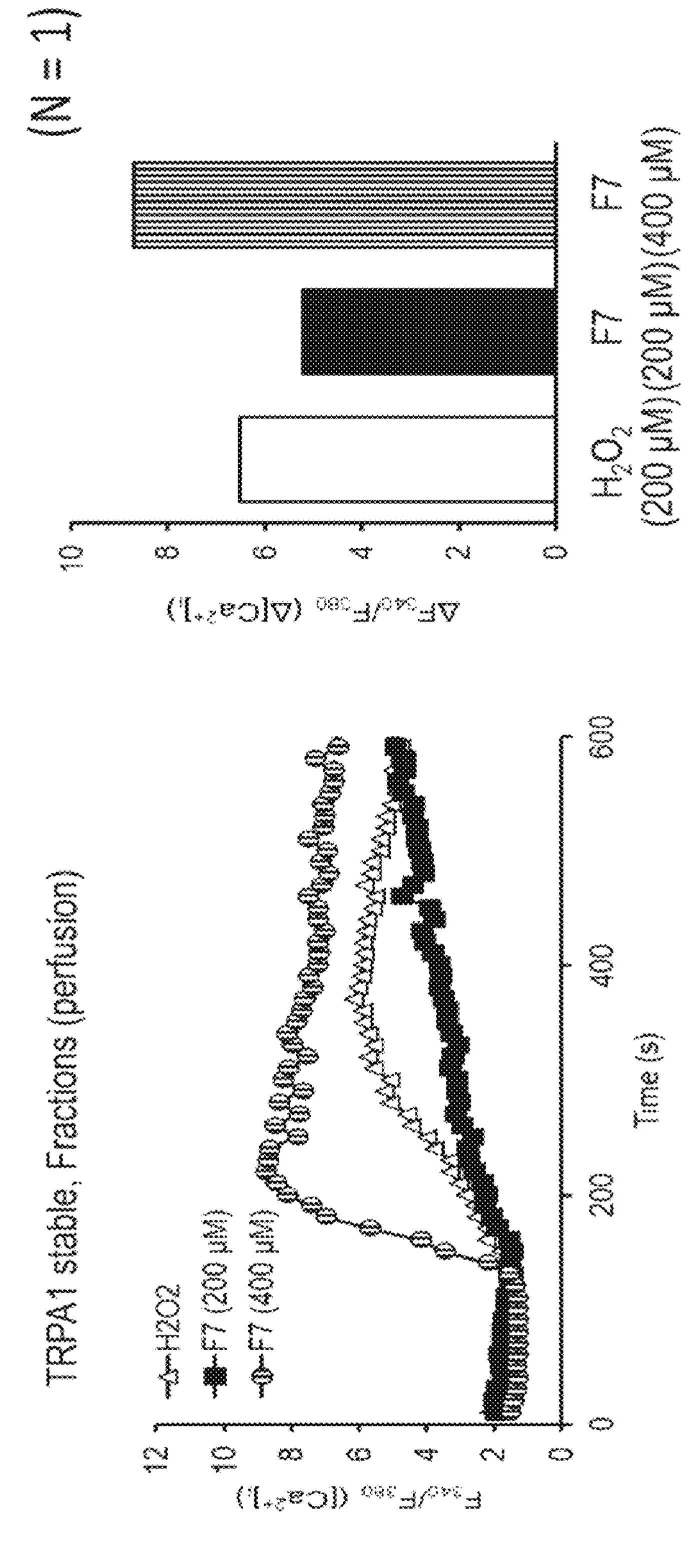
Figures 1, 2:
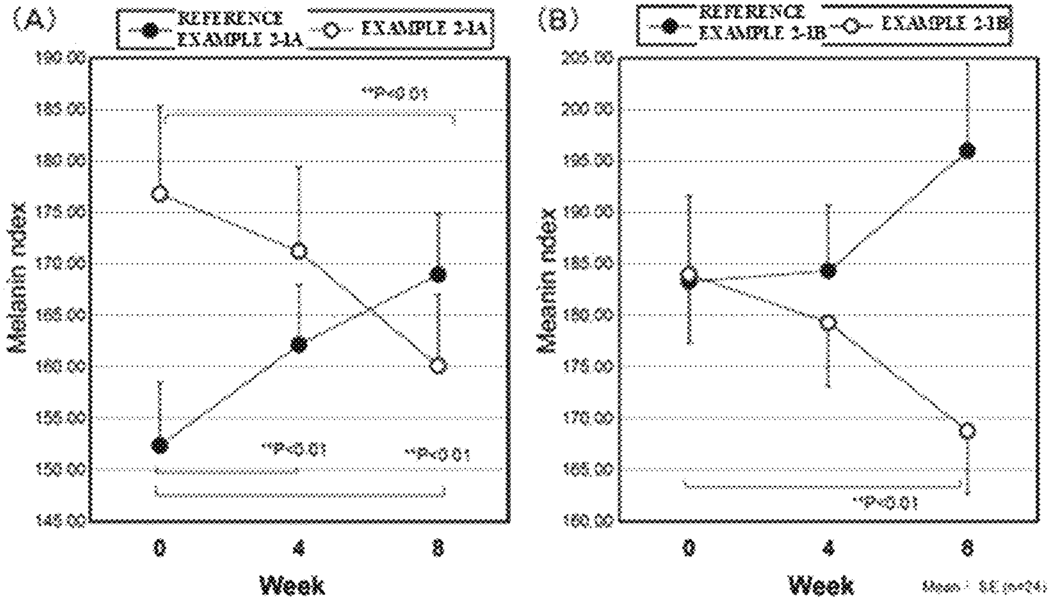
Figure 2:
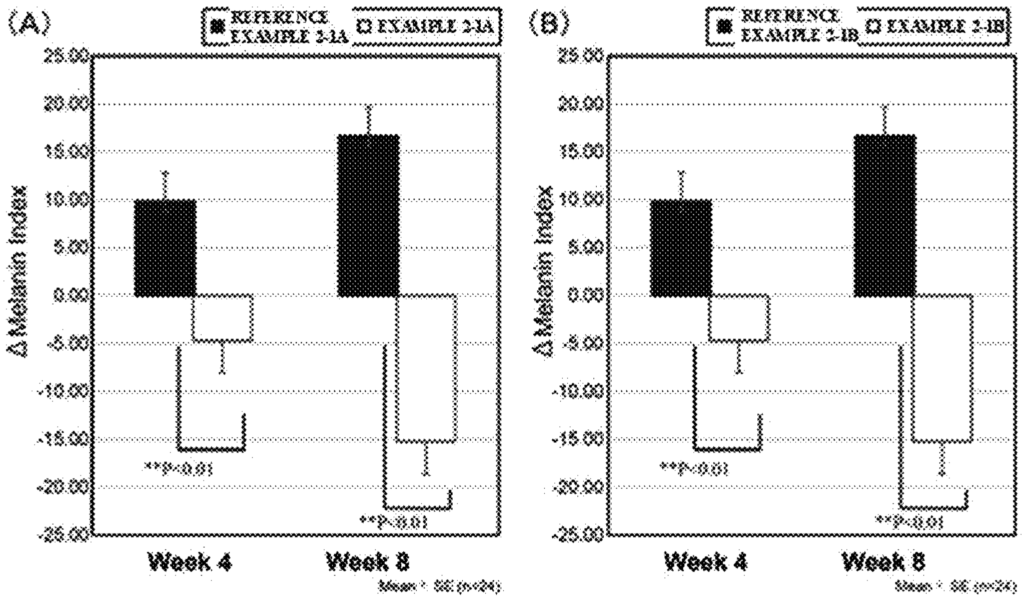
Figures 2, 3:
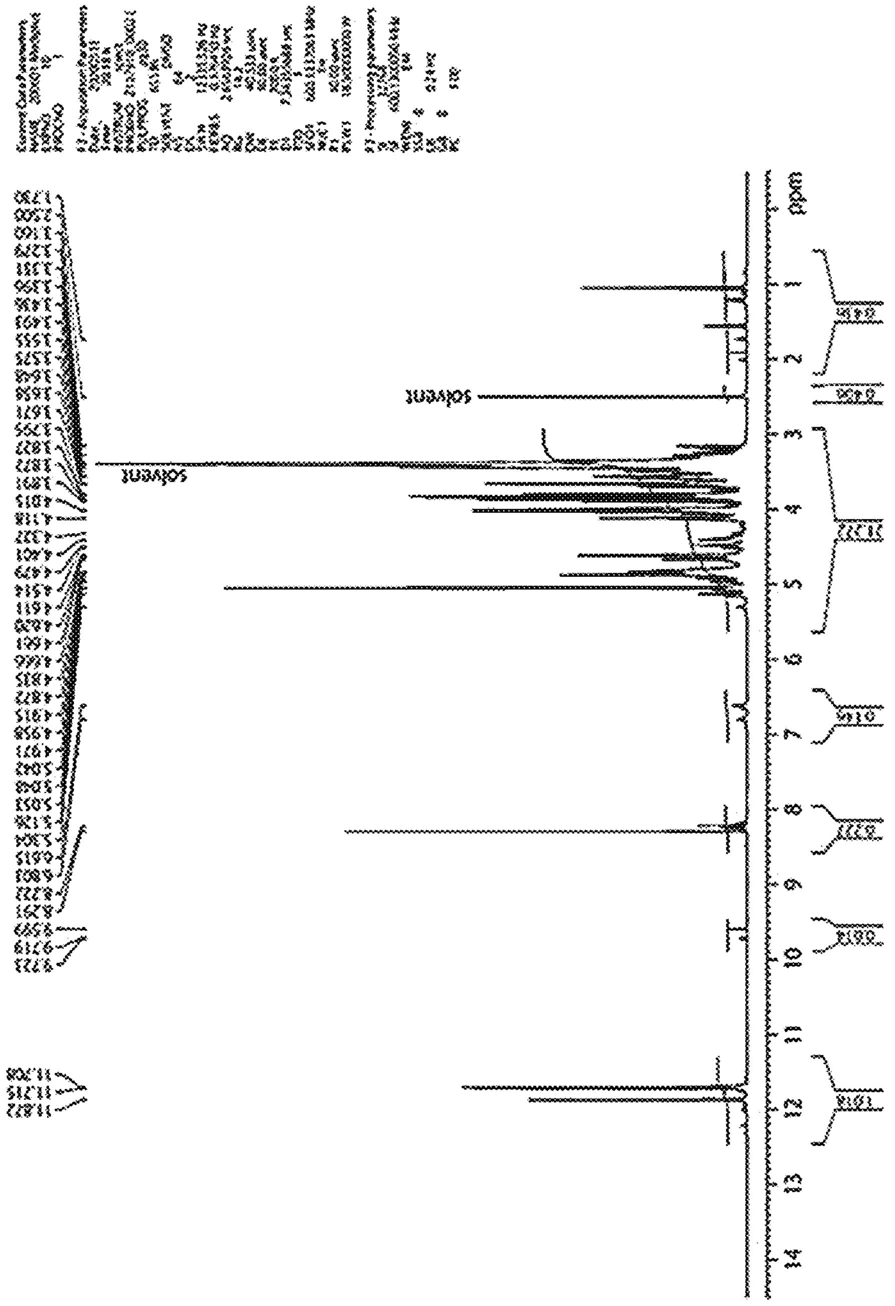
Figures 2, 3, 4:
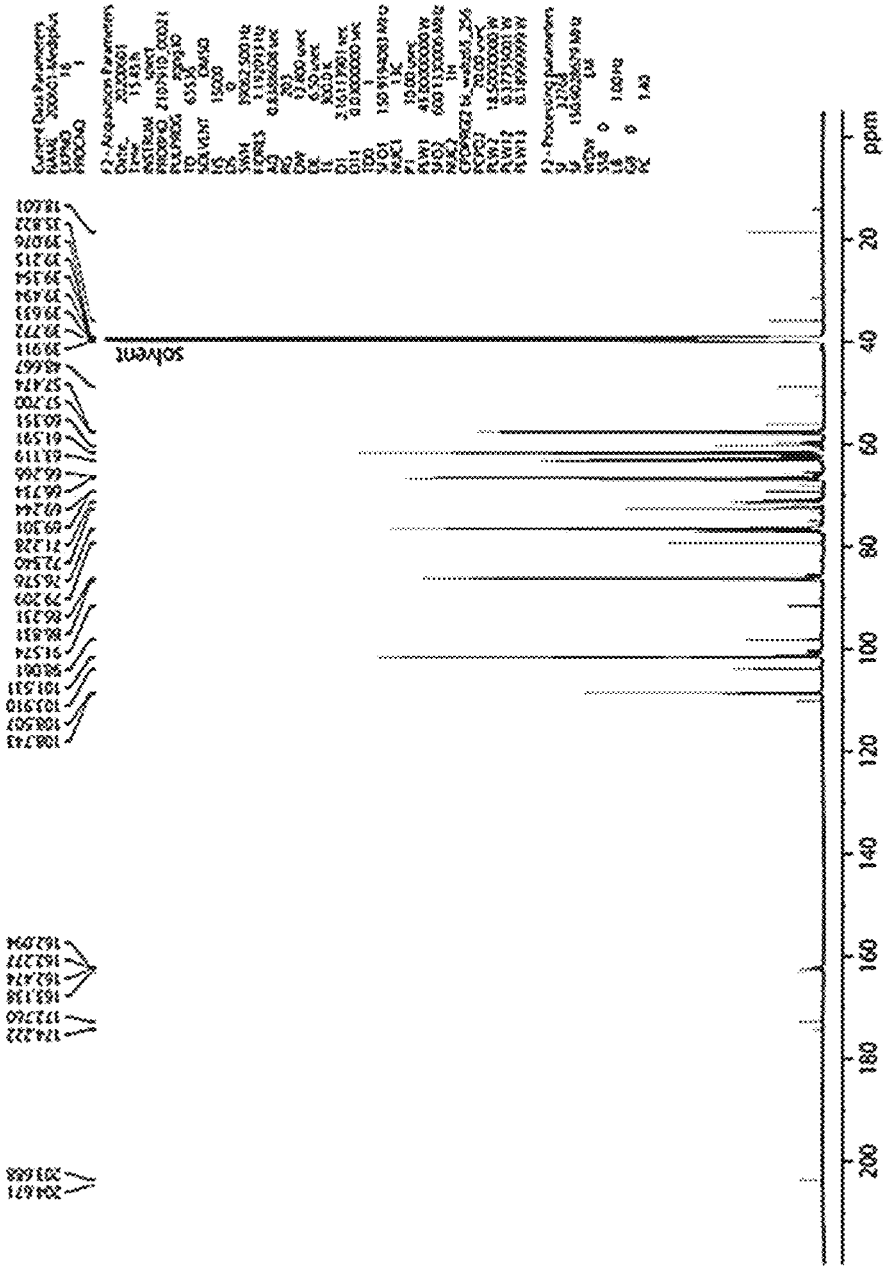
Figures 2, 3, 4, 5:
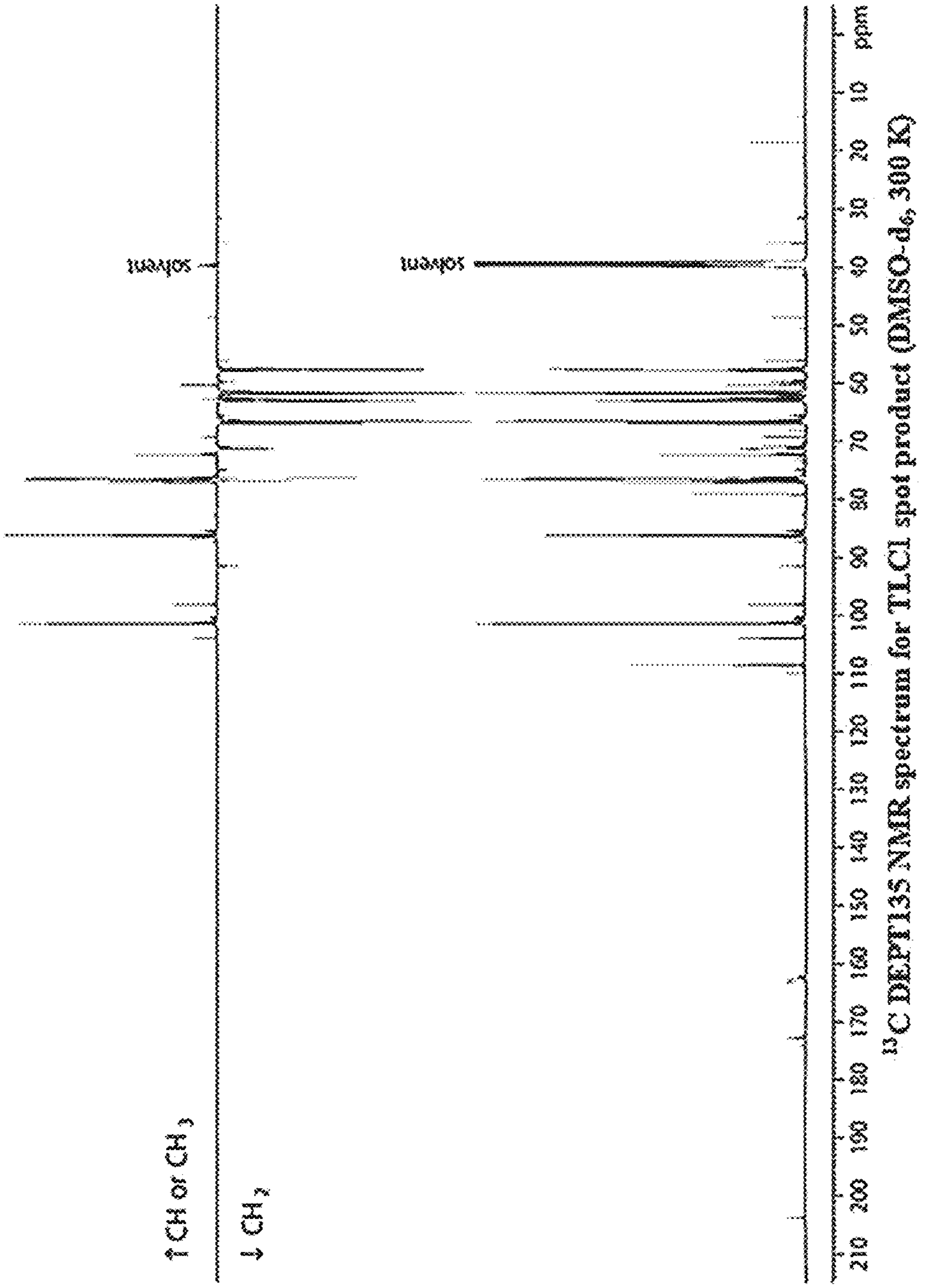
Figures 2, 3, 4, 5, 6:
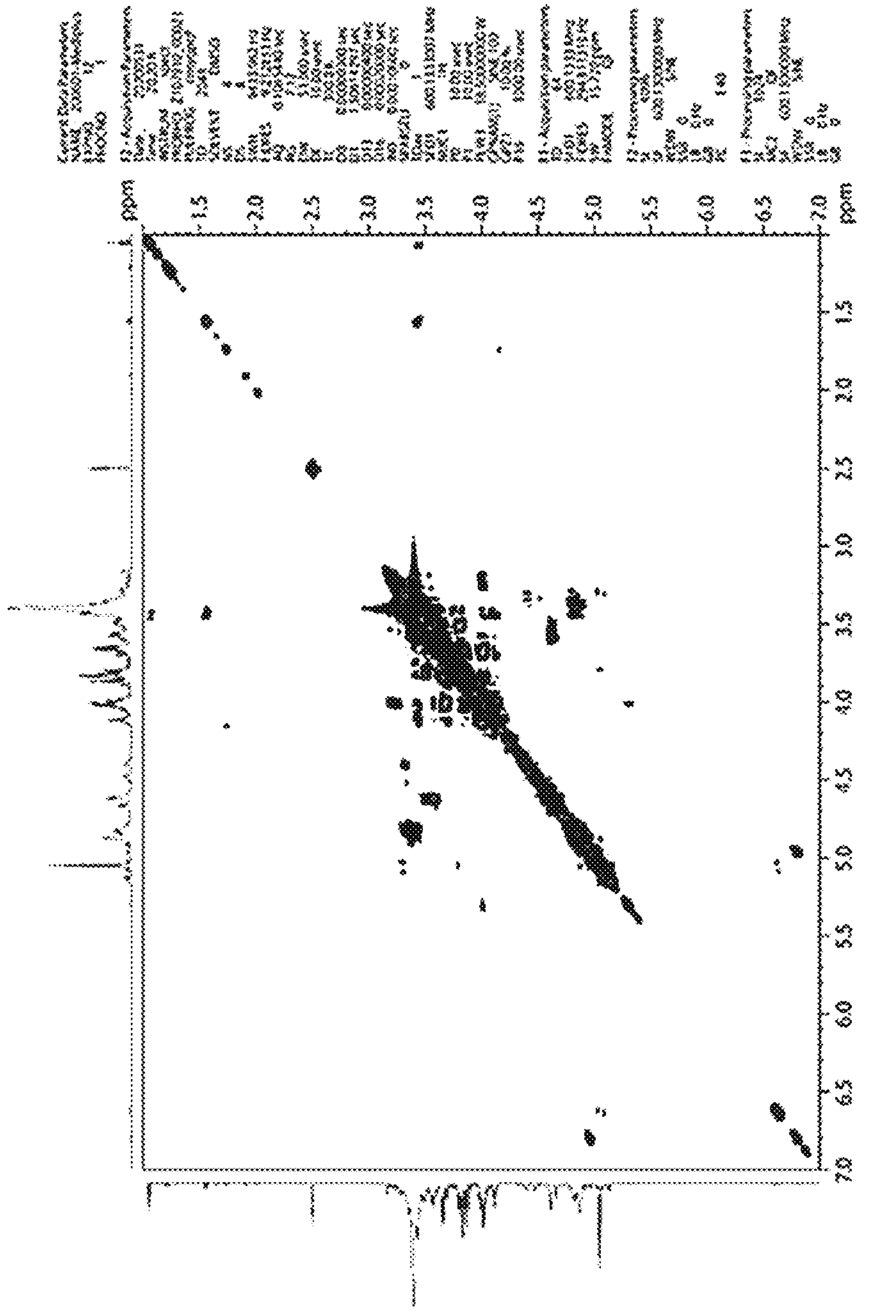
Figures 2, 3, 4, 5, 6, 7:
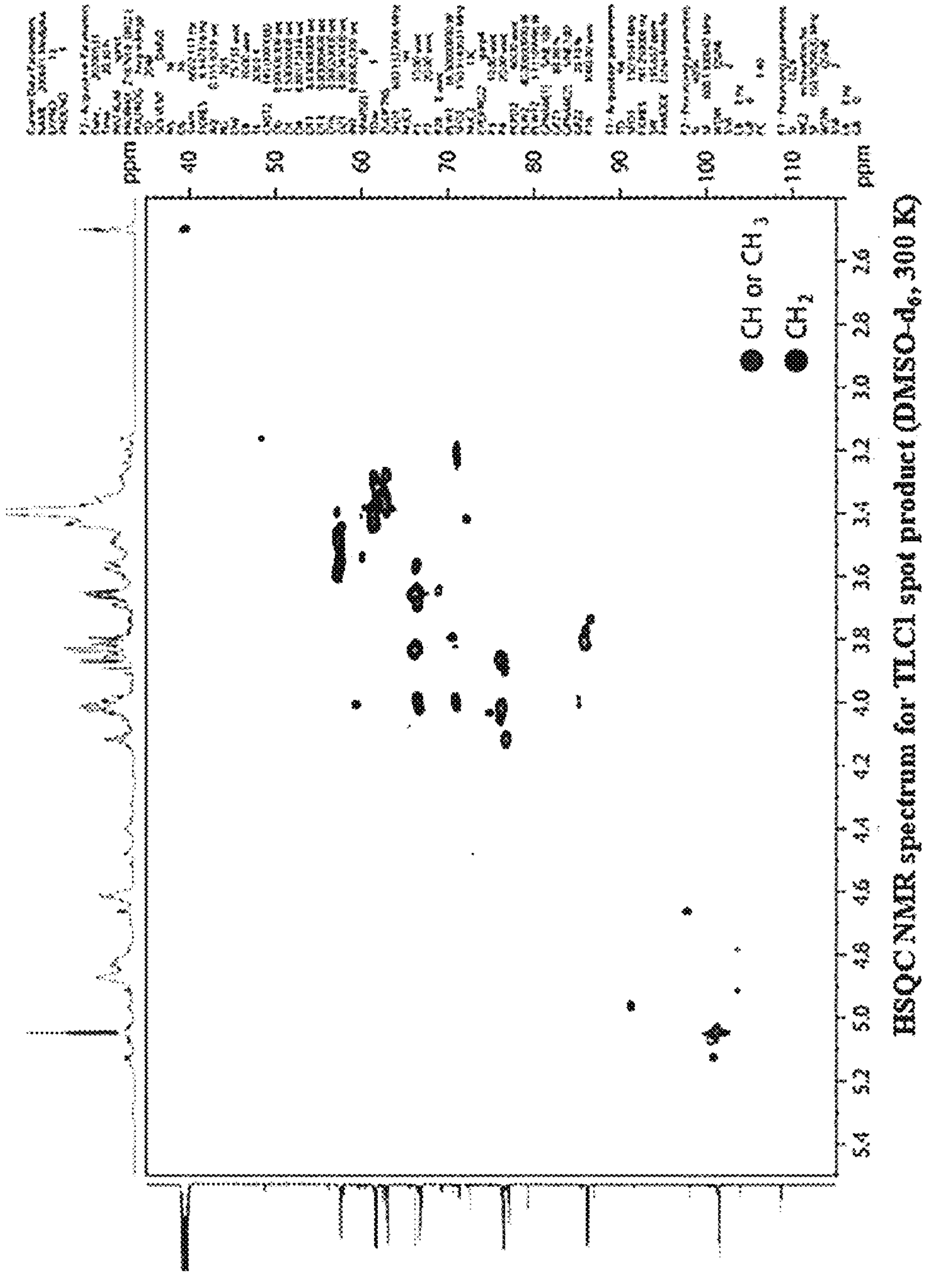
Figures 2, 3, 4, 5, 6, 7, 8:
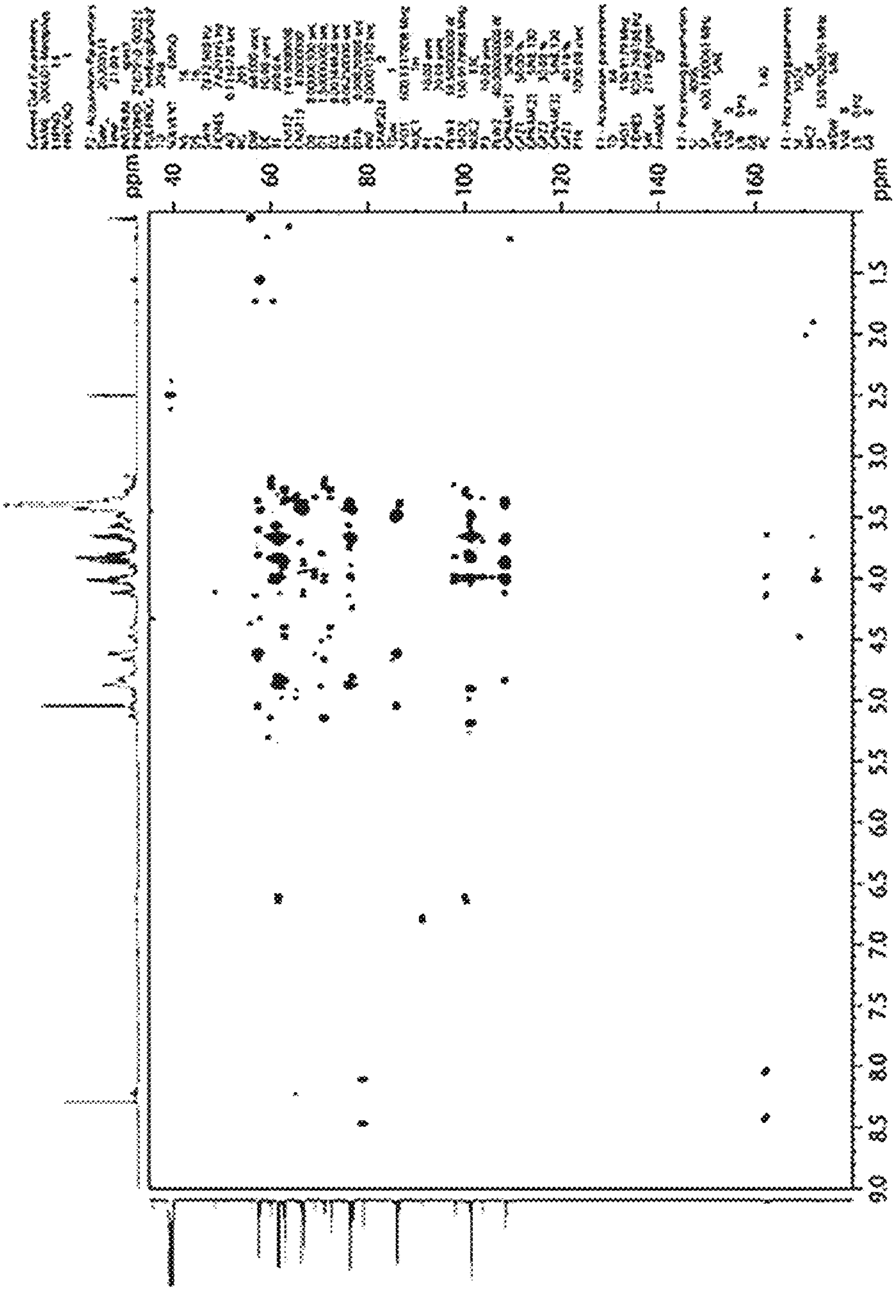
Figures 2, 3, 4, 5, 6, 7, 8, 9:
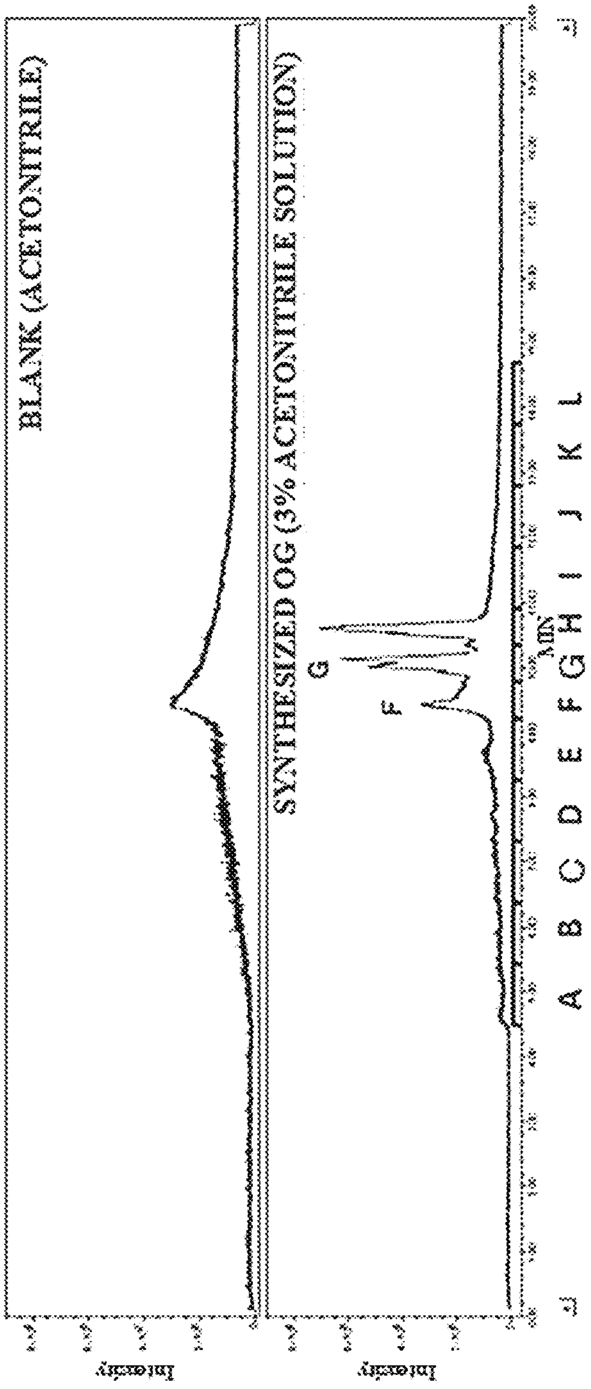
Figures 2, 3, 4, 5, 6, 7, 8, 9, 10:
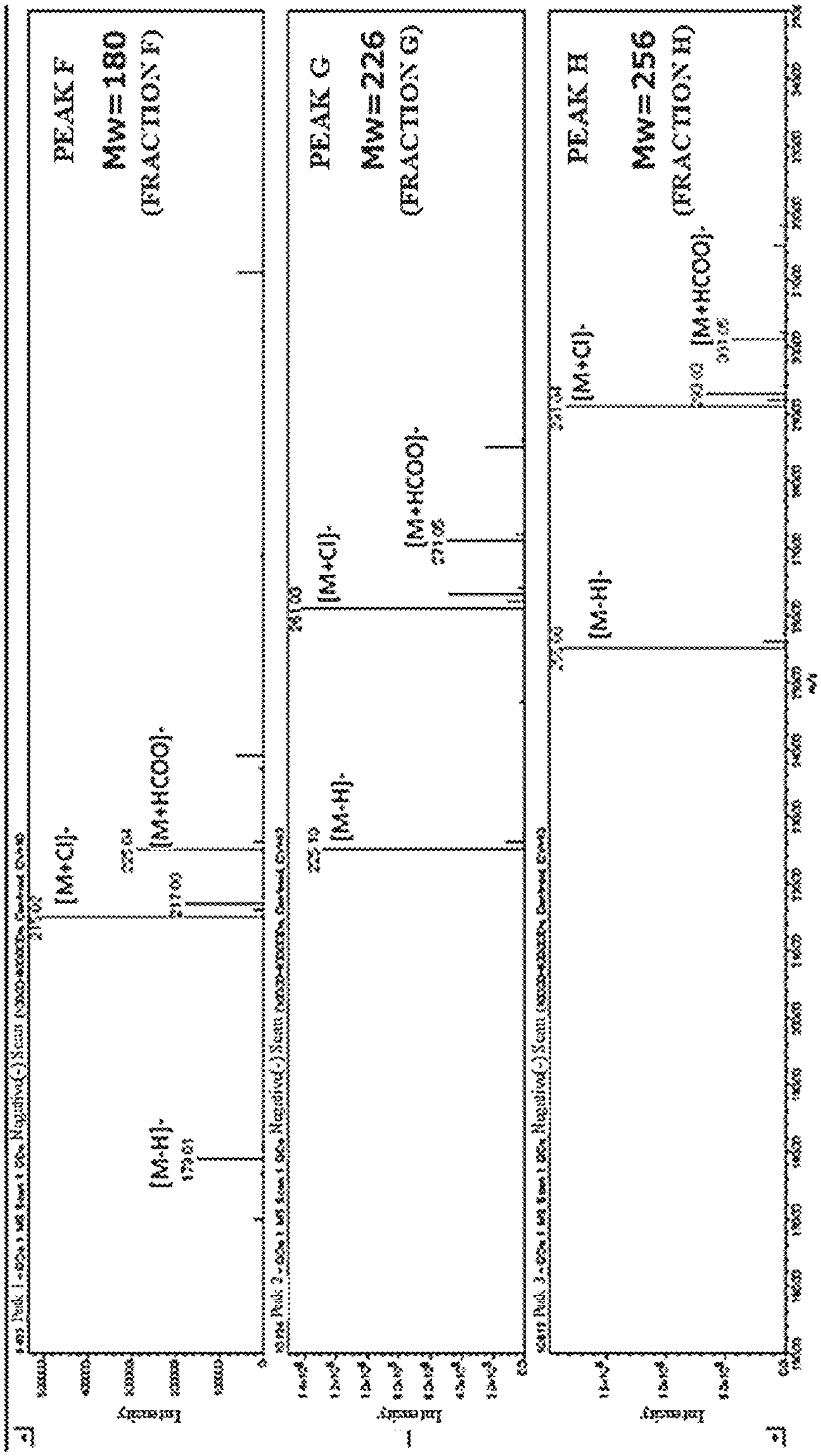
Figures 2, 3, 4, 5, 6, 7, 8, 9, 10, 11:
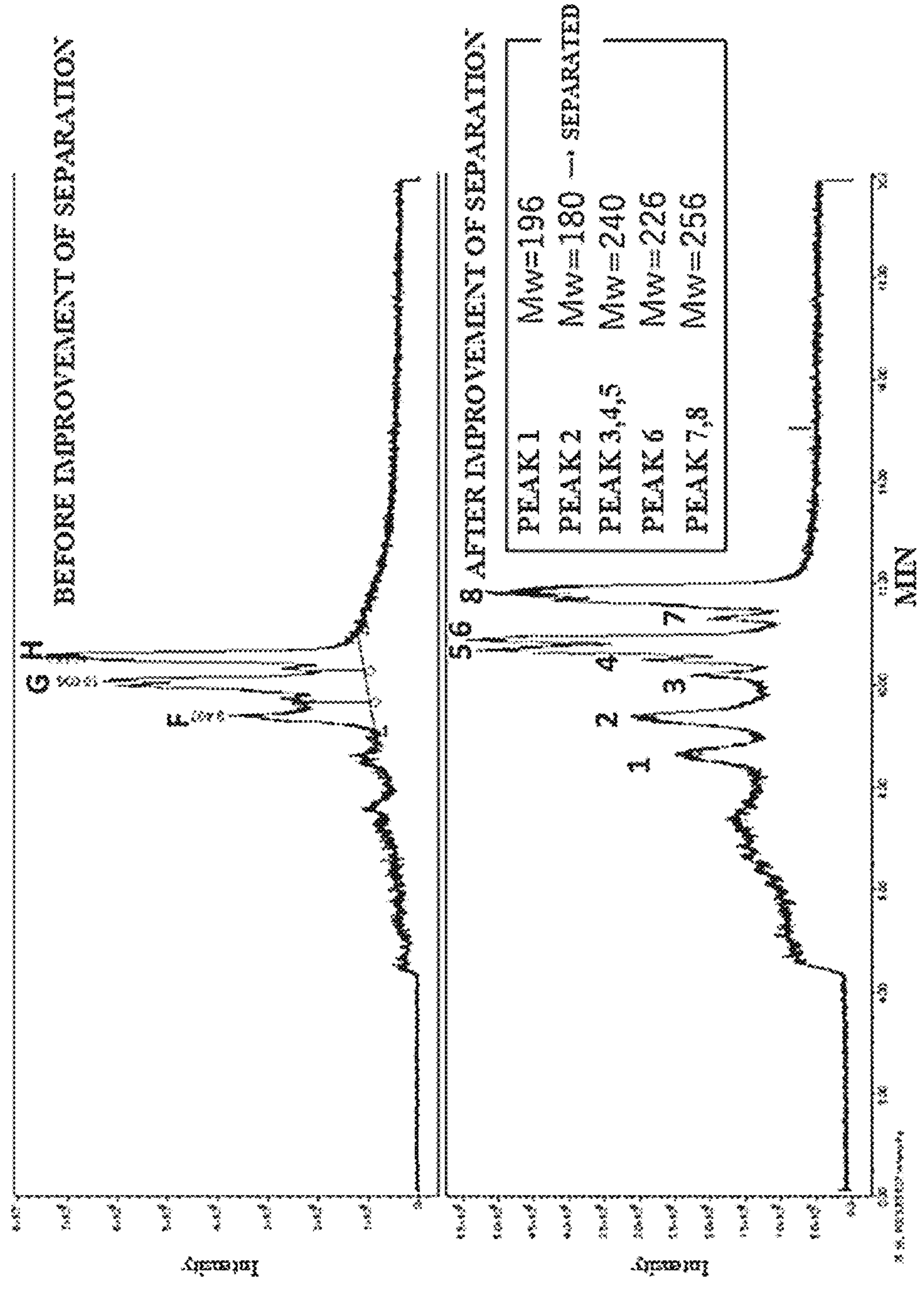
Figures 2, 3, 4, 5, 6, 7, 8, 9, 10, 11, 12:
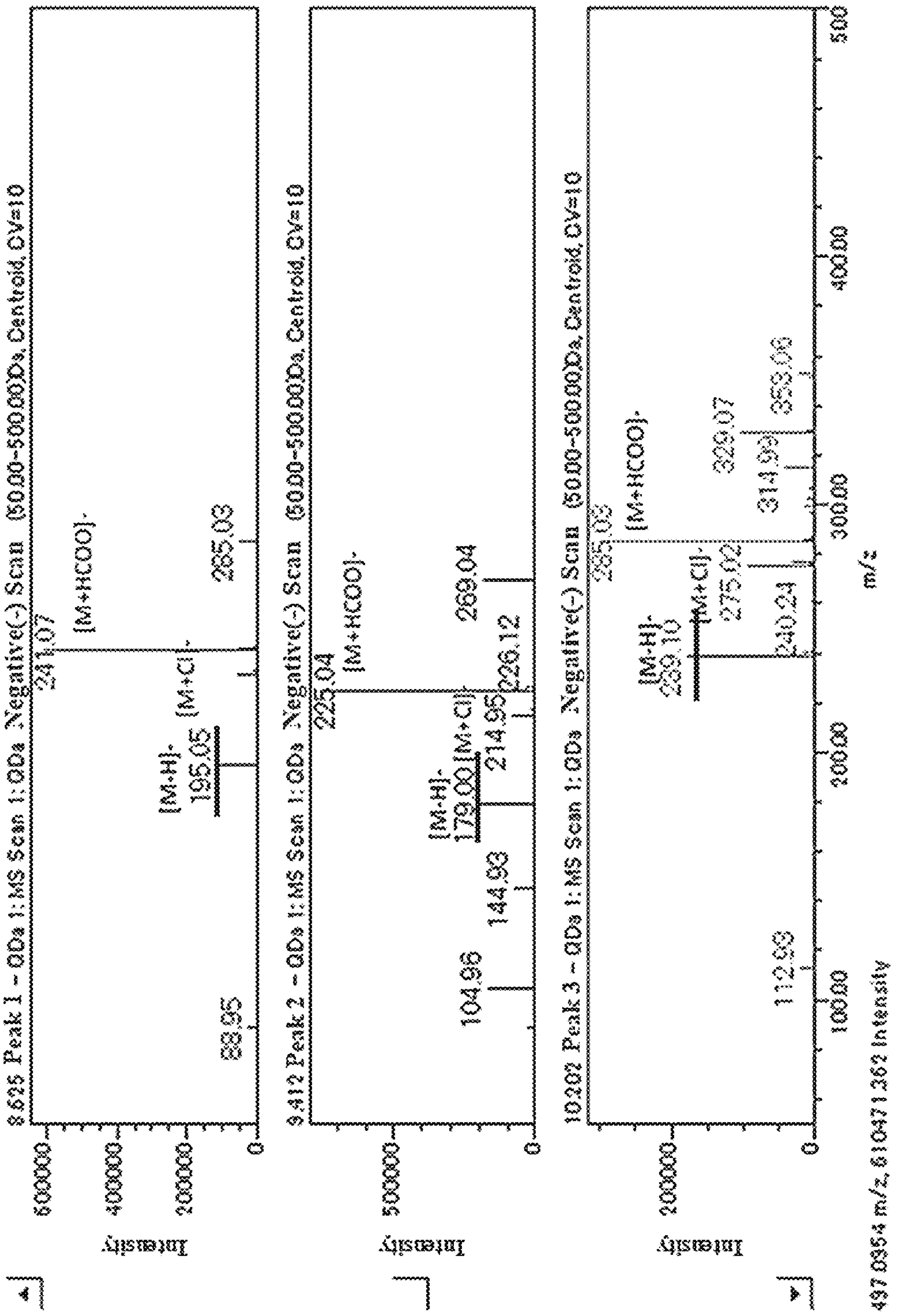
Figures 2, 3, 4, 5, 6, 7, 8, 9, 10, 11, 12, 13:
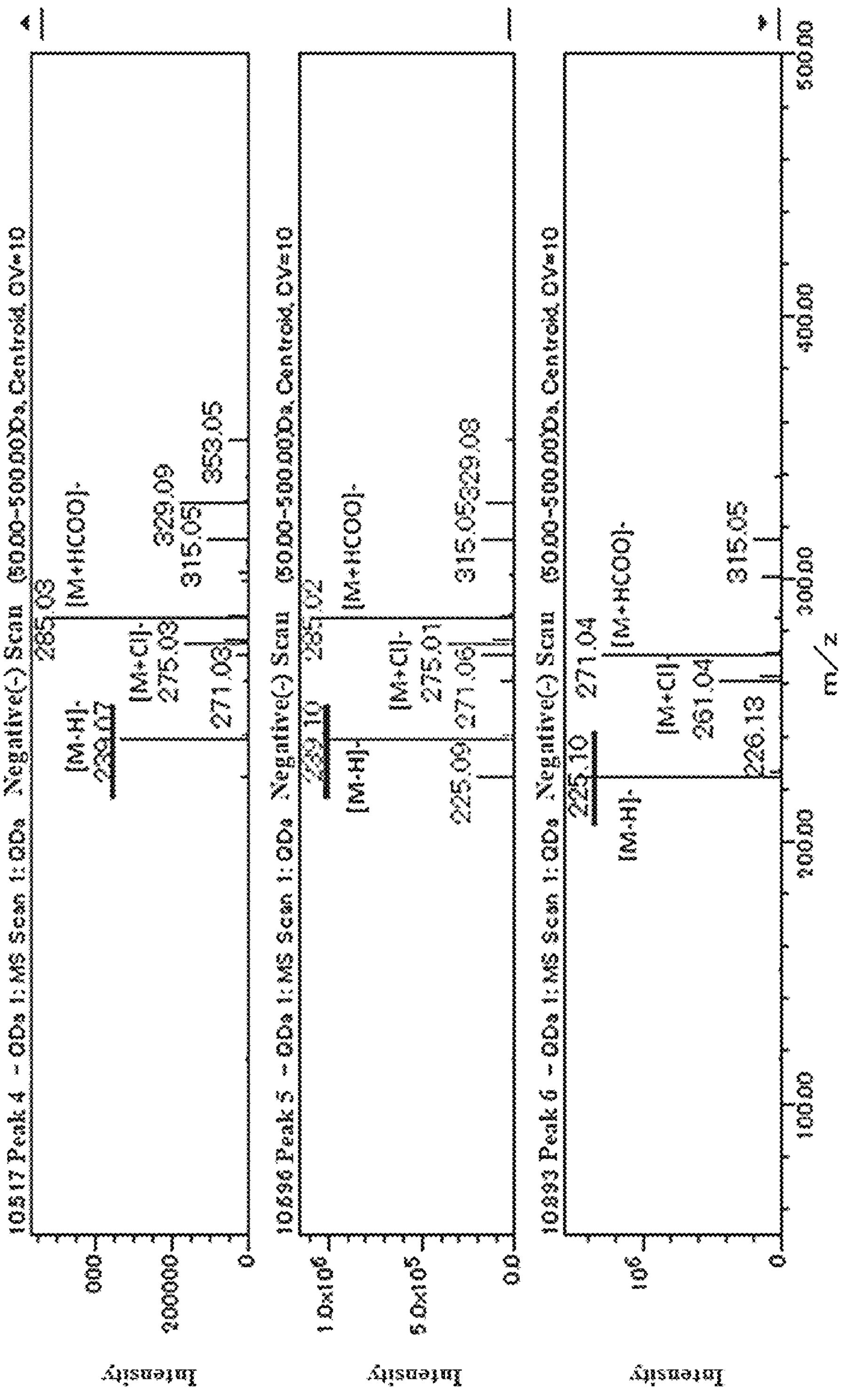
Figures 2, 3, 4, 5, 6, 7, 8, 9, 10, 11, 12, 13, 14:
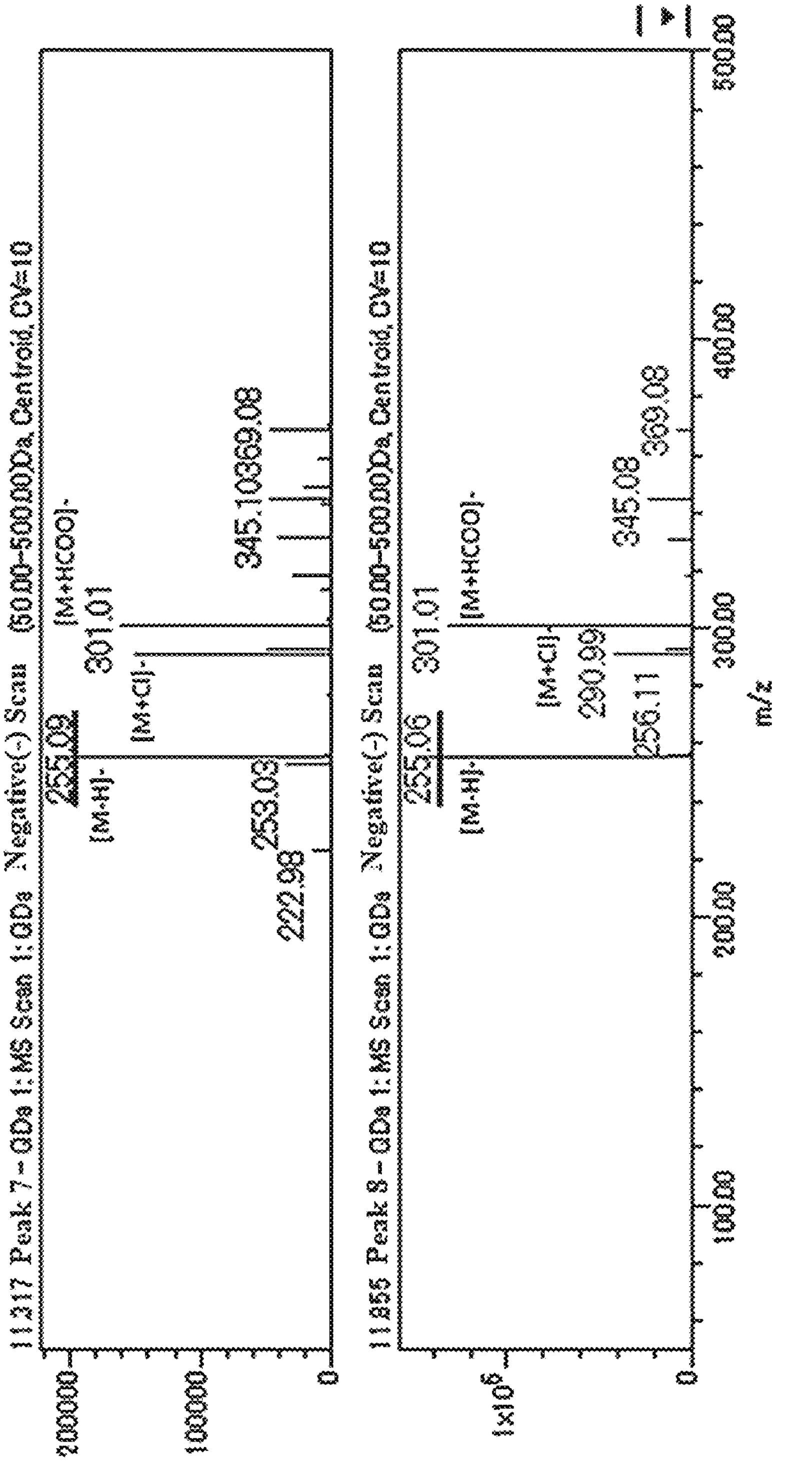
Figures 2, 3, 4, 5, 6, 7, 8, 9, 10, 11, 12, 13, 14, 15:
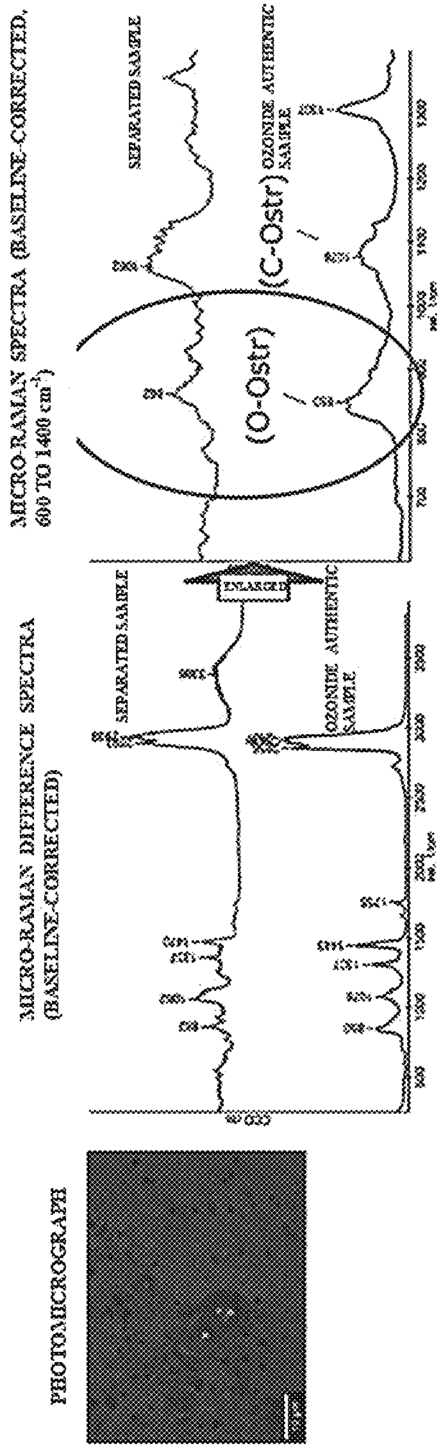
Figures 2, 3, 4, 5, 6, 7, 8, 9, 10, 11, 12, 13, 14, 15, 16:
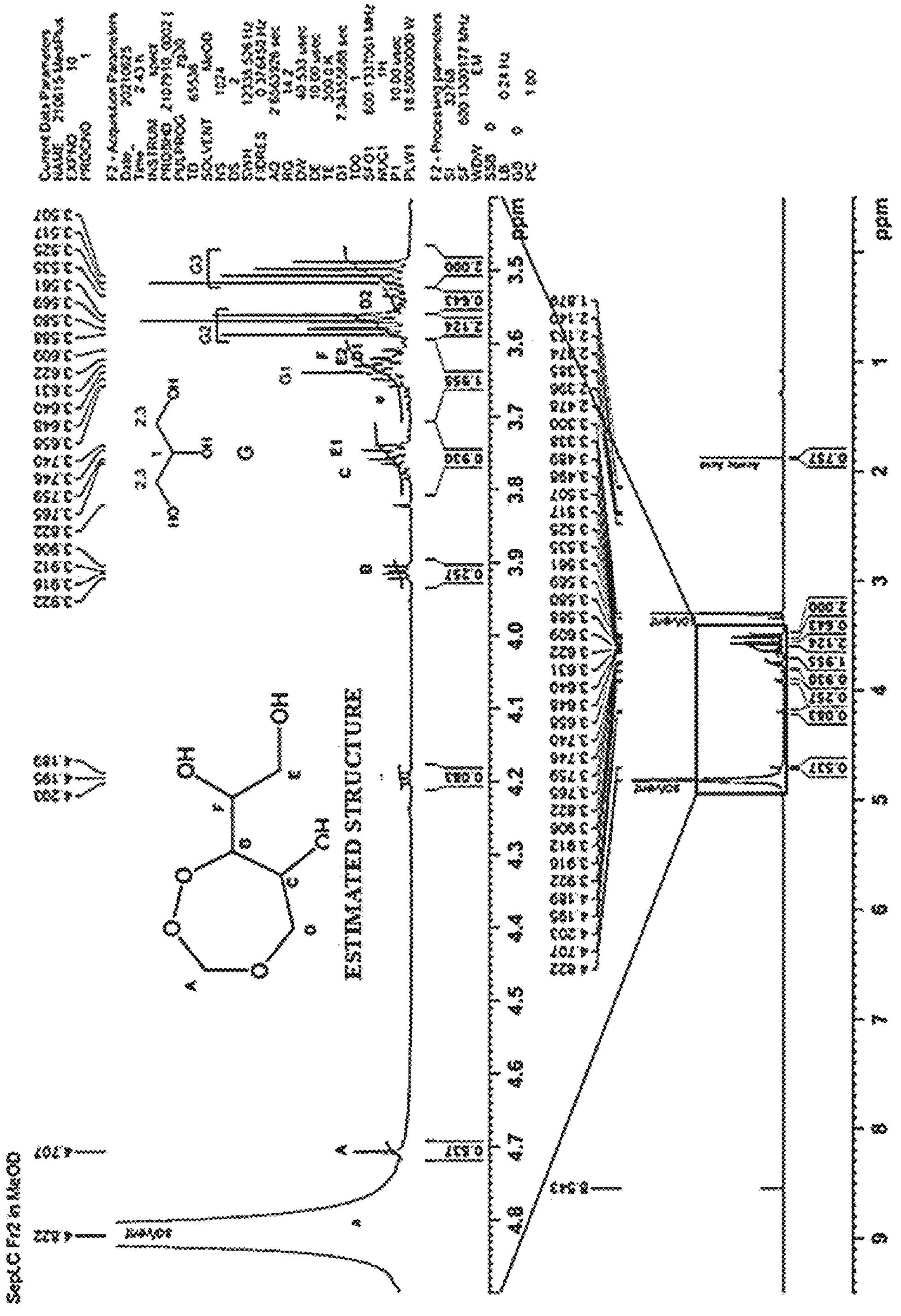
Figures 2, 3, 4, 5, 6, 7, 8, 9, 10, 11, 12, 13, 14, 15, 16, 17:
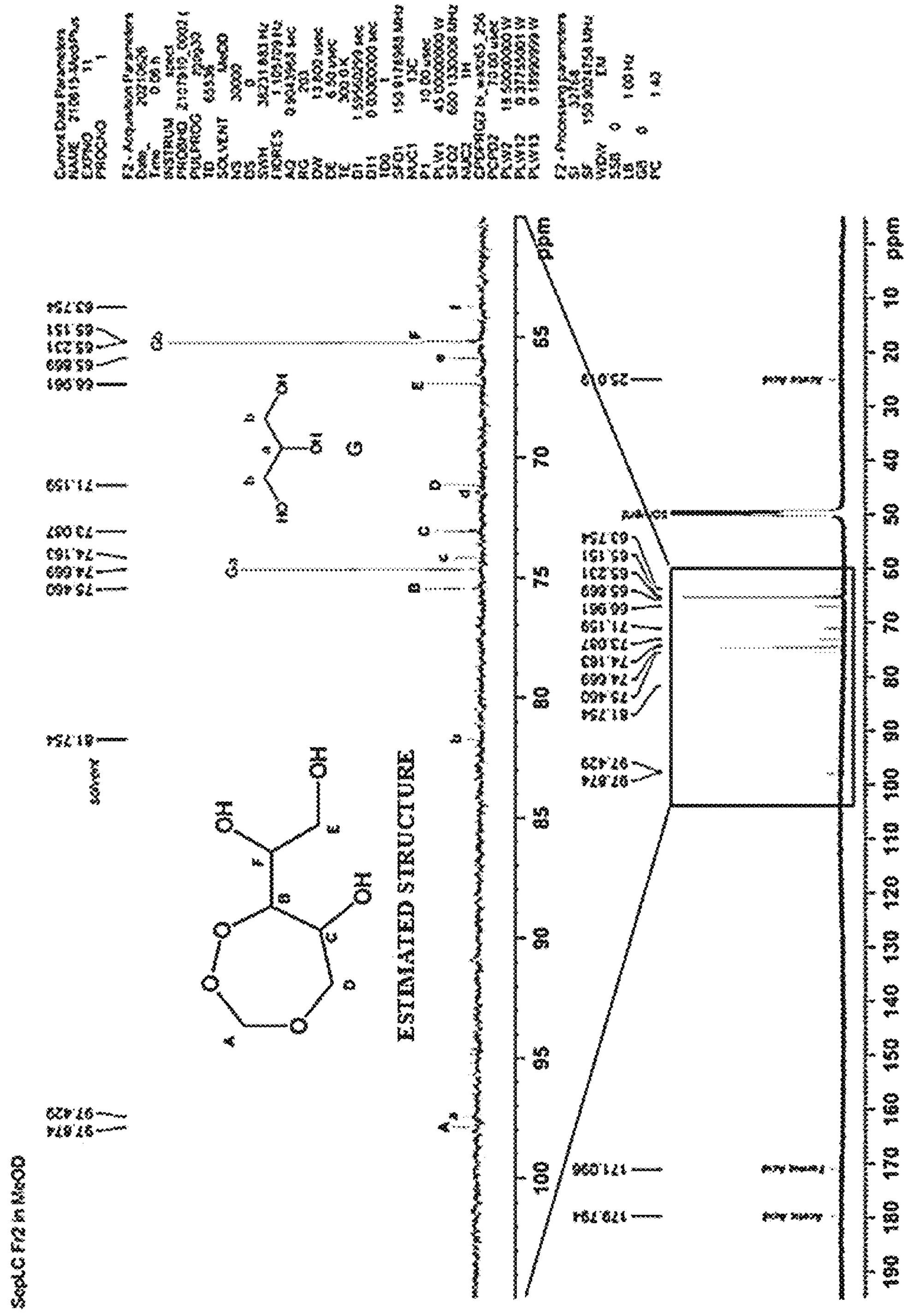
Figures 2, 3, 4, 5, 6, 7, 8, 9, 10, 11, 12, 13, 14, 15, 16, 17, 18:
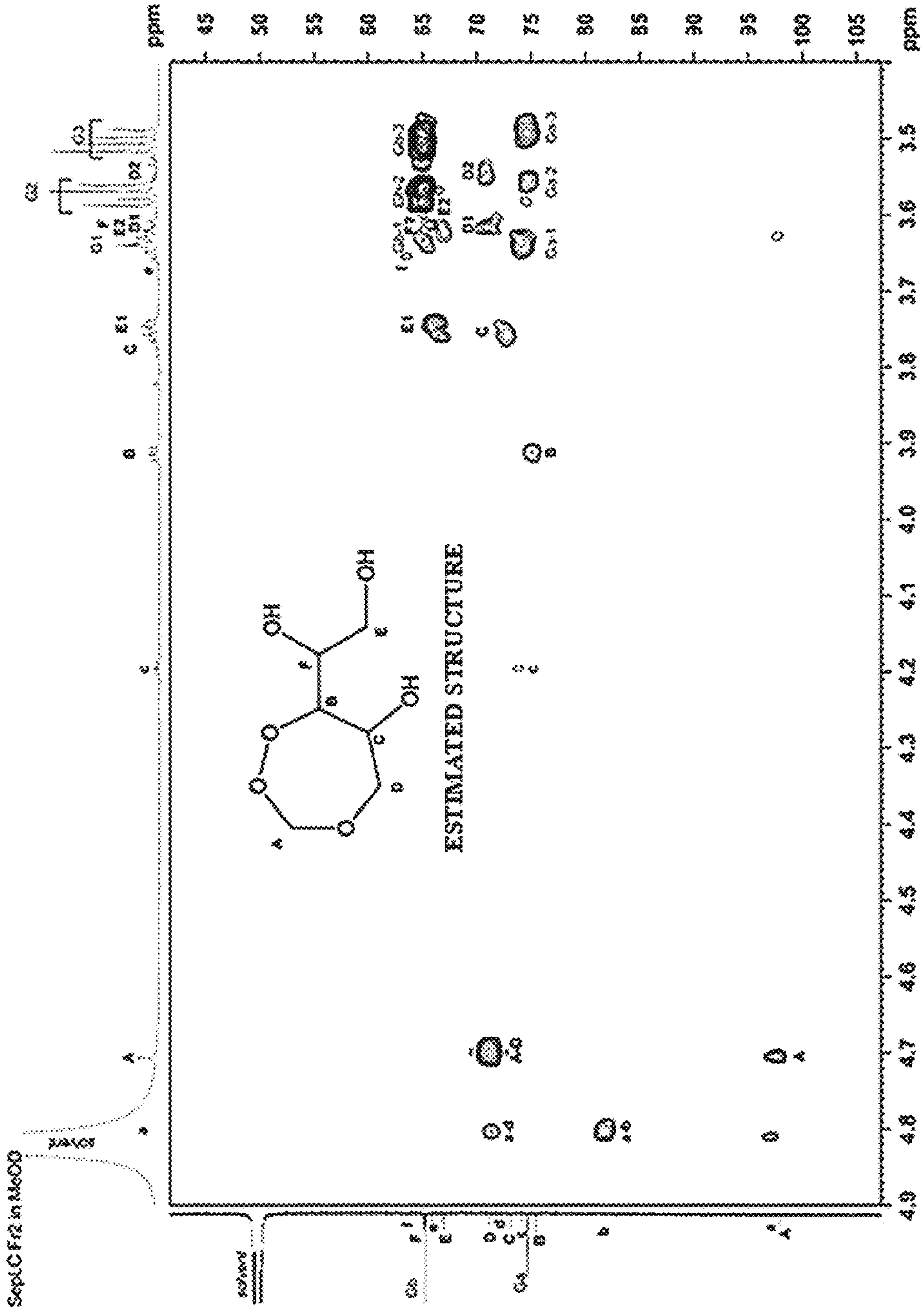
Figures 2, 3, 4, 5, 6, 7, 8, 9, 10, 11, 12, 13, 14, 15, 16, 17, 18, 19:
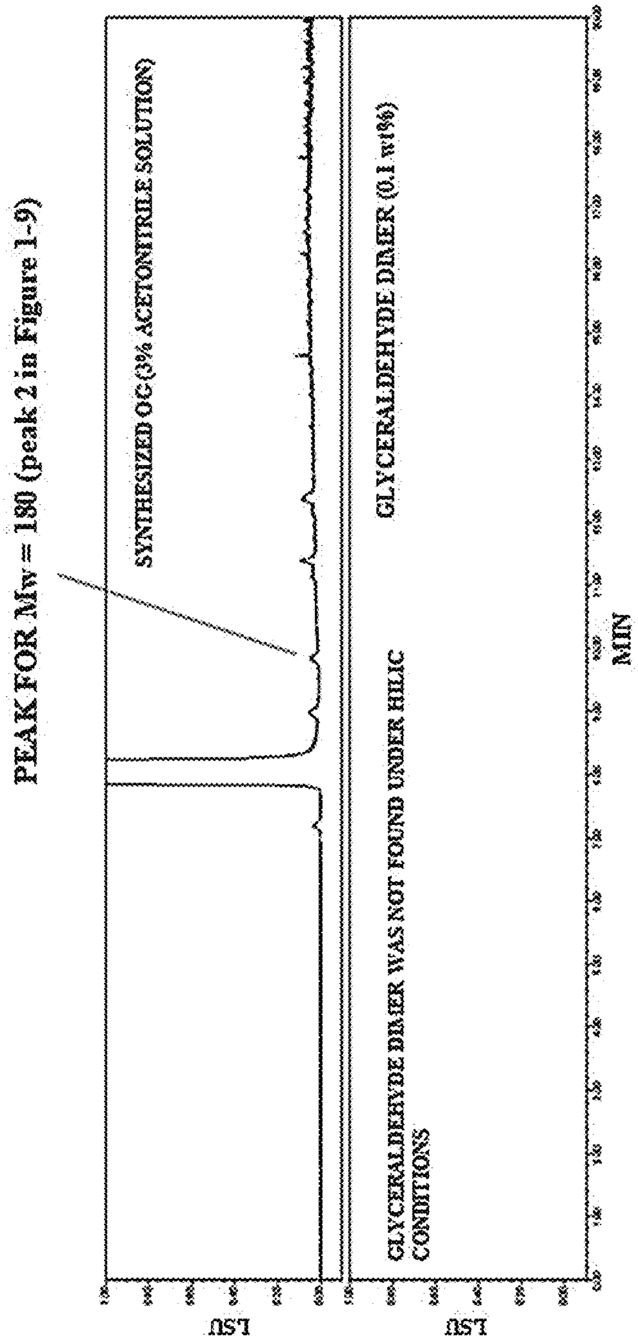
Figures 2, 3, 4, 5, 6, 7, 8, 9, 10, 11, 12, 13, 14, 15, 16, 17, 18, 19, 20:
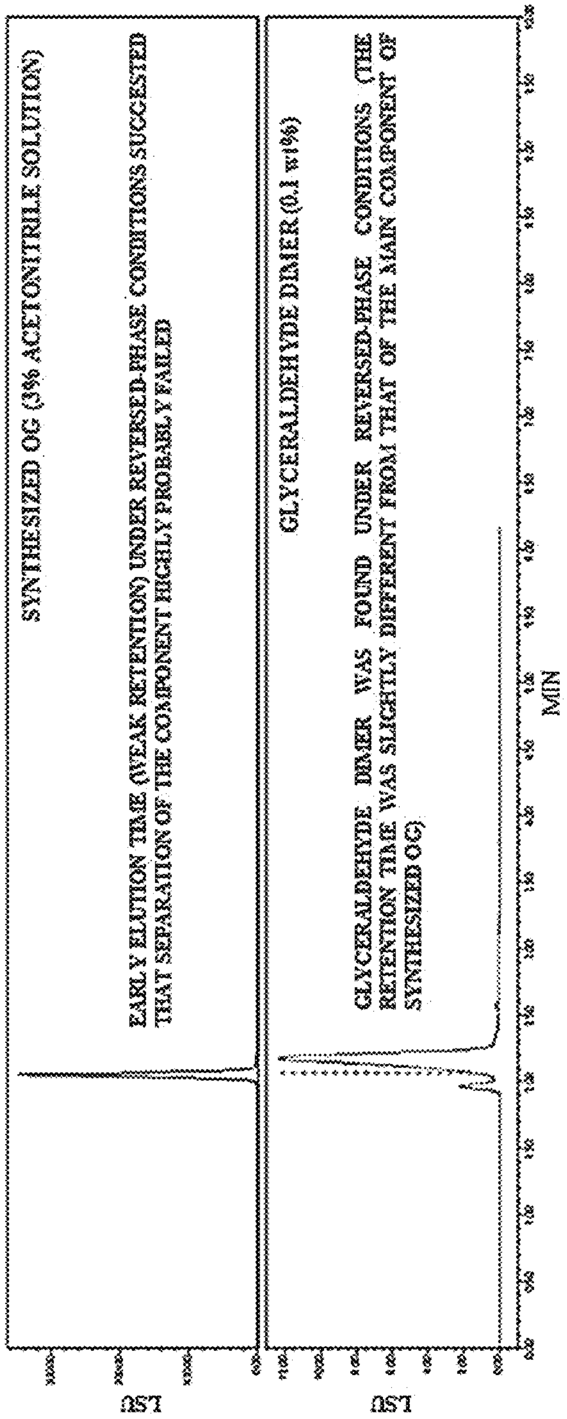
Figures 2, 3, 4, 5, 6, 7, 8, 9, 10, 11, 12, 13, 14, 15, 16, 17, 18, 19, 20, 21:
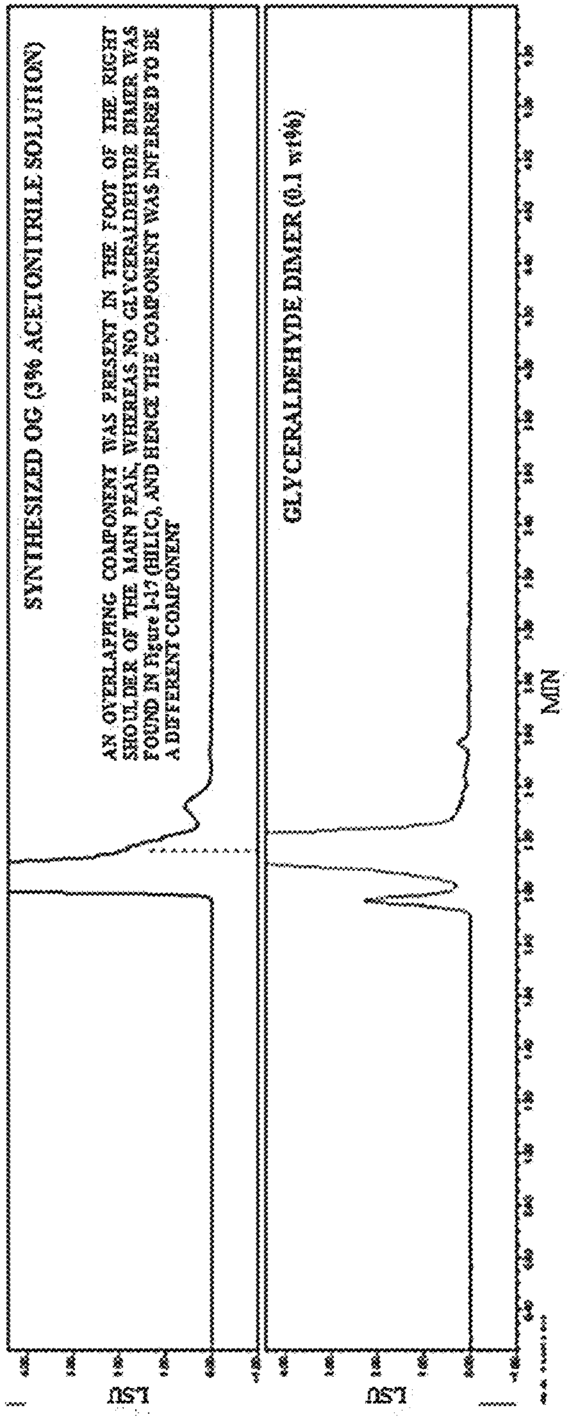
Figures 2, 3, 4, 5, 6, 7, 8, 9, 10, 11, 12, 13, 14, 15, 16, 17, 18, 19, 20, 21, 22:
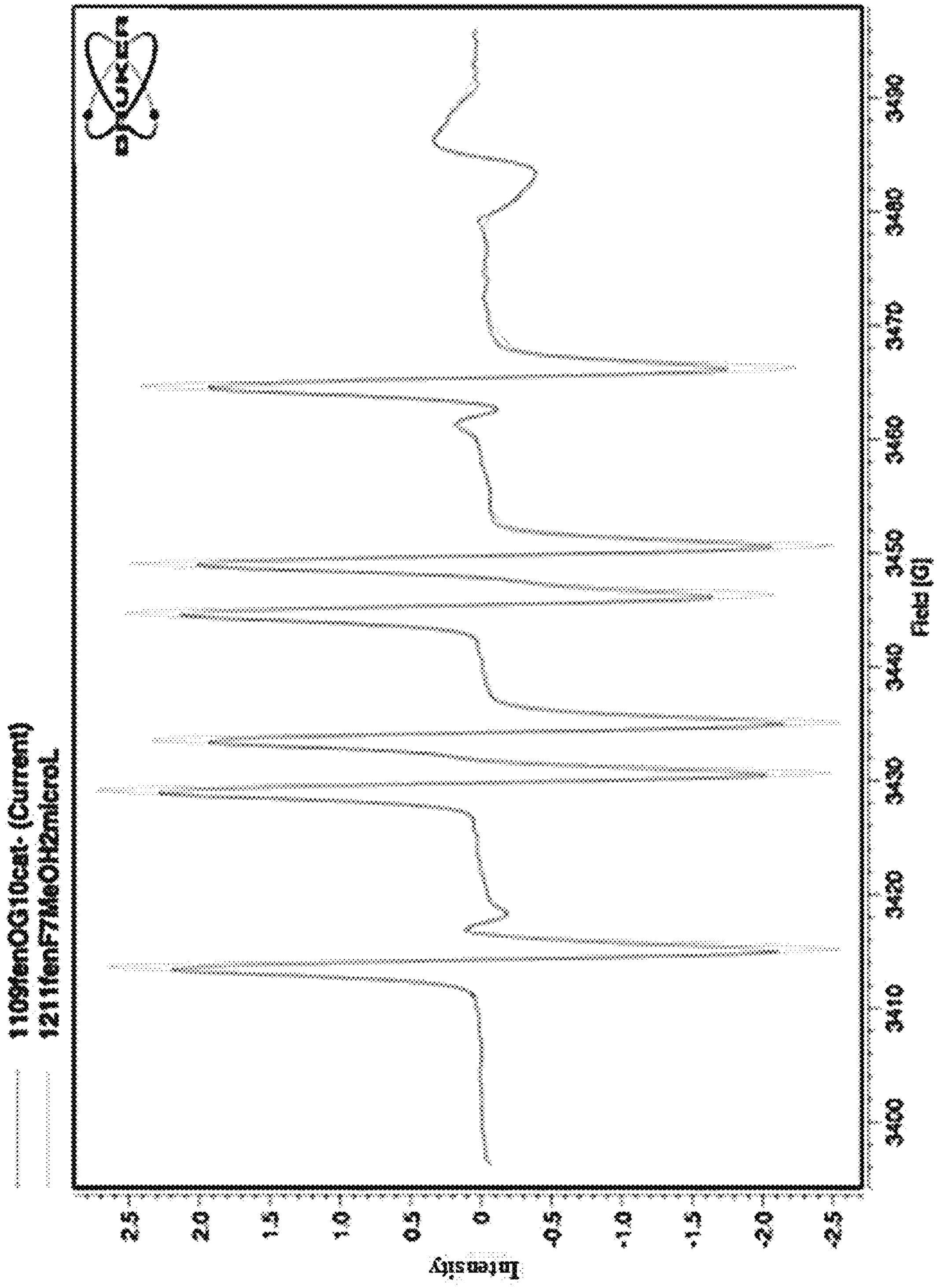
Figures 2, 3, 4, 5, 6, 7, 8, 9, 10, 11, 12, 13, 14, 15, 16, 17, 18, 19, 20, 21, 22, 23:
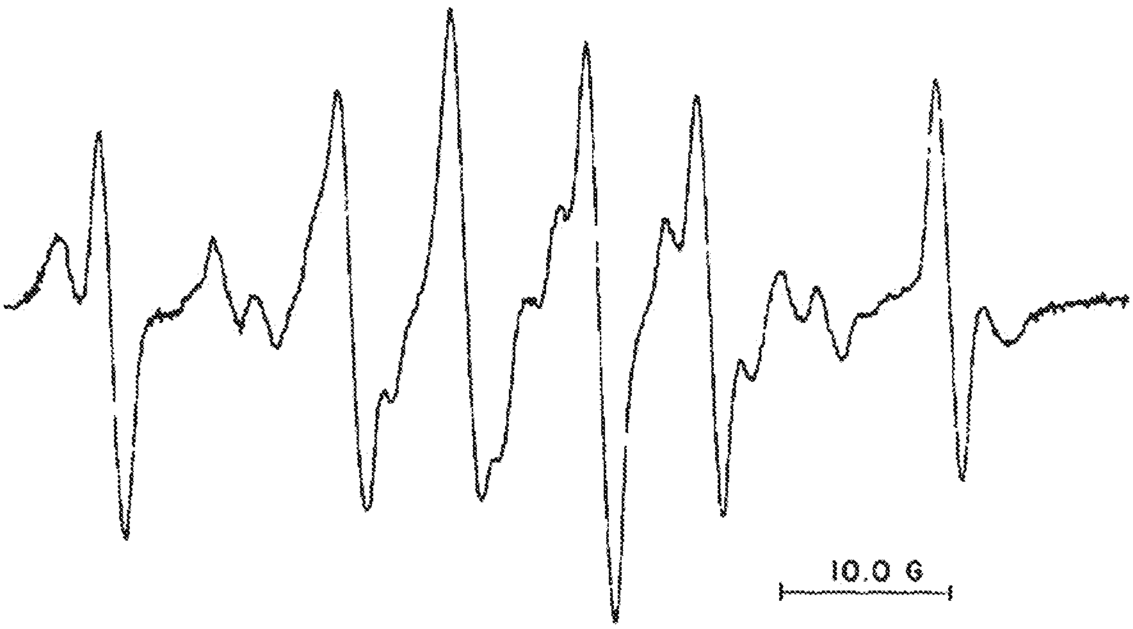
Figures 2, 3, 4, 5, 6, 7, 8, 9, 10, 11, 12, 13, 14, 15, 16, 17, 18, 19, 20, 21, 22, 23, 24:
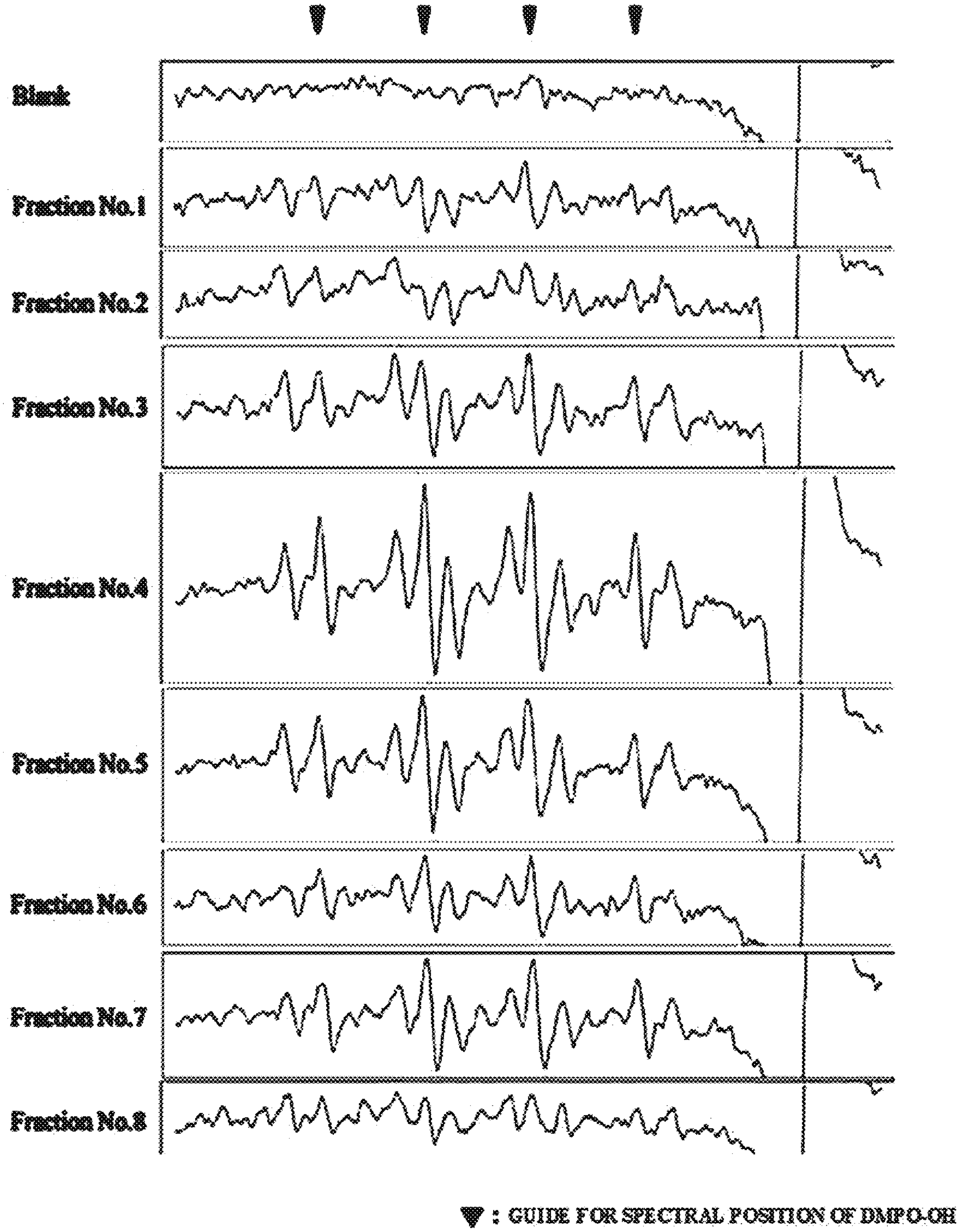
Figures 2, 3, 4, 5, 6, 7, 8, 9, 10, 11, 12, 13, 14, 15, 16, 17, 18, 19, 20, 21, 22, 23, 24, 25:
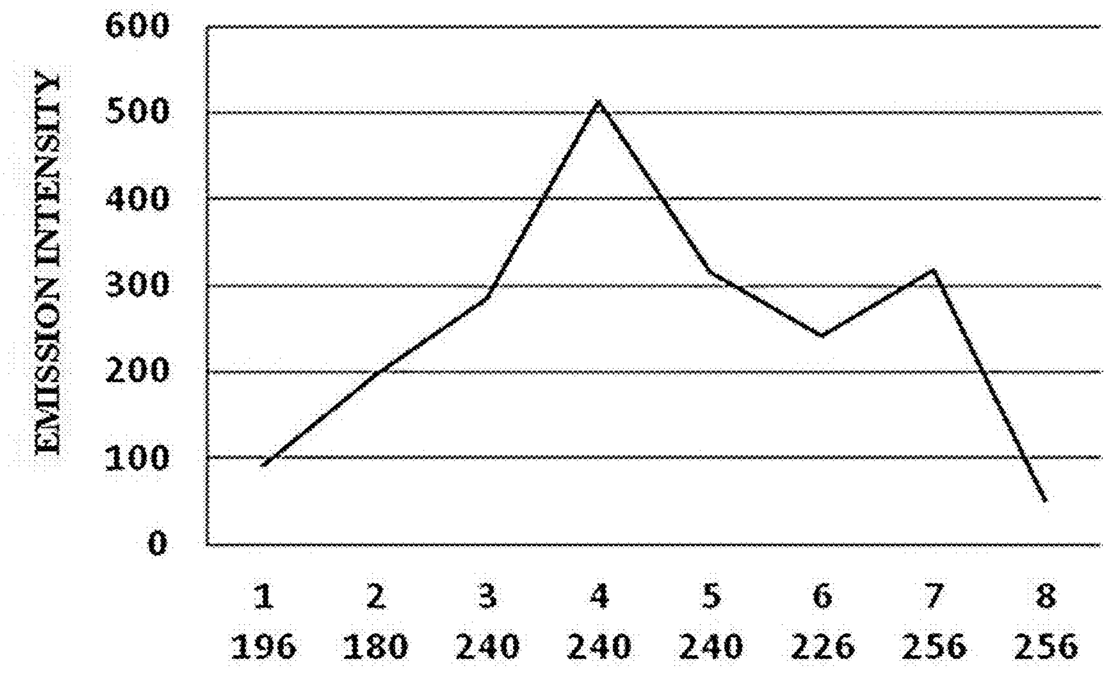
Figures 1, 3:
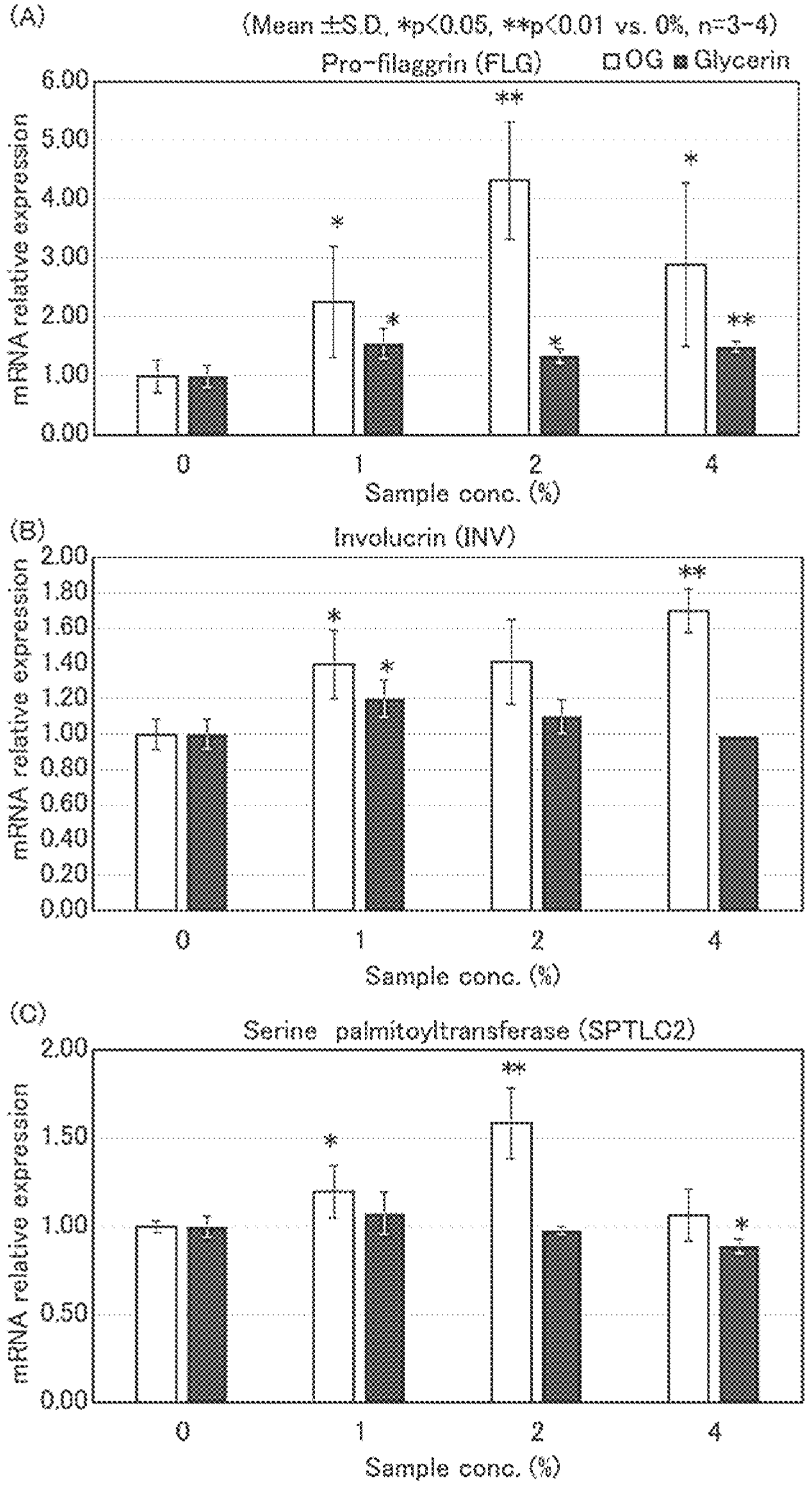
Figures 2, 3:
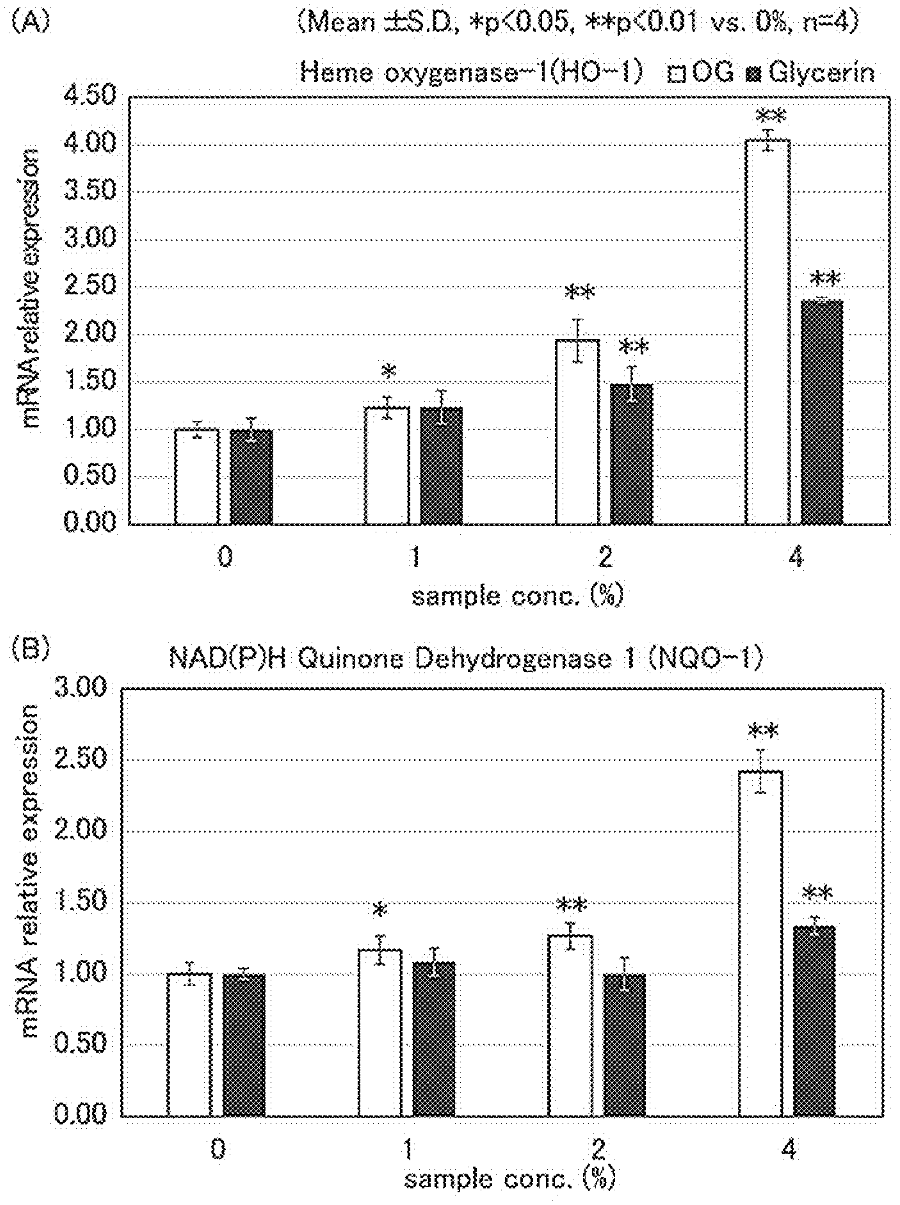
Figure 3:
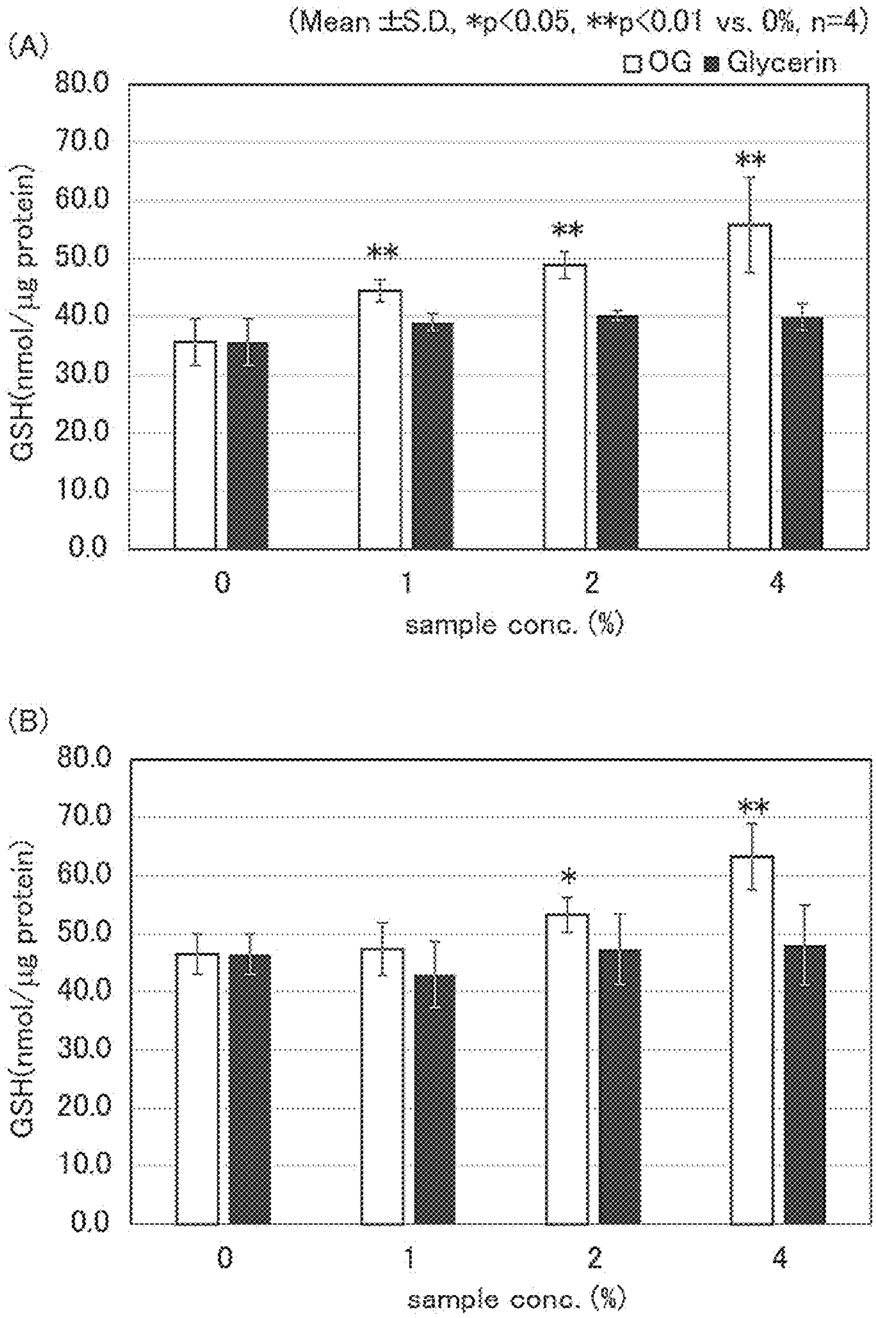
Figures 3, 4:
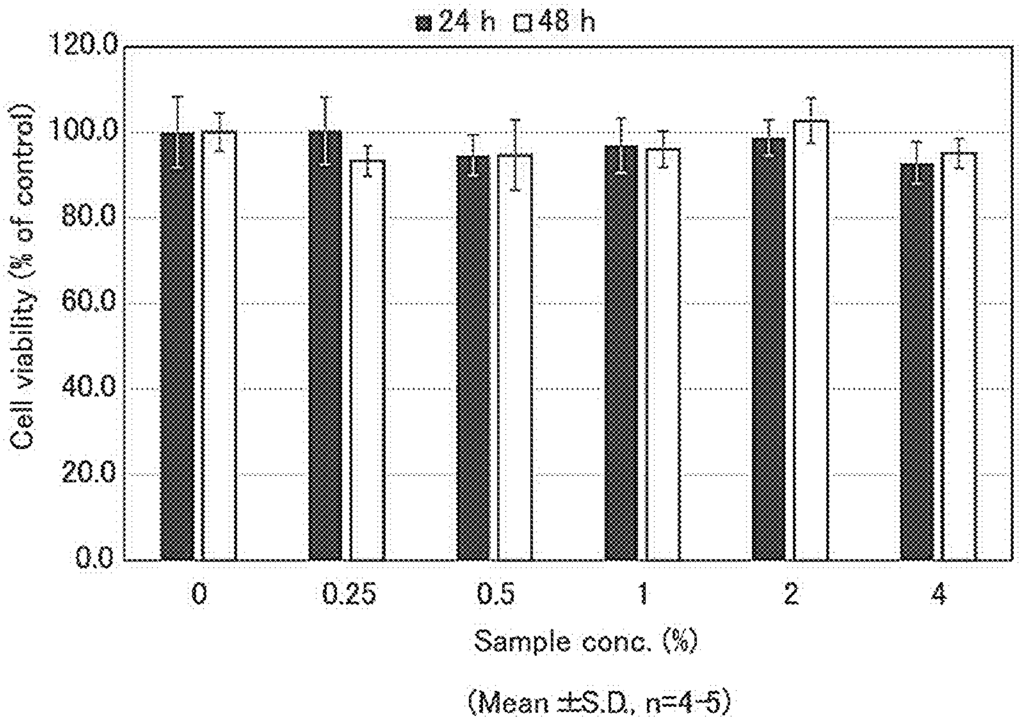
Figures 3, 4, 5:
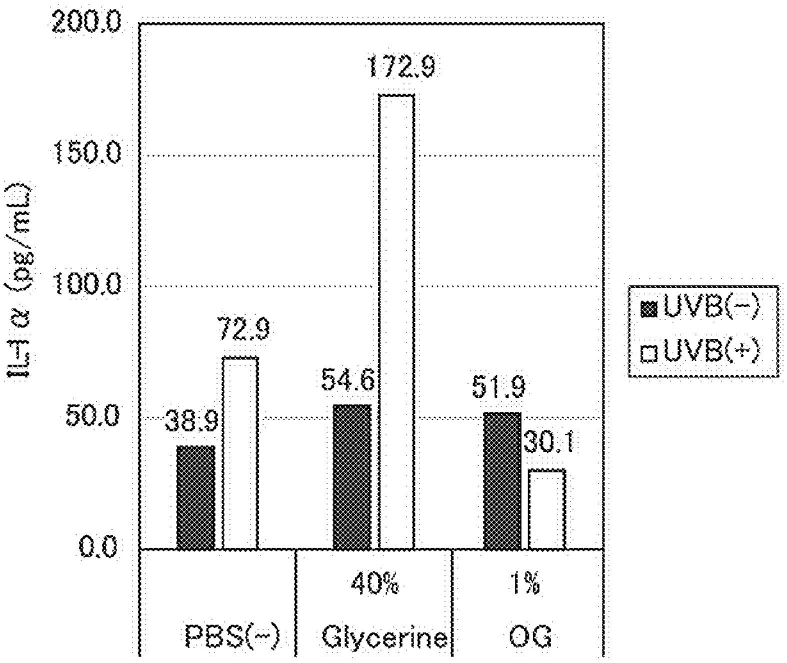
Figures 3, 4, 5, 6:
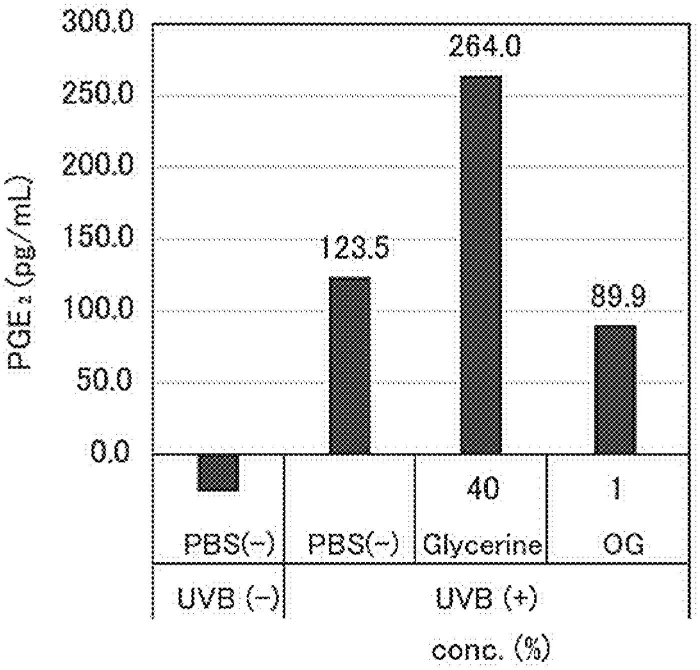
Figures 3, 4, 5, 6, 7:
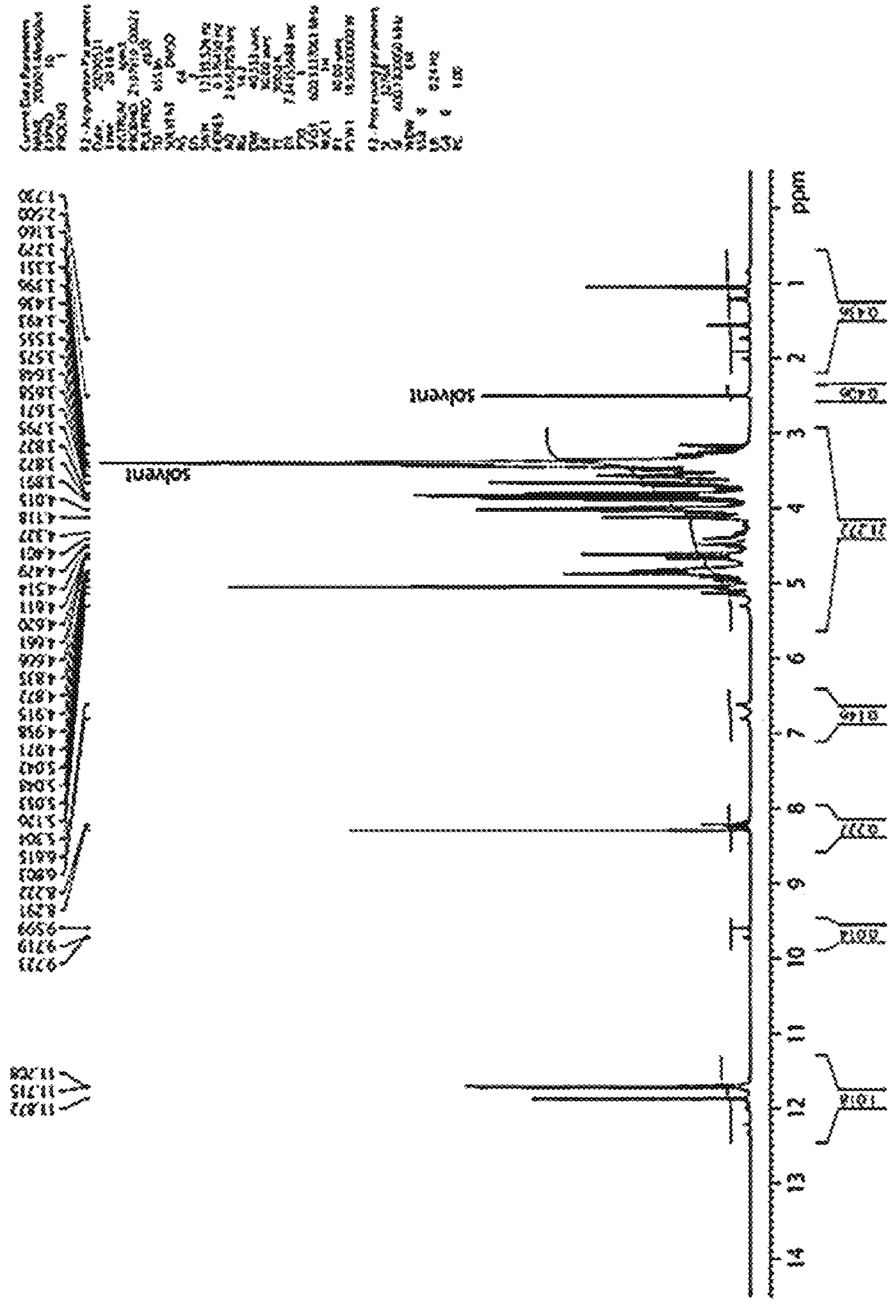
Figures 3, 4, 5, 6, 7, 8:
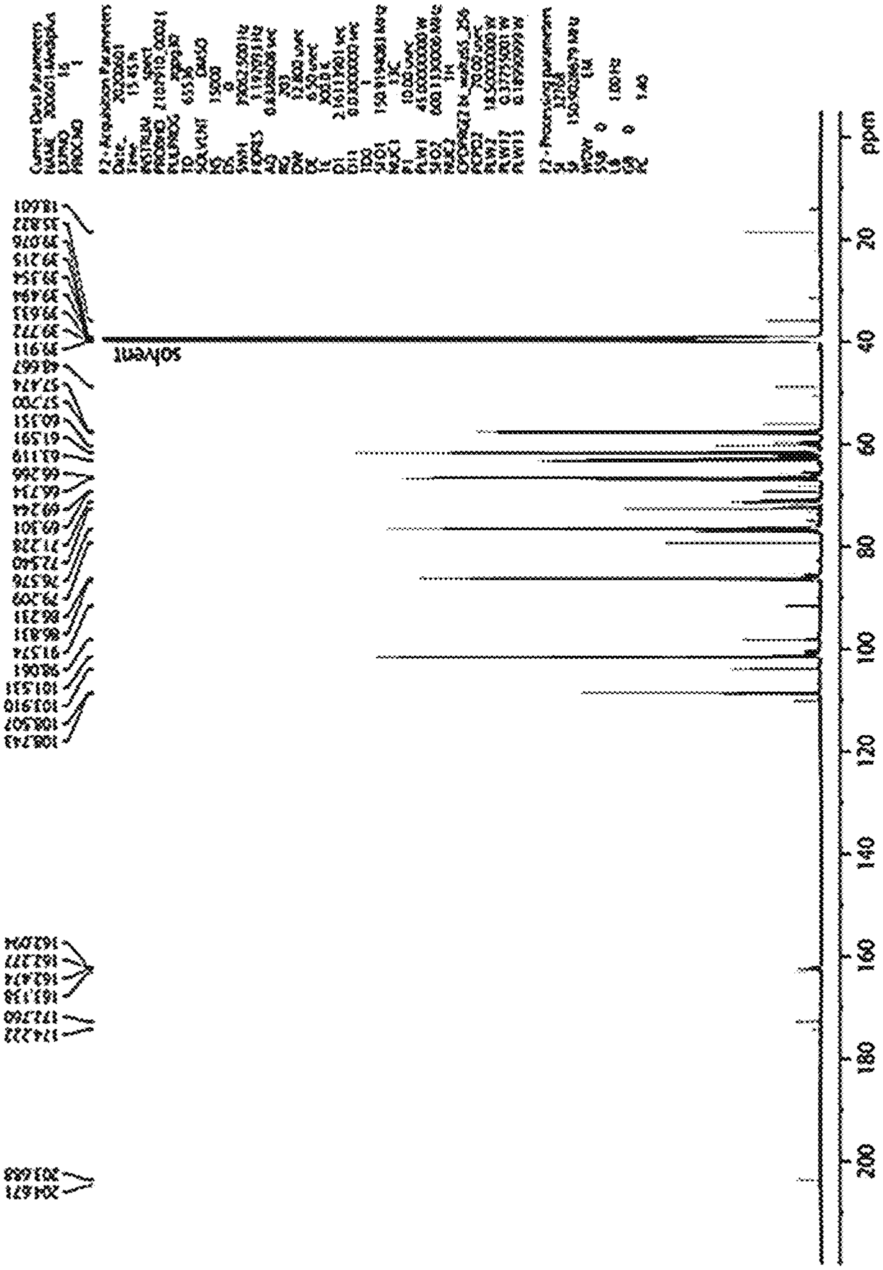
Figures 3, 4, 5, 6, 7, 8, 9:
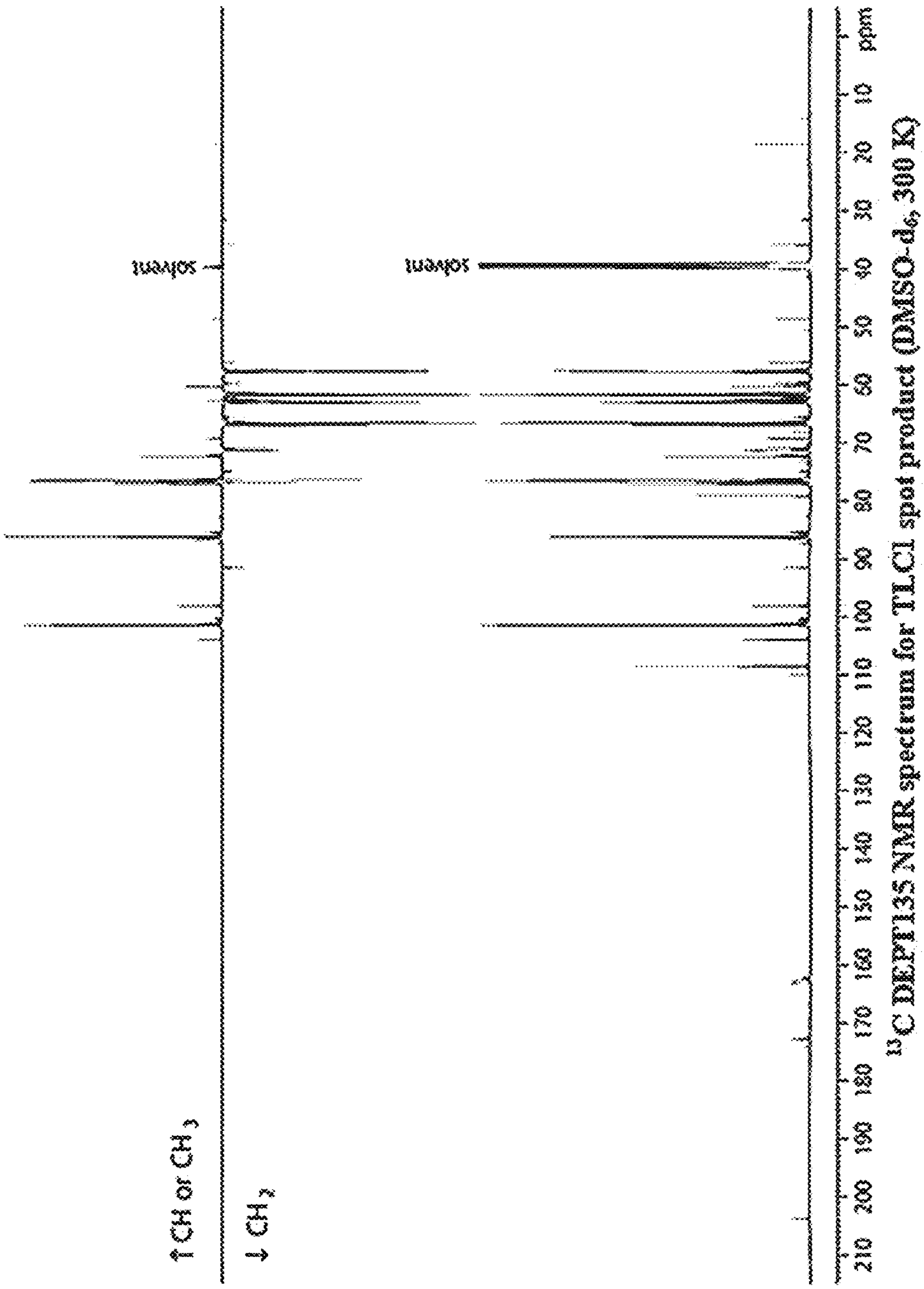
Figures 3, 4, 5, 6, 7, 8, 9, 10:
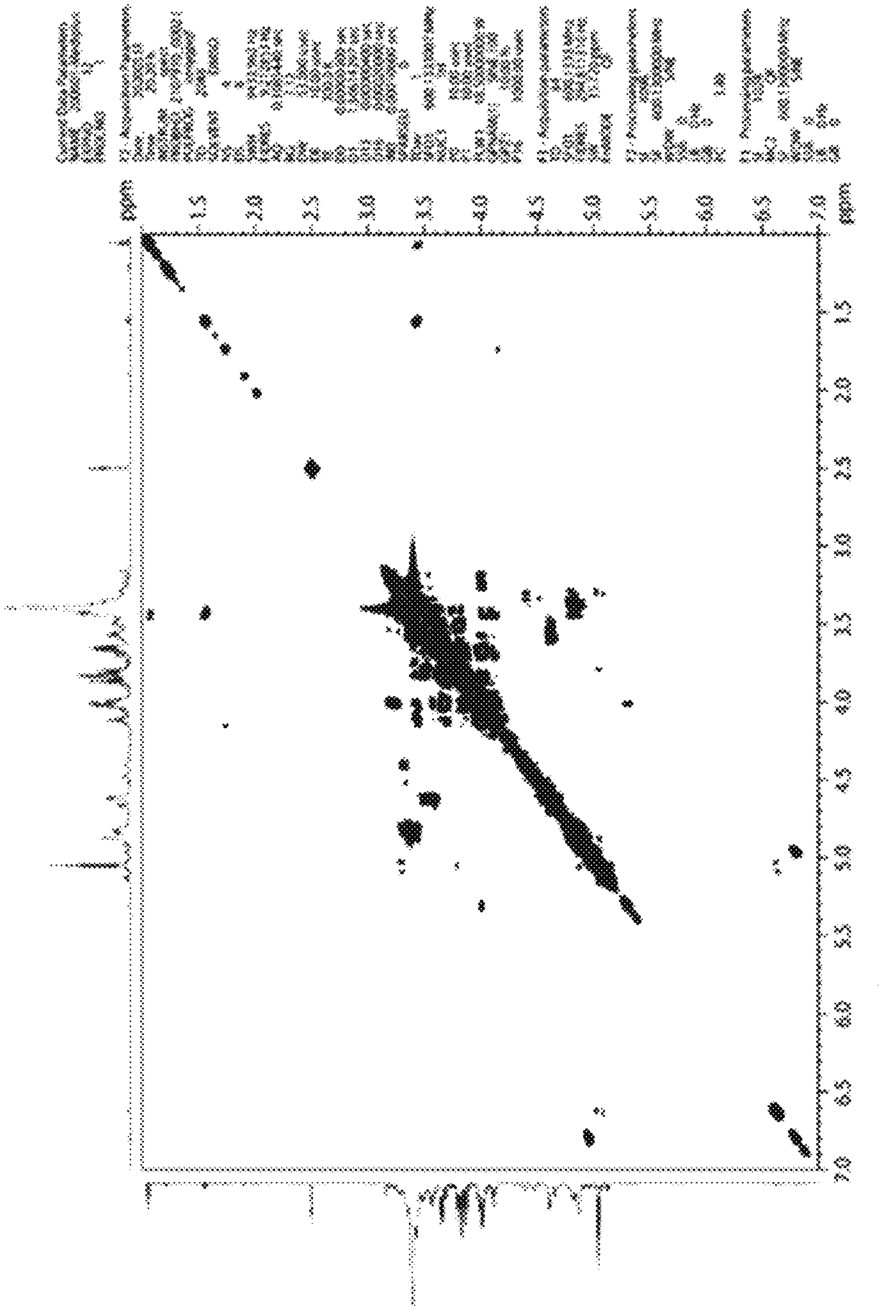
Figures 3, 4, 5, 6, 7, 8, 9, 10, 11:
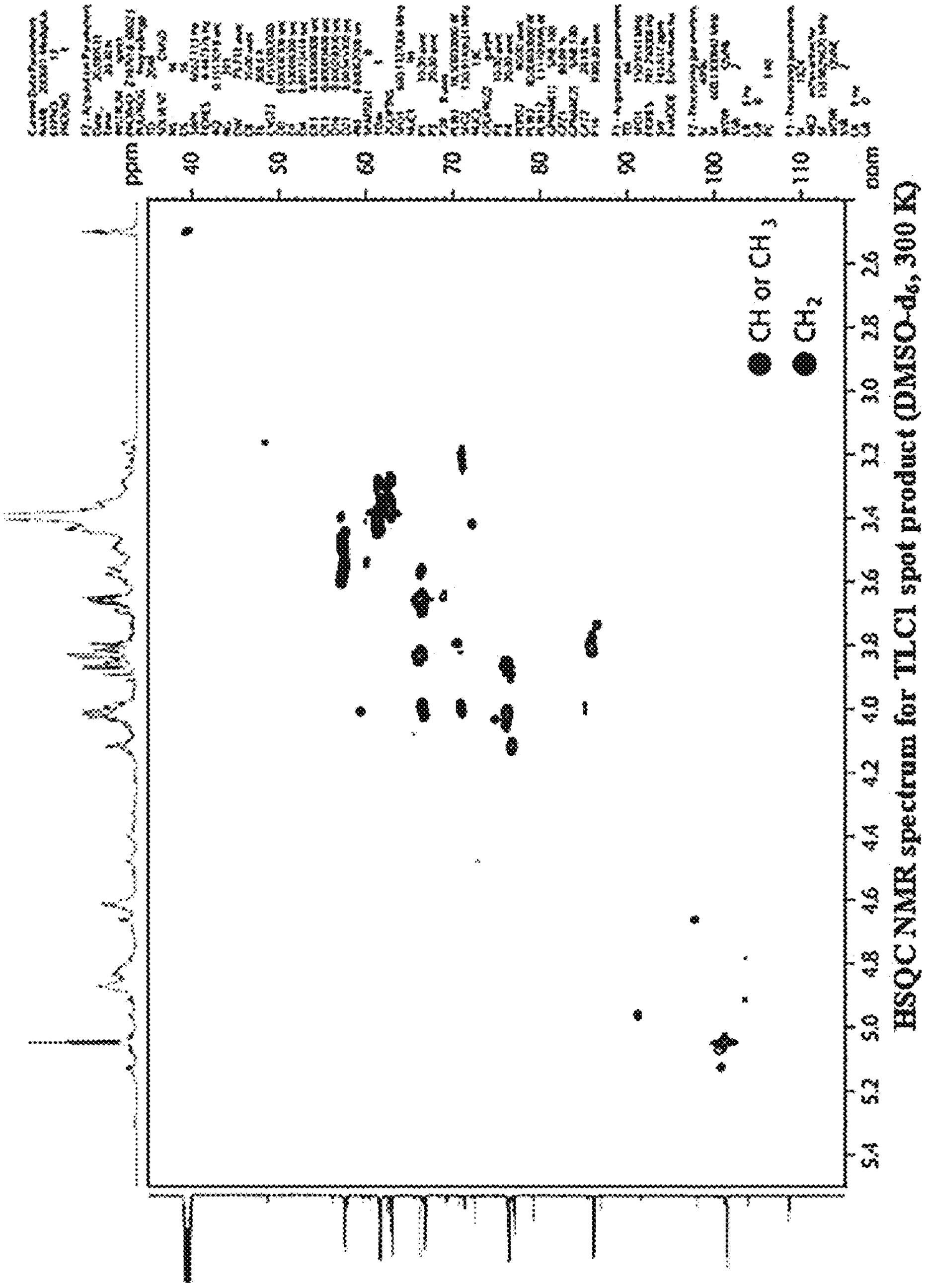
Figures 3, 4, 5, 6, 7, 8, 9, 10, 11, 12:
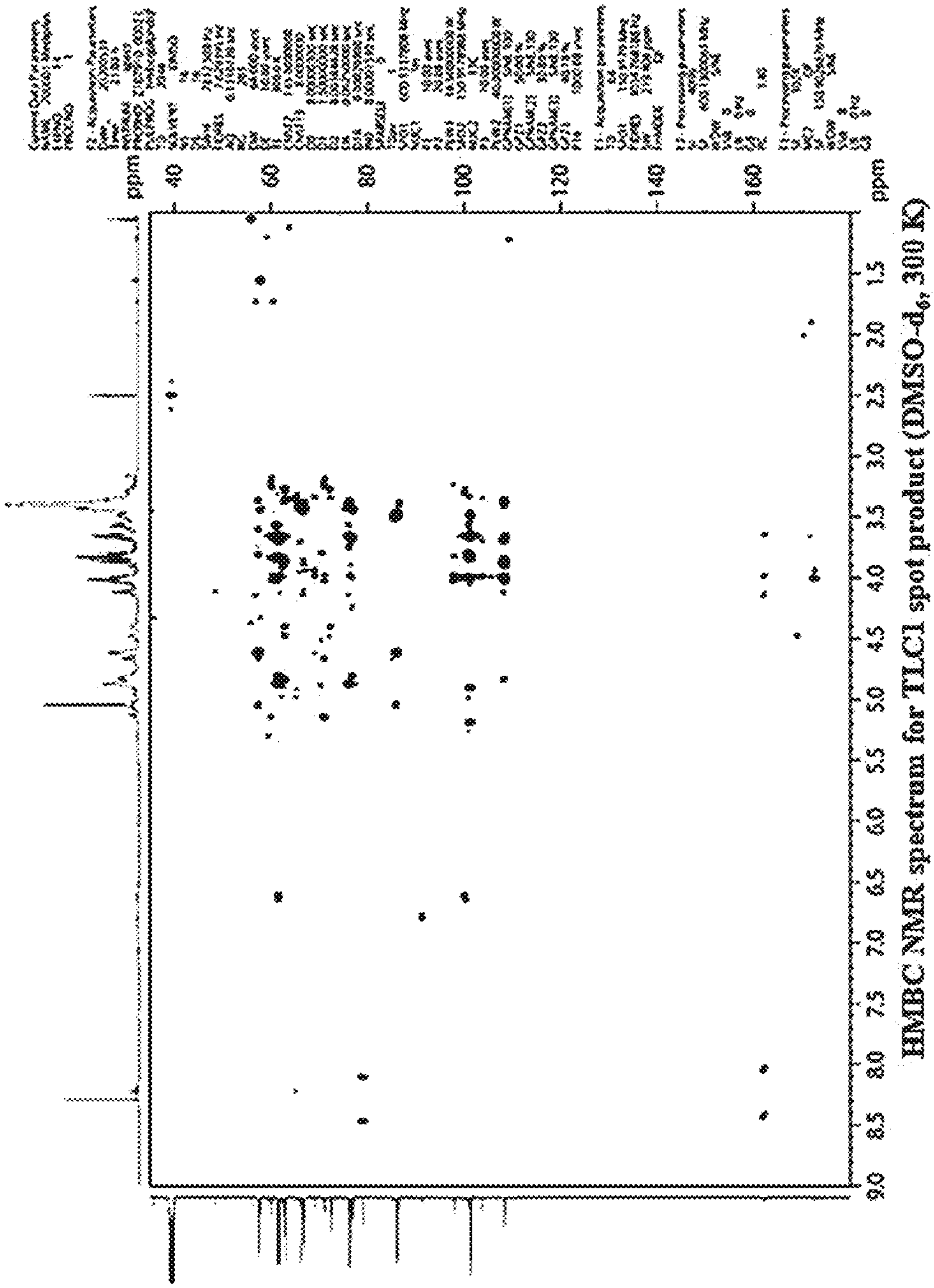
Figures 3, 4, 5, 6, 7, 8, 9, 10, 11, 12, 13:
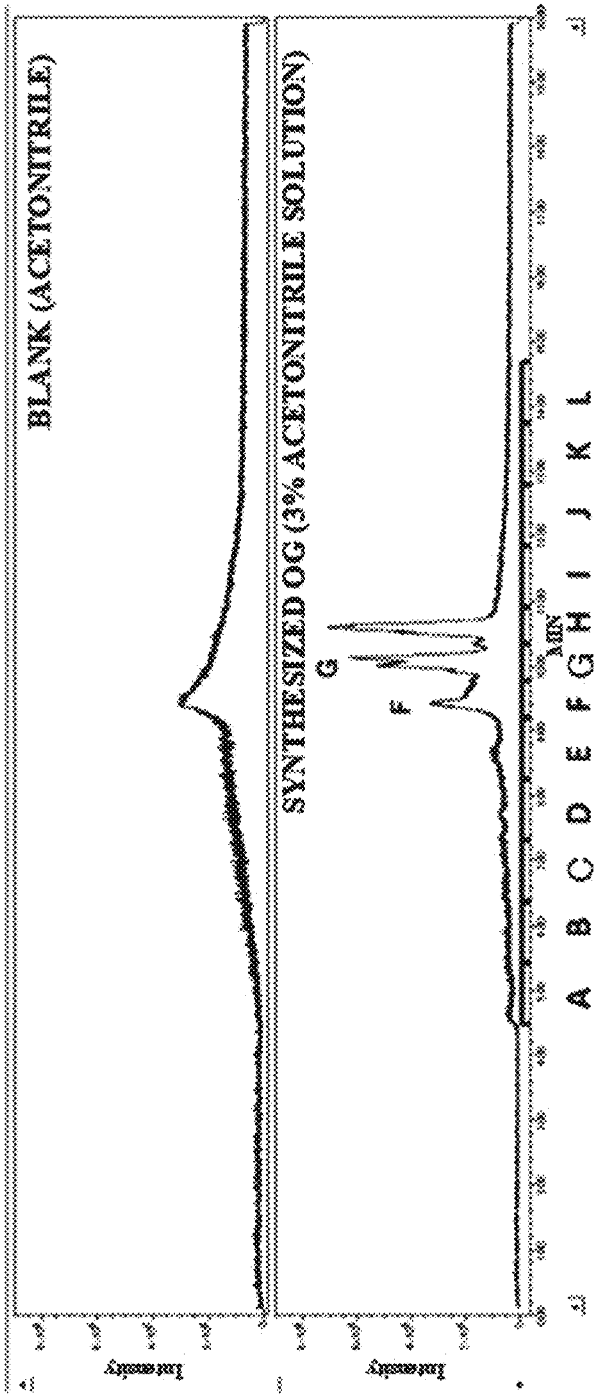
Figures 3, 4, 5, 6, 7, 8, 9, 10, 11, 12, 13, 14:
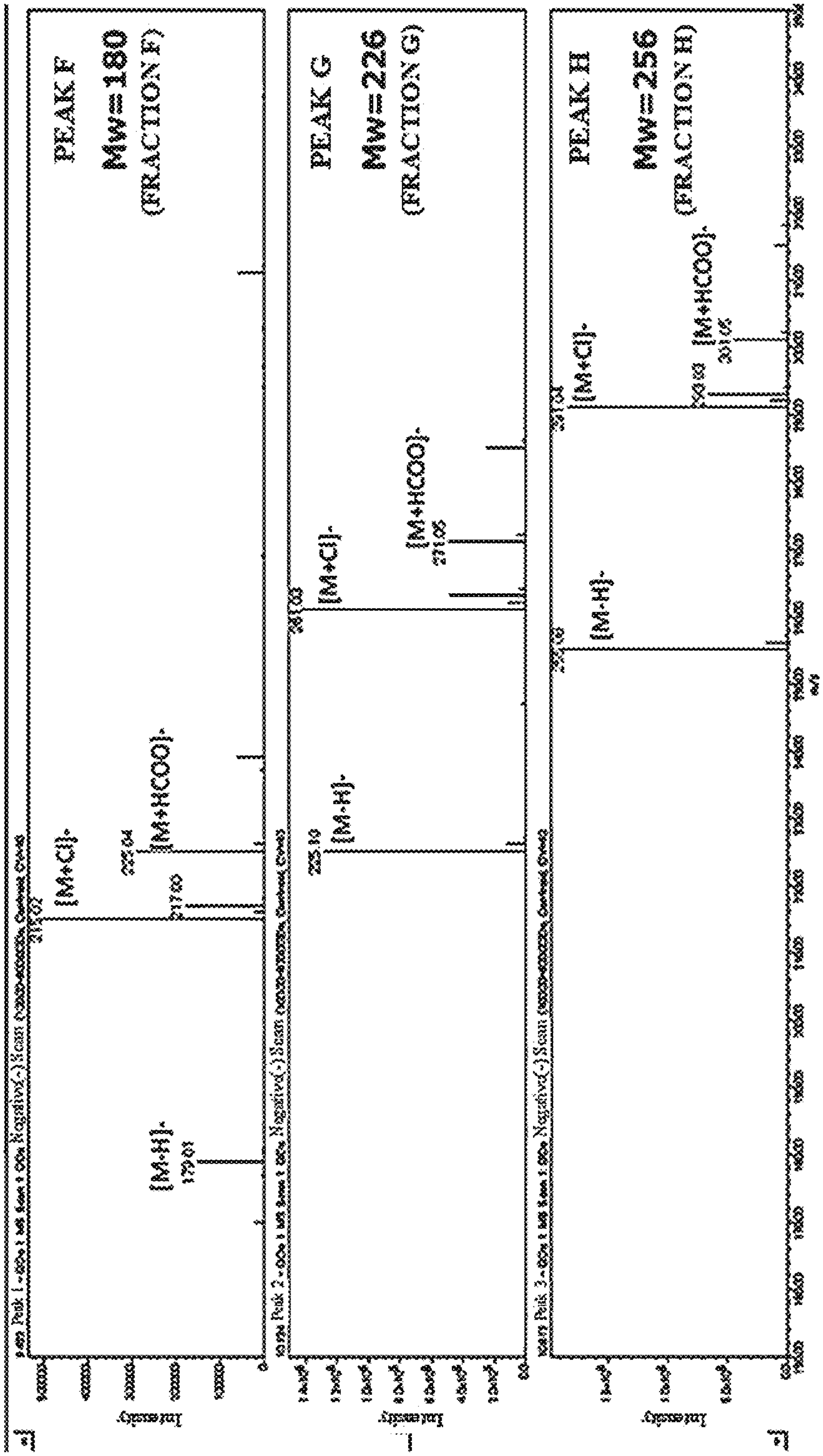
Figures 3, 4, 5, 6, 7, 8, 9, 10, 11, 12, 13, 14, 15:
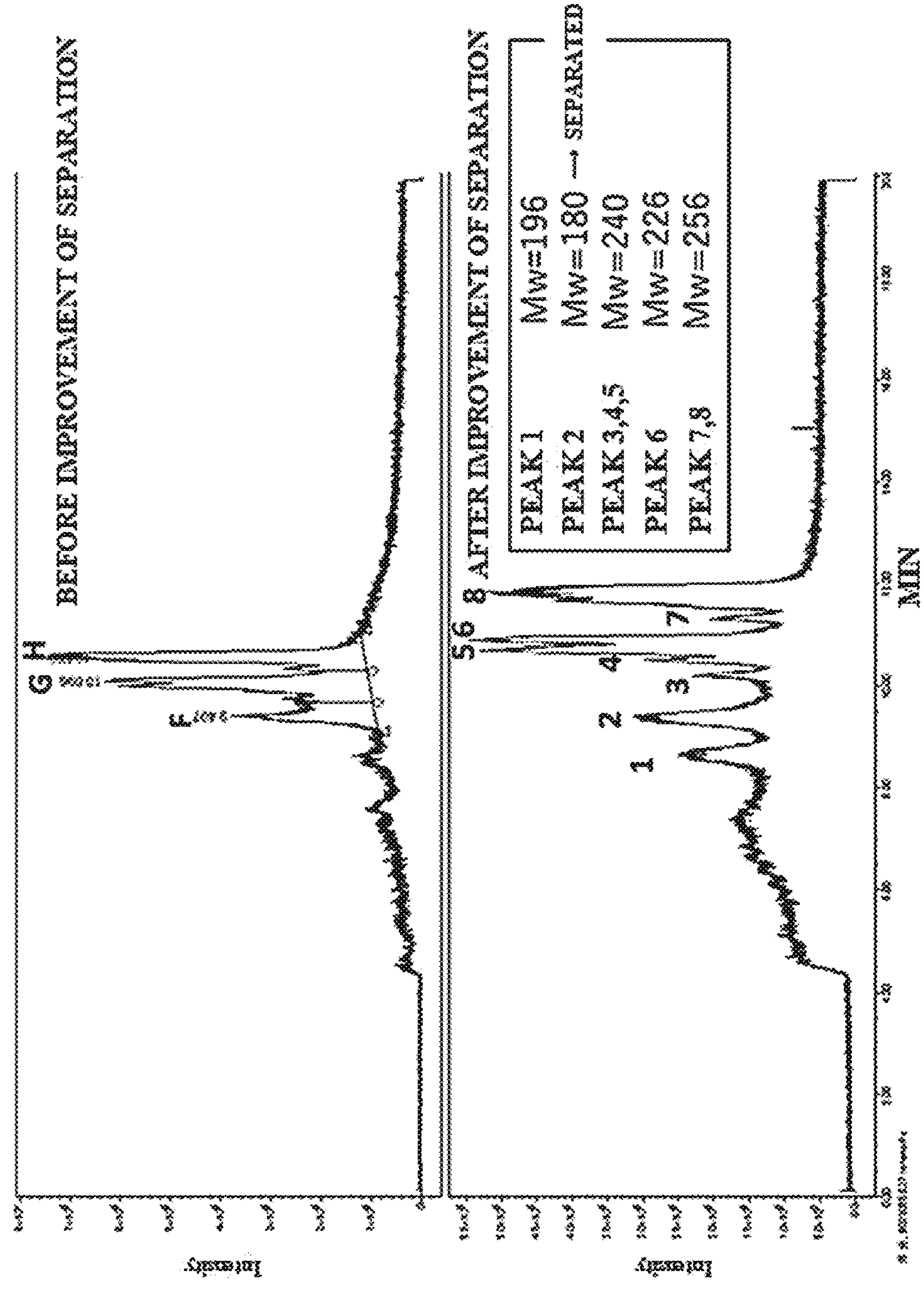
Figures 3, 4, 5, 6, 7, 8, 9, 10, 11, 12, 13, 14, 15, 16:
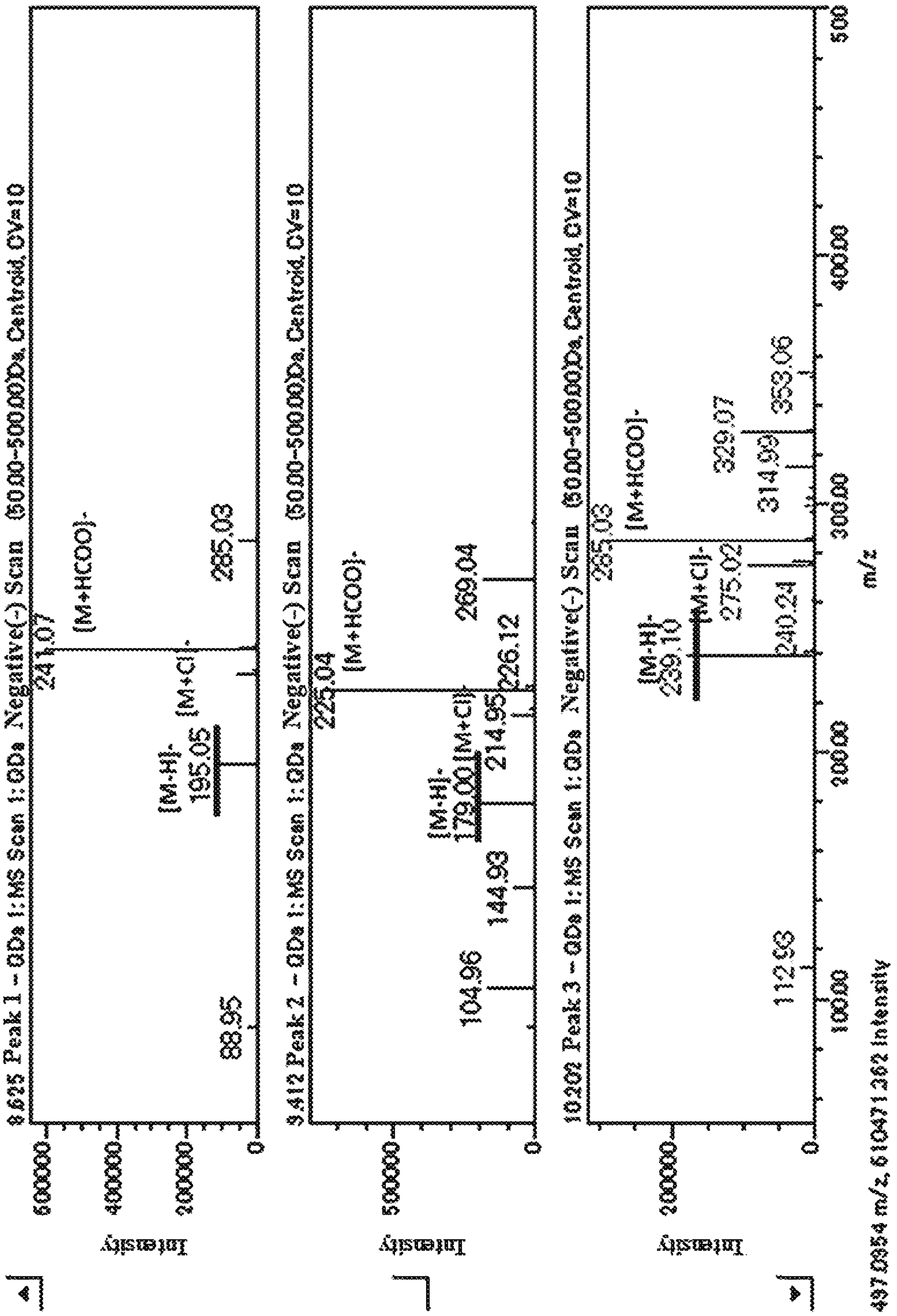
Figures 3, 4, 5, 6, 7, 8, 9, 10, 11, 12, 13, 14, 15, 16, 17:
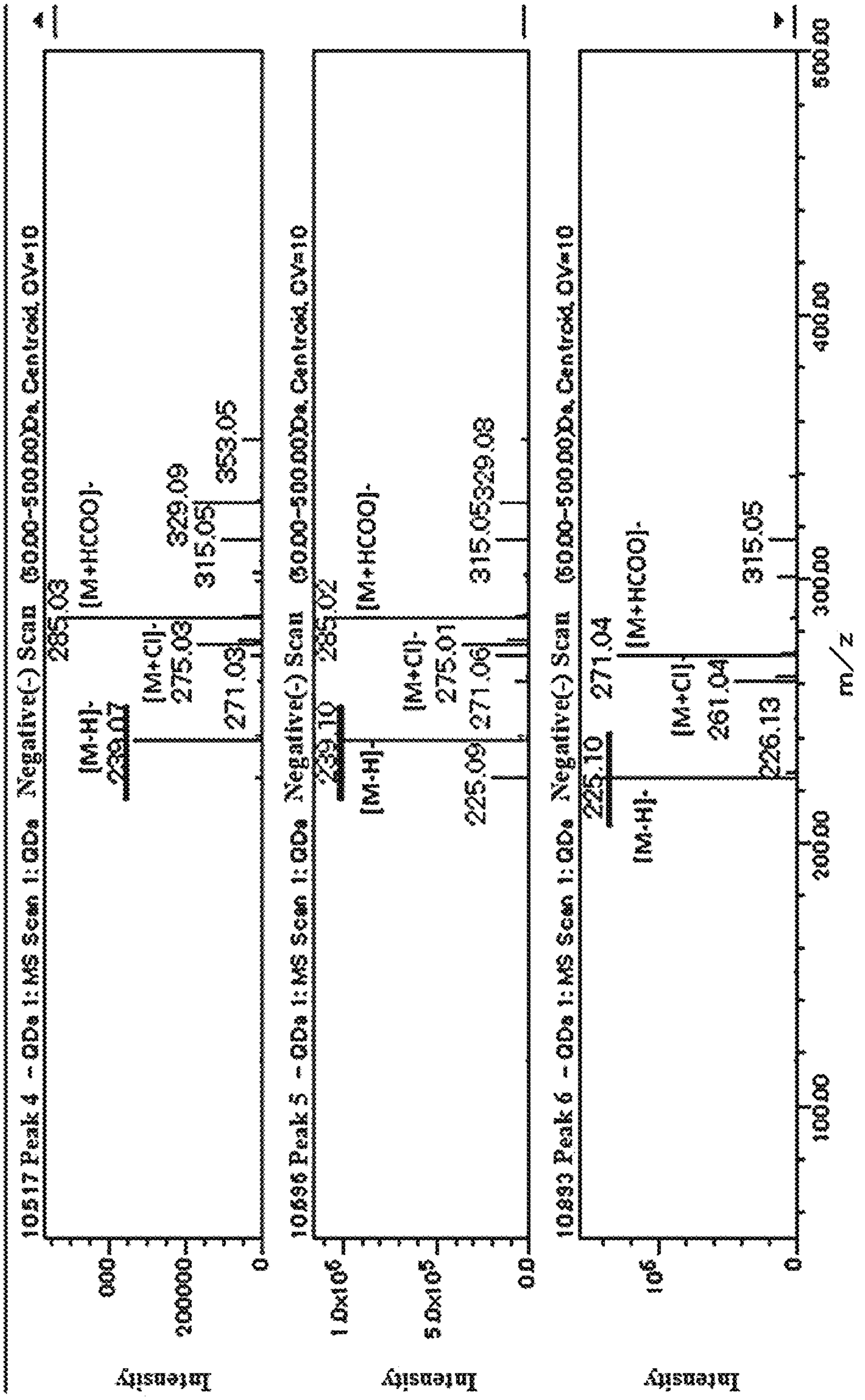
Figures 3, 4, 5, 6, 7, 8, 9, 10, 11, 12, 13, 14, 15, 16, 17, 18:
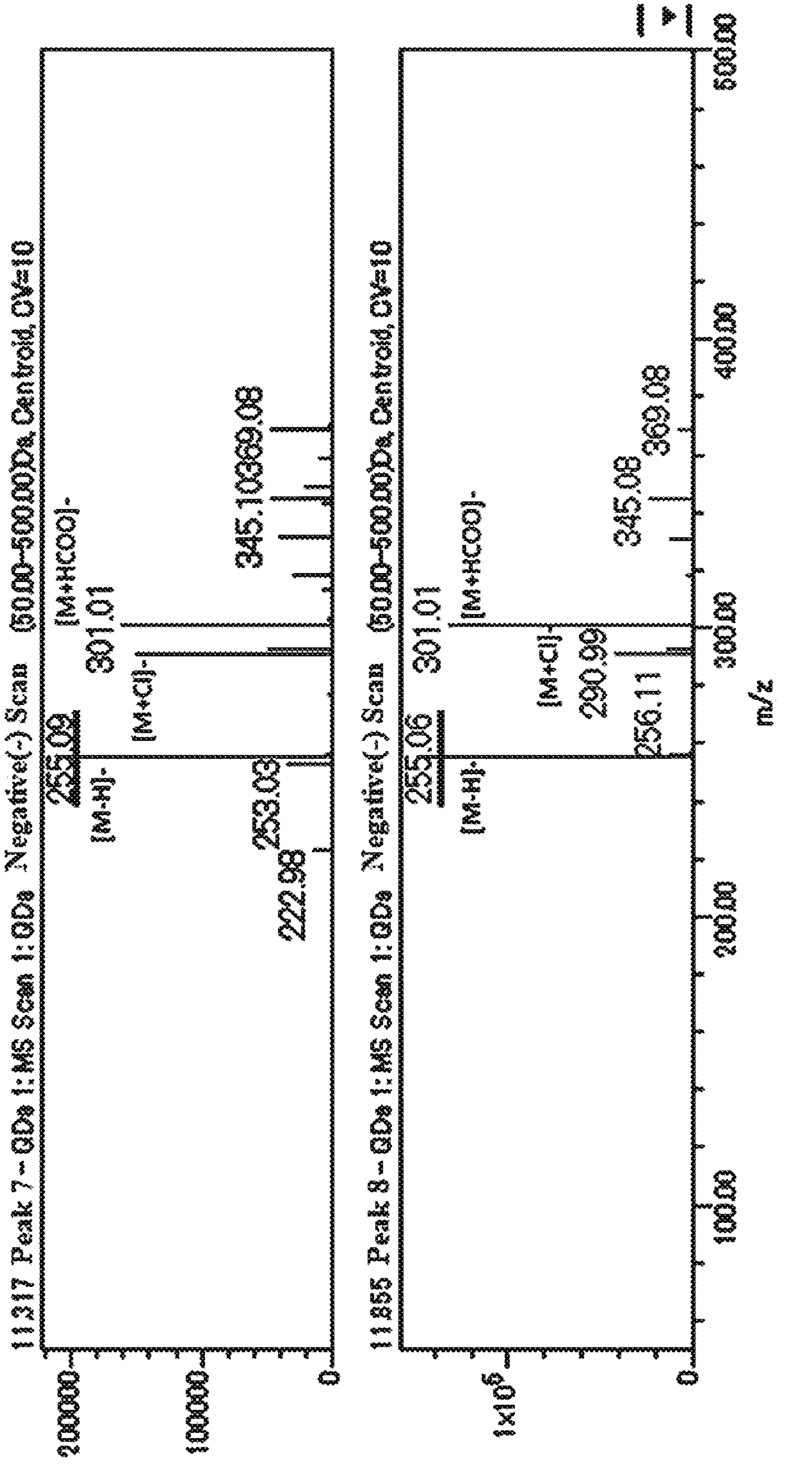
Figures 3, 4, 5, 6, 7, 8, 9, 10, 11, 12, 13, 14, 15, 16, 17, 18, 19:
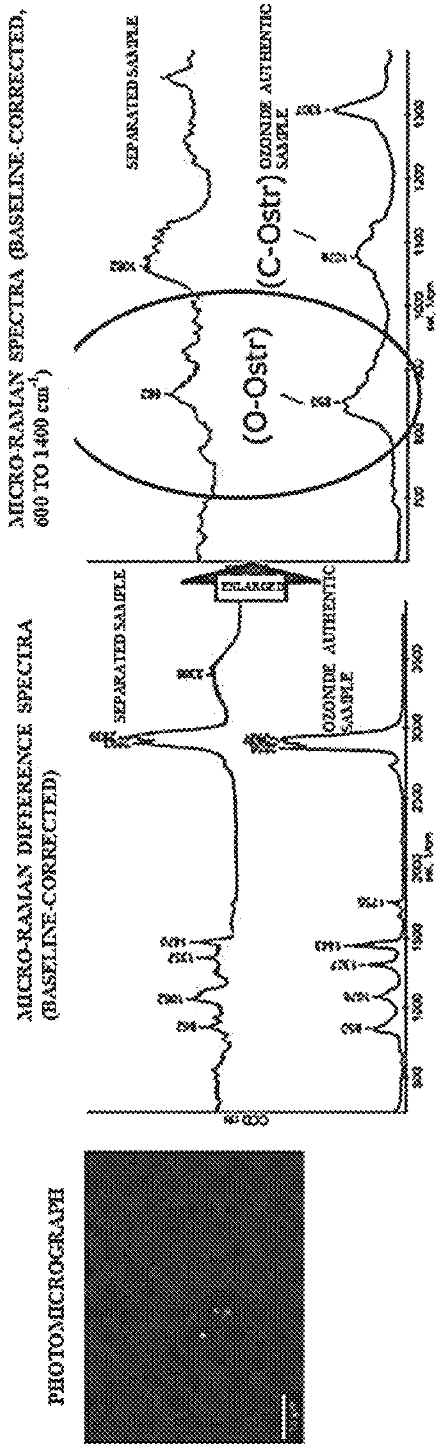
Figures 3, 4, 5, 6, 7, 8, 9, 10, 11, 12, 13, 14, 15, 16, 17, 18, 19, 20:
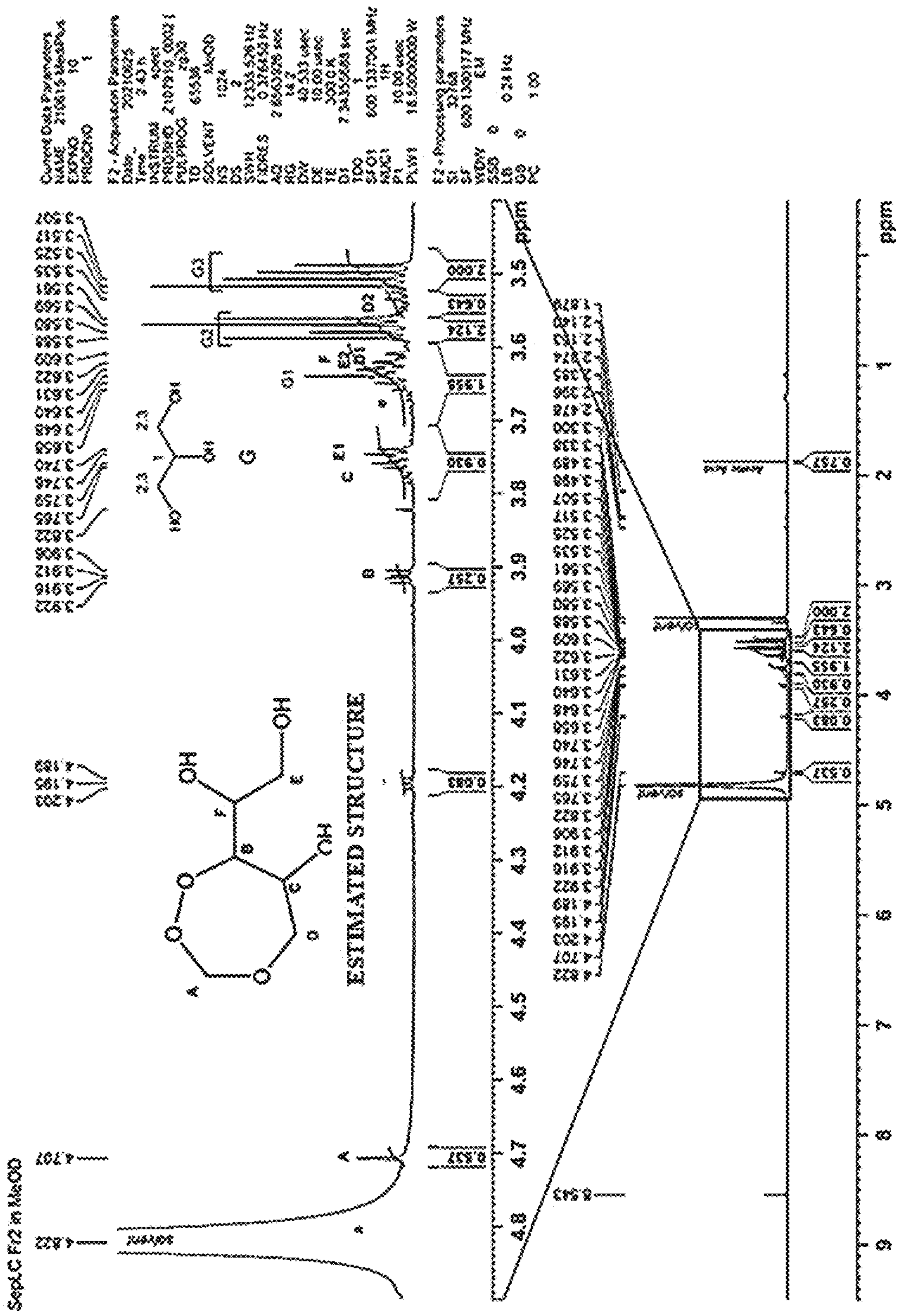
Figures 3, 4, 5, 6, 7, 8, 9, 10, 11, 12, 13, 14, 15, 16, 17, 18, 19, 20, 21:
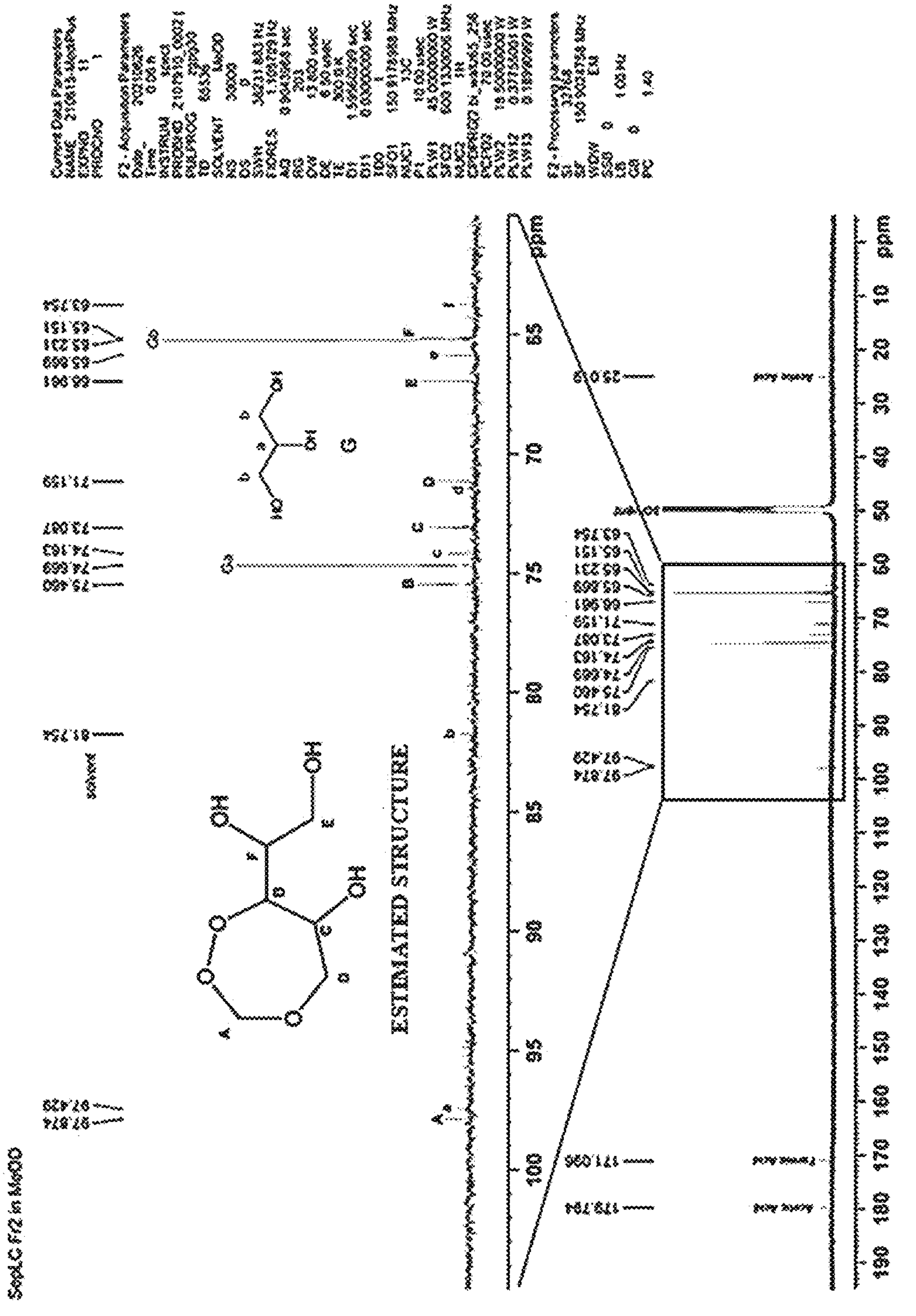
Figures 3, 4, 5, 6, 7, 8, 9, 10, 11, 12, 13, 14, 15, 16, 17, 18, 19, 20, 21, 22:
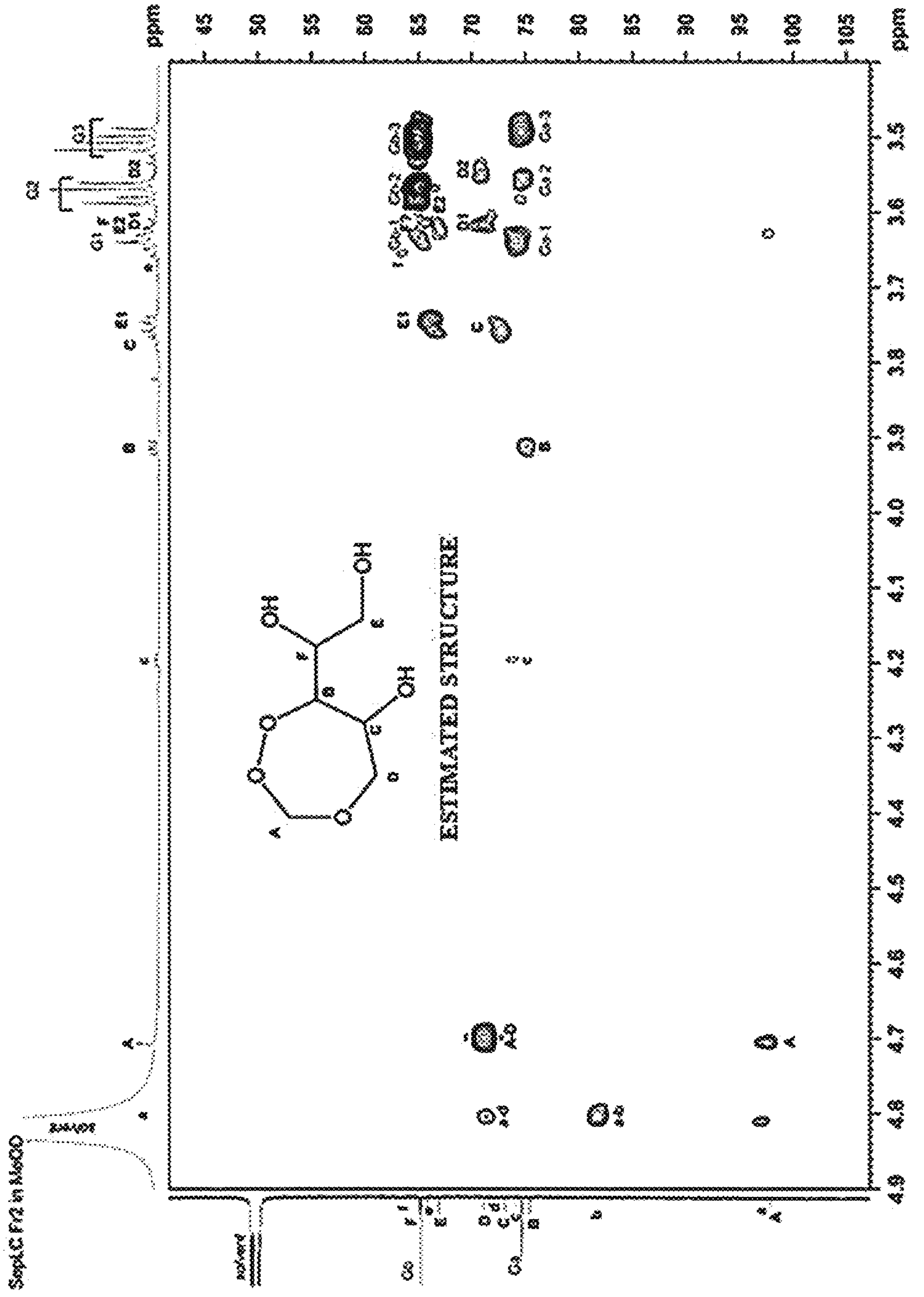
Figures 3, 4, 5, 6, 7, 8, 9, 10, 11, 12, 13, 14, 15, 16, 17, 18, 19, 20, 21, 22, 23:
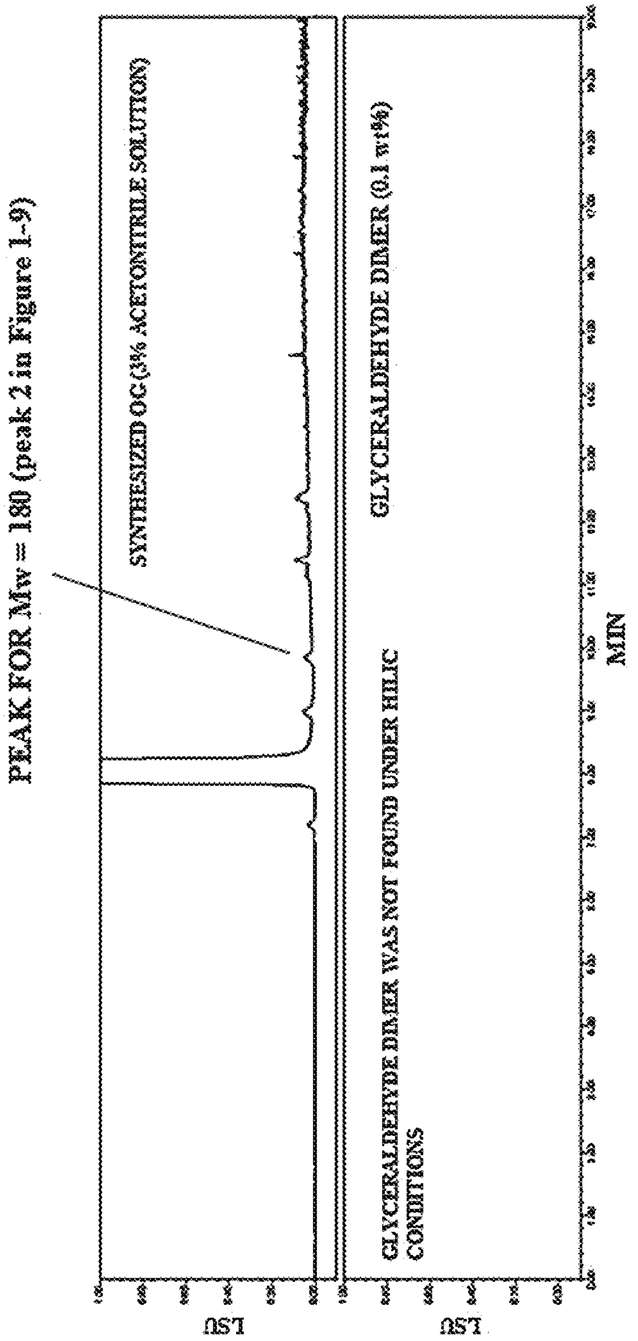
Figures 3, 4, 5, 6, 7, 8, 9, 10, 11, 12, 13, 14, 15, 16, 17, 18, 19, 20, 21, 22, 23, 24:
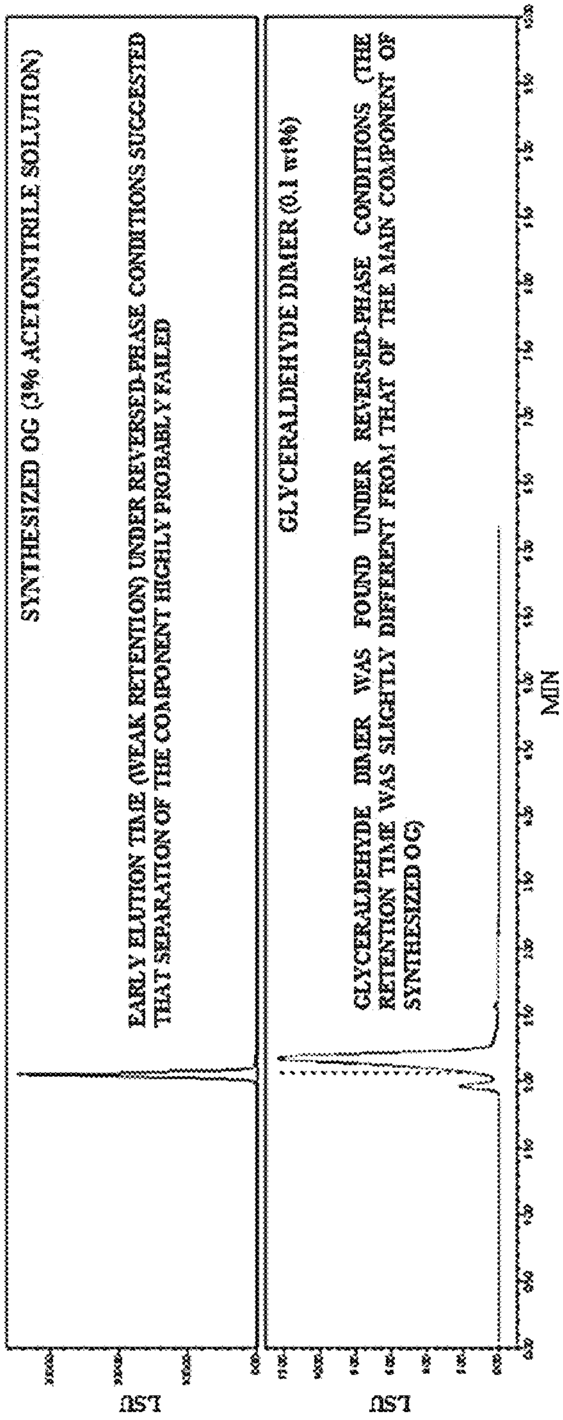
Figures 3, 4, 5, 6, 7, 8, 9, 10, 11, 12, 13, 14, 15, 16, 17, 18, 19, 20, 21, 22, 23, 24, 25:
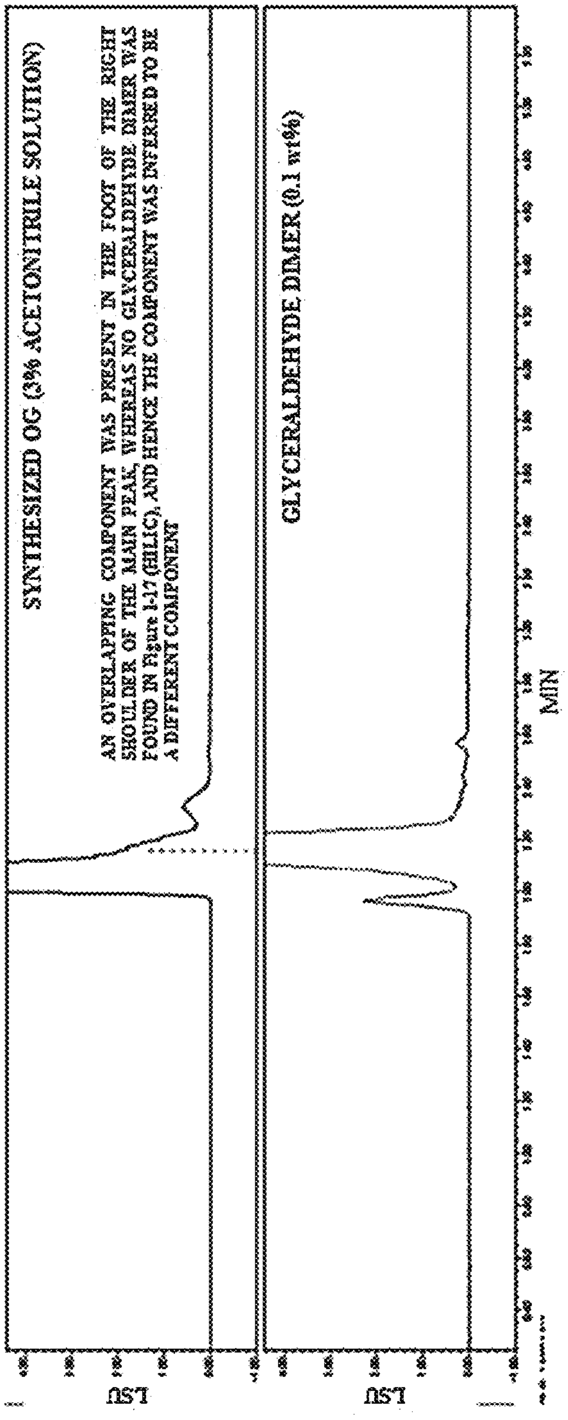
Figures 3, 4, 5, 6, 7, 8, 9, 10, 11, 12, 13, 14, 15, 16, 17, 18, 19, 20, 21, 22, 23, 24, 25, 26:
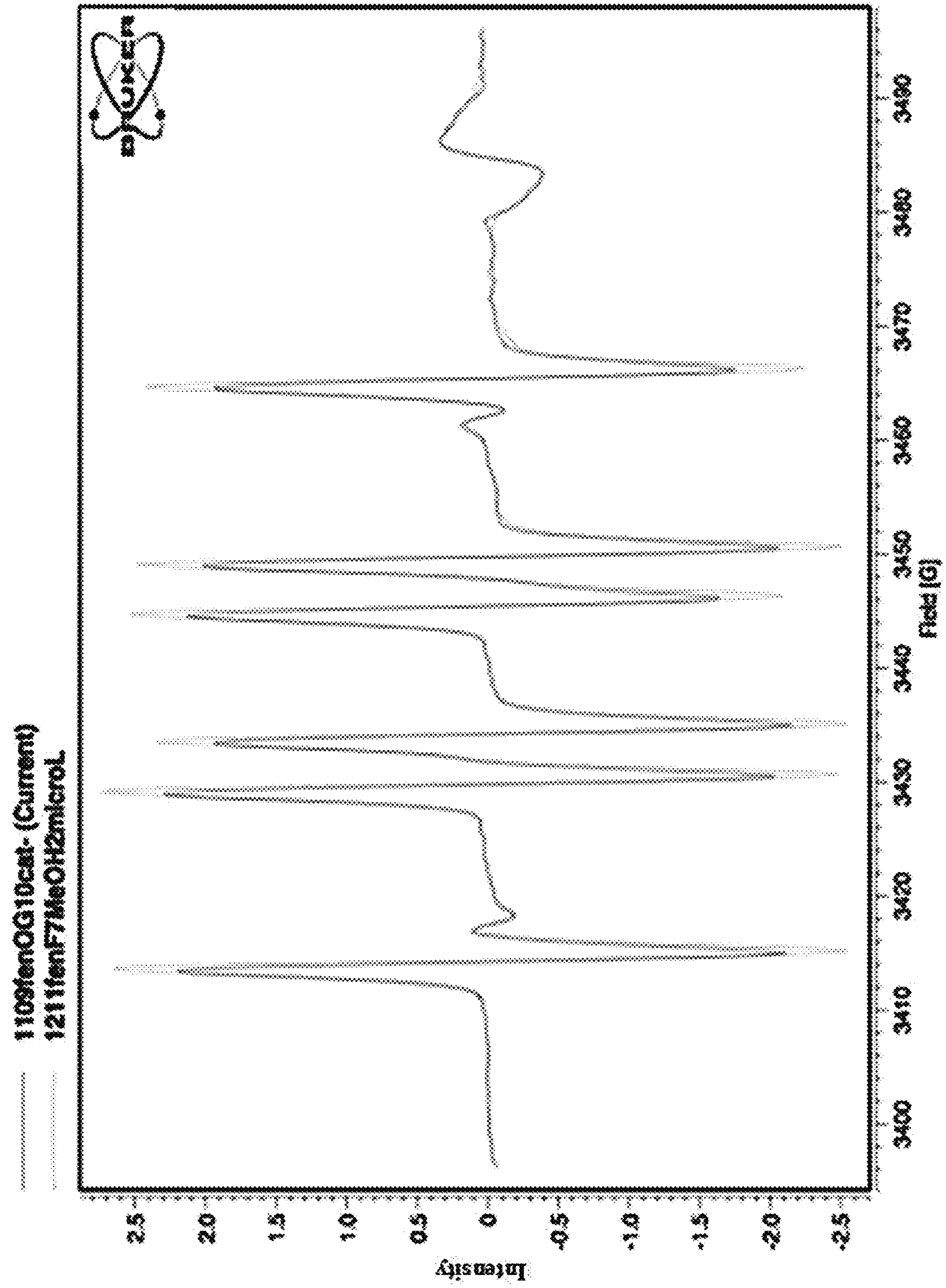
Figures 3, 4, 5, 6, 7, 8, 9, 10, 11, 12, 13, 14, 15, 16, 17, 18, 19, 20, 21, 22, 23, 24, 25, 26, 27:
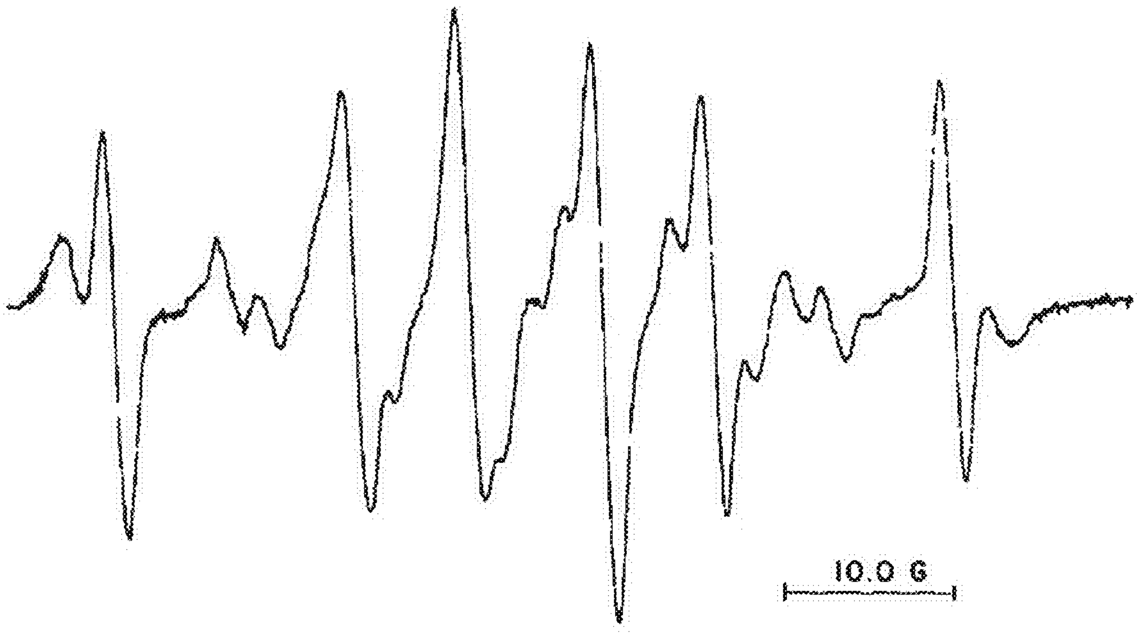
Figures 3, 4, 5, 6, 7, 8, 9, 10, 11, 12, 13, 14, 15, 16, 17, 18, 19, 20, 21, 22, 23, 24, 25, 26, 27, 28:
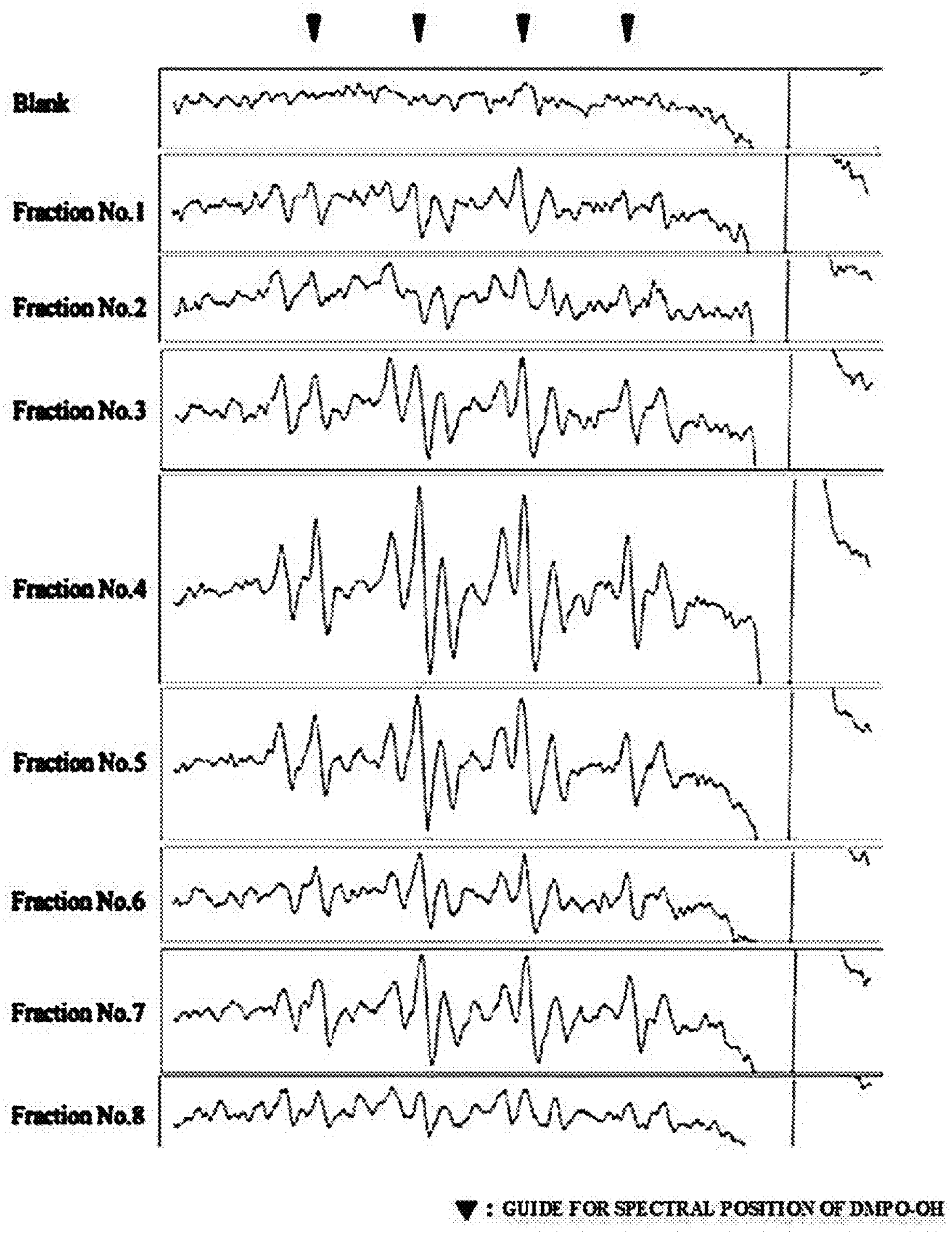
Figures 3, 4, 5, 6, 7, 8, 9, 10, 11, 12, 13, 14, 15, 16, 17, 18, 19, 20, 21, 22, 23, 24, 25, 26, 27, 28, 29:
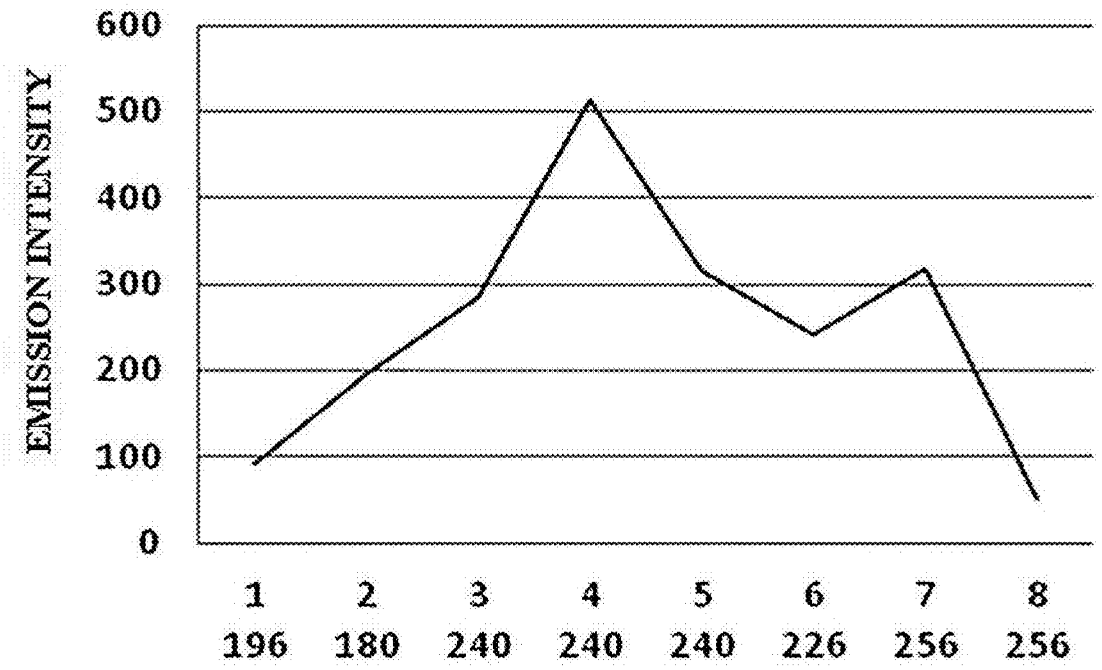
Figures 1, 4:
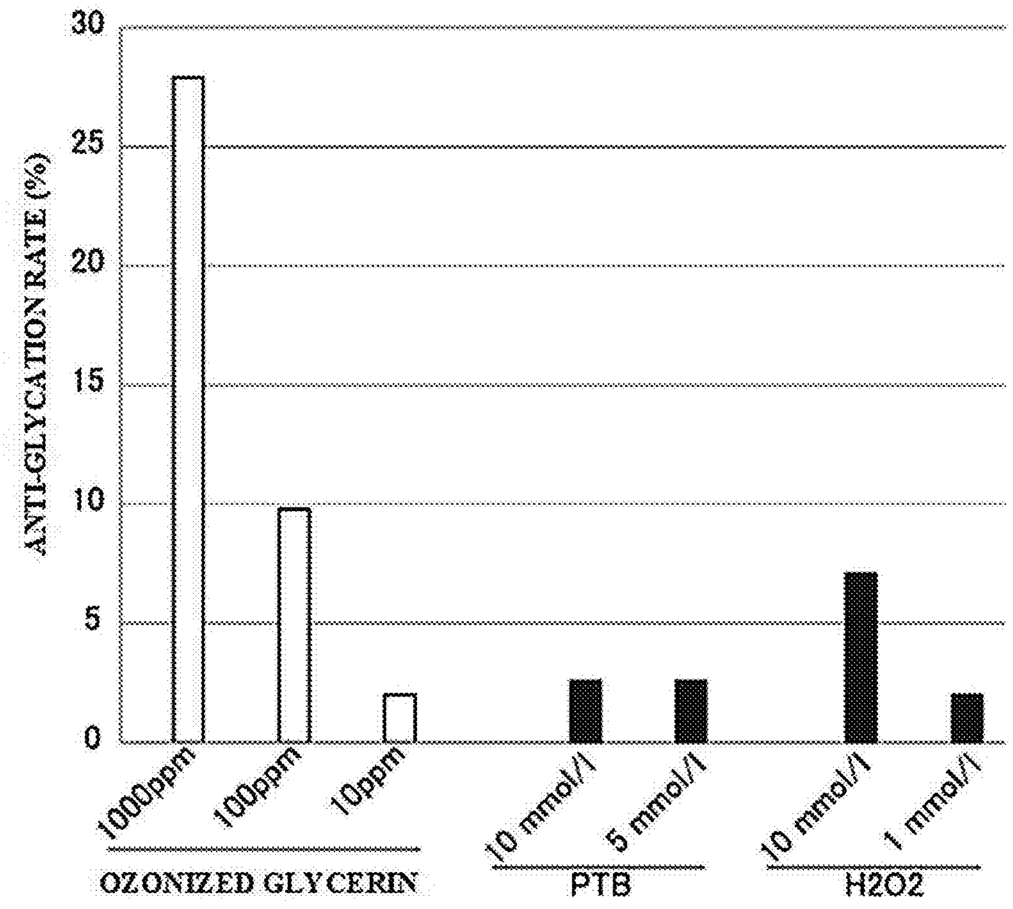
Figures 2, 4:
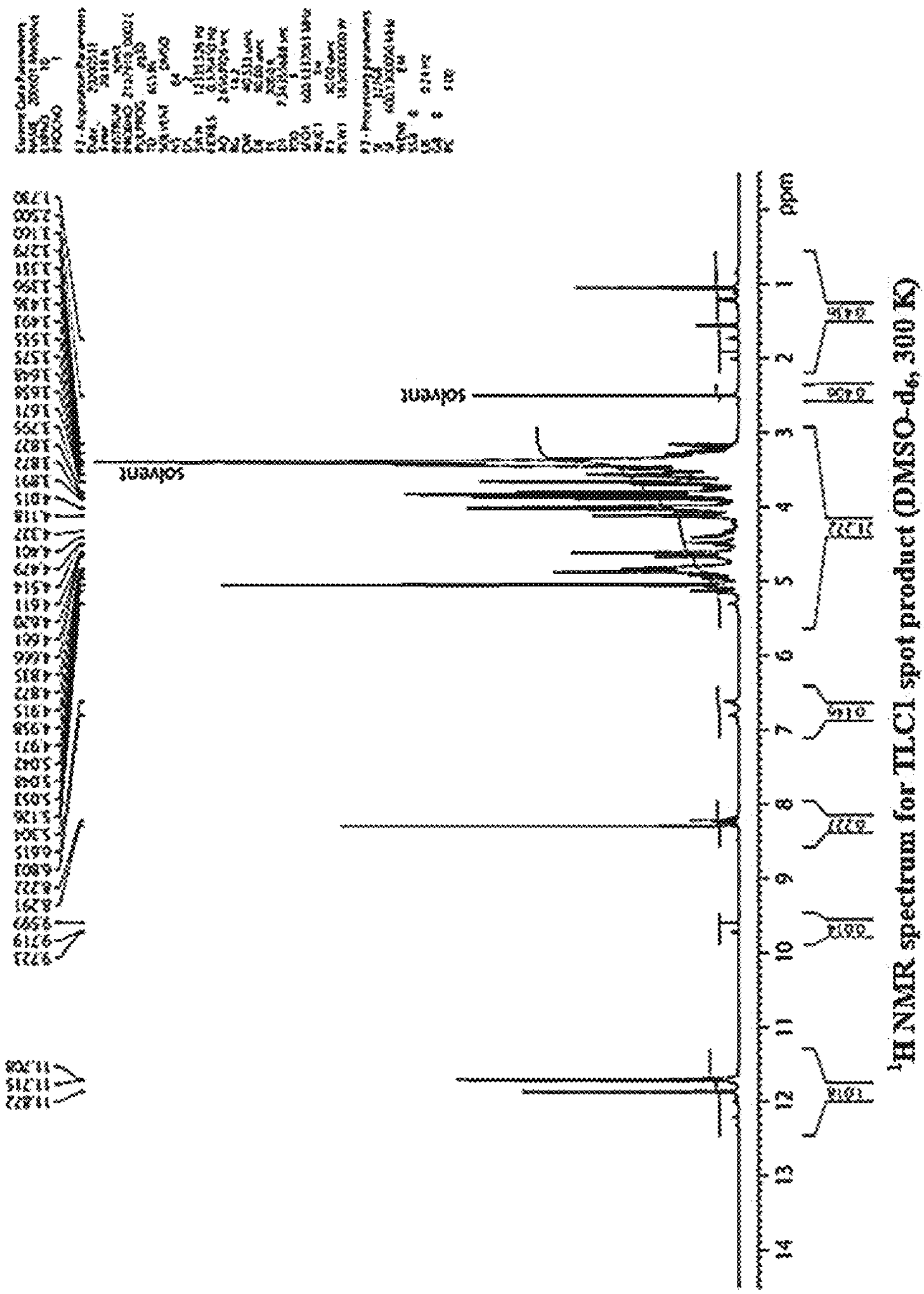
Figures 3, 4:
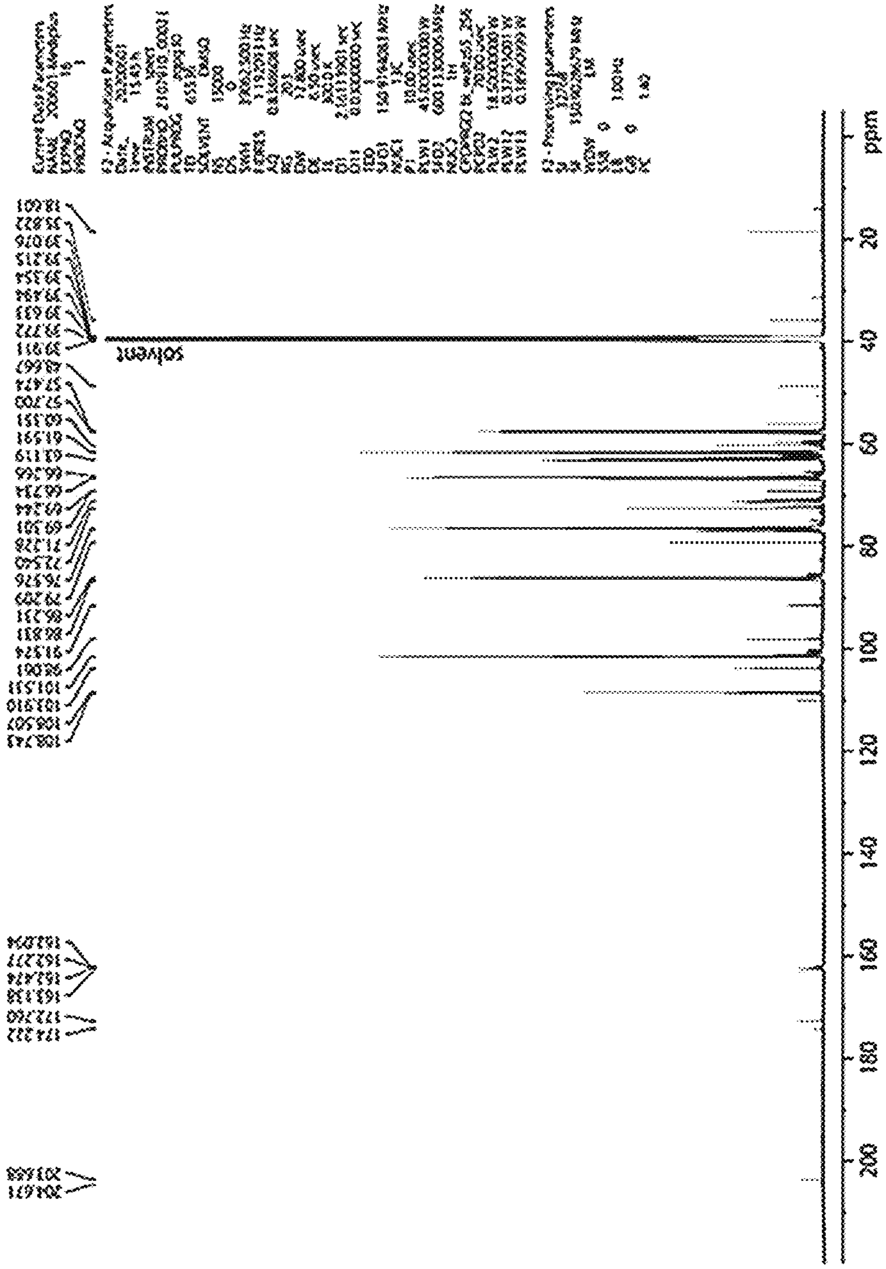
Figure 4:
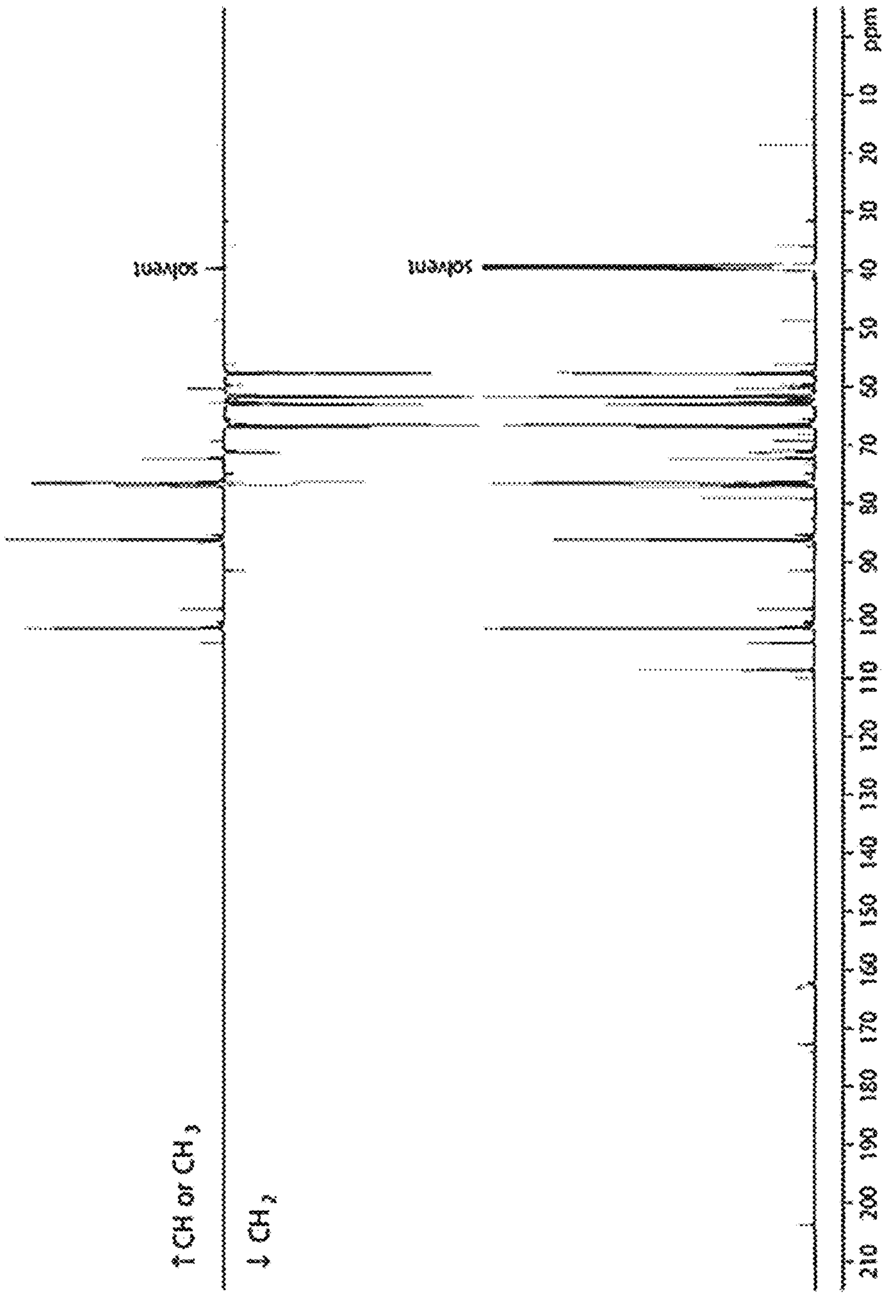
Figures 4, 5:
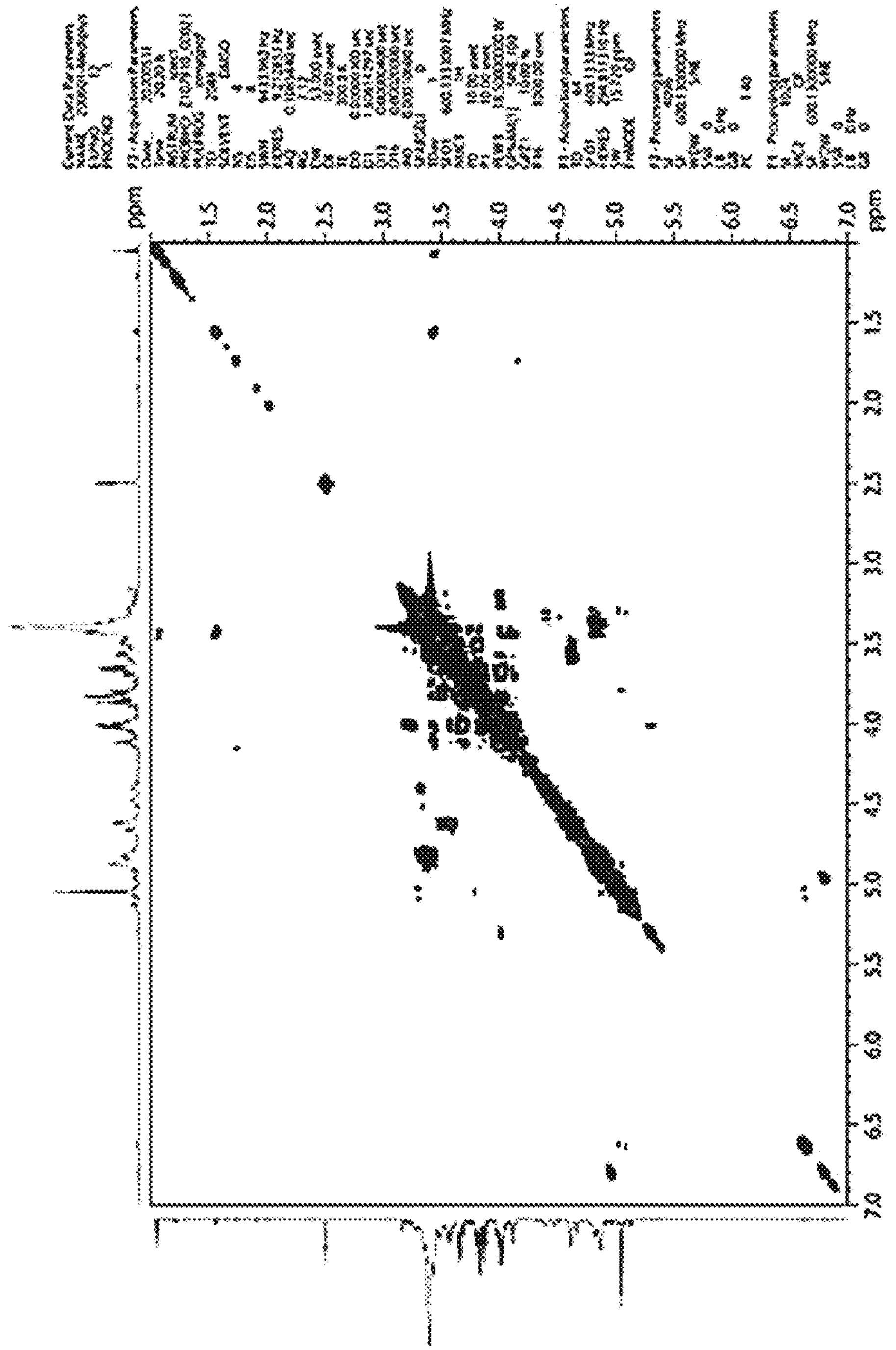
Figures 4, 5, 6:
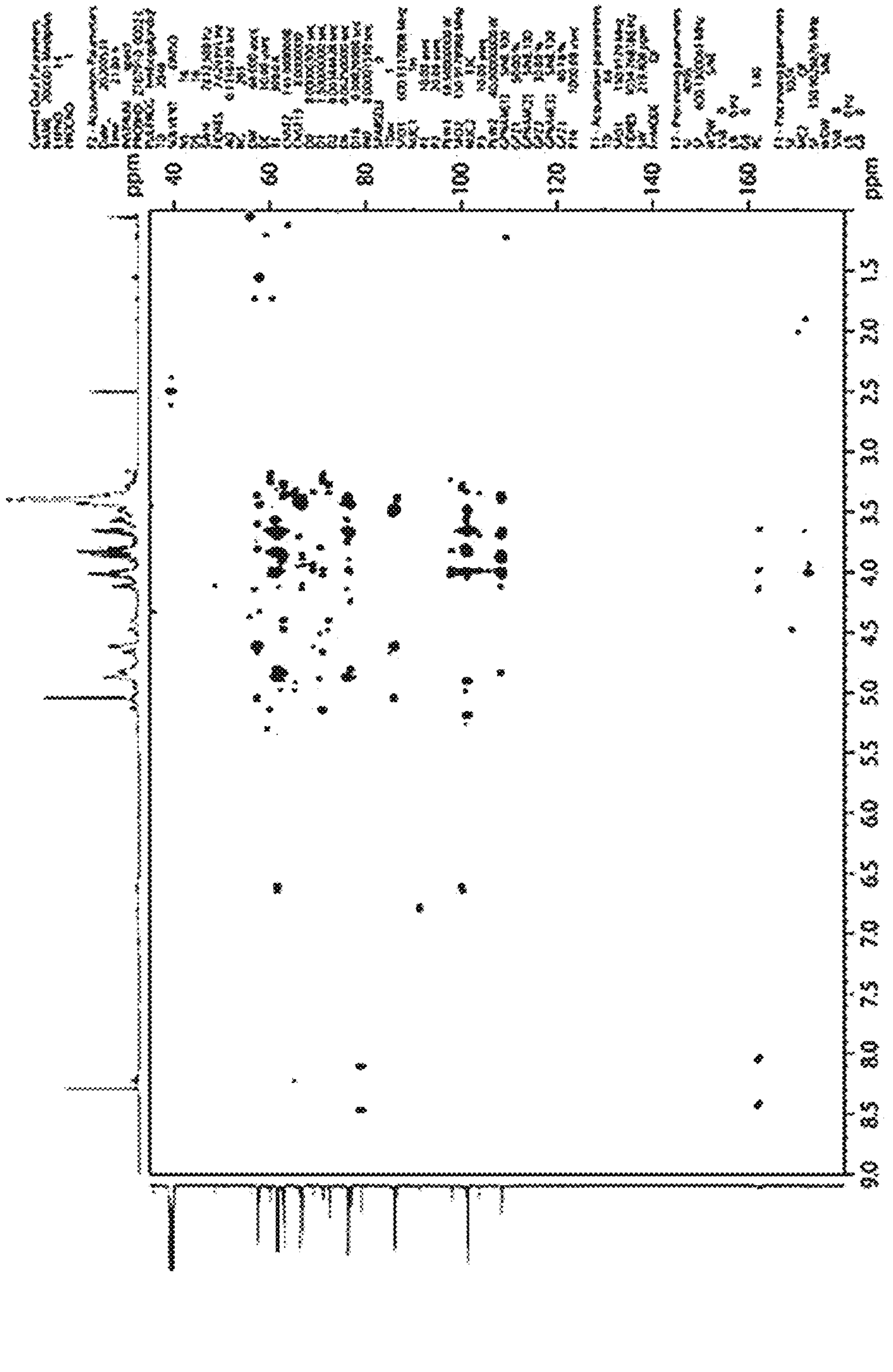
Figures 4, 5, 6, 7:
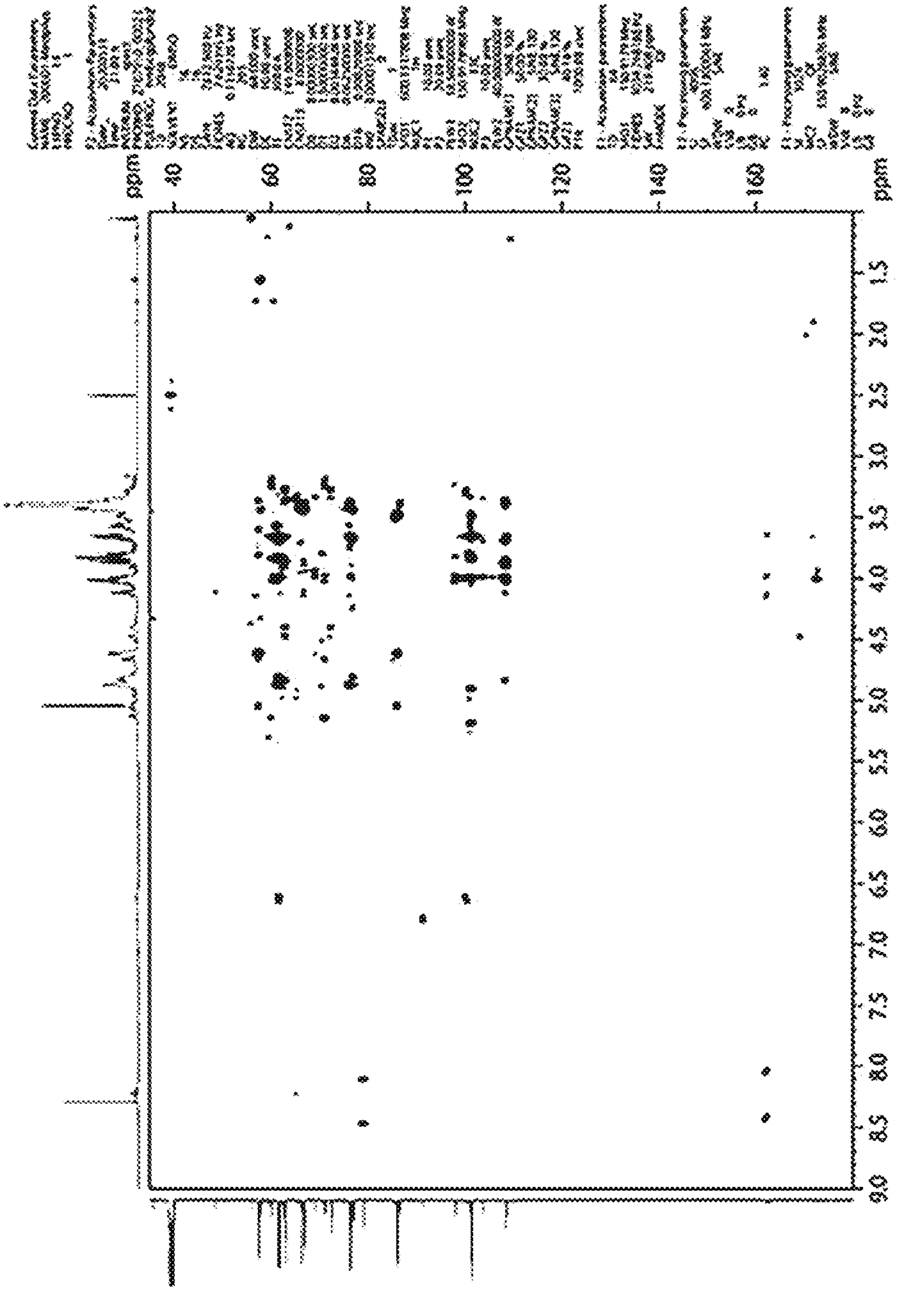
Figures 4, 5, 6, 7, 8:
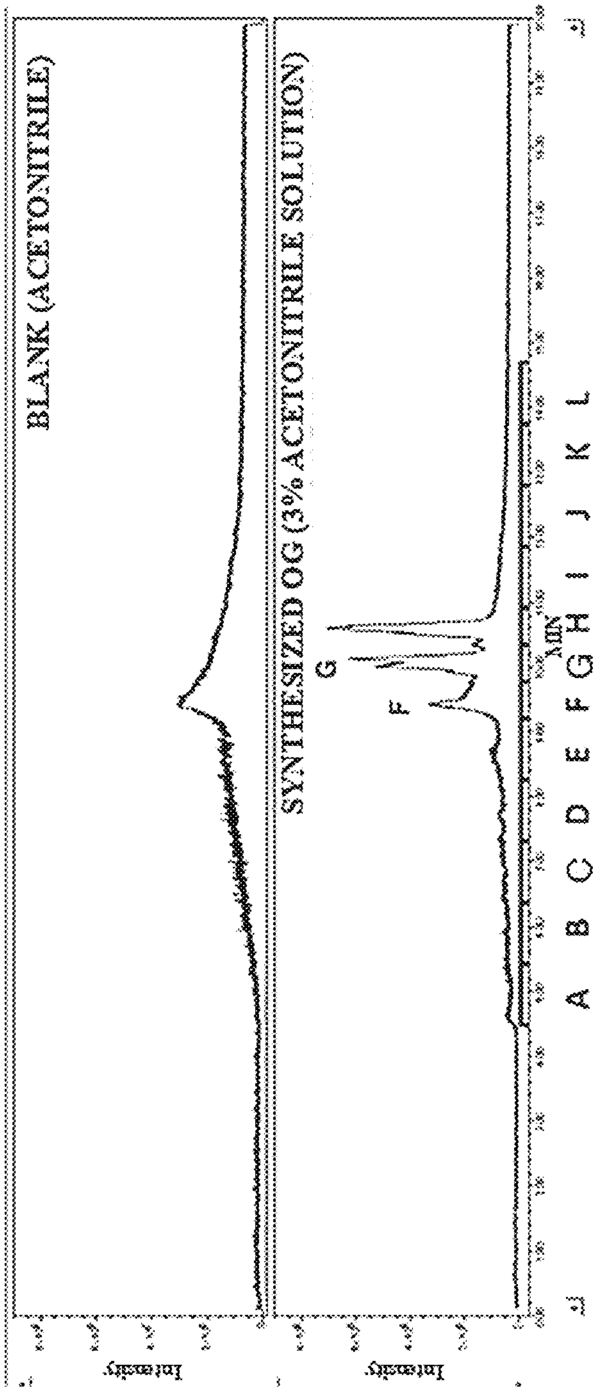
Figures 4, 5, 6, 7, 8, 9:
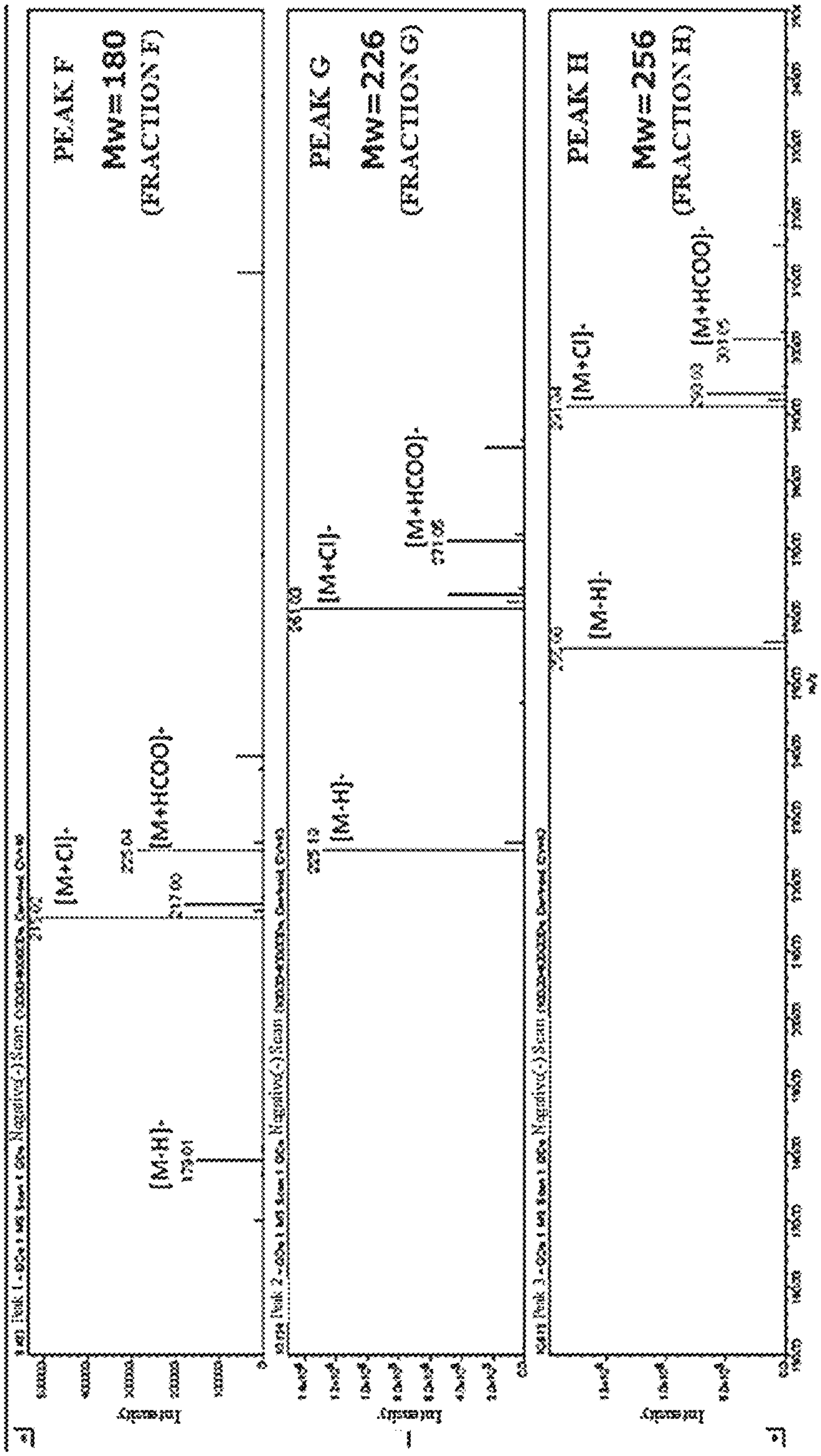
Figures 4, 5, 6, 7, 8, 9, 10:
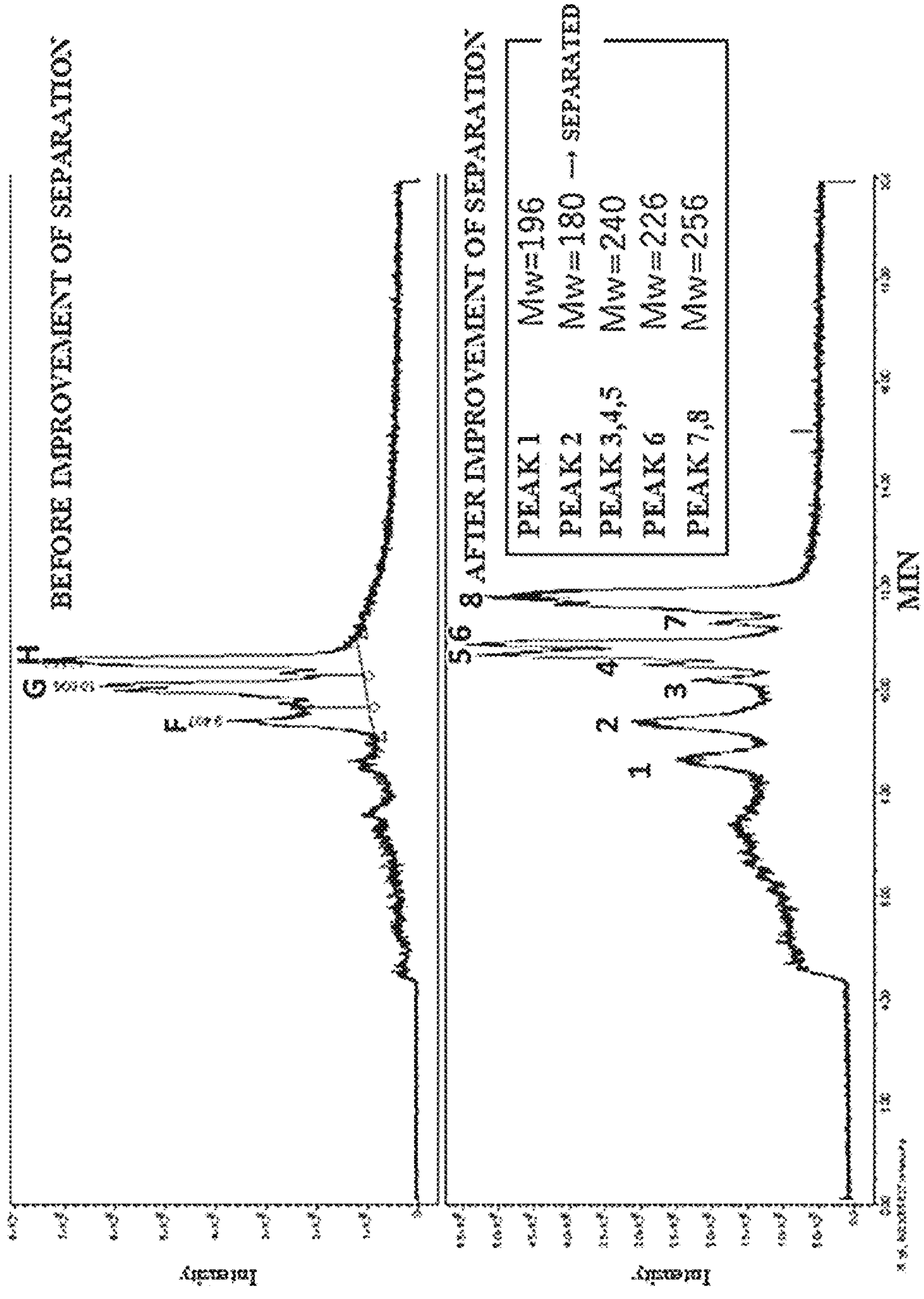
Figures 4, 5, 6, 7, 8, 9, 10, 11:
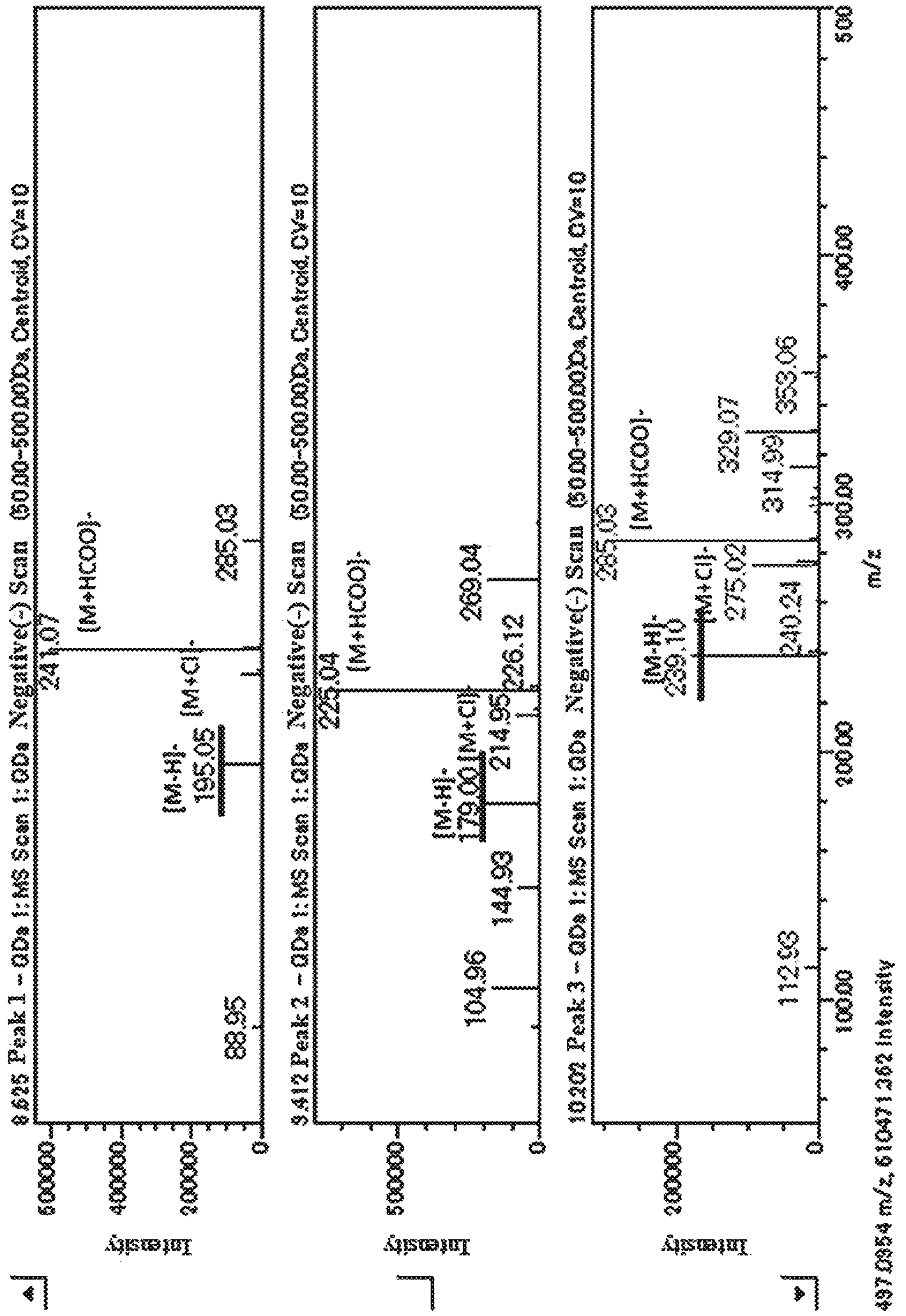
Figures 4, 5, 6, 7, 8, 9, 10, 11, 12:
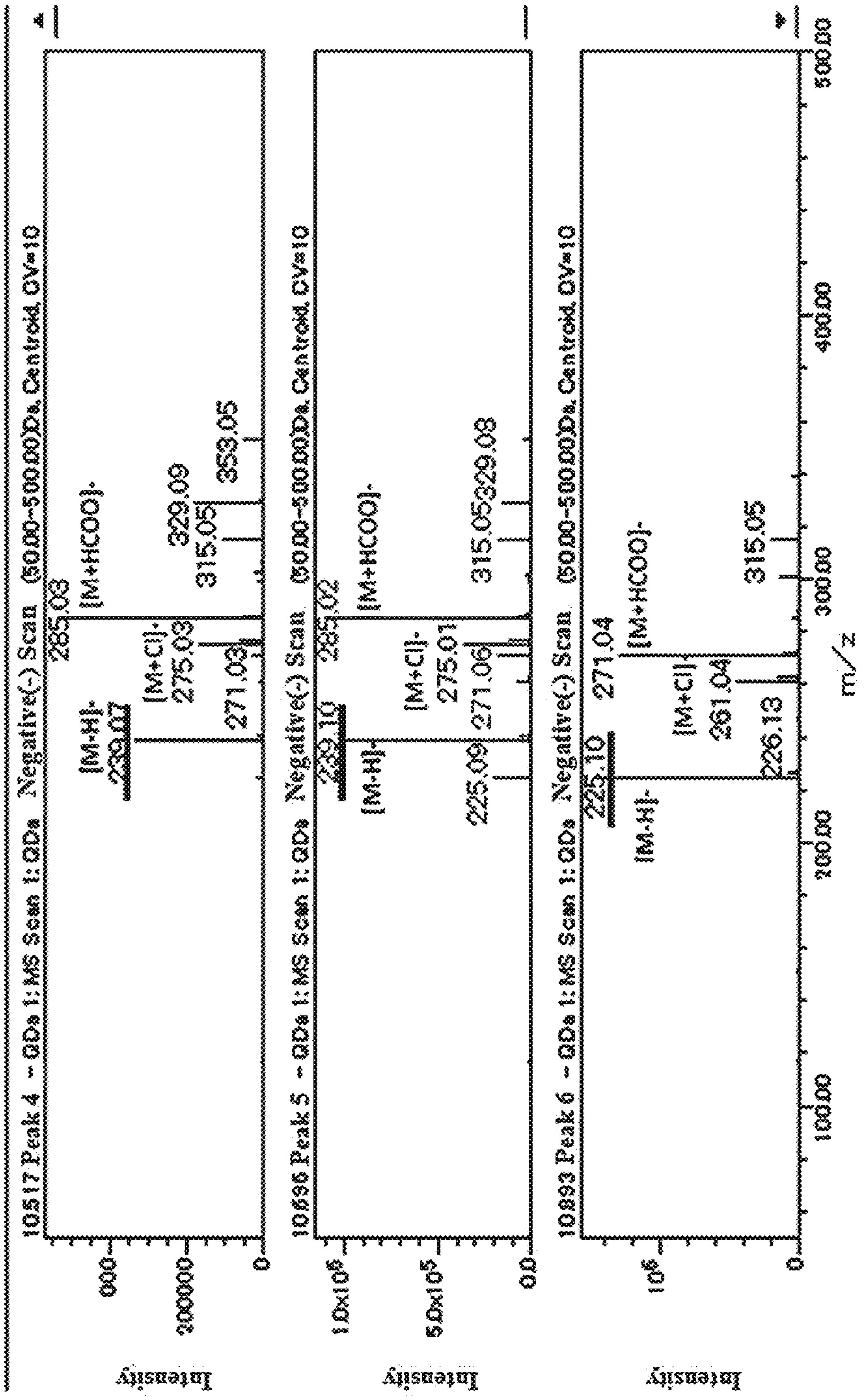
Figures 4, 5, 6, 7, 8, 9, 10, 11, 12, 13:
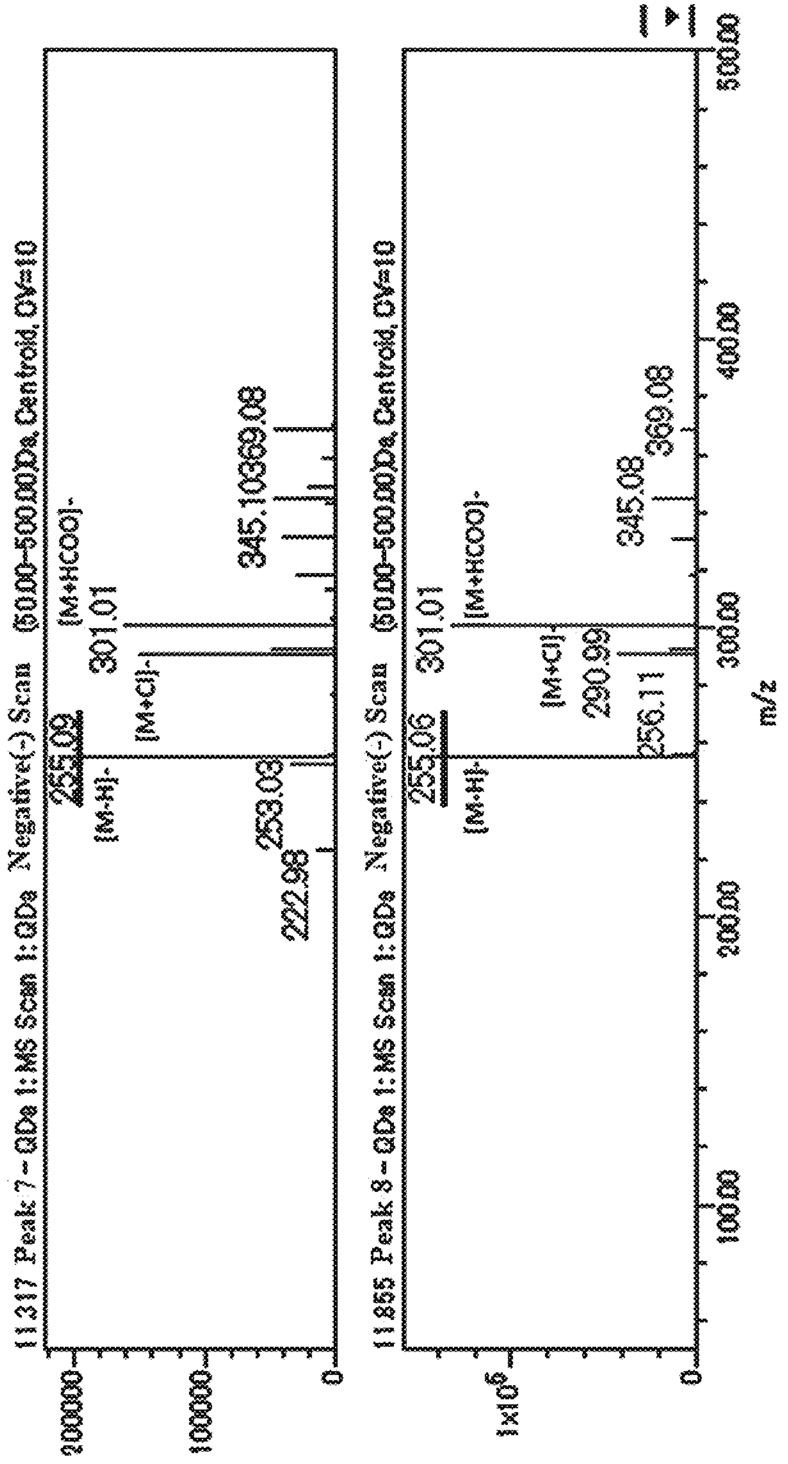
Figures 4, 5, 6, 7, 8, 9, 10, 11, 12, 13, 14:
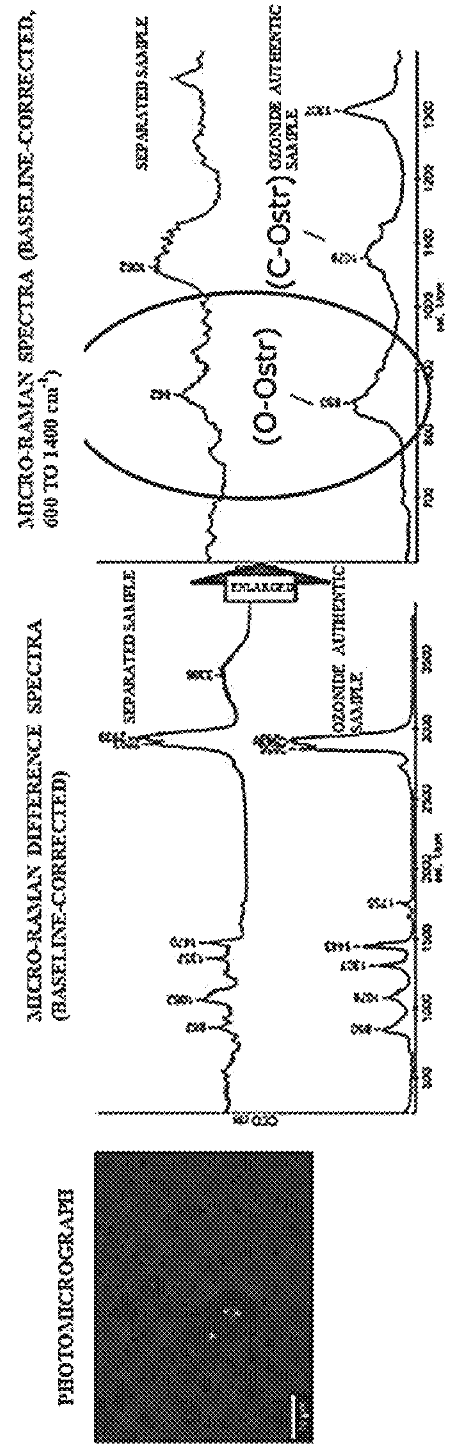
Figures 4, 5, 6, 7, 8, 9, 10, 11, 12, 13, 14, 15:
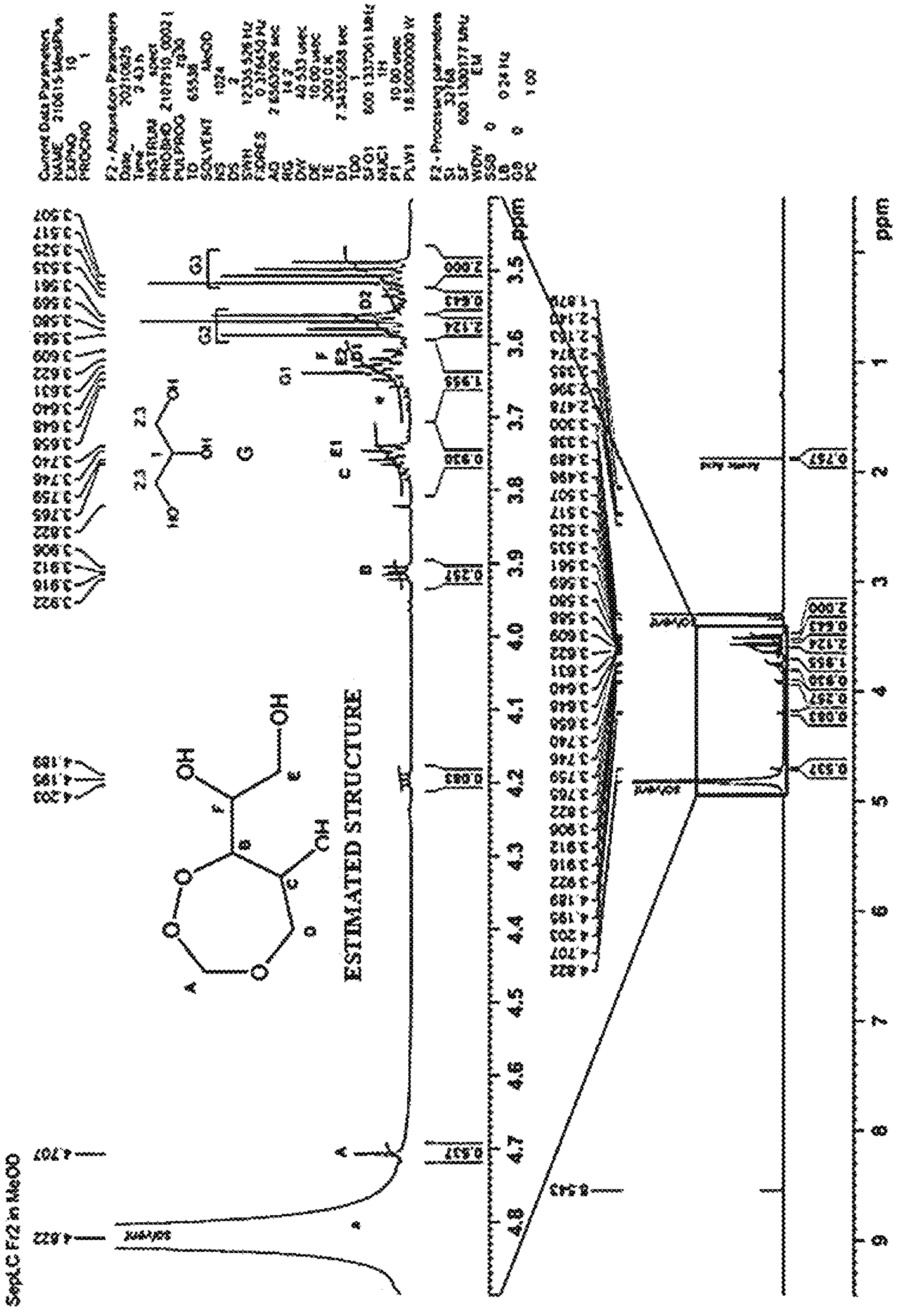
Figures 4, 5, 6, 7, 8, 9, 10, 11, 12, 13, 14, 15, 16:
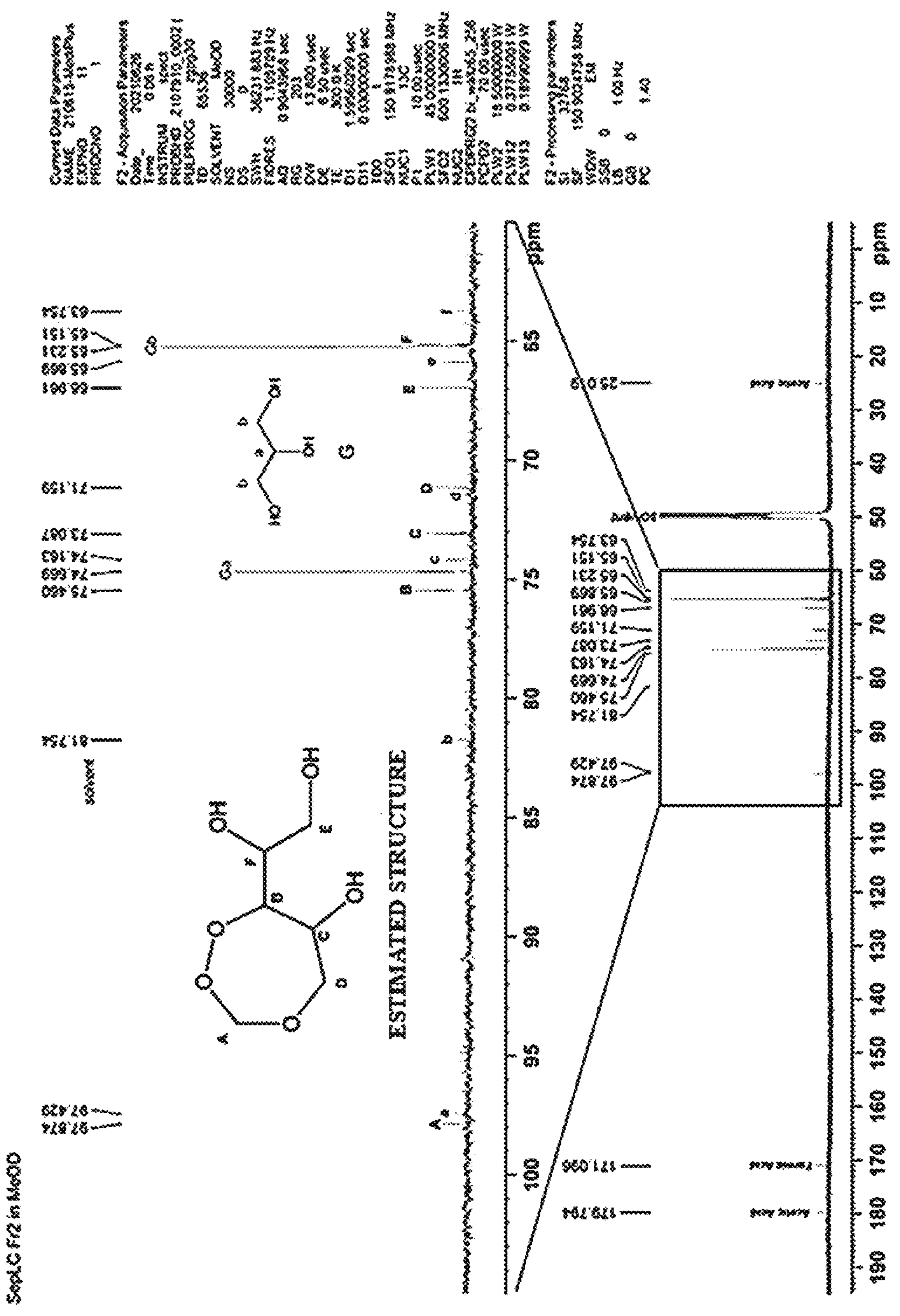
Figures 4, 5, 6, 7, 8, 9, 10, 11, 12, 13, 14, 15, 16, 17:
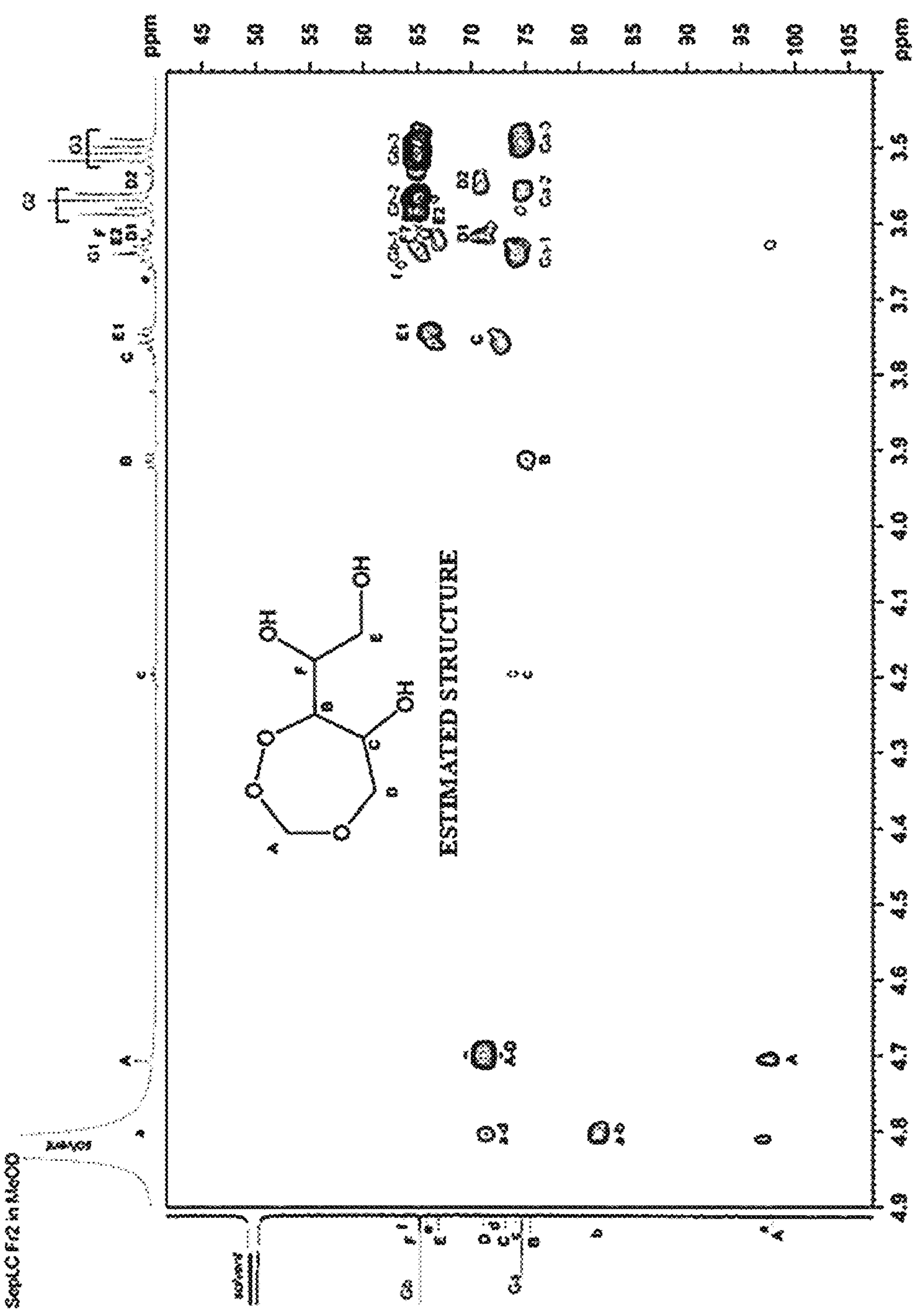
Figures 4, 5, 6, 7, 8, 9, 10, 11, 12, 13, 14, 15, 16, 17, 18:
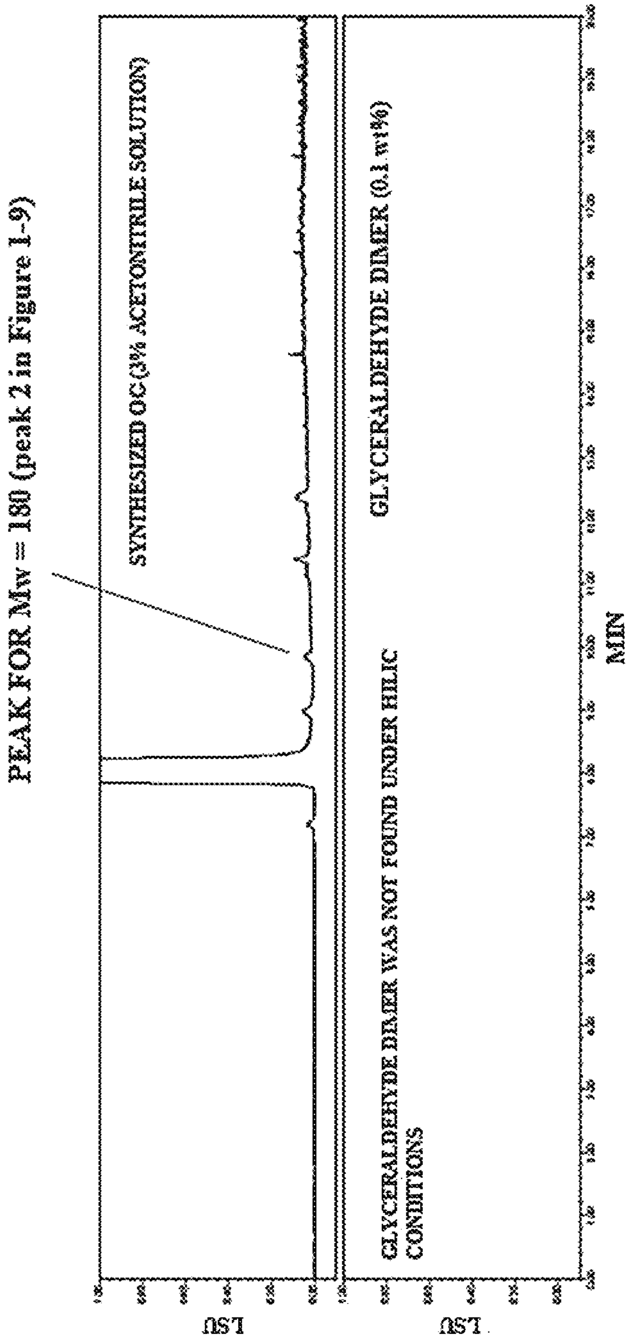
Figures 4, 5, 6, 7, 8, 9, 10, 11, 12, 13, 14, 15, 16, 17, 18, 19:
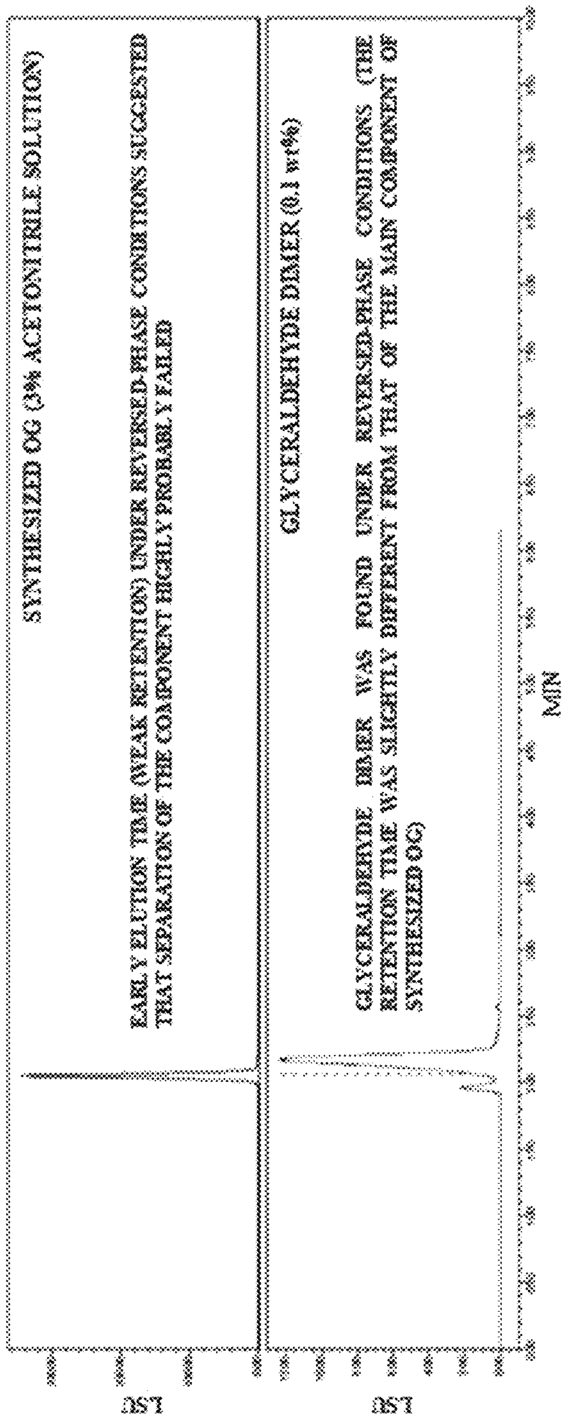
Figures 4, 5, 6, 7, 8, 9, 10, 11, 12, 13, 14, 15, 16, 17, 18, 19, 20:
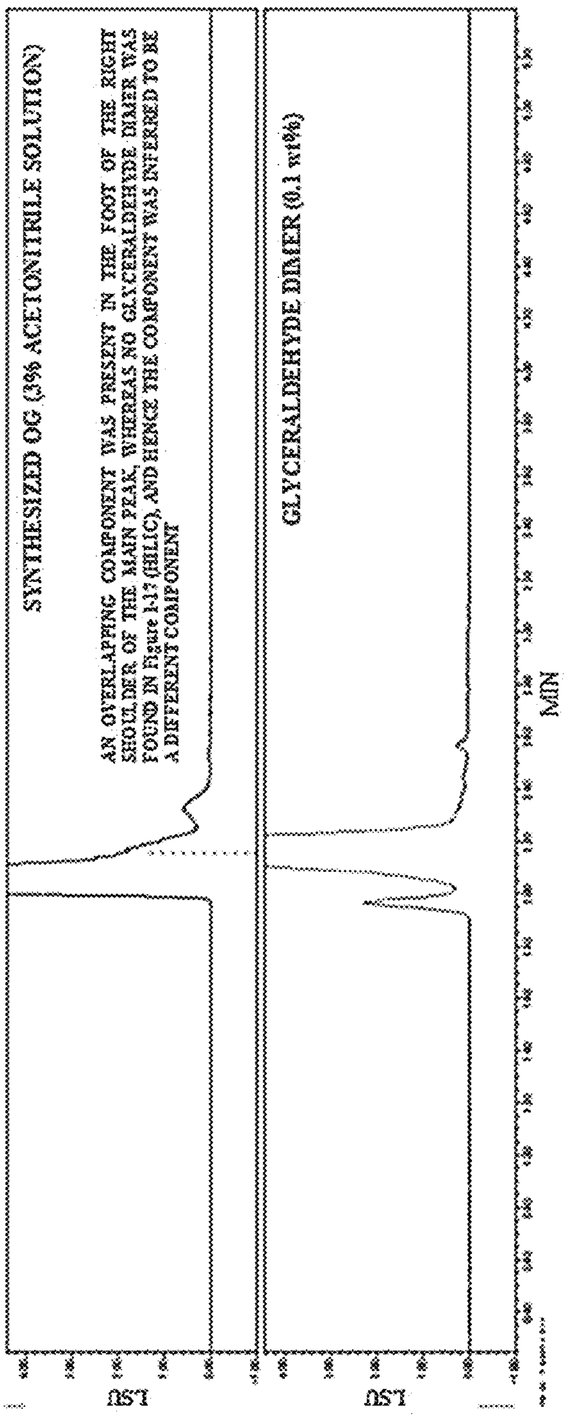
Figures 4, 5, 6, 7, 8, 9, 10, 11, 12, 13, 14, 15, 16, 17, 18, 19, 20, 21:
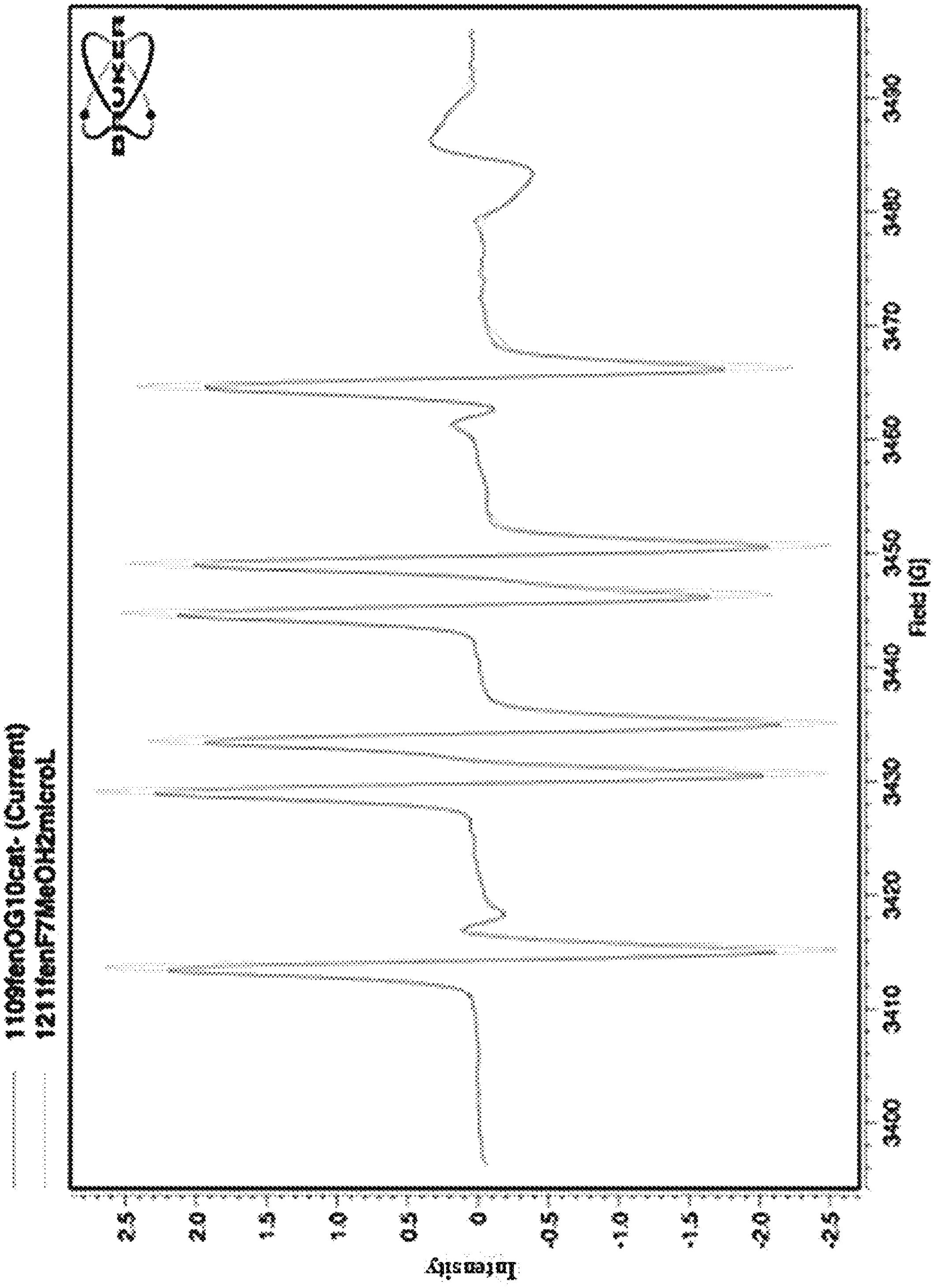
Figures 4, 5, 6, 7, 8, 9, 10, 11, 12, 13, 14, 15, 16, 17, 18, 19, 20, 21, 22:
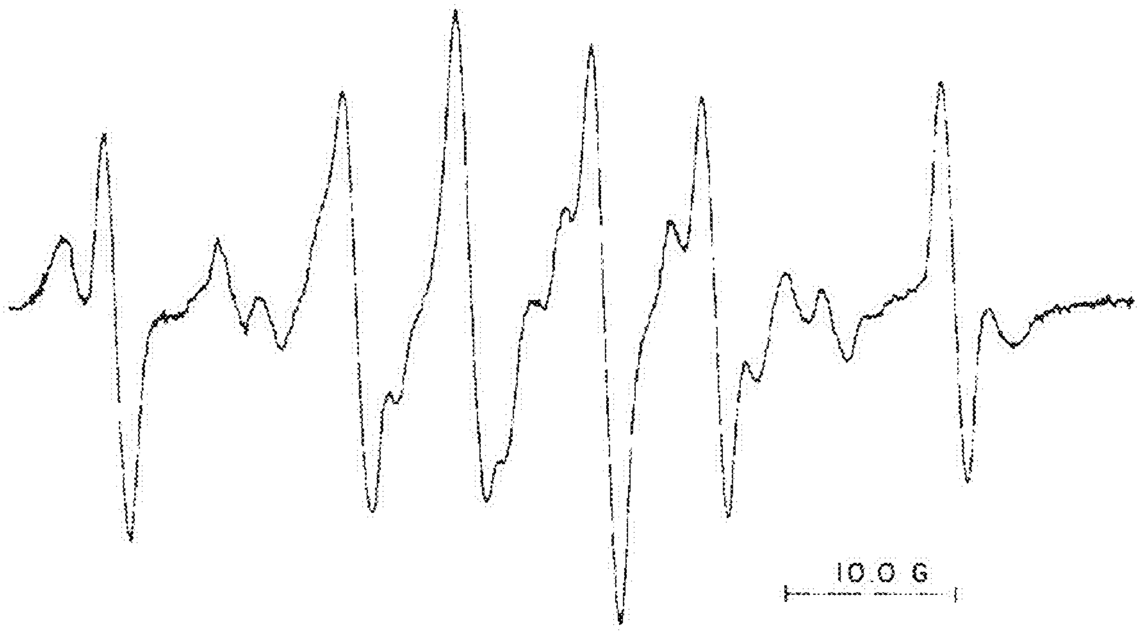
Figures 4, 5, 6, 7, 8, 9, 10, 11, 12, 13, 14, 15, 16, 17, 18, 19, 20, 21, 22, 23:
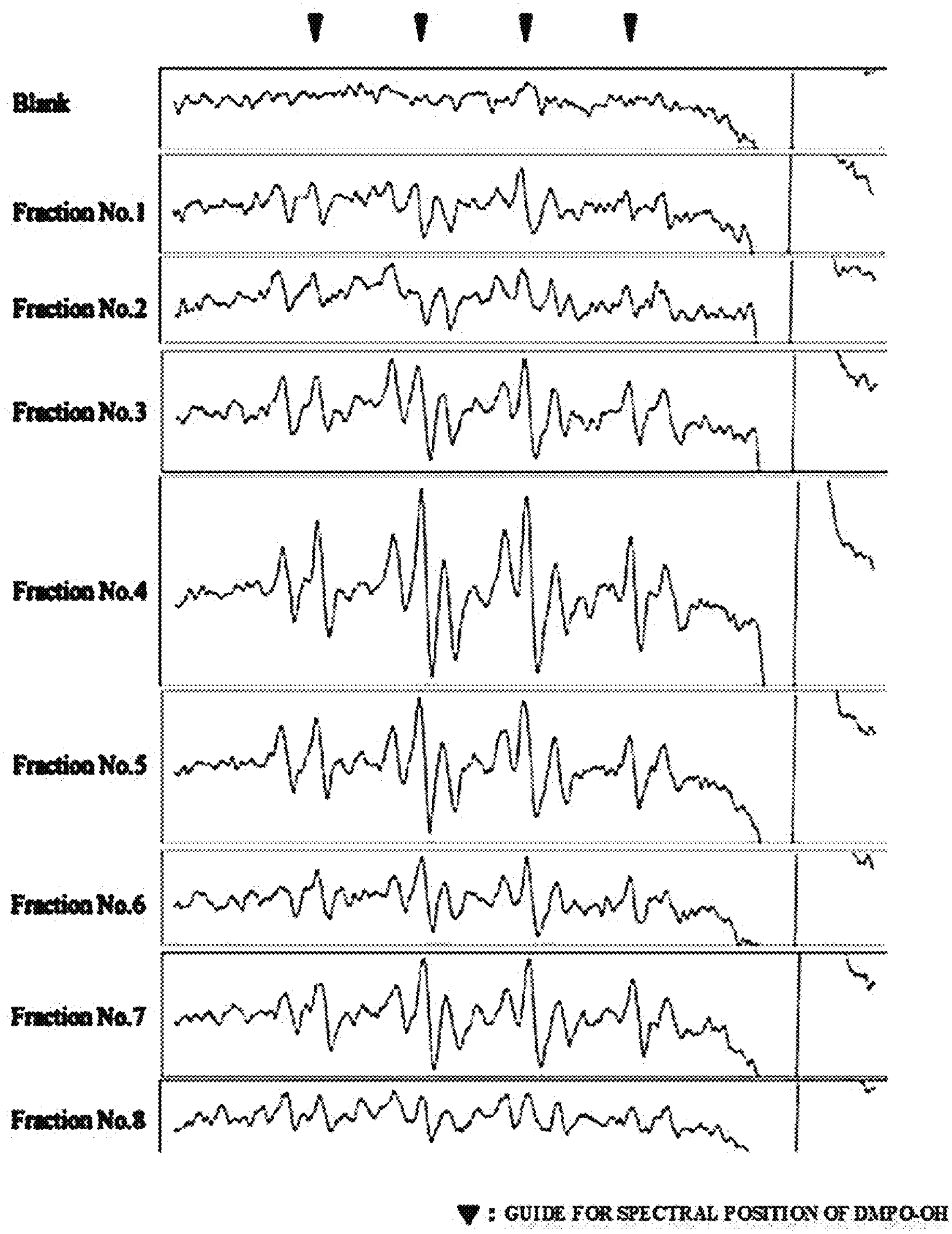
Figures 4, 5, 6, 7, 8, 9, 10, 11, 12, 13, 14, 15, 16, 17, 18, 19, 20, 21, 22, 23, 24:
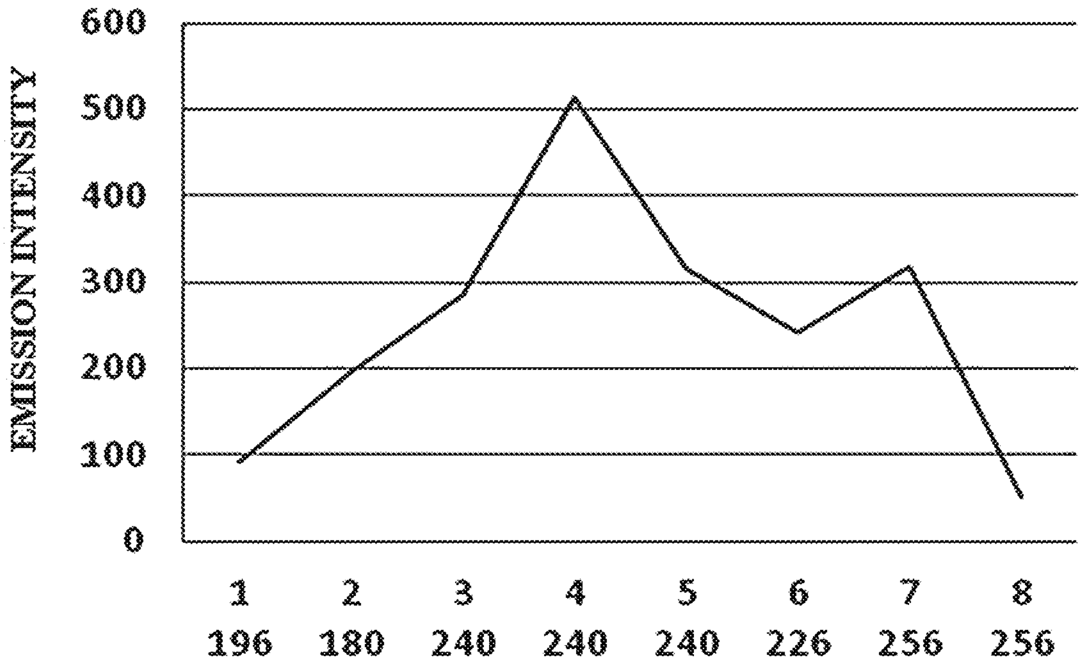

NMR spectra for the reaction mixture (TLC1 spot product) were determined with use of DMSO-$d_6$ as a solvent at a temperature of 300 K (27° C.). FIG. 4-2 to FIG. 4-7 show the spectrum diagrams. FIG. 4-2 is the $^1$H NMR spectrum diagram. FIG. 4-3 is the $^{13}$C NMR spectrum diagram. FIG. 4-4 is the $^{13}$C DEPT135 NMR spectrum diagram. FIG. 4-5 is the COSY NMR spectrum diagram. FIG. 4-6 is the HSQC NMR spectrum diagram. FIG. 4-7 is the HMBC NMR spectrum diagram. Complex peaks were observed as shown in FIG. 4-2 to FIG. 4-7, and hence the TLC1 spot product was expected to be a mixture of a plurality of substances. LCMS found that the TLC1 spot product contained a component of m/z 198,203.

(2) Separation and Analysis of Reaction Mixture

The reaction mixture (TLC1 spot product) was adjusted (diluted) to approximately 3% by mass with acetonitrile, and filtered through a membrane filter, and the resulting filtrate was subjected to LC measurement for optimization of separation conditions. Subsequently, peaks found in LC measurement under the optimized conditions were checked for mass, and precise separation was performed for Mw=180 (peak 2). Thereafter, the resulting fractionated solution was freeze-dried, and the dried product of the fraction was subjected to microscopic LR measurement and various NMR measurements. The measurement apparatuses (analyzers) and measurement conditions were as follows.

[Measurement Apparatuses (Analyzers)]

1) Precise preparative LC: Waters, ACQUITY UPLC H-class Bio

2) Microscopic LR: SNOM/AFM/Raman multifunction apparatus, alpha300RSA manufactured by WITec 3) NMR: Bruker Biospin, AVANCE 111-600 with Cryo Probe

[Measurement Conditions]

1) Precise Preparative LC

Column: Shodex Asahipak NH2P-50 (4.6 mmφ×250 mm, 5 μm)

Composition of eluent: water/acetonitrile gradient

Time (min): 0 5 15 20

Water: 5 10 50 50

Acetonitrile: 95 90 50 50

Flow rate: 1.0 mL/min

Detector: MS (QDa)

Column temperature: 40° C.

Injection volume: 50 μL

Ionization method: ESI (NEG.)

Mass range in measurement (m/z): 50 to 500

2) Microscopic LR

Excitation wavelength: 532 nm

Wavelength range in measurement: approximately 125 to 3800 $cm^{-1}$

Objective lens: ×100

Detector: EMCCD

3) NMR

Observation frequency: 600 MHz ($^1$H), 150 MHz ($^{13}$C)

Solvent for measurement: methanol-$d_4$

Measurement temperature: 300 K

Chemical shift standard: solvent for measurement [3.30 ppm ($^1$H), 49.80 ppm ($^{13}$C)]

FIG. 4-8 shows total ion chromatograms (ESI-negative mode) from the precise preparative LC (liquid chromatography) for the sample and a blank, the sample being obtained by adjusting (diluting) the reaction mixture (TLC1 spot product) to approximately 3% by mass with acetonitrile. In FIG. 4-8, the ordinate shows intensity and the abscissa shows retention time (minutes). In FIG. 4-8, “Synthesized OG” in the bottom shows a chromatogram for the sample of the TLC1 spot product, and the top shows a chromatogram for the blank (acetonitrile). As shown in the figure, components of A to L were found from the TLC1 spot product. These components A to L were separated and checked for the presence or absence of coloring with potassium iodide starch test paper, and the result showed that component H exhibited the strongest coloring.

FIG. 4-9 shows mass spectra for peaks F, G, and H (fraction F, fraction G, and fraction H) in FIG. 4-8 in combination. In FIG. 4-9, the ordinate shows intensity and the abscissa shows mass-charge ratios (m/z). As shown in the figure, it was found that peak F had Mw=180, peak G had Mw=226, and peak H had Mw=256.

Moreover, FIG. 4-10 shows results of examination on improvement of separation (improvement of separation conditions) in HILIC (high-performance liquid chromatography). In FIG. 4-10, the ordinate shows intensity and the abscissa shows retention time (minutes), and the same applies to FIG. 4-18 to FIG. 4-20. In FIG. 4-10, the top is a chromatogram before improvement of separation (under the same conditions as for FIG. 4-9), and the bottom is a chromatogram after improvement of separation. As shown in the figure, peaks 1 to 8 were found after improvement of separation. The molecular weights of the peaks were confirmed to be those as shown in FIG. 4-10 from mass spectra shown later.

FIG. 4-11 shows mass spectra for peaks 1 to 3 in FIG. 4-10 (after improvement of separation). In FIG. 4-11, the top, middle, and bottom are mass spectra for peak 1, peak 2, and peak 3, respectively. As shown in the figure, it was found that peak 1 had Mw=196, peak 2 had Mw=180, and peak 3 had Mw=240.

FIG. 4-12 shows mass spectra for peaks 4 to 6 in FIG. 4-10 (after improvement of separation). In FIG. 4-12, the top, middle, and bottom are mass spectra for peak 4, peak 5, and peak 6, respectively. As shown in the figure, it was found that peak 4 had Mw=240, peak 5 had Mw=240, and peak 6 had Mw=226.

FIG. 4-13 shows mass spectra for peaks 7 and 8 in FIG. 4-10 (after improvement of separation). In FIG. 4-13, the top and bottom are mass spectra for peak 7 and peak 8, respectively. As shown in the figure, it was found that peaks 7 and 8 both had Mw=256.

FIG. 4-14 shows micro-Raman spectrum diagrams for a separated sample obtained from peak 2 (Mw=180) in FIG. 4-10 and an ozonide authentic sample (ozonized oleic acid) in combination. In FIG. 4-14, the ordinate shows intensity and the abscissa shows Raman shifts (1/cm). As shown in FIG. 4-14, peak 2 (Mw=180) exhibited a micro-Raman spectrum similar to that for ozonide, and hence expected to have a structure similar to that of ozonide. The micro-Raman spectrum for peak 2 (Mw=180) exhibited a pattern differing from that for peroxide, and hence peak 2 (Mw=180) was expected not to correspond to peroxide. From NMR shown later, peak 2 (Mw=180) was found to correspond to the cyclic peroxide.

FIG. 4-15 shows a $^{1}H$ NMR spectrum diagram for peak 2 (Mw=180) in FIG. 4-10. Methanol-$d_4$ ($CD_3OD$) was used for the solvent for measurement. In the figure, the top spectrum diagram is an enlarged view of a part around 3.4 to 4.9 ppm in the bottom spectrum diagram. From the attribution of the $^{1}H$ NMR, the result of Mw=180, and other instrumental analysis data, the structure of the oxidation reaction product for peak 2 (Mw=180) was demonstrated to be that of a cyclic peroxide represented by a chemical formula (1) below. The peaks indicated with signs A to F in the $^{1}H$ NMR spectrum diagram in FIG. 4-15 were attributed to peaks for hydrogen bound to the carbon atoms indicated with the same signs A to F in a chemical formula (1) below, which is shown in FIG. 4-15. It was expected that a slight amount of the raw material glycerin remained, and the peak was also detected.

[Chemical Formula 1M]

(1)

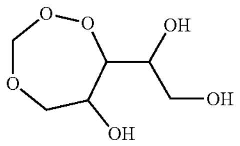

Molecular Weight: 180.16

FIG. 4-16 shows a $^{13}C$ NMR spectrum diagram for peak 2 (Mw=180) in FIG. 4-10. Methanol-$d_4$ ($CD_3OD$) was used for the solvent for measurement. In the figure, the top spectrum diagram is an enlarged view of a part around 60 to 105 ppm in the bottom spectrum diagram. From the attribution of the $^{13}C$ NMR, the result of Mw=180, and other instrumental analysis data, the structure of the oxidation reaction product for peak 2 (Mw=180) was demonstrated to be that of the cyclic peroxide represented by the chemical formula (1). The peaks indicated with signs A to F in the $^{13}C$ NMR spectrum diagram in FIG. 4-16 were attributed to peaks for the carbon atoms indicated with the same signs A to F in a chemical formula (1) below, which is shown in FIG. 4-16. It was expected that a slight amount of the raw material glycerin remained, and the peak was also detected.

FIG. 4-17 shows a two-dimensional ($^{1}H$-$^{13}C$ COSY) NMR spectrum diagram for peak 2 (Mw=180) in FIG. 4-10. Methanol-$d_4$ ($CD_3OD$) was used for the solvent for measurement. From the attribution of the two-dimensional NMR, the result of Mw=180, and other instrumental analysis data, the structure of the oxidation reaction product for peak 2 (Mw=180) was demonstrated to be that of the cyclic peroxide represented by the chemical formula (1). The peaks indicated with signs A to F in the two-dimensional NMR spectrum diagram in FIG. 4-17 were attributed to peaks for the carbon atoms indicated with the same signs A to F and hydrogen atoms bound to the carbon atoms in a chemical formula (1) below, which is shown in FIG. 4-17. It was expected that a slight amount of the raw material glycerin remained, and the peak was also detected.

FIG. 4-18 shows HILIC chromatograms for the TLC1 spot product and glyceraldehyde dimer under the HILIC (high-performance liquid chromatography) conditions in FIG. 4-10 in combination. In FIG. 4-18, the "Synthesized OG" in the top shows a HILIC chromatogram for the TLC1 spot product. The bottom is a HILIC chromatogram for glyceraldehyde dimer. As shown in the figure, no glyceraldehyde dimer was detected under the HILIC conditions in FIG. 4-18.

FIG. 4-19 shows HILIC chromatograms for the TLC1 spot product and glyceraldehyde dimer under reversed-phase HILIC (high-performance liquid chromatography) conditions in combination. FIG. 4-20 shows an enlarged view of a part of FIG. 4-19. The "Synthesized OG" in the top in each of FIG. 4-19 and FIG. 4-20 is a HILIC chromatogram for the TLC1 spot product. The bottom is a HILIC chromatogram for glyceraldehyde dimer. As shown in the figures, the component separation of the TLC1 spot product was not found under the reversed-phase HILIC conditions. This was probably because the retention power of the column was weak and as a result the elution time of the TLC1 spot product was short. On the other hand, the retention time of glyceraldehyde dimer was slightly different from that of the TLC1 spot product (Synthesized OG). From the results, the TLC1 spot product was inferred to contain no glyceraldehyde dimer.

FIG. 4-21 shows ESR spectrum diagrams for the TLC1 spot product and peak 2 (Mw=180) in FIG. 4-10 in combination. In FIG. 4-21, the ordinate shows intensity and the abscissa shows magnetic flux density (G). Water was used for the solvent for measurement. As shown in the figure, the spectrum for the TLC1 spot product and that for the peak 2 (Mw=180) component in FIG. 4-10 almost completely matched, and the positions of the appearance of peaks in the former were almost identical to those in the latter. The TLC1 spot product and the peak 2 (Mw=180) component in FIG. 4-10 both exhibited a spectrum for DMPO (spin-trapping agent), the spectrum characterized by six lines. This spectral pattern is similar to that for ozonide.

FIG. 4-22 shows an ESR spectrum diagram for ozonized methyl linolenate. Acetone was used for the solvent for measurement. Ozonized methyl linolenate is a known ozonide. As shown in the figure, the ESR spectrum diagram for ozonized methyl linolenate exhibited a spectrum for DMPO (spin-trapping agent), the spectrum characterized by six lines characteristic to ozonide. This spectral pattern is similar to those for the TLC1 spot product and peak 2 (Mw=180) in FIG. 4-21.

FIG. 4-23 shows ESR spectrum diagrams for peaks 1 to 8 in FIG. 4-10. Water was used for the solvent for measurement. The uppermost is an ESR spectrum diagram for a blank (only the solvent) for comparison. As shown in the figure, the components of peaks 1 to 8 were all found to have radical activity.

The graph in FIG. 4-24 shows results of measurement of activity for peaks 1 to 8 in FIG. 4-10 through chemiluminescence. In the figure, the ordinate shows all-wavelength emission intensity (relative intensity). The numbers "1" to "8" in the abscissa indicate fractions of peaks 1 to 8. The numerical values under the numbers indicate the molecular weights of the fractions found from mass spectra. As shown in the figure, it was found from the chemiluminescence that components with activity were generated in addition to the component having a molecular weight of 180.

Thus, the present invention has been described with reference to embodiments and examples, but the present invention is not limited to the embodiments and examples. Various modifications understandable for those skilled in the art within the scope of the invention of the present application may be made for the configurations and details of the present invention.

The present application claims priority to Japanese Patent Application No. 2021-134732 filed on Aug. 20, 2021, Japanese Patent Application No. 2021-195536 filed on Dec. 1, 2021, Japanese Patent Application No. 2021-202053 filed on Dec. 13, 2021, and Japanese Patent Application No. 2021-212094 filed on Dec. 27, 2021, and all of the disclosures are incorporated herein.

CLAUSES

Some or all of the embodiments and examples can be described as the following clauses, but the description is not limited to the followings.

(Clause 1)

A cyclic peroxide represented by the following chemical formula (I):

[Chemical Formula I]

(I)

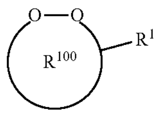

wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 2)

The cyclic peroxide according to clause 1, wherein, in the chemical formula (I), $R^{100}$ is a cyclic structure having 5 to 10 ring members.

(Clause 3)

The cyclic peroxide according to clause 1 or 2, represented by the following chemical formula (II):

[Chemical Formula II]

(II)

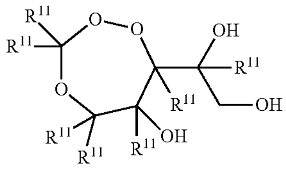

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 4)

The cyclic peroxide according to clause 3, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 5)

The cyclic peroxide according to any of clauses 1 to 4, represented by the following chemical formula (1):

[Chemical Formula I]

(1)

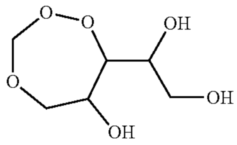

(Clause 6)

An oxidation reaction product comprising a cyclic peroxide, wherein the oxidation reaction product is obtained through oxidation of an alcohol.

(Clause 7)

The oxidation reaction product according to clauses 6, wherein the oxidation of an alcohol is at least one of ozone oxidation and hydrogen peroxide oxidation.

(Clause 8)

The oxidation reaction product according to clause 6 or 7, wherein the oxidation reaction product is a mixture containing a plurality of oxidation reaction products.

(Clause 9)

The oxidation reaction product according to any of clauses 6 to 8, wherein the oxidation reaction product has oxidative capacity.

(Clause 10)

The oxidation reaction product according to any of clauses 6 to 9, wherein the oxidation reaction product has reductive capacity.

(Clause 11)

The oxidation reaction product according to any of clauses 6 to 10, wherein the oxidation reaction product comprises a TRP channel activator.

(Clause 12)

The oxidation reaction product according to any of clauses 6 to 11, wherein the alcohol is a saturated alcohol.

(Clause 13)

The oxidation reaction product according to any of clauses 6 to 12, wherein the alcohol is a polyhydric alcohol.

(Clause 14)

The oxidation reaction product according to any of clauses 6 to 13, wherein the alcohol is at least one of glycerin and a glycerin derivative.

(Clause 15)

The oxidation reaction product according to any of clauses 6 to 14, comprising an oxidation reaction product formed by binding of two or more molecules of the alcohol.

(Clause 16)

The oxidation reaction product according to any of clauses 6 to 15, comprising the cyclic peroxide according to any of clauses 1 to 5.

(Clause 17)

A method for producing the oxidation reaction product according to any of clauses 6 to 16, the method comprising an alcohol oxidation step of oxidating the alcohol.

(Clause 18)

The method for producing an oxidation reaction product according to clause 17, wherein the alcohol is oxidized through at least one of ozone oxidation and hydrogen peroxide oxidation in the alcohol oxidation step.

(Clause 19)

The method for producing an oxidation reaction product according to clause 17 or 18, wherein reaction time in the alcohol oxidation step is 24 hours or more.

<Whitening Composition>

(Clause 20)

A whitening composition comprising glycerin and/or a glycerin derivative, and a whitening component, wherein the whitening component comprises, as an active ingredient, a cyclic peroxide represented by the following chemical formula (I):

[Chemical Formula I]

(I)

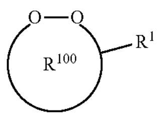

or a salt thereof, wherein $R^{10}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 21)

The whitening composition according to clause 20, wherein, in the chemical formula (I), $R^{100}$ is a cyclic structure having 5 to 10 ring members.

(Clause 22)

The whitening composition according to clause 20 or 21, wherein the cyclic peroxide represented by the chemical formula (I) is represented by the following chemical formula (II):

[Chemical Formula II]

(II)

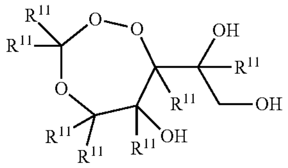

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 23)

The whitening composition according to clause 22, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 24)

The whitening composition according to any of clauses 20 to 23, wherein the cyclic peroxide represented by the chemical formula (I) is represented by the following chemical formula (1):

[Chemical Formula I]

(1)

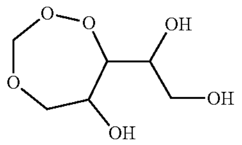

(Clause 25)

A whitening composition comprising glycerin and/or a glycerin derivative, and a whitening component, wherein the whitening component comprises, as an active ingredient, an oxidation reaction product containing a cyclic peroxide or a salt thereof, wherein the oxidation reaction product is obtained through oxidation of an alcohol.

(Clause 26)

The whitening composition according to clause 25, wherein the oxidation of an alcohol is at least one of ozone oxidation and hydrogen peroxide oxidation.

(Clause 27)

The whitening composition according to clause 25 or 26, wherein the whitening composition is a mixture containing a plurality of oxidation reaction products.

(Clause 28)

The whitening composition according to any of clauses 25 to 27, wherein the oxidation reaction product has oxidative capacity.

(Clause 29)

The whitening composition according to any of clauses 25 to 28, wherein the oxidation reaction product has reductive capacity.

(Clause 30)

The whitening composition according to any of clauses 25 to 29, wherein the oxidation reaction product has melanin decomposition activity, melanin generation-suppressing activity, and/or melanin excretion-promoting activity.

(Clause 31)

The whitening composition according to any of clauses 25 to 30, wherein the alcohol is a saturated alcohol.

(Clause 32)

The whitening composition according to any of clauses 25 to 31, wherein the alcohol is a polyhydric alcohol.

(Clause 33)

The whitening composition according to any of clauses 25 to 32, wherein the alcohol is at least one of glycerin and a glycerin derivative.

(Clause 34)

The whitening composition according to any of clauses 25 to 33, comprising an oxidation reaction product formed by binding of two or more molecules of the alcohol.

(Clause 35)

The whitening composition according to any of clauses 25 to 34, comprising the cyclic peroxide described in any of clauses 20 to 24.

(Clause 36)

The whitening composition according to any of clauses 20 to 35, for use for skin.

(Clause 37)

The whitening composition according to any of clauses 20 to 36, wherein the composition is a cosmetic.

<Whitening Agent>

(Clause 38)

A whitening agent comprising a cyclic peroxide represented by the following chemical formula (I):

[Chemical Formula I]

(I)

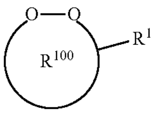

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 39)

The whitening agent according to clause 38, wherein, in the chemical formula (I), $R^{100}$ is a cyclic structure having 5 to 10 ring members.

(Clause 40)

The whitening agent according to clause 38 or 39, wherein the cyclic peroxide represented by the chemical formula (I) is represented by the following chemical formula (II):

[Chemical Formula II]

(II)

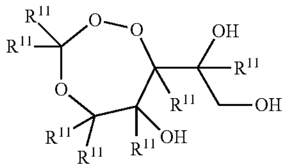

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 41)

The whitening agent according to clause 40, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 42)

The whitening agent according to any of clauses 38 to 41, wherein the cyclic peroxide represented by the chemical formula (I) is represented by the following chemical formula (1):

[Chemical Formula I]

(1)

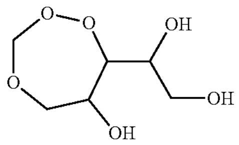

(Clause 43)

A whitening agent comprising an oxidation reaction product comprising a cyclic peroxide or a salt thereof, wherein the oxidation reaction product is obtained through oxidation of an alcohol.

(Clause 44)

The whitening agent according to clause 43, wherein the oxidation of an alcohol is at least one of ozone oxidation and hydrogen peroxide oxidation.

(Clause 45)

The whitening agent according to clause 43 or 44, wherein the whitening agent is a mixture containing a plurality of oxidation reaction products.

(Clause 46)

The whitening agent according to any of clauses 43 to 45, wherein the oxidation reaction product has oxidative capacity.

(Clause 47)

The whitening agent according to any of clauses 43 to 46, wherein the oxidation reaction product has reductive capacity.

(Clause 48)

The whitening agent according to any of clauses 43 to 47, wherein the oxidation reaction product has melanin decomposition activity, melanin generation-suppressing activity, and/or melanin excretion-promoting activity.

(Clause 49)

The whitening agent according to any of clauses 43 to 48, wherein the alcohol is a saturated alcohol.

(Clause 50)

The whitening agent according to any of clauses 43 to 49, wherein the alcohol is a polyhydric alcohol.

(Clause 51)

The whitening agent according to any of clauses 43 to 50, wherein the alcohol is at least one of glycerin and a glycerin derivative.

(Clause 52)

The whitening agent according to any of clauses 43 to 51, comprising an oxidation reaction product formed by binding of two or more molecules of the alcohol.

(Clause 53)

The whitening agent according to any of clauses 43 to 52, comprising the cyclic peroxide described in any of clauses 38 to 42.

(Clause 54)

The whitening agent according to any of clauses 38 to 53, for use for skin.

<Whitening Method>

(Clause 55)

A whitening method using the whitening composition according to any of clauses 20 to 37 and/or the whitening agent according to any of clauses 38 to 54.

(Clause 56)

The whitening method according to clause 55, wherein the whitening composition and/or the whitening agent is used for skin of a subject.

<Use>

(Clause 57)

The whitening composition according to any of clauses 20 to 37 and/or the whitening agent according to any of clauses 38 to 54 for use in whitening.

<Composition for Inducing Expression of Skin Barrier Function-Related Gene>

(Clause 58)

A composition for inducing expression of a skin barrier function-related gene, the composition comprising glycerin and/or a glycerin derivative, and a component for inducing expression of a skin barrier function-related gene, wherein the component for inducing expression of a skin barrier function-related gene comprises, as an active ingredient, a cyclic peroxide represented by the following chemical formula (I):

[Chemical Formula I]

(I)

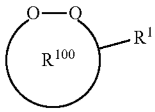

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 59)

The composition for inducing the expression according to clause 58, wherein, in the chemical formula (I), $R^{100}$ is a cyclic structure having 5 to 10 ring members.

(Clause 60)

The composition for inducing the expression according to clause 58 or 59, wherein the cyclic peroxide represented by the chemical formula (I) is represented by the following chemical formula (II):

[Chemical Formula II]

(II)

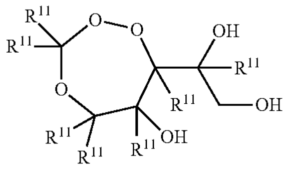

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 61)

The composition for inducing the expression according to clause 60, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 62)

The composition for inducing the expression according to any of clauses 58 to 61, wherein the cyclic peroxide represented by the chemical formula (I) is represented by the following chemical formula (1):

[Chemical Formula I]

(1)

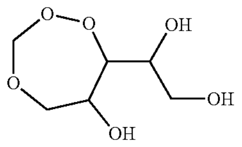

(Clause 63)

The composition for inducing the expression according to any of clauses 58 to 62, for use for skin.

(Clause 64)

The composition for inducing the expression according to any of clauses 58 to 63, wherein the composition is a cosmetic.

(Clause 65)

The composition for inducing the expression according to any of clauses 58 to 64, wherein the skin barrier function-related gene is a pro-filaggrin gene, an involucrin gene, and/or a serine palmitoyltransferase gene.

(Clause 66)

The composition for inducing the expression according to any of clauses 58 to 64, wherein the skin barrier function-related gene is a pro-filaggrin gene.

<Composition for Improving Skin Barrier Function>

(Clause 67)

A composition for improving a skin barrier function, the composition comprising the composition for inducing expression of a skin barrier function-related gene according to any of clauses 58 to 66.

(Clause 68)

The improving composition according to clause 67, for use in a method for improving a skin barrier function in a subject by inducing expression of a skin barrier function-related gene in skin of the subject through transdermal administration.

<Agent for Inducing Expression of Skin Barrier Function-Related Gene>

(Clause 69)

An agent for inducing a skin barrier function-related gene, the agent comprising a cyclic peroxide represented by the following chemical formula (I):

[Chemical Formula I]

(I)

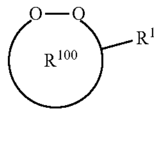

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 70)

The inducing agent according to clause 69, wherein, in the chemical formula (I), $R^{100}$ is a cyclic structure having 5 to 10 ring members.

(Clause 71)

The inducing agent according to clause 69 or 70, wherein the cyclic peroxide represented by the chemical formula (I) is represented by the following chemical formula (II):

[Chemical Formula II]

(II)

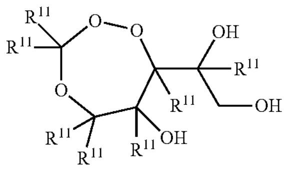

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 72)

The inducing agent according to clause 71, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 73)

The inducing agent according to any of clauses 69 to 72, wherein the cyclic peroxide represented by the chemical formula (I) is represented by the following chemical formula (1):

[Chemical Formula 1]

(1)

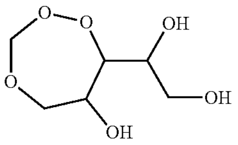

(Clause 74)

The inducing agent according to any of clauses 69 to 73, for use for skin.

(Clause 75)

The inducing agent according to any of clauses 69 to 74, wherein the skin barrier function-related gene is a pro-filaggrin gene, an involucrin gene, and/or a serine palmitoyltransferase gene.

(Clause 76)

The inducing agent according to any of clauses 69 to 75, wherein the skin barrier function-related gene is a profilaggrin gene.

<Agent for Improving Skin Barrier Function>

(Clause 77)

An agent for improving a skin barrier function, the agent comprising the agent for inducing a skin barrier function-related gene according to any of clauses 69 to 76.

(Clause 78)

The improving agent according to clause 77, for use in a method for improving a skin barrier function in a subject by inducing expression of a skin barrier function-related gene in skin of the subject through transdermal administration.

<Composition for Inducing Expression of Anti-Oxidative Stress Response Gene>

(Clause 79)

A composition for inducing expression of an anti-oxidative stress response gene, the composition comprising glycerin and/or a glycerin derivative, and a component for inducing expression of an anti-oxidative stress response gene, wherein the component for inducing expression of an anti-oxidative stress response gene comprises, as an active ingredient, a cyclic peroxide represented by the following chemical formula (I):

[Chemical Formula I]

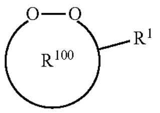

(I)

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 80)

The composition for inducing the expression according to clause 79, wherein, in the chemical formula (I), $R^{100}$ is a cyclic structure having 5 to 10 ring members.

(Clause 81)

The composition for inducing the expression according to clause 79 or 80, wherein the cyclic peroxide represented by the chemical formula (I) is represented by the following chemical formula (II):

[Chemical Formula II]

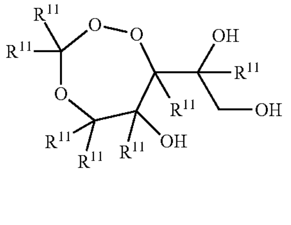

(II)

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 82)

The composition for inducing the expression according to clause 81, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 83)

The composition for inducing the expression according to any of clauses 79 to 82, wherein the cyclic peroxide represented by the chemical formula (I) is represented by the following chemical formula (1):

[Chemical Formula 1]

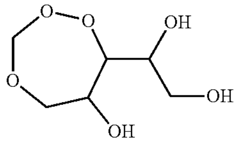

(1)

(Clause 84)

The composition for inducing the expression according to any of clauses 79 to 83, for use for skin.

(Clause 85)

The composition for inducing the expression according to any of clauses 79 to 84, wherein the composition for inducing the expression is a cosmetic.

(Clause 86)

The composition for inducing the expression according to any of clauses 79 to 85, wherein the anti-oxidative stress response gene is a heme oxygenase-1 gene, an NAD(P)H quinone oxidoreductase-1 gene, and/or a glutathione gene.

(Clause 87)

The composition for inducing the expression according to any of clauses 79 to 86, wherein the composition for inducing expression of an anti-oxidative stress response gene is a composition for inducing expression of an anti-oxidative stress response gene in an epidermal keratinocyte.

<Agent for Inducing Expression of Anti-Oxidative Stress Response Gene>

(Clause 88)

An agent for inducing expression of an anti-oxidative stress response gene, the agent comprising a cyclic peroxide represented by the following chemical formula (I):

[Chemical Formula I]

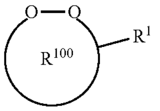

(I)

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 89)

The inducing agent according to clause 88, wherein, in the chemical formula (I), $R^{100}$ is a cyclic structure having 5 to 10 ring members.

(Clause 90)

The inducing agent according to clause 88 or 89, wherein the cyclic peroxide represented by the chemical formula (I) is represented by the following chemical formula (II):

[Chemical Formula II]

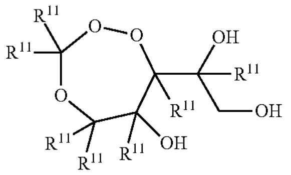

(II)

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 91)

The inducing agent according to clause 90, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 92)

The inducing agent according to any of clauses 88 to 91, wherein the cyclic peroxide represented by the chemical formula (I) is represented by the following chemical formula (1):

[Chemical Formula 1]

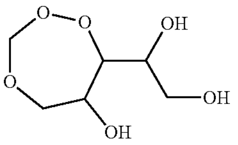

(1)

(Clause 93)

The inducing agent according to any of clauses 88 to 92, for use for skin.

(Clause 94)

The inducing agent according to any of clauses 88 to 93, wherein the anti-oxidative stress response gene is a heme oxygenase-1 gene, an NAD(P)H quinone oxidoreductase-1 gene, and/or a glutathione gene.

<Anti-Inflammatory Composition>

(Clause 95)

An anti-inflammatory composition comprising glycerin and/or a glycerin derivative, and an anti-inflammatory component, wherein the anti-inflammatory component comprises, as an active ingredient, a cyclic peroxide represented by the following chemical formula (I):

[Chemical Formula I]

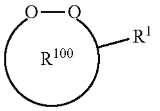

(I)

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 96)

The anti-inflammatory composition according to clause 95, wherein, in the chemical formula (I), $R^{100}$ is a cyclic structure having 5 to 10 ring members.

(Clause 97)

The anti-inflammatory composition according to clause 95 or 96, wherein the cyclic peroxide represented by the chemical formula (I) is represented by the following chemical formula (II):

[Chemical Formula II]

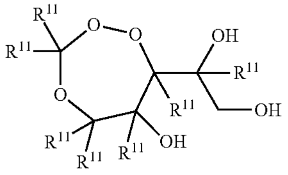

(II)

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 98)

The anti-inflammatory composition according to clause 97, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 99)

The anti-inflammatory composition according to any of clauses 95 to 98, wherein the cyclic peroxide represented by the chemical formula (I) is represented by the following chemical formula (1):

[Chemical Formula 1]

(1)

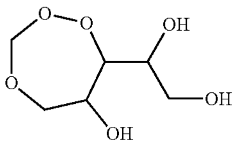

(Clause 100)

The anti-inflammatory composition according to any of clauses 95 to 99, for use for skin.

(Clause 101)

The anti-inflammatory composition according to any of clauses 95 to 100, wherein the composition for inducing the expression is a cosmetic.

(Clause 102)

The anti-inflammatory composition according to any of clauses 95 to 101, wherein the anti-inflammatory composition is a composition for suppressing expression of an IL-1α gene, a composition for suppressing production of IL-1α, and/or a composition for suppressing production of prostaglandin E2.

(Clause 103)

The anti-inflammatory composition according to any of clauses 95 to 102, wherein the anti-inflammatory composition is a composition for suppressing inflammation in an epidermal keratinocyte.

<Anti-Inflammatory Agent>

(Clause 104)

An anti-inflammatory agent comprising a cyclic peroxide represented by the following chemical formula (I):

[Chemical Formula I]

(I)

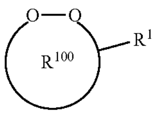

or a salt thereof, wherein

- $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and
- $R^1$ is a substituent, wherein one $R^1$ group, a plurality of $R^1$ groups, or no $R^1$ group is present, and if a plurality of $R^1$ groups is present, the $R^1$ groups are the same or different.

(Clause 105)

The anti-inflammatory agent according to clause 104, wherein, in the chemical formula (I), $R^{100}$ is a cyclic structure having 5 to 10 ring members.

(Clause 106)

The anti-inflammatory agent according to clause 104 or 105, wherein the cyclic peroxide represented by the chemical formula (I) is represented by the following chemical formula (II):

[Chemical Formula II]

(II)

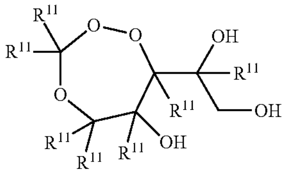

wherein

- the $R^{11}$ groups are the same or different, each being a hydrogen atom or a substituent, and two $R^{11}$ groups bound to the same carbon atom optionally together form an oxo group (=O) or a thioxo group (=S).

(Clause 107)

The anti-inflammatory agent according to clause 106, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 108)

The anti-inflammatory agent according to any of clauses 104 to 107, wherein the cyclic peroxide represented by the chemical formula (I) is represented by the following chemical formula (1):

[Chemical Formula 1]

(1)

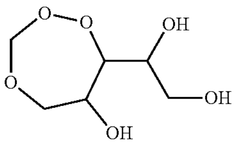

(Clause 109)

The anti-inflammatory agent according to any of clauses 104 to 108, for use for skin.

(Clause 110)

The anti-inflammatory agent according to any of clauses 104 to 109, wherein the anti-inflammatory agent is an agent for suppressing expression of an IL-1α gene, an agent for suppressing production of IL-1α, and/or an agent for suppressing production of prostaglandin E2.

(Clause 111)

The anti-inflammatory agent according to any of clauses 104 to 110, wherein the anti-inflammatory agent is an agent for suppressing inflammation in an epidermal keratinocyte.

<Method for Inducing Expression of Skin Barrier Function-Related Gene>

(Clause 112)

A method for inducing expression of a skin barrier function-related gene using the induced expression promotor composition for a skin barrier function-related gene according to any of clauses 58 to 66 and/or the induced expression promotor for a skin barrier function-related gene according to any of clauses 69 to 76.

(Clause 113)

The method for inducing the expression according to clause 112, wherein the induced expression promotor composition and/or the induced expression promotor are/is administered to a subject.

(Clause 114)

The method for inducing the expression according to clause 113, wherein the administration is performed to skin of the subject.

(Clause 115)

The method for inducing the expression according to any of clauses 112 to 114, to be used in vitro or in vivo.

<Method for Improving Skin Barrier Function>

(Clause 116)

A method for improving a skin barrier function, using the composition for improving a skin barrier function according to clause 67 or 68 and/or the agent for improving a skin barrier function according to clause 77 or 78.

(Clause 117)

The improving method according to clause 116, wherein the composition for improving a skin barrier function and/or the agent for improving a skin barrier function are/is administered to a subject.

(Clause 118)

The improving method according to clause 117, wherein the administration is performed to skin of the subject.

(Clause 119)

The improving method according to any of clauses 116 to 118, to be used in vitro or in vivo.

<Method for Inducing Expression of Anti-Oxidative Stress Response Gene>

(Clause 120)

A method for inducing expression of an anti-oxidative stress response gene using the induced expression promotor composition for an anti-oxidative stress response gene according to any of clauses 79 to 87 and/or the induced expression promotor for an anti-oxidative stress response gene according to any of clauses 88 to 94.

(Clause 121)

The method for inducing the expression according to clause 120, wherein the induced expression promotor composition and/or the induced expression promotor are/is administered to a subject.

(Clause 122)

The method for inducing the expression according to clause 121, wherein the administration is performed to skin of the subject.

(Clause 123)

The method for inducing the expression according to any of clauses 120 to 122, to be used in vitro or in vivo.

<Method for Suppressing Inflammation>

(Clause 124)

A method for suppressing inflammation using the anti-inflammatory composition according to any of clauses 95 to 103 and/or the anti-inflammatory agent according to any of clauses 104 to 111.

(Clause 125)

The suppressing method according to clause 124, wherein the anti-inflammatory composition and/or the anti-inflammatory agent are/is administered to a subject.

(Clause 126)

The method for inducing the expression according to clause 125, wherein the administration is performed to skin of the subject.

(Clause 127)

The suppressing method according to any of clauses 124 to 126, to be used in vitro or in vivo.

<Method for Treating Inflammatory Disease>

(Clause 128)

A method for treating an inflammatory disease, wherein the anti-inflammatory composition according to any of clauses 95 to 103 and/or the anti-inflammatory agent according to any of clauses 104 to 111 are/is administered to a subject.

(Clause 129)

The treating method according to clause 128, wherein the administration is performed to skin of the subject.

(Clause 130)

The treating method according to clause 128 or 129, to be used in vitro or in vivo.

<Use>

(Clause 131)

A composition for use in inducing expression of a skin barrier function-related gene, wherein the composition comprises the composition for inducing expression of a skin barrier function-related gene according to any of clauses 58 to 66.

(Clause 132)

An agent for use in inducing expression of a skin barrier function-related gene, wherein the agent comprises the agent for inducing expression of a skin barrier function-related gene according to any of clauses 69 to 76.

(Clause 133)

A composition for use in improving a skin barrier function, wherein the composition comprises the composition for improving a skin barrier function according to clause 67 or 68.

(Clause 134)

An agent for use in improving a skin barrier function, wherein the agent comprises the agent for improving a skin barrier function according to clause 77 or 78.

(Clause 135)

A composition for use in inducing expression of an anti-oxidative stress response gene, wherein the composition comprises the composition for inducing expression of an anti-oxidative stress response gene according to any of clauses 79 to 87.

(Clause 136)

An agent for use in inducing expression of an anti-oxidative stress response gene, wherein the agent comprises the agent for inducing expression of an anti-oxidative stress response gene according to any of clauses 88 to 94.

(Clause 137)

A composition for use in anti-inflammation, wherein the composition comprises the anti-inflammatory composition according to any of clauses 95 to 103.

(Clause 138)

An agent for use in anti-inflammation, wherein the agent comprises the anti-inflammatory agent according to any of clauses 104 to 111.

(Clause 139)

A composition for use in treating an inflammatory disease, wherein the composition comprises the anti-inflammatory composition according to any of clauses 95 to 103.

(Clause 140)

An agent for use in treating an inflammatory disease, wherein the agent comprises the anti-inflammatory agent according to any of clauses 104 to 111.

<Anti-Glycation Composition>

(Clause 141)

An anti-glycation composition comprising glycerin and/or a glycerin derivative, and an anti-glycation component, wherein the anti-glycation component comprises, as an active ingredient, a cyclic peroxide represented by the following chemical formula (I):

[Chemical Formula I]

(I)

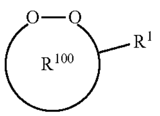

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 142)

The anti-glycation composition according to clause 141, wherein in the chemical formula (I), $R^{100}$ is a cyclic structure having 5 to 10 ring members.

(Clause 143)

The anti-glycation composition according to clause 141 or 142, wherein the cyclic peroxide represented by the chemical formula (I) is represented by the following chemical formula (II):

[Chemical Formula II]

(II)

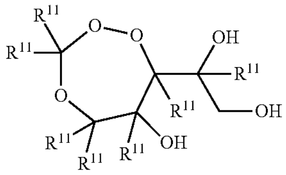

wherein the $R^{11}$ groups are the same or different, each being a hydrogen atom or a substituent, and two $R^{11}$ groups bound to the same carbon atom optionally together form an oxo group (=O) or a thioxo group (=S).

(Clause 144)

The anti-glycation composition according to clause 143, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 145)

The anti-glycation composition according to any of clauses 141 to 144, wherein the cyclic peroxide represented by the chemical formula (I) is represented by the following chemical formula (1):

[Chemical Formula 1]

(1)

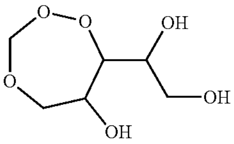

(Clause 146)

The anti-glycation composition according to any of clauses 141 to 145, for cleaving a crosslinking structure generated through glycation reaction across a polypeptide and/or a protein.

(Clause 147)

The anti-glycation composition according to any of clauses 141 to 146, for use for skin.

(Clause 148)

The anti-glycation composition according to any of clauses 141 to 147, wherein the composition is a cosmetic.

<Anti-Glycation Agent>

(Clause 149)

An anti-glycation agent comprising acyclic peroxide represented by the following chemical formula (I):

[Chemical Formula I]

(I)

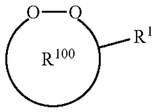

or a salt thereof, wherein $R^{100}$ is a cyclic structure having three or more ring members, being saturated or unsaturated, being an aromatic ring or a nonaromatic ring, having or not having a heteroatom other than the oxygen atoms in the chemical formula (I) in the cyclic structure, and being a monocyclic ring or a fused ring, and $R^1$ is a substituent, wherein one $R^1$ group, a plurality of $R^1$ groups, or no $R^1$ group is present, and if a plurality of $R^1$ groups is present, the $R^1$ groups are the same or different.

(Clause 150)

The anti-glycation agent according to clause 149, wherein, in the chemical formula (I), $R^{100}$ is a cyclic structure having 5 to 10 ring members.

(Clause 151)

The anti-glycation agent according to clause 149 or 150, wherein the cyclic peroxide represented by the chemical formula (I) is represented by the following chemical formula (II):

[Chemical Formula II]

(II)

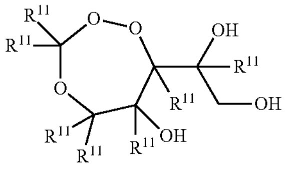

wherein the $R^{11}$ groups are the same or different, each being a hydrogen atom or a substituent, and two $R^{11}$ groups bound to the same carbon atom optionally together form an oxo group (═O) or a thioxo group (═S).

(Clause 152)

The anti-glycation agent according to clause 151, wherein the substituent for each of the $R^{11}$ groups in the chemical formula (II) is a hydroxy group (—OH), an aldehyde group (formyl group), a hydroxyalkyl group, a sulfo group, a nitro group, a diazo group, an alkyl group, an unsaturated aliphatic hydrocarbon group, an aryl group, a heteroaryl group, a halogen, a mercapto group (—SH), or an alkylthio group (—SR, wherein R is an alkyl group).

(Clause 153)

The anti-glycation agent according to any of clauses 149 to 152, wherein the cyclic peroxide represented by the chemical formula (I) is represented by the following chemical formula (1):

[Chemical Formula 1]

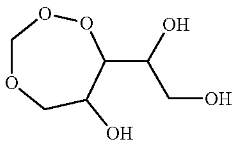

(1)

(Clause 154)

The anti-glycation agent according to any of clauses 149 to 153, for cleaving a crosslinking structure generated through glycation reaction across a polypeptide and/or a protein.

(Clause 155)

The anti-glycation agent according to any of clauses 149 to 154, for use for skin.

<Anti-Glycation Method>

(Clause 156)

An anti-glycation method using the glycation-inhibitory composition according to any of clauses 141 to 148 and/or the anti-glycation agent according to any of clauses 149 to 155.

(Clause 157)

The anti-glycation method according to clause 156, wherein the glycation-inhibitory composition and/or the anti-glycation agent are/is administered to a subject.

(Clause 158)

The anti-glycation method according to clause 157, wherein the administration is performed to skin of the subject.

(Clause 159)

The anti-glycation method according to any of clauses 156 to 158, to be used in vitro or in vivo.

<Use>

(Clause 160)

A composition for use in anti-glycation, wherein the composition comprises the anti-glycation composition according to any of clauses 141 to 148.

(Clause 161)

An agent for use in anti-glycation, wherein the agent comprises the anti-glycation agent according to any of clauses 149 to 155.

INDUSTRIAL APPLICABILITY

Industrial Applicability of First Mode

As described above, the cyclic peroxide, the oxidation reaction product, and the method for producing an oxidation reaction product according to the first mode of the present invention are highly safe, hence being very useful, for example, in the field of medicaments, cosmetic products, foods, and dietary supplements.

Industrial Applicability of Second Mode

As described above, the whitener composition according to the second mode of the present invention is very useful, for example, in the field of cosmetics.

Industrial Applicability of Third Mode

As described above, the expression-inducing composition for a skin barrier function-related gene according to the third mode of the present invention is capable of inducing expression of a skin barrier function-related gene, hence being very useful, for example, in the field of cosmetics.

Industrial Applicability of Fourth Mode

As described above, the anti-glycation composition according to the fourth mode of the present invention has anti-glycation activity, hence being very useful, for example, in the field of cosmetics.

SEQUENCE LISTING

TF21091WO.xml

What is claimed is:

1. A cyclic-peroxide represented by the following chemical formula (1):

[Chemical Formula 1]

(1)

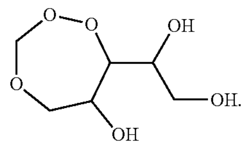

2. An oxidation reaction product comprising the cyclic peroxide according to claim 1, wherein the oxidation reaction product is obtained through oxidation of an alcohol.

3. The oxidation reaction product according to claim 2, wherein the oxidation of an alcohol is at least one of ozone oxidation and hydrogen peroxide oxidation.

4. The oxidation reaction product according to claim 2, wherein the alcohol is at least one of glycerin and a glycerin derivative.

5. A method for producing an oxidation reaction product, wherein the oxidation reaction product is the oxidation reaction product according to claim 2, the method comprising:

an alcohol oxidation step of oxidizing an alcohol.

6. The method for producing an oxidation reaction product according to claim 5, wherein the alcohol is oxidized through at least one of ozone oxidation and hydrogen peroxide oxidation in the alcohol oxidation step.

7. A whitening agent comprising the cyclic peroxide to claim 1 or salt thereof.

8. A whitening composition comprising glycerin and/or a glycerin derivative, and a whitening component, wherein the whitening component comprises the whitening agent according to claim 7 as an active ingredient.

9. An agent for inducing a skin barrier function-related gene, the agent comprising the cyclic peroxide according to claim 1 or a salt thereof.

10. A composition for inducing expression of a skin barrier function-related gene, the composition comprising glycerin and/or a glycerin derivative, and a component for inducing expression of a skin barrier function-related gene, wherein the component for inducing expression of a skin barrier function-related gene comprises the agent for inducing a skin barrier function-related gene according to claim 9.

11. A composition for improving a skin barrier function, the composition comprising the composition for inducing expression of a skin barrier function-related gene according to claim 10.

12. The improving agent composition for a skin barrier function according to claim 11, for use in a method for improving a skin barrier function in a subject by inducing expression of a skin barrier function-related gene in skin of the subject through transdermal administration.

13. The agent for inducing a skin barrier function-related gene according to claim 9, wherein the skin barrier function-related gene is a pro-filaggrin gene, an involucrin gene, and/or a serine palmitoyltransferase gene.

14. An agent for improving a skin barrier function, the agent comprising the agent for inducing a skin barrier function-related gene according to claim 9.

15. The agent for improving a skin barrier function according to claim 14, for use in a method for improving a skin barrier function in a subject by inducing expression of a skin barrier function-related gene in skin of the subject through transdermal administration.

16. An agent for inducing expression of an anti-oxidative stress response gene, the agent comprising the cyclic peroxide according to claim 1 or a salt thereof.

17. A composition for inducing expression of an anti-oxidative stress response gene, the composition comprising glycerin and/or a glycerin derivative, and a component for inducing expression of an anti-oxidative stress response gene, wherein the component for inducing expression of an anti-oxidative stress response gene comprises the agent for inducing an anti-oxidative stress response gene according to claim 16 as an active ingredient.

18. The agent for inducing expression of an anti-oxidative stress response gene according to claim 16, wherein the anti-oxidative stress response gene is a heme oxygenase-1 gene, an NAD(P)H quinone oxidoreductase-1 gene, and/or a glutathione gene.

19. An anti-inflammatory agent comprising the cyclic peroxide according to claim 1 or a salt thereof.

20. An anti-inflammatory composition comprising glycerin and/or a glycerin derivative, and an anti-inflammatory component, wherein the anti-inflammatory component comprises the anti-inflammatory agent according to claim 19 as an active ingredient.

21. The anti-inflammatory agent according to claim 19, wherein the anti-inflammatory agent is an agent for suppressing expression of an IL-1α gene, an agent for suppressing production of IL-1α, and/or an agent for suppressing production of prostaglandin E2.

22. The anti-inflammatory agent according to claim 19, wherein the anti-inflammatory agent is an agent for suppressing inflammation in an epidermal keratinocyte.

23. An anti-glycation agent comprising the cyclic peroxide according to claim 1 or a salt thereof.

24. An anti-glycation composition comprising glycerin and/or a glycerin derivative, and an anti-glycation component, wherein the anti-glycation component comprises the anti-glycation agent according to claim 23 as an active ingredient.

25. The anti-glycation agent according to claim 23, wherein the anti-glycation agent cleaves a crosslinking structure generated through glycation reaction across a polypeptide and/or a protein.

* * * * *

```
                              SEQUENCE LISTING


Sequence total quantity: 12
SEQ ID NO: 1              moltype = DNA  length = 23
FEATURE                   Location/Qualifiers
misc_feature              1..23
                          note = profilaggrin_fw primer
source                    1..23
                          mol_type = other DNA
                          organism = synthetic construct
SEQUENCE: 1
catggcagct atggtagtgc aga                                          23

SEQ ID NO: 2              moltype = DNA  length = 23
FEATURE                   Location/Qualifiers
misc_feature              1..23
                          note = profilaggrin_rv primer
```

```
source                  1..23
                        mol_type = other DNA
                        organism = synthetic construct
SEQUENCE: 2
accaaacgca cttgctttac aga                                              23

SEQ ID NO: 3            moltype = DNA  length = 20
FEATURE                 Location/Qualifiers
misc_feature            1..20
                        note = involucrin_fw primer
source                  1..20
                        mol_type = other DNA
                        organism = synthetic construct
SEQUENCE: 3
gctggagcag cctgtgtttg                                                  20

SEQ ID NO: 4            moltype = DNA  length = 20
FEATURE                 Location/Qualifiers
misc_feature            1..20
                        note = involucrin_rv primer
source                  1..20
                        mol_type = other DNA
                        organism = synthetic construct
SEQUENCE: 4
ctggacactg cgggtggtta                                                  20

SEQ ID NO: 5            moltype = DNA  length = 22
FEATURE                 Location/Qualifiers
misc_feature            1..22
                        note = serine palmitoyltransferase_fw primer
source                  1..22
                        mol_type = other DNA
                        organism = synthetic construct
SEQUENCE: 5
gcctgtcagc agctcatacc aa                                               22

SEQ ID NO: 6            moltype = DNA  length = 23
FEATURE                 Location/Qualifiers
misc_feature            1..23
                        note = serine palmitoyltransferase_rv primer
source                  1..23
                        mol_type = other DNA
                        organism = synthetic construct
SEQUENCE: 6
ggcctgtcca gtagaggtac caa                                              23

SEQ ID NO: 7            moltype = DNA  length = 20
FEATURE                 Location/Qualifiers
misc_feature            1..20
                        note = GAPDH_fw primer
source                  1..20
                        mol_type = other DNA
                        organism = synthetic construct
SEQUENCE: 7
gcaccgtcaa ggctgagaac                                                  20

SEQ ID NO: 8            moltype = DNA  length = 19
FEATURE                 Location/Qualifiers
misc_feature            1..19
                        note = GAPDH_rv primer
source                  1..19
                        mol_type = other DNA
                        organism = synthetic construct
SEQUENCE: 8
tggtgaagac gccagtgga                                                   19

SEQ ID NO: 9            moltype = DNA  length = 20
FEATURE                 Location/Qualifiers
misc_feature            1..20
                        note = heme oxygenase 1_fw primer
source                  1..20
                        mol_type = other DNA
                        organism = synthetic construct
SEQUENCE: 9
ttgccagtgc caccaagttc                                                  20

SEQ ID NO: 10           moltype = DNA  length = 20
FEATURE                 Location/Qualifiers
misc_feature            1..20
```

-continued

```
                        note = heme oxygenase 1_rv primer
source                  1..20
                        mol_type = other DNA
                        organism = synthetic construct
SEQUENCE: 10
tcagcagctc ctgcaactcc                                          20

SEQ ID NO: 11           moltype = DNA  length = 22
FEATURE                 Location/Qualifiers
misc_feature            1..22
                        note = NAD(P)H quinone oxidoreductase 1_fw primer
source                  1..22
                        mol_type = other DNA
                        organism = synthetic construct
SEQUENCE: 11
gtggcagtgg ctccatgtac tc                                       22

SEQ ID NO: 12           moltype = DNA  length = 25
FEATURE                 Location/Qualifiers
misc_feature            1..25
                        note = NAD(P)H quinone oxidoreductase 1_rv primer
source                  1..25
                        mol_type = other DNA
                        organism = synthetic construct
SEQUENCE: 12
gagtgtgccc aatgctatat gtcag                                    25
```